(12) United States Patent
Stoermer et al.

(10) Patent No.: US 9,938,275 B2
(45) Date of Patent: *Apr. 10, 2018

(54) SUBSTITUTED IMIDAZOQUINOLINES, IMIDAZOPYRIDINES, AND IMIDAZONAPHTHYRIDINES

(71) Applicant: 3M INNOVATIVE PROPERTIES COMPANY, St. Paul, MN (US)

(72) Inventors: Doris Stoermer, Newbury Park, CA (US); Joseph F. Dellaria, Jr., Woodbury, MN (US); David T. Amos, St. Paul, MN (US); Bernhard M. Zimmermann, Apple Valley, MN (US); Luke T. Dressel, Somerset, WI (US); Jason D. Bonk, Hudson, WI (US); Matthew R. Radmer, Robbinsdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,850

(22) Filed: Jan. 23, 2017

(65) Prior Publication Data

US 2017/0129891 A1 May 11, 2017

Related U.S. Application Data

(60) Continuation of application No. 14/684,871, filed on Apr. 13, 2015, now Pat. No. 9,550,773, which is a division of application No. 14/021,197, filed on Sep. 9, 2013, now Pat. No. 9,006,264, which is a continuation of application No. 12/974,459, filed on Dec. 21, 2010, now Pat. No. 8,541,438, which is a division of application No. 11/570,707, filed as application No. PCT/US2005/021445 on Jun. 17, 2005, now Pat. No. 7,884,207.

(60) Provisional application No. 60/581,274, filed on Jun. 18, 2004.

(51) Int. Cl.
*C07D 471/04* (2006.01)
*C07D 471/14* (2006.01)

(52) U.S. Cl.
CPC .......... *C07D 471/04* (2013.01); *C07D 471/14* (2013.01)

(58) Field of Classification Search
CPC ............................ C07D 471/04; C07D 471/14
USPC ........................................................ 514/300
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,753,951 A | 6/1988 | Takada et al. |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,348,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS

Wozniak et al., "The Amination of 3-nitro-1, 5-naphthyridines by Liquid Ammonia/Potassium Perrnanganate[1,2]. A New and Convenient Amination Method." *Journal of the Royal Netherlands Chemical Society*, 102, pp. 511-513, Dec. 12, 1983.

(Continued)

*Primary Examiner* — Rita J Desai

(57) ABSTRACT

Imidazo-quinoline, -pyridine, and -naphthyridine ring systems (particularly quinolines, tetrahydroquinolines, pyridines, [1,5]naphthyridines, [1,5]tetrahydronaphthyridines) substituted at the 1-position with a cyclic substituent, pharmaceutical compositions containing the compounds, methods of making these compounds, and methods of use of these compounds as immunomodulators, for inducing cytokine biosynthesis in animals and in the treatment of diseases including viral and neoplastic diseases are disclosed.

20 Claims, No Drawings

(56) References Cited

U.S. PATENT DOCUMENTS

| | | | |
|---|---|---|---|
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,698,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,841,878 B1 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,255 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,228,928 B2 | 6/2007 | Mitre et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,655,872 B2 | 2/2010 | Statham et al. |
| 7,687,628 B2 | 3/2010 | Gutman et al. |
| 7,696,159 B2 | 4/2010 | Owens et al. |
| 7,698,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 * | 2/2011 | Stoermer ............ C07D 471/14 546/82 |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 | 3/2011 | Griesgraber et al. |
| 7,915,281 B2 | 3/2011 | Moser et al. |
| 7,939,526 B2 | 5/2011 | Radmer et al. |
| 7,943,609 B2 | 5/2011 | Griesgraber et al. |
| 7,943,610 B2 | 5/2011 | Hays et al. |
| 7,943,636 B2 | 5/2011 | Hays et al. |
| 7,943,809 B2 | 5/2011 | Griesgraber et al. |
| 7,968,562 B2 | 6/2011 | Skwierczynski et al. |
| 7,968,563 B2 | 6/2011 | Kshirsagar et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,028,366 B2 | 9/2011 | Prince et al. |
| 8,034,938 B2 | 10/2011 | Griesgraber et al. |
| 8,138,173 B2 | 3/2012 | Merrill et al. |
| 8,143,270 B2 | 3/2012 | Kshirsager et al. |
| 8,158,794 B2 | 4/2012 | Kshirsager et al. |
| 8,178,677 B2 | 5/2012 | Kshirsager et al. |
| 8,263,594 B2 | 9/2012 | Lindstrom et al. |
| 8,343,993 B2 | 1/2013 | Kshirsager et al. |
| 8,541,438 B2 * | 9/2013 | Stoermer ............ A61K 31/341 514/290 |
| 8,658,666 B2 | 2/2014 | Rice et al. |
| 8,673,932 B2 | 3/2014 | Kshirsager et al. |
| 8,691,837 B2 | 4/2014 | Krepski et al. |
| 8,697,873 B2 | 4/2014 | Krepski et al. |
| 8,735,421 B2 | 5/2014 | Bonk et al. |
| 8,802,853 B2 | 8/2014 | Bonk et al. |
| 8,846,710 B2 | 9/2014 | Kshirsager et al. |
| 8,871,782 B2 | 10/2014 | Lindstrom et al. |
| 9,006,264 B2 * | 4/2015 | Stoermer ............ A61K 31/341 514/293 |

(56) References Cited

U.S. PATENT DOCUMENTS

| | | |
|---|---|---|
| 9,107,958 B2 | 8/2015 | Wightman |
| 9,475,804 B2 | 10/2016 | Wightman |
| 9,550,773 B2 | 1/2017 | Stoermer et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0068839 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0017078 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0221558 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | |
|---|---|---|
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| WO | WO 02/36592 | 5/2002 |
| WO | WO 05/003064 | 1/2005 |
| WO | 2005/094531 | * 10/2005 |
| WO | 2005/123079 | * 12/2005 |
| WO | WO 06/028451 | 3/2006 |
| WO | WO 06/063072 | 6/2006 |
| WO | WO 06/121528 | 11/2006 |
| WO | WO 07/030775 | 3/2007 |

OTHER PUBLICATIONS

Baranov et al., "Pyrazoles, Imidazoles, and Other 5-Membered Rings.", *Chem. Abs.* 85 94362, (1976).

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

(56) References Cited

OTHER PUBLICATIONS

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).
Gerster et al. "Synthesis and Structure" *J. Med Chem.* 2005, 48, 3481-3491.

\* cited by examiner

SUBSTITUTED IMIDAZOQUINOLINES, IMIDAZOPYRIDINES, AND IMIDAZONAPHTHYRIDINES

CROSS-REFERENCE TO RELATED APPLICATIONS

This application is a continuation U.S. patent application Ser. No. 14/684,871, filed Apr. 13, 2015, now U.S. Pat. No. 9,550,773, which is a divisional of U.S. patent application Ser. No. 14/021,197, filed Sep. 9, 2013, now U.S. Pat. No. 9,006,264, which is a continuation of Ser. No. 12/974,459, filed Dec. 21, 2010, now U.S. Pat. No. 8,541,438, which is a divisional of U.S. Ser. No. 11/570,707, filed Dec. 15, 2006, now U.S. Pat. No. 7,884,207, which is a National Stage Filing of International Application No. PCT/US2005/021445, filed Jun. 17, 2005, which claims priority to U.S. Provisional Application Ser. No. 60/581,274, filed Jun. 18, 2004, all of which are incorporated herein by reference.

BACKGROUND

In the 1950's the 1H-imidazo[4,5-c]quinoline ring system was developed and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo [4,5-c]quinoline was synthesized as a possible anticonvulsant and cardiovascular agent. Also, several 2-oxoimidazo [4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo [4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in the imidazoquinoline ring system, as well as other imidazo ring systems, and there is a continuing need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula (I):

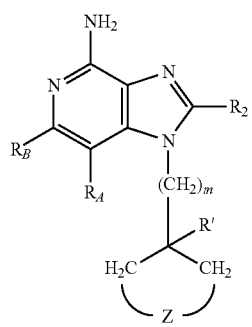

wherein $R_A$, $R_B$, $R_2$, R', Z, and m are as defined below.

Compounds of Formula (I) include imidazo-quinoline, -pyridine, and -naphthyridine ring systems, particularly quinolines, tetrahydroquinolines, pyridines, 1,5-naphthyridines, and 1,5-tetrahydronaphthyridines, substituted at the 1-position with a cyclic substituent.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula (I):

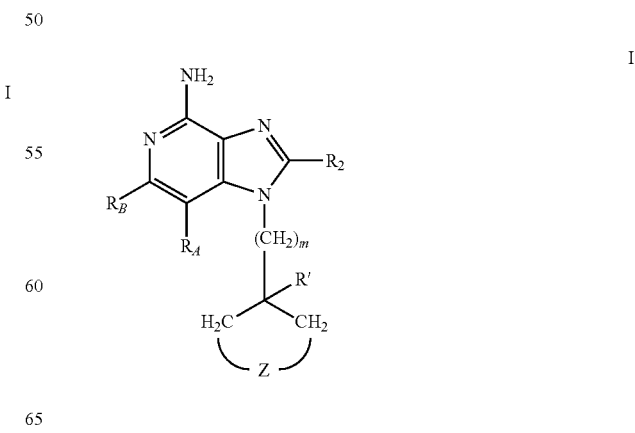

as well as more specific compounds of the following Formulas (II, III, IV, V, VI, VII, VIII, IX, and X):

II 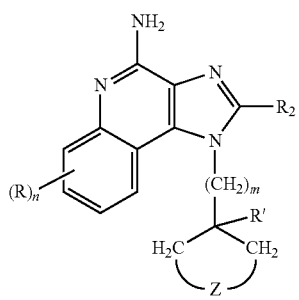
III 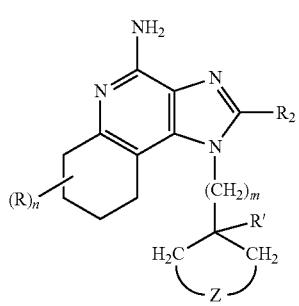
IV 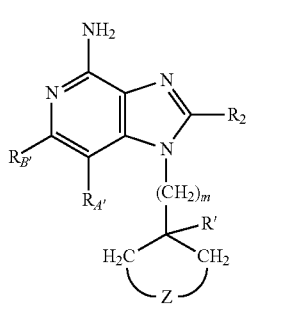
V 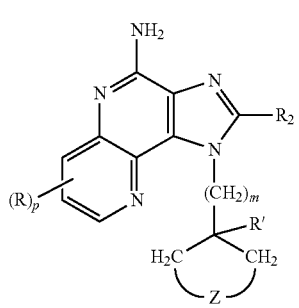
VI 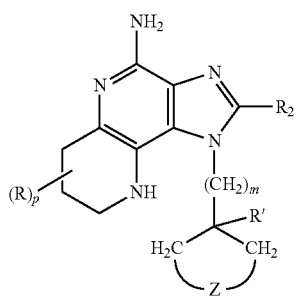
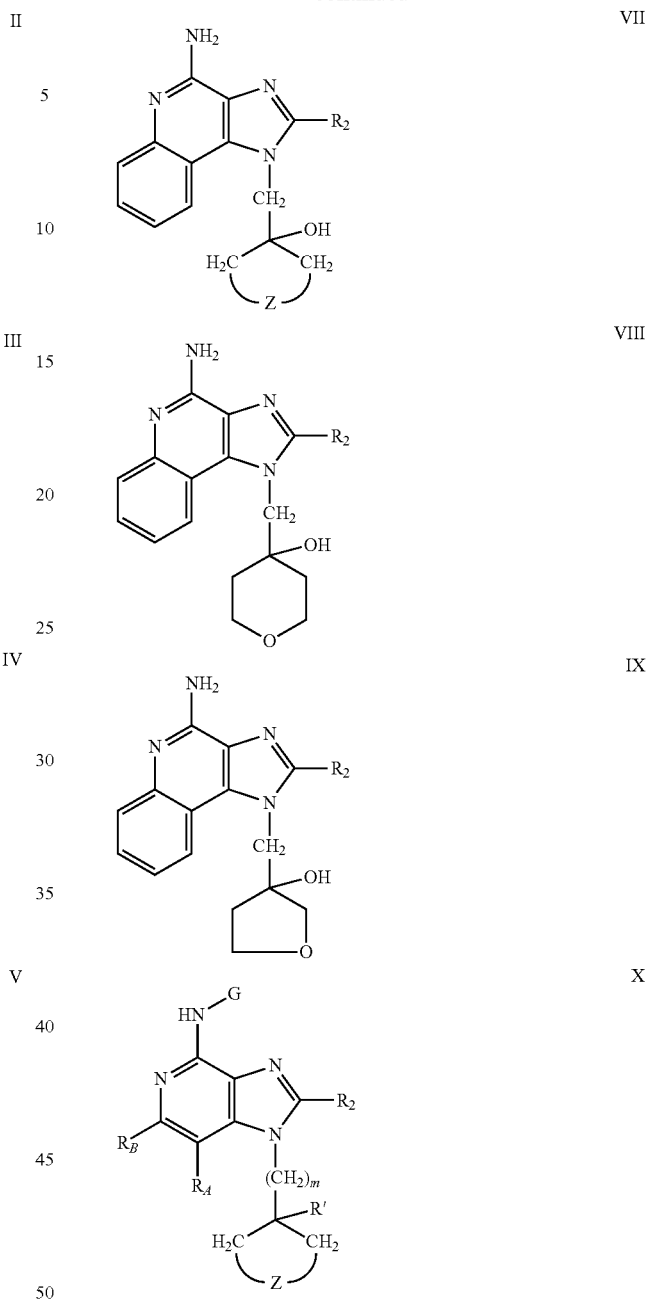
as well as intermediates of the following Formulas (XI) and (XII):
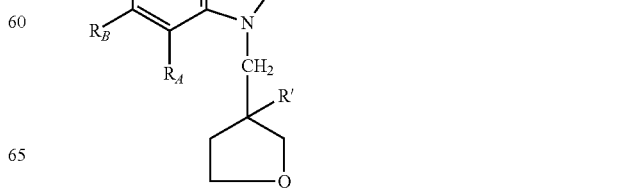

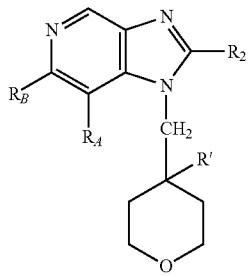

and pharmaceutically acceptable salts thereof.

In one embodiment, there is provided a compound of the Formula (I):

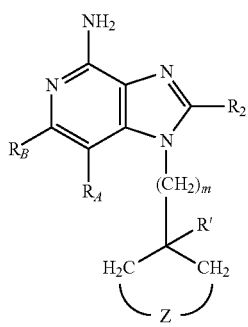

wherein:
m is an integer from 1 to 5;
R' is selected from the group consisting of:
hydroxy,
thiol,
—S(O)$_{0-2}$-alkyl,
—S(O)$_2$—NH—R$_9$,
alkoxy,
—O—C$_{1-3}$ alkylene-S(O)$_2$-alkyl,
—N(R$_9$)$_2$, and
—NH-Q-R$_4$;
Z is selected from the group consisting of:
a bond,
C$_{1-5}$-alkylene,

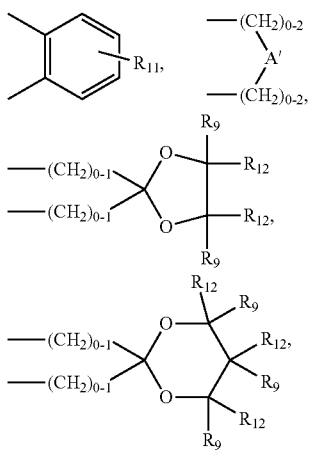

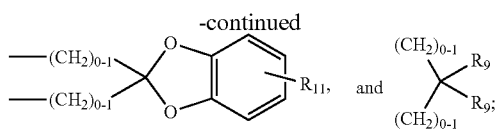

A' is selected from the group consisting of:
—O—,
—C(O)—,
—N(R$_8$)—,
—N(Q-R$_4$)—,
—N(C$_{1-5}$ alkylene-NH-Q-R$_4$)—,
—N(C$_{1-5}$ alkylene-W—NH—R$_8$)—, and
—S(O)$_{0-2}$—;
R$_2$ is selected from the group consisting of:
—R$_4$,
—X—R$_4$,
—X—Y—R$_4$, and
—X—R$_5$;
R$_A$ and R$_B$ are each independently selected from the group consisting of:
hydrogen,
halogen,
alkyl,
alkenyl,
alkoxy,
alkylthio, and
—N(R$_9$)$_2$;
or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups;
or when taken together, R$_A$ and R$_B$ form a fused 5 to 7 membered saturated ring, optionally containing one heteroatom selected from the group consisting of N and S, and unsubstituted or substituted by one or more R groups;
R is selected from the group consisting of:
halogen,
hydroxy,
alkyl,
alkenyl,
haloalkyl,
alkoxy,
alkylthio, and
—N(R$_9$)$_2$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

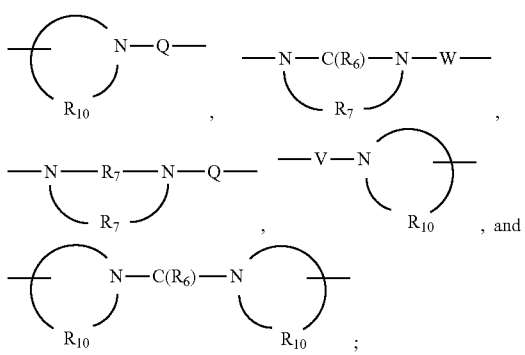

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

R₅ is selected from the group consisting of:

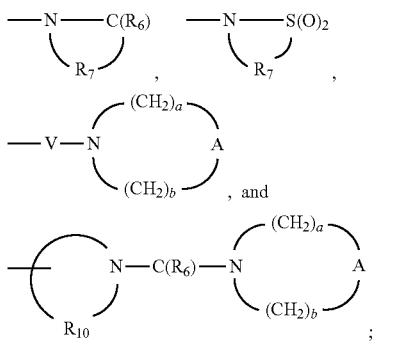

R₆ is selected from the group consisting of =O and =S;
R₇ is $C_{2-7}$ alkylene;
R₈ is selected from the group consisting of hydrogen, alkyl, alkoxyalkylenyl, and arylalkylenyl;
R₉ is selected from the group consisting of hydrogen and alkyl;
R₁₀ is $C_{3-8}$ alkylene;
R₁₁ is selected from the group consisting of hydrogen, alkyl, halogen, and trifluoromethyl;
R₁₂ is selected from the group consisting of hydrogen, alkyl, phenyl, 2-pyridyl, 3-pyridyl, and 4-pyridyl;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that when Z is a bond or $C_{1-5}$ alkylene then R' is other than —O—$C_{1-3}$ alkylene-S(O)$_2$-alkyl, and with the further proviso that when Z is a bond or $C_{1-5}$ alkylene and R$_2$ is —X—Y—R$_4$ and Y is —N(R$_8$)-Q-, then Q is other than —C(R$_6$)—N(R$_8$)—W—;

or a pharmaceutically acceptable salt thereof.

In another embodiment, there is provided a compound of the Formula (II):

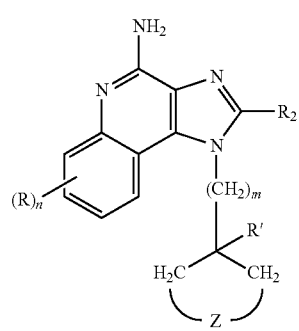

II wherein:
m is an integer from 1 to 5;
n is an integer from 0 to 4;
R' is selected from the group consisting of:
  hydroxy,
  thiol,
  —S(O)$_{0-2}$-alkyl,
  —S(O)$_2$—NH—R$_9$,
  alkoxy,
  —O—$C_{1-3}$ alkylene-S(O)$_2$-alkyl,
  —N(R$_9$)$_2$, and
  —NH-Q-R$_4$;
Z is selected from the group consisting of:
  a bond,
  $C_{1-5}$ alkylene,

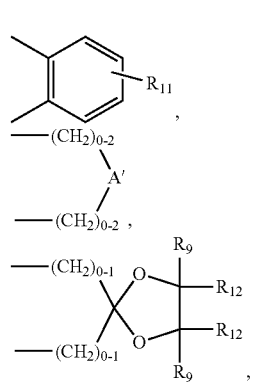

-continued

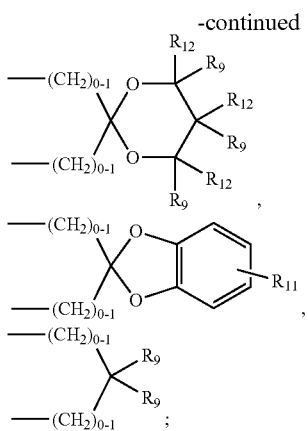
, and

A' is selected from the group consisting of:
—O—,
—N(R$_8$)—,
—N(Q-R$_4$)—,
—N(C$_{1-5}$ alkylene-NH-Q-R$_4$)—,
—N(C$_{1-5}$ alkylene-W—NH—R$_8$)—, and
—S(O)$_{0-2}$—;

R$_2$ is selected from the group consisting of:
—R$_4$,
—X—R$_4$,
—X—Y—R$_4$, and
—X—R$_8$;

R is selected from the group consisting of:
halogen,
hydroxy,
alkyl,
alkenyl,
haloalkyl,
alkoxy,
alkylthio, and
—N(R$_9$)$_2$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

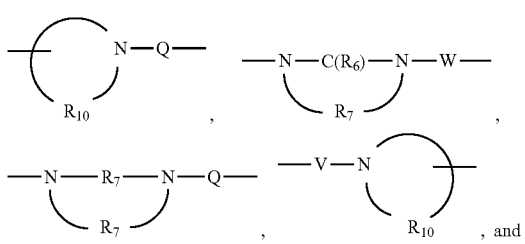

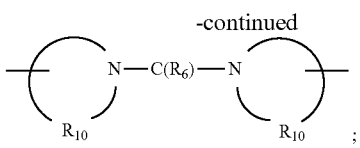
;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

R$_5$ is selected from the group consisting of:

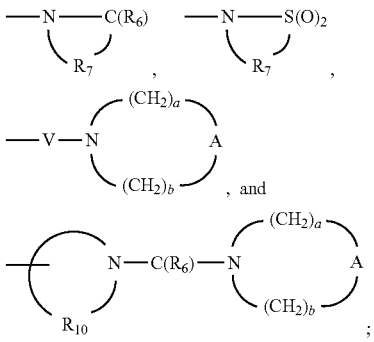
;

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
R$_{11}$ is selected from the group consisting of hydrogen, alkyl, halogen, and trifluoromethyl;
R$_{12}$ is selected from the group consisting of hydrogen, alkyl, phenyl, 2-pyridyl, 3-pyridyl, and 4-pyridyl;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that when Z is a bond or C$_{1-5}$ alkylene then R' is other than —O—C$_{1-3}$ alkylene-S(O)$_2$-alkyl, and with the further proviso that when Z is a bond or $C_{1-5}$ alkylene and $R_2$ is —X—Y—$R_4$ and Y is —N($R_8$)-Q-, then Q is other than —C($R_6$)—N($R_8$)—W—;

or a pharmaceutically acceptable salt thereof.

In another embodiment, there is provided a compound of the Formula (III):

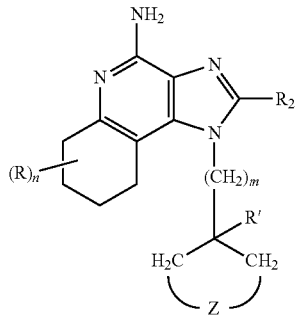

III wherein:
m is an integer from 1 to 5;
n is an integer from 0 to 4;
R' is selected from the group consisting of:
  hydroxy,
  thiol,
  —S(O)$_{0-2}$-alkyl,
  —S(O)$_2$—NH—$R_9$,
  alkoxy,
  —O—$C_{1-3}$ alkylene-S(O)$_2$-alkyl,
  —N($R_9$)$_2$, and
  —NH-Q-$R_4$;
Z is selected from the group consisting of:
  a bond,
  $C_{1-5}$ alkylene,

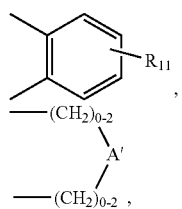,

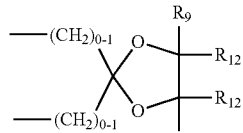,

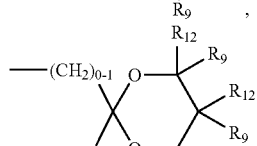,

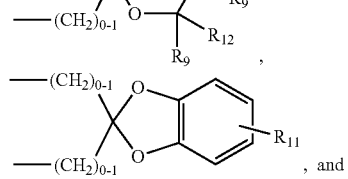, and

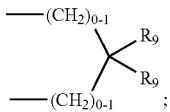;

A' is selected from the group consisting of:
  —O—,
  —C(O)—,
  —N($R_8$)—,
  —N(Q-$R_4$)—,
  —N($C_{1-5}$ alkylene-NH-Q-$R_4$)—,
  —N($C_{1-5}$ alkylene-W—NH—$R_8$)—, and
  —S(O)$_{0-2}$—;
$R_2$ is selected from the group consisting of:
  —$R_4$,
  —X—$R_4$,
  —X—Y—$R_4$, and
  —X—$R_8$;
R is selected from the group consisting of:
  halogen,
  hydroxy,
  alkyl,
  alkenyl,
  haloalkyl,
  alkoxy,
  alkylthio, and
  —N($R_9$)$_2$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
  —S(O)$_{0-2}$—,
  —S(O)$_2$—N($R_8$)—,
  —C($R_6$)—,
  —C($R_6$)—O—,
  —O—C($R_6$)—,
  —O—C(O)—O—,
  —N($R_8$)-Q-,
  —C($R_6$)—N($R_8$)—,
  —O—C($R_6$)—N($R_8$)—,
  —C($R_6$)—N(O$R_9$)—,

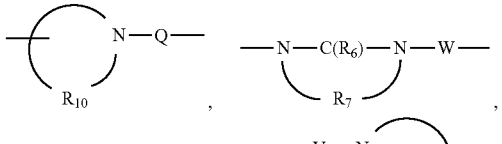

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_5$ is selected from the group consisting of:

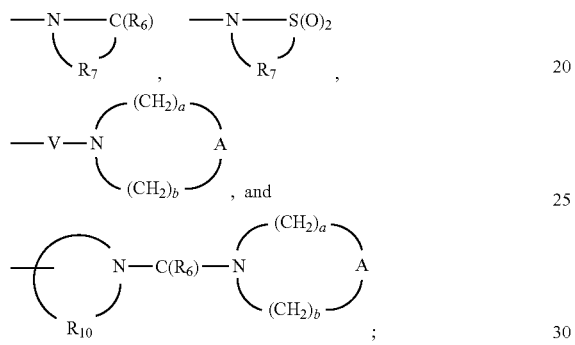

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

$R_{11}$ is selected from the group consisting of hydrogen, alkyl, halogen, and trifluoromethyl;

$R_{12}$ is selected from the group consisting of hydrogen, alkyl, phenyl, 2-pyridyl, 3-pyridyl, and 4-pyridyl;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that when Z is a bond or $C_{1-5}$ alkylene then R' is other than —O—$C_{1-3}$ alkylene-S(O)$_2$-alkyl, and with the further proviso that when Z is a bond or $C_{1-5}$ alkylene and $R_2$ is —X—Y—$R_4$ and Y is —N(R$_8$)-Q-, then Q is other than —C(R$_6$)—N(R$_8$)—W—;

or a pharmaceutically acceptable salt thereof.

In another embodiment, the present invention provides a compound of the Formula (IV):

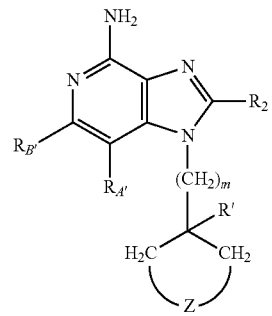

IV wherein:
m is an integer from 1 to 5;
R' is selected from the group consisting of:
hydroxy,
thiol,
—S(O)$_{0-2}$-alkyl,
—S(O)$_2$—NH—R$_9$,
alkoxy,
—O—$C_{1-3}$ alkylene-S(O)$_2$-alkyl,
—N(R$_9$)$_2$, and
—NH-Q-R$_4$;

Z is selected from the group consisting of:
a bond,
$C_{1-5}$ alkylene,

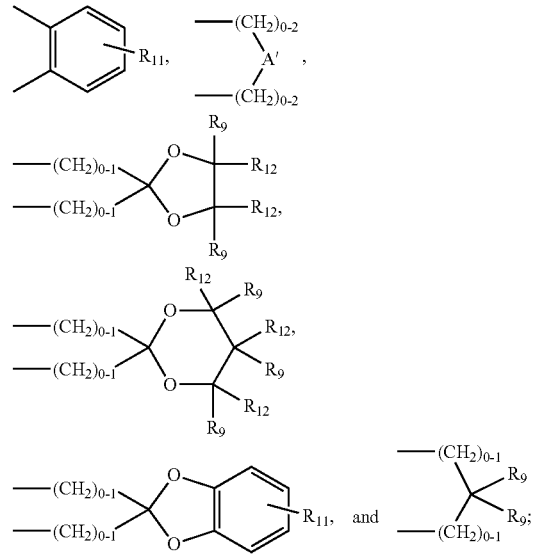

A' is selected from the group consisting of:
—O—,
—C(O)—,
—N(R$_8$)—,
—N(Q-R$_4$)—,
—N($C_{1-5}$ alkylene-NH-Q-R$_4$)—,
—N($C_{1-5}$ alkylene-W—NH—R$_8$)—, and
—S(O)$_{0-2}$—;

$R_2$ is selected from the group consisting of:
—R$_4$,
—X—R$_4$,
—X—Y—R$_4$, and
—X—R$_8$;

$R_{A'}$ and $R_{B'}$ are each independently selected from the group consisting of:
hydrogen,
halogen,
alkyl,
alkenyl,
alkoxy,
alkylthio, and
—N(R$_9$)$_2$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_5$ is selected from the group consisting of:

$R_6$ is selected from the group consisting of =O and =S;
$R_7$ is C$_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is C$_{3-8}$ alkylene;
$R_{11}$ is selected from the group consisting of hydrogen, alkyl, halogen, and trifluoromethyl;
$R_{12}$ is selected from the group consisting of hydrogen, alkyl, phenyl, 2-pyridyl, 3-pyridyl, and 4-pyridyl;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that when Z is a bond or C$_{1-5}$ alkylene and R$_2$ is —X—Y—R$_4$ and Y is —N(R$_8$)-Q-, then Q is other than —C(R$_6$)—N(R$_8$)—W—;

or a pharmaceutically acceptable salt thereof.

In another embodiment, there is provided a compound of the Formula (V):

wherein:
m is an integer from 1 to 5;
p is an integer from 0 to 3;
R' is selected from the group consisting of:
hydroxy,
thiol,
—S(O)$_{0-2}$-alkyl,
—S(O)$_2$—NH—R$_9$,
alkoxy,
—O—C$_{1-3}$ alkylene-S(O)$_2$-alkyl,
—N(R$_9$)$_2$, and
—NH-Q-R$_4$;
Z is selected from the group consisting of:
a bond,
C$_{1-5}$ alkylene,

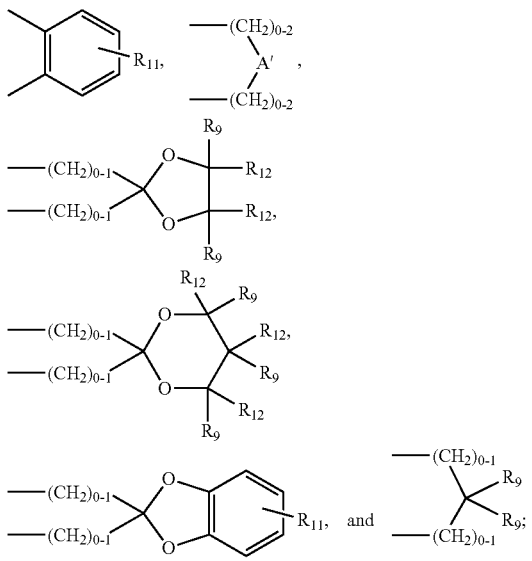
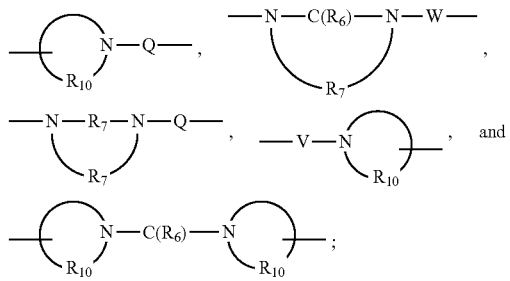

A' is selected from the group consisting of:
—O—,
—C(O)—,
—N(R_8)—,
—N(Q-R_4)—,
—N($C_{1-5}$ alkylene-NH-Q-R_4)—,
—N($C_{1-5}$ alkylene-W—NH—R_8)—, and
—S(O)$_{0-2}$—;

$R_2$ is selected from the group consisting of:
—R_4,
—X—R_4,
—X—Y—R_4, and
—X—R_8;

R is selected from the group consisting of:
halogen,
hydroxy,
alkyl,
alkenyl,
haloalkyl,
alkoxy,
alkylthio, and
—N(R_9)_2;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)_2—N(R_8)—,
—C(R_6)—,
—C(R_6)—O—,
—O—C(R_6)—,
—O—C(O)—O—,
—N(R_8)-Q-,
—C(R_6)—N(R_8)—,
—O—C(R_6)—N(R_8)—,
—C(R_6)—N(OR_9)—,

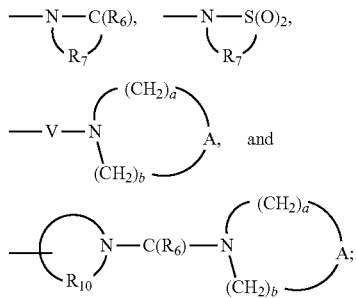

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_5$ is selected from the group consisting of:

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
$R_{11}$ is selected from the group consisting of hydrogen, alkyl, halogen, and trifluoromethyl;
$R_{12}$ is selected from the group consisting of hydrogen, alkyl, phenyl, 2-pyridyl, 3-pyridyl, and 4-pyridyl;
A is selected from the group consisting of —O—, —C(O)—, —S(O)$_{0-2}$—, —CH_2—, and —N(R_4)—;
Q is selected from the group consisting of a bond, —C(R_6)—, —C(R_6)—C(R_6), —S(O)_2—, —C(R_6)—N(R_8)—W—, —S(O)_2—N(R_8)—, —C(R_6)—O—, and —C(R_6)—N(OR_9)—;
V is selected from the group consisting of —C(R_6)—, —O—C(R_6)—, —N(R_8)—C(R_6)—, and —S(O)_2—;
W is selected from the group consisting of a bond, —C(O)—, and —S(O)_2—; and a and b are independently integers from 1 to 6 with the proviso that a+b is ≤7;
with the proviso that when Z is a bond or $C_{1-5}$ alkylene then R' is other than —O—$C_{1-3}$ alkylene-S(O)$_2$-alkyl, and with the further proviso that when Z is a bond or $C_{1-5}$ alkylene and $R_2$ is —X—Y—$R_4$ and Y is —N($R_8$)-Q-, then Q is other than —C($R_6$)—N($R_8$)—W—;
or a pharmaceutically acceptable salt thereof.

In another embodiment, there is provided a compound of the Formula (VI):

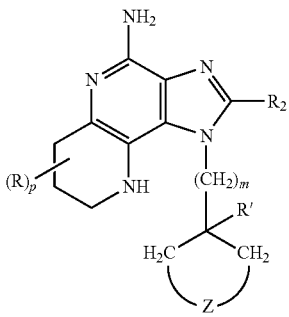

VI wherein:
m is an integer from 1 to 5;
p is an integer from 0 to 3;
R' is selected from the group consisting of:
  hydroxy,
  thiol,
  —S(O)$_{0-2}$-alkyl,
  —S(O)$_2$—NH—$R_9$,
  alkoxy,
  —O—$C_{1-3}$ alkylene-S(O)$_2$-alkyl,
  —N($R_9$)$_2$, and
  —NH-Q-$R_4$;
Z is selected from the group consisting of:
  a bond,
  $C_{1-5}$ alkylene,

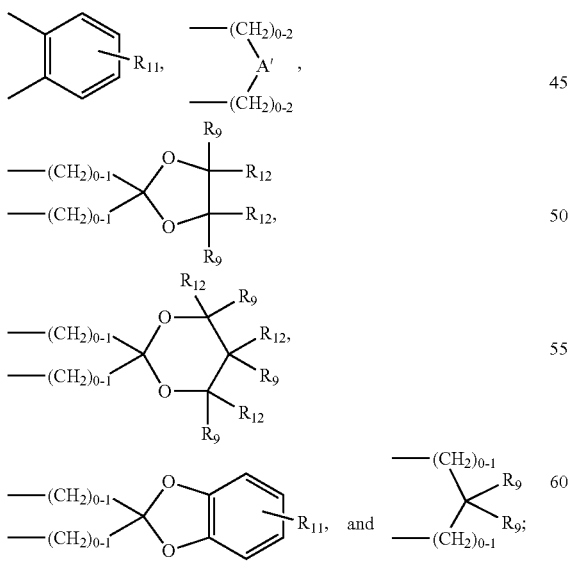

A' is selected from the group consisting of:
  —O—,
  —C(O)—,
  —N($R_8$)—,
  —N(Q-$R_4$)—,
  —N($C_{1-5}$ alkylene-NH-Q-$R_4$)—,
  —N($C_{1-5}$ alkylene-W—NH—$R_8$)—, and
  —S(O)$_{0-2}$—;
$R_2$ is selected from the group consisting of:
  —$R_4$,
  —X—$R_4$,
  —X—Y—$R_4$, and
  —X—$R_5$;
R is selected from the group consisting of:
  halogen,
  hydroxy,
  alkyl,
  alkenyl,
  haloalkyl,
  alkoxy,
  alkylthio, and
  —N($R_9$)$_2$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
  —S(O)$_{0-2}$—,
  —S(O)$_2$—N($R_6$)—,
  —C($R_6$)—,
  —C($R_6$)—O—,
  —O—C($R_6$)—,
  —O—C(O)—O—,
  —N($R_8$)-Q-,
  —C($R_6$)—N($R_8$)—,
  —O—C($R_6$)—N($R_9$)—,

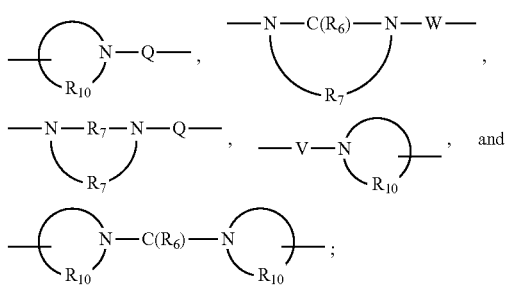

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_5$ is selected from the group consisting of:

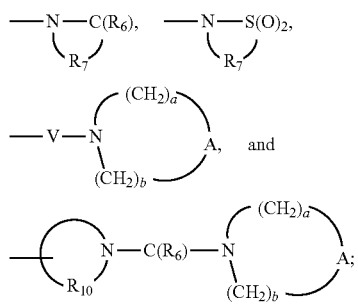

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
$R_{11}$ is selected from the group consisting of hydrogen, alkyl, halogen, and trifluoromethyl;
$R_{12}$ is selected from the group consisting of hydrogen, alkyl, phenyl, 2-pyridyl, 3-pyridyl, and 4-pyridyl;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that when Z is a bond or $C_{1-5}$ alkylene then R' is other than —O—$C_{1-3}$ alkylene-S(O)$_2$-alkyl, and with the further proviso that when Z is a bond or $C_{1-5}$ alkylene and $R_2$ is —X—Y—$R_4$ and Y is —N(R$_8$)-Q-, then Q is other than —C(R$_6$)—N(R$_8$)—W—;
or a pharmaceutically acceptable salt thereof.

In another embodiment, there is provided a compound of the Formula (VII):

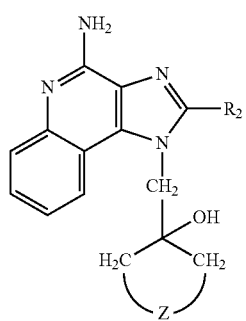

wherein:
Z is a bond or $C_{1-3}$ alkylene; and
$R_2$ is selected from the group consisting of hydrogen, $C_{1-4}$ alkyl, HO—$C_{1-4}$ alkylenyl and $C_{1-4}$ alkyl-O—$C_{1-4}$ alkylenyl;
or a pharmaceutically acceptable salt thereof.

In another embodiment, there is provided a compound of the Formula (VIII):

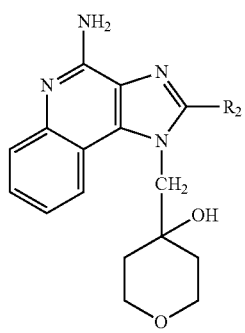

wherein $R_2$ is selected from the group consisting of hydrogen, $C_{1-4}$ alkyl, HO—$C_{1-4}$ alkylenyl and $C_{1-4}$ alkyl-O—$C_{1-4}$ alkylenyl; or a pharmaceutically acceptable salt thereof.

In another embodiment, there is provided a compound of the Formula (IX):

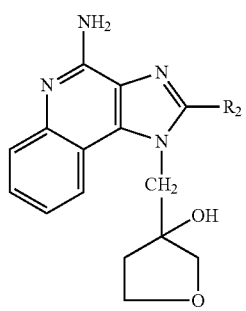

wherein $R_2$ is selected from the group consisting of hydrogen, $C_{1-4}$ alkyl, HO—$C_{1-4}$ alkylenyl and $C_{1-4}$ alkyl-O—$C_{1-4}$ alkylenyl; or a pharmaceutically acceptable salt thereof.

In another embodiment, there is provided a compound (which is a prodrug) of the Formula (X):

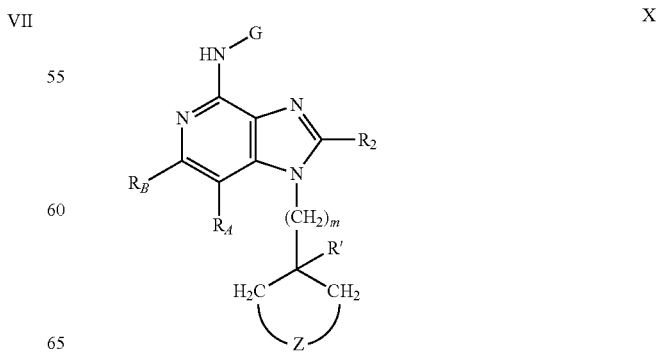

wherein:
m is an integer from 1 to 5;
R' is selected from the group consisting of:
hydroxy,
thiol,
—S(O)$_{0-2}$-alkyl,
—S(O)$_2$—NH—R$_9$,
alkoxy,
—O—C$_{1-3}$ alkylene-S(O)$_2$-alkyl,
—N(R$_9$)$_2$, and
—NH-Q-R$_4$;
Z is selected from the group consisting of:
a bond,
C$_{1-5}$ alkylene,

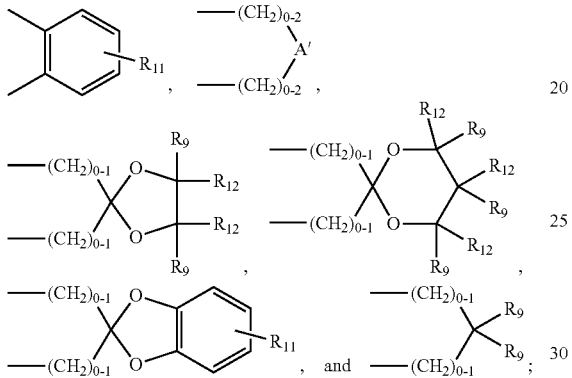

A' is selected from the group consisting of:
—O—,
—C(O)—,
—N(R$_8$)—,
—N(Q-R$_4$)—,
—N(C$_{1-5}$ alkylene-NH-Q-R$_4$)—,
—N(C$_{1-5}$ alkylene-W—NH—R$_8$)—, and
—S(O)$_{0-2}$—;
R$_2$ is selected from the group consisting of:
—R$_4$,
—X—R$_4$,
—X—Y—R$_4$, and
—X—R$_5$;
R$_A$ and R$_B$ are each independently selected from the group consisting of:
hydrogen,
halogen,
alkyl,
alkenyl,
alkoxy,
alkylthio, and
—N(R$_9$)$_2$;
or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups;
or when taken together, R$_A$ and R$_B$ form a fused 5 to 7 membered saturated ring, optionally containing one heteroatom selected from the group consisting of N and S, and unsubstituted or substituted by one or more R groups;
R is selected from the group consisting of:
halogen,
hydroxy,
alkyl,
alkenyl,
haloalkyl,
alkoxy,
alkylthio, and
—N(R$_9$)$_2$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

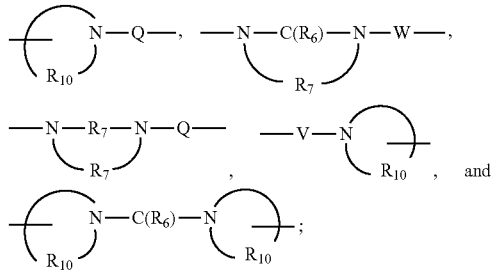

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;
R$_5$ is selected from the group consisting of:

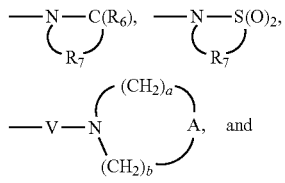

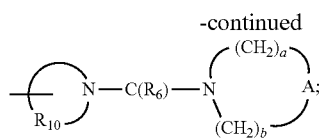

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
R$_{11}$ is selected from the group consisting of hydrogen, alkyl, halogen, and trifluoromethyl;
R$_{12}$ is selected from the group consisting of hydrogen, alkyl, phenyl, 2-pyridyl, 3-pyridyl, and 4-pyridyl;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
G is selected from the group consisting of:
 —C(O)—R'',
 α-aminoacyl,
 α-aminoacyl-α-aminoacyl,
 —C(O)—O—R'',
 —C(O)—N(R''')R'',
 —C(=NY')—R'',
 —CH(OH)—C(O)—OY',
 —CH(OC$_{1-4}$ alkyl)Y$_0$,
 —CH$_2$Y$_1$, and
 —CH(CH$_3$)Y$_1$;
R'' and R''' are independently selected from the group consisting of C$_{1-10}$ alkyl, C$_{3-7}$ cycloalkyl, and benzyl, each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R''' can also be hydrogen;
α-aminoacyl is an acyl group derived from an amino acid selected from the group consisting of racemic, D-, and L-amino acids;
Y' is selected from the group consisting of hydrogen, C$_{1-6}$ alkyl, and benzyl;
Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl;
Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;
with the proviso that when Z is a bond or C$_{1-5}$ alkylene then R' is other than —O—C$_{1-3}$ alkylene-S(O)$_2$-alkyl, and with the further proviso that when Z is a bond or C$_{1-5}$ alkylene and R$_2$ is —X—Y—R$_4$ and Y is —N(R$_8$)-Q-, then Q is other than —C(R$_6$)—N(R$_8$)—W—;
or a pharmaceutically acceptable salt thereof.

In another embodiment, there is provided a compound of the Formula (XI):

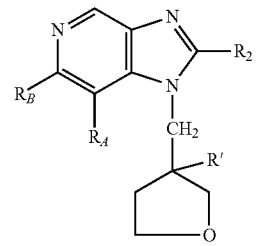

wherein:
R' is selected from the group consisting of:
 hydroxy,
 thiol,
 —S(O)$_{0-2}$-alkyl,
 —S(O)$_2$—NH—R$_9$,
 alkoxy,
 —O—C$_{1-3}$ alkylene-S(O)$_2$-alkyl,
 —N(R$_9$)$_2$, and
 —NH-Q-R$_4$;
R$_2$ is selected from the group consisting of:
 —R$_4$,
 —X—R$_4$,
 —X—Y—R$_4$, and
 —X—R$_5$;
R$_A$ and R$_B$ are each independently selected from the group consisting of:
 hydrogen,
 halogen,
 alkyl,
 alkenyl,
 alkoxy,
 alkylthio, and
 —N(R$_9$)$_2$;
or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups;
or when taken together, R$_A$ and R$_B$ form a fused 5 to 7 membered saturated ring, optionally containing one heteroatom selected from the group consisting of N and S, and unsubstituted or substituted by one or more R groups;
R is selected from the group consisting of:
 halogen,
 hydroxy,
 alkyl,
 alkenyl,
 haloalkyl,
 alkoxy,
 alkylthio, and
 —N(R$_9$)$_2$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—N(R$_8$)-Q-,
—C(R$_6$)—N(R$_8$)—,
—O—C(R$_6$)—N(R$_8$)—,
—C(R$_6$)—N(OR$_9$)—,

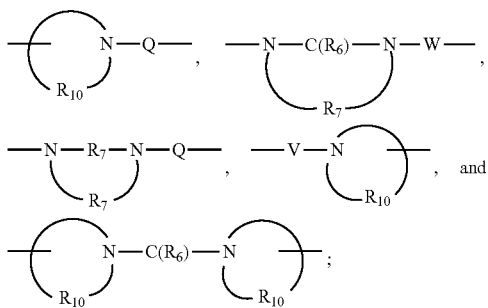

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;
R$_5$ is selected from the group consisting of:

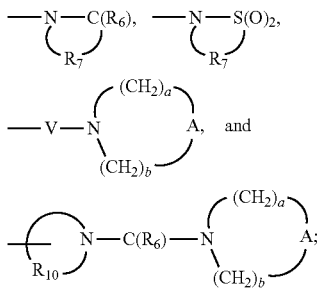

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;

A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_6$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof.

In another embodiment, there is provided a compound of the Formula (XII):

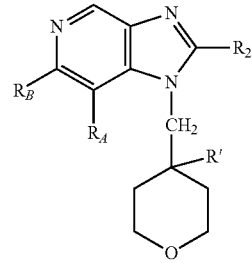

XII wherein:
R' is selected from the group consisting of:
hydroxy,
thiol,
—S(O)$_{0-2}$-alkyl,
—S(O)$_2$—NH—R$_9$,
alkoxy,
—O—C$_{1-3}$ alkylene-S(O)$_2$-alkyl,
—N(R$_9$)$_2$, and
—NH-Q-R$_4$;
R$_2$ is selected from the group consisting of:
—R$_4$,
—X—R$_4$,
—X—Y—R$_4$, and
—X—R$_5$;
R$_A$ and R$_B$ are each independently selected from the group consisting of:
hydrogen,
halogen,
alkyl,
alkenyl,
alkoxy,
alkylthio, and
—N(R$_9$)$_2$;
or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups;
or when taken together, R$_A$ and R$_B$ form a fused 5 to 7 membered saturated ring, optionally containing one heteroatom selected from the group consisting of N and S, and unsubstituted or substituted by one or more R groups;
R is selected from the group consisting of:
halogen,
hydroxy, alkyl,
alkenyl,
haloalkyl,
alkoxy,
alkylthio, and
—N($R_9$)$_2$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

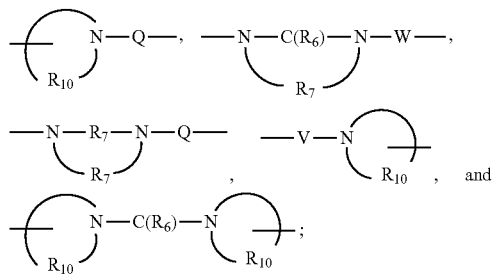

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_5$ is selected from the group consisting of:

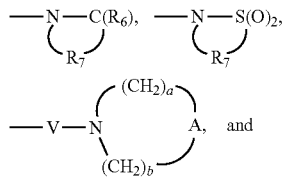

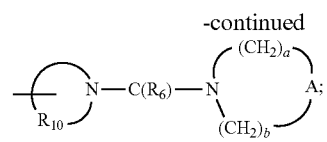

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N($R_4$)—;
Q is selected from the group consisting of a bond, —C($R_6$)—, —C($R_6$)—C($R_6$), —S(O)$_2$—, —C($R_6$)—N($R_8$)—W—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof.

For any of the compounds presented herein, each one of the following variables (e.g., Z, X, Y, R, R', $R_A$, $R_B$, $R_{A'}$, $R_{B'}$, $R_2$, Q, W, m, n, p, G, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, m is an integer from 1 to 5. For certain embodiments, m is 1, 2, or 3. For certain embodiments, m is 1 or 2. Preferably, m is 1.

For certain embodiments, n is an integer from 0 to 4. Preferably, n is 0.

For certain embodiments, p is an integer from 0 to 3. Preferably, p is 0.

For certain embodiments, R' is selected from the group consisting of hydroxy, thiol, —S(O)$_{0-2}$-alkyl, —S(O)$_2$—NH—$R_9$, alkoxy, —O—$C_{1-3}$ alkylene-S(O)$_2$-alkyl, —N($R_9$)$_2$, and —NH-Q-$R_4$. For certain embodiments, particularly when Z is a bond or $C_{1-5}$ alkylene, R' is other than —O—$C_{1-3}$ alkylene-S(O)$_2$-alkyl.

For certain embodiments, R' is selected from the group consisting of hydroxy, methoxy, and amino. For certain embodiments, R' is selected from the group consisting of hydroxy and methoxy. For certain embodiments R' is hydroxy. For certain embodiments, R' is —O—$C_{1-3}$ alkylene-S(O)$_2$-alkyl. For certain alternative embodiments, R' is selected from the group consisting of —NH$_2$ and —NH-Q-$R_4$. In such embodiments, preferably Q is selected from the group consisting of —C(O)—, —S(O)$_2$—, —C(O)—O—, and —C(O)—NH—, and $R_4$ is selected from the group consisting of alkyl and alkoxyalkylene. Alternatively, in such embodiments, preferably Q is selected from the group consisting of —C(O)—, —C(O)—O—, —S(O)$_2$—, and —C($R_6$)—N($R_8$)—, $R_8$ is selected from hydrogen and $C_{1-4}$ alkyl, and $R_4$ is alkyl, aryl, arylalkylene, heteroaryl, and heterocyclyl, wherein the aryl group can be unsubstituted or substituted by acetylamino, alkyl, alkoxy, cyano, and halogen. More preferably, Q is selected from the group consisting of —C(O)—, —S(O)$_2$—, —C(O)—O—, and —C(O)—NH—, and R$_4$ is selected from the group consisting of alkyl and alkoxyalkylene.

For certain embodiments, Z is selected from the group consisting of a bond, C$_{1-5}$ alkylene

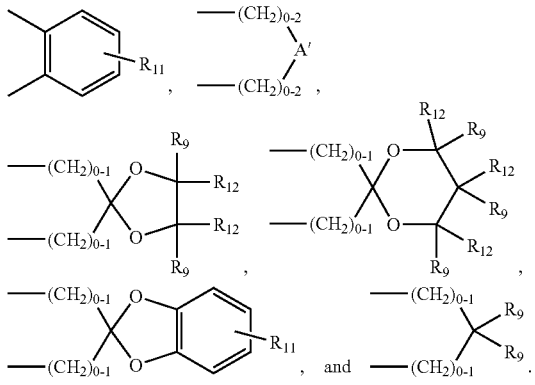

For certain embodiments, Z is selected from the group consisting of a bond and C$_{1-5}$ alkylene. In such embodiments, preferably R' is other than —O—C$_{1-3}$ alkylene-S(O)$_2$-alkyl. Alternatively or additionally, in such embodiments, preferably, when Z is a bond or C$_{1-5}$ alkylene and R$_2$ is —X—Y—R$_4$ and Y is —N(R$_8$)-Q-, then Q is other than —C(R$_6$)—N(R$_8$)—W—

For certain embodiments, Z is selected from the group consisting of a bond and C$_{1-3}$ alkylene.

For certain alternative embodiments, Z is —(CH$_2$)$_{0-1}$-A'—(CH$_2$)$_{0-1}$—. In some of these embodiments Z is —(CH$_2$)-A'—(CH$_2$)—. In some embodiments, preferably, A' is —O—. In some embodiments, preferably, A' is —S(O)$_2$—. In some embodiments, preferably, A' is selected from the group consisting of —N(R$_8$)— and —N(Q-R$_4$)—. In some embodiments, In some embodiments, preferably, A' is selected from the group consisting of —O—, —N(R$_8$)—, and —N(Q-R$_4$)—. In such embodiments, preferably, Q is selected from the group consisting of —C(O)—, —C(O)—O—, —S(O)$_2$—, and —C(R$_6$)—N(R$_8$)—, wherein, preferably, R$_8$ is selected from hydrogen and C$_{1-4}$ alkyl. In such embodiments, preferably, R$_4$ is selected from the group consisting of alkyl, aryl, arylalkylene, heteroaryl, and heterocyclyl, wherein the aryl group can be unsubstituted or substituted by acetylamino, alkyl, alkoxy, cyano, and halogen. In such embodiments, more preferably, Q is —S(O)$_2$— and R$_4$ is C$_{1-4}$ alkyl.

For certain embodiments, Z is selected from the group consisting of a bond, —CH$_2$—, —CH$_2$CH$_2$—, —CH$_2$CH$_2$CH$_2$—, and —CH$_2$—O—CH$_2$—. For certain embodiments Z is —CH$_2$CH$_2$CH$_2$— or —CH$_2$—O—CH$_2$—.

For certain embodiments, R$_2$ is selected from the group consisting of —R$_4$, —X—R$_4$, —X—Y—R$_4$, and —X—R$_5$. For certain embodiments, R$_2$ is —X—Y—R$_4$.

For certain embodiments, R$_2$ is selected from the group consisting of hydrogen, alkyl, alkoxyalkylenyl, hydroxyalkylenyl, and —X—Y—R$_4$ wherein X is C$_{1-2}$ alkylene; Y is selected from the group consisting of —S(O)$_{0-2}$—, —S(O)$_2$—N(R$_8$)—, —C(R$_6$)—, —C(R$_6$)—O—, —O—C(R$_6$)—, —O—C(R$_6$)—, —O—C(O)—O—, —N(R$_8$)-Q-, —C(R$_6$)—N(R$_8$)—, —O—C(R$_6$)—N(R$_8$)—, and —C(R$_6$)—N(OR$_9$)—; and R$_4$ is alkyl.

For certain embodiments, R$_2$ is selected from the group consisting of hydrogen, alkyl, alkoxyalkylenyl, and —X—Y—R$_4$ wherein X is C$_{1-2}$ alkylene; Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, and —C(R$_6$)—N(OR$_9$)—; and R$_4$ is alkyl. Preferably, R$_2$ is selected from the group consisting of hydrogen, C$_{1-4}$ alkyl, and C$_{1-4}$ alkyl-O—C$_{1-4}$ alkylenyl. For certain embodiments, R$_2$ is hydrogen or C$_{1-4}$ alkyl. For certain embodiments, R$_2$ is C$_{1-4}$ alkyl. More preferably, R$_2$ is selected from the group consisting of hydrogen, methyl, ethyl, n-propyl, n-butyl, ethoxymethyl, and 2-methoxyethyl. For certain embodiments, R$_2$ is selected from the group consisting of hydrogen, methyl, ethyl, n-propyl, and n-butyl.

For certain embodiments, R$_2$ is HO—C$_{1-4}$ alkylenyl or C$_{1-4}$ alkyl-O—C$_{1-4}$ alkylenyl. For certain embodiments, R$_2$ is selected from the group consisting of hydroxymethyl, 2-hydroxyethyl, ethoxymethyl, and 2-methoxyethyl. For certain embodiments, R$_2$ is selected from the group consisting of hydrogen, C$_{1-4}$ alkyl, HO—C$_{1-4}$ alkylenyl and C$_{1-4}$ alkyl-O—C$_{1-4}$ alkylenyl.

For certain embodiments, R$_{A'}$ and R$_{B'}$ are each independently selected from the group consisting of hydrogen, halogen, alkyl, alkenyl, alkoxy, alkylthio, and —N(R$_9$)$_2$.

For certain embodiments, R$_{A'}$ and R$_{B'}$ are independently hydrogen or alkyl. Preferably, R$_{A'}$ and R$_{B'}$ are both methyl.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups. For certain embodiments, particularly in —X—Y—R$_4$, X is C$_{1-2}$ alkylene.

For certain embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

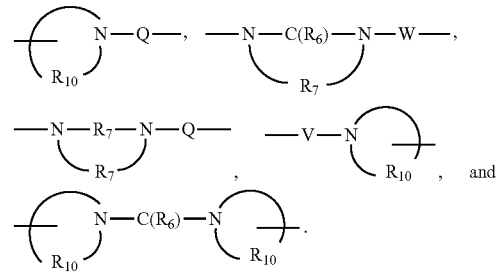

For certain embodiments, Y is selected from the group consisting of —S(O)$_{0-2}$—, —S(O)$_2$—N(R$_6$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, and —C(R$_6$)—N(OR$_9$)—. For certain embodiments, Y is —N(R$_8$)-Q-.

For certain embodiments, R$_A$ and R$_B$ are each independently selected from the group consisting of hydrogen, halogen, alkyl, alkenyl, alkoxy, alkylthio, and —N(R$_9$)$_2$. Alternatively, for certain embodiments, when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups. Alternatively, when taken together, $R_A$ and $R_B$ form a fused 5 to 7 membered saturated ring, optionally containing one heteroatom selected from the group consisting of N and S, and unsubstituted or substituted by one or more R groups. For certain embodiments, $R_A$ and $R_B$ join to form a fused benzene ring. For certain embodiments, $R_A$ and $R_B$ join to form a fused pyridine ring.

For certain embodiments, R is selected from the group consisting of halogen, hydroxy, alkyl, alkenyl, haloalkyl, alkoxy, alkylthio, and —$N(R_9)_2$.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo.

For certain embodiments, $R_4$ is alkyl, aryl, arylalkylene, heteroaryl, and heterocyclyl, wherein the aryl group can be unsubstituted or substituted by acetylamino, alkyl, alkoxy, cyano, and halogen. For certain embodiments, $R_4$ is selected from the group consisting of alkyl and alkoxyalkylene.

For certain embodiments, $R_4$ is alkyl. For certain embodiments, $R_4$ is methyl, ethyl, isopropyl, or phenyl. For certain embodiments, $R_4$ is methyl or ethyl.

For certain embodiments, $R_5$ is selected from the group consisting of

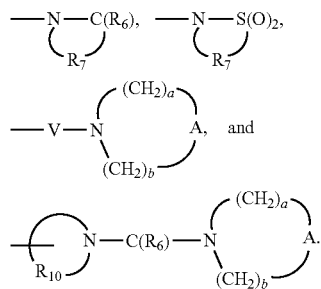

For certain embodiments, $R_6$ is selected from the group consisting of =O and =S. For certain embodiments, $R_6$ is =O.

For certain embodiments, $R_7$ is $C_{2-7}$ alkylene. For certain embodiments, particularly embodiments where Y is

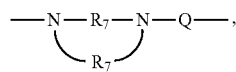

$R_7$ is selected such that the total number of ring atoms is from 6 to 8.

For certain embodiments, $R_8$ is selected from the group consisting of hydrogen, alkyl, alkoxyalkylenyl, and arylalkylenyl. For certain embodiments, $R_8$ is hydrogen or alkyl. For certain embodiments, $R_8$ is selected from hydrogen and $C_{1-4}$ alkyl.

For certain embodiments, $R_9$ is hydrogen or alkyl. For certain embodiments, $R_9$ is hydrogen.

For certain embodiments, $R_{10}$ is $C_{3-8}$ alkylene.

For certain embodiments, R is selected from the group consisting of hydrogen, alkyl, halogen, and trifluoromethyl.

For certain embodiments, $R_{12}$ is selected from the group consisting of hydrogen, alkyl, phenyl, 2-pyridyl, 3-pyridyl, and 4-pyridyl.

For certain embodiments, A is selected from the group consisting of —O—, —C(O)—, —$S(O)_{0-2}$—, —$CH_2$—, and —$N(R_4)$—.

For certain embodiments, A' is selected from the group consisting of —O—, —C(O)—, —$N(R_8)$—, —$N(Q-R_4)$—, —$N(C_{1-5}$ alkylene-NH-Q-$R_4)$—, —$N(C_{1-5}$ alkylene-W—NH—$R_8)$—, and —$S(O)_{0-2}$—. For certain embodiments, A' is —O—, —$N(R_8)$—, or —$N(Q-R_4)$—. For certain embodiments, A' is —O—. For certain embodiments, A' is —$S(O)_2$—.

For certain embodiments, A' is —$N(R_8)$— or —$N(Q-R_4)$—. In such embodiments, preferably, Q is selected from the group consisting of —C(O)—, —C(O)—O—, —$S(O)_2$—, and —$C(R_6)$—$N(R_8)$—, $R_8$ is selected from hydrogen and $C_{1-4}$ alkyl, and $R_4$ is selected from the group consisting of alkyl, aryl, arylalkylene, heteroaryl, and heterocyclyl, wherein the aryl group can be unsubstituted or substituted by acetylamino, alkyl, alkoxy, cyano, and halogen. In such embodiments, more preferably, Q is —$S(O)_2$— and $R_4$ is $C_{1-4}$ alkyl.

For certain embodiments, Q is selected from the group consisting of a bond, —$C(R_6)$—, —$C(R_6)$—$C(R_6)$, —$S(O)_2$—, —$C(R_6)$—$N(R_8)$—W—, —$S(O)_2$—$N(R_8)$—, —$C(R_6)$—O—, and —$C(R_6)$—$N(OR_9)$—. For certain embodiments, Q is —C(O)—, —C(O)—O—, —$S(O)_2$—, or —$C(R_6)$—$N(R_8)$—. For certain embodiments, Q is selected from the group consisting of —C(O)—, —$S(O)_2$—, —C(O)—O—, and —C(O)—NH—. For certain embodiments, Q is a bond, —C(O)—, —$S(O)_2$—, or —C(O)—NH—. For certain embodiments, Q is —$S(O)_2$—.

For certain embodiments, particularly when Z is a bond or $C_{1-5}$ alkylene and $R_2$ is —X—Y—$R_4$ and Y is —$N(R_8)$-Q-, then Q is other than —$C(R_6)$—$N(R_8)$—W—.

For certain embodiments, V is selected from the group consisting of —$C(R_6)$—, —O—$C(R_6)$—, —$N(R_8)$—C$(R_6)$—, and —$S(O)_2$—.

For certain embodiments, W is selected from the group consisting of a bond, —C(O)—, and —$S(O)_2$—. For certain embodiments, W is a bond.

For certain embodiments, a and b are independently integers from 1 to 6 with the proviso that a+b is ≤7.

For certain embodiments of the compounds of Formulas (I) through (IX), the —$NH_2$ group can be replaced by an —NH-G group to form prodrugs. In such embodiments, G is selected from the group consisting of: —C(O)—R", α-aminoacyl, α-aminoacyl-α-aminoacyl, —C(O)—O—R", —C(O)—N(R''')R", —C(=NY')—R", —CH(OH)—C(O)—OY', —CH(O$C_{1-4}$ alkyl)$Y_0$, —$CH_2Y_1$, and —CH$(CH_3)Y_1$. In some of these embodiments G is —C(O)—R", α-aminoacyl, α-aminoacyl-α-aminoacyl, or —C(O)—O—R". Preferably, R" and R''' are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$. R''' can also be hydrogen. Preferably, α-aminoacyl is an acyl group derived from an amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl. Preferably, Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

As used herein, the terms "alkyl, "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, up to 5 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. Likewise, "alkylenyl," "alkenylenyl," and "alkynylenyl" are the divalent forms of the "alkyl," "alkenyl," and "alkynyl" groups defined above. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclic groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "fused heteroaryl ring" includes the fused forms of 5 or 6 membered aromatic rings that contain one heteroatom selected from S and N.

The term "fused 5 to 7 membered saturated ring" includes rings which are fully saturated except for the bond where the ring is fused.

When a group (or substituent or variable) is present more than once in any Formula described herein, each group (or substituent or variable) is independently selected, whether explicitly stated or not. For example, for the formula —N(R$_9$)$_2$ each R$_9$ group is independently selected. In another example, when an R' and an A' group both contain an R$_4$ group, each R$_4$ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyldimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the Formula II where R, R', $R_2$, n, m, and Z are as defined above can be prepared starting from 2,4-dichloro-3-nitroquinoline XV as shown in Reaction Scheme I. The route shown in Reaction Scheme I is especially useful when Z, R', and $R_2$ contain functional groups that are easily oxidized by reagents used in step (4) of Reaction Scheme II. Easily oxidizable groups include —S—, heteroaryl groups, and amines. In step (1) of Reaction Scheme I, a 2,4-dichloro-3-nitroquinoline of Formula XV is reacted with an amine of the Formula XVI or hydrochloride salt thereof to form a compound of Formula XVII. This reaction is carried out by adding a compound of Formula XVI or a salt thereof to a solution of 2,4-dichloro-3-nitroquinoline of Formula XV in the presence of a base such as triethylamine. The reaction is carried out in a suitable solvent, such as dichloromethane or chloroform. Amines of the Formula XVI and hydrochloride salts thereof can be obtained commercially or prepared according to published procedures or modified versions thereof, and according to Schemes III-V and XI. Compounds of Formula XV are known or can be prepared using known synthetic methods, see for example, U.S. Pat. No. 4,988,815 and the documents cited therein.

The resultant compound of Formula XVII is reduced in step (2) of Reaction Scheme I to provide a quinoline-3,4-diamine of Formula XVIII. The reaction can be carried out by hydrogenation using a heterogeneous hydrogenation catalyst such as platinum on carbon or palladium on carbon. The hydrogenation is conveniently carried out in a Parr apparatus in a suitable solvent such as acetonitrile, ethyl acetate, or ethanol. The reaction can be carried out at ambient temperature, and the product can be isolated using conventional methods.

Alternatively step (2) can be carried out using a one- or two-phase sodium dithionite reduction. The reaction is conveniently carried out using the conditions described by K. K. Park et al., W. K.; *Tetrahedron Lett.*, 34, 7445-7446 (1993) by adding sodium dithionite to a compound of Formula XVII in a mixture of dichloromethane and water at ambient temperature in the presence of potassium carbonate and ethyl viologen dibromide, ethyl viologen diiodide, or 1,1'-di-n-octyl-4,4'-bipyridinium dibromide. The product can be isolated using conventional methods.

In step (3) of Reaction Scheme I, a quinoline-3,4-diamine of Formula XVIII is treated with a carboxylic acid equivalent to provide a 1H-imidazo[4,5-c]quinoline of Formula XIX. Suitable carboxylic acid equivalents include orthoesters of Formula $R_2C(O-alkyl)_3$, 1,1-dialkoxyalkyl alkanoates of Formula $R_2C(O-alkyl)_2(O—C(O)-alkyl)$, and acid chlorides of Formula $R_2C(O)Cl$. The selection of the carboxylic acid equivalent is determined by the desired substituent at $R_2$. For example, ethoxyacetyl chloride will provide a compound where $R_2$ is an ethoxymethyl group, and acetyl chloride will provide a compound where $R_2$ is a methyl group. Step (3) can be carried out in two steps when an acid chloride of Formula $R_2C(O)Cl$ is used as the carboxylic acid equivalent. The first step is conveniently carried out by adding the acid chloride to a solution of a quinoline-3,4-diamine of Formula XVIII in a suitable solvent such as dichloromethane in the presence of a base such as triethylamine, pyridine, or 4-dimethylaminopyridine to afford an amide. Optionally, the reaction can be performed without a tertiary amine. The reaction can be carried out starting at a sub-ambient temperature, such as 0° C., with warming to ambient temperature or at ambient temperature. The amide product can be isolated and optionally purified using conventional techniques before it is heated and cyclized to provide a 1H-imidazo[4,5-c]quinoline of Formula XIX. The cyclization reaction is conveniently carried out in a solvent such as ethanol or methanol in the presence of a base such as triethylamine and may be carried out at an elevated temperature, such as the reflux temperature of the solvent. The 1H-imidazo[4,5-c]quinoline of Formula XIX can be isolated using conventional methods.

Alternatively, step (3) can be carried out in one step when orthoesters of Formula $R_2C(O-alkyl)_3$ or 1,1-dialkoxyalkyl alkanoates of Formula $R_2C(O-alkyl)_2(O—C(O)-alkyl)$ are used. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a quinoline-3,4-diamine of Formula XVIII in a suitable solvent such as toluene. Optionally, catalytic pyridine hydrochloride or pyridium p-toluenesulfonate can be added. The reaction is carried out at an elevated temperature, such as at reflux.

In step (4) of Reaction Scheme I, a compound of Formula XIX is reacted with ammonia in a suitable solvent at elevated temperature and pressure. The product of Formula II or a pharmaceutically acceptable salt thereof can be isolated by conventional methods.

methods, see for example, U.S. Pat. Nos. 4,689,338; 5,175,296; 5,367,076; and 5,389,640; and the documents cited therein. Step (1) of Reaction Scheme II is carried out as described for step (1) of Reaction Scheme I, as are steps (2) and (3).

In step (4) of Reaction Scheme II, a 1H-imidazo[4,5-c]quinoline of Formula XXIII is oxidized to provide a 1H-imidazo[4,5-c]quinoline-5N-oxide of Formula XXIV using a conventional oxidizing agent capable of forming N-oxides. The reaction is conveniently carried out by adding 3-chloroperoxybenzoic acid to a solution of a compound of Formula XXIII in a solvent such as dichloromethane or chloro- Reaction Scheme I

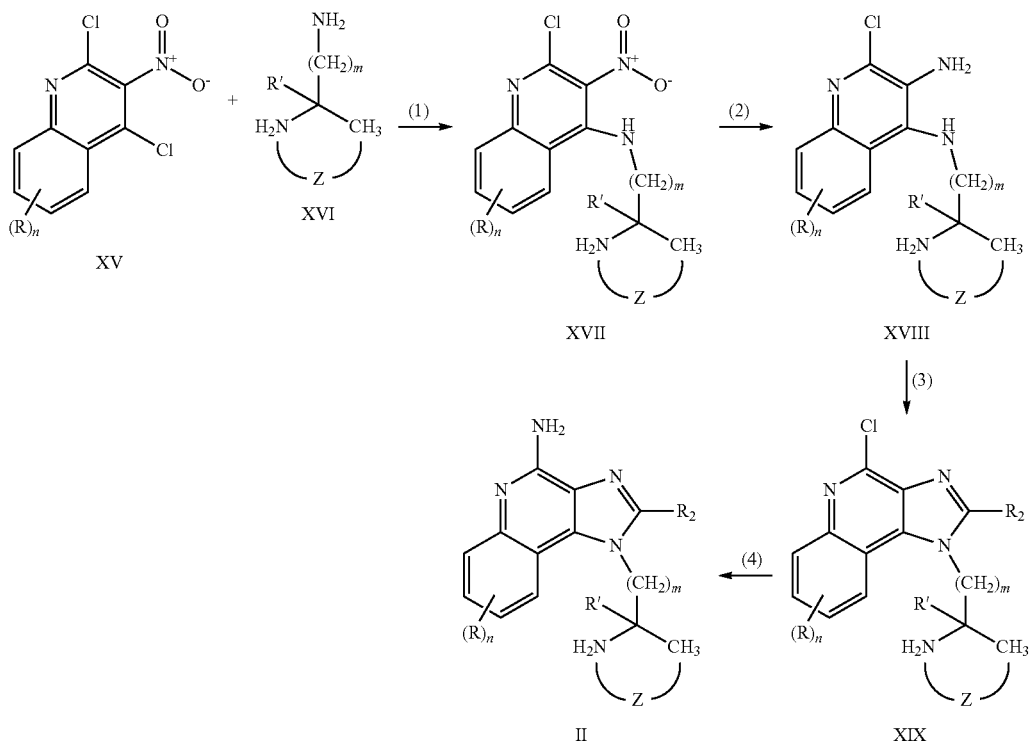

Compounds of Formula IIa can be prepared according to Reaction Scheme II, wherein R, n, and m are as defined above, and $Z_a$ and $R_{2a}$ are subsets of Z and $R_2$ as defined above that do not include those substitutents that one skilled in the art would recognize as being susceptible to the oxidation in step (4) or incompatible with other functional groups present. Those substitutents include —S—, heteroaryl groups, and alkyl amines. One exception is that —S— is included in the set of $Z_a$ and is oxidized to a sulfone during step (4). Therefore, $Z_b$ is a subset of Z that contains —S(O)$_2$— and all of $Z_a$ except for —S—. In step (1) of Reaction Scheme II, a 4-chloro-3-nitroquinoline of Formula XX is reacted with an amine of the Formula XVIa or hydrochloride salt thereof to form a compound of Formula XXI. Amines of the Formula XVIa and hydrochloride salts thereof can be obtained commercially or prepared according to published procedures or modified versions thereof, and according to Schemes III-V. Many compounds of Formula XX are known or can be prepared using known synthetic roform. The reaction can be carried out at ambient temperature, and the product can be isolated using conventional methods.

In step (5) of Reaction Scheme II, a 1H-imidazo[4,5-c]quinoline-5N-oxide of Formula XXIV is aminated to provide a 1H-imidazo[4,5-c]quinolin-4-amine of Formula IIa. Step (5) can be carried out by the activation of an N-oxide of Formula XXIV by conversion to an ester and then reacting the ester with an aminating agent. Suitable activating agents include alkyl- or arylsulfonyl chlorides such as benzenesulfonyl chloride, methanesulfonyl chloride, orp-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXIV in a suitable solvent such as dichloromethane or chloroform and then adding p-toluenesulfonyl chloride. The reaction can be carried out at ambient temperature. The product or pharmaceutically acceptable salt thereof can be isolated using conventional methods.

Alternatively step (5) can be carried out by the reaction of a 1H-imidazo[4,5-c]quinoline-5N-oxide of Formula XXIV with trichloroacetyl isocyanate followed by base-promoted hydrolysis of the resulting intermediate to provide a 1H-imidazo[4,5-c]quinolin-4-amine of Formula IIa. The reaction is conveniently carried out in two steps by (i) adding trichloroacetyl isocyanate to a solution of the N-oxide of Formula XXIV in a solvent such as dichloromethane and stirring at ambient temperature to provide an amide intermediate which may be isolated. In step (ii), a solution of the intermediate in methanol is treated with a base such as sodium methoxide or ammonium hydroxide at ambient temperature. The product or a pharmaceutically acceptable salt thereof can be isolated using conventional methods.

Steps (4) and (5) of Reaction Scheme II may be carried out as a one-pot procedure by adding 3-chloroperoxybenzoic acid to a solution of a compound of Formula XXIII in a solvent such as dichloromethane or chloroform and then adding ammonium hydroxide and p-toluenesulfonyl chloride without isolating the N-oxide compound of Formula XXIV. The product of Formula IIa or pharmaceutically acceptable salt thereof can be isolated by conventional methods.

may also be applied toward the synthesis of many amines of Formula XVI where m is 2 and R' is —OH. In a publication by I. L. Lysenko et al., *Russ. J. Org. Chem.*, 37, 1238-1243 (2001), the synthesis of the amine of Formula XVI where m is 1, R' is —OH, and Z is a bond has been described. The synthesis of the amine of Formula XVI where m is 3, R is —OH, and Z is a bond from butyrolactone has been published by A. Esposito et al., *J. Org. Chem.*, 65, 9245-9248 (2000). The method described by A. Esposito et al. may be applied toward the synthesis of amines of Formula XVI where m is 2, 4, and 5, R' is —OH, and Z is a bond starting from the appropriate commercially available lactones. Other amines of Formula XVI where R is —OH may be prepared according to Schemes III-V.

Amines of the Formula XVIb where Z is defined as above and hydrochloride salts thereof can be prepared according to Reaction Scheme III. In step (1) of Reaction Scheme III, a ketone of Formula XXV can be treated with excess nitromethane in a suitable solvent such as ethanol or methanol in the presence of a catalytic amount of base such as sodium ethoxide or sodium hydroxide to provide a compound of Formula XXVI. A wide variety of ketones of Formula XXV can be obtained from commercial sources or can be synthesized using known synthetic methods. The reaction can be carried out at ambient temperature. The product of Formula XXVI can be isolated using conventional methods.

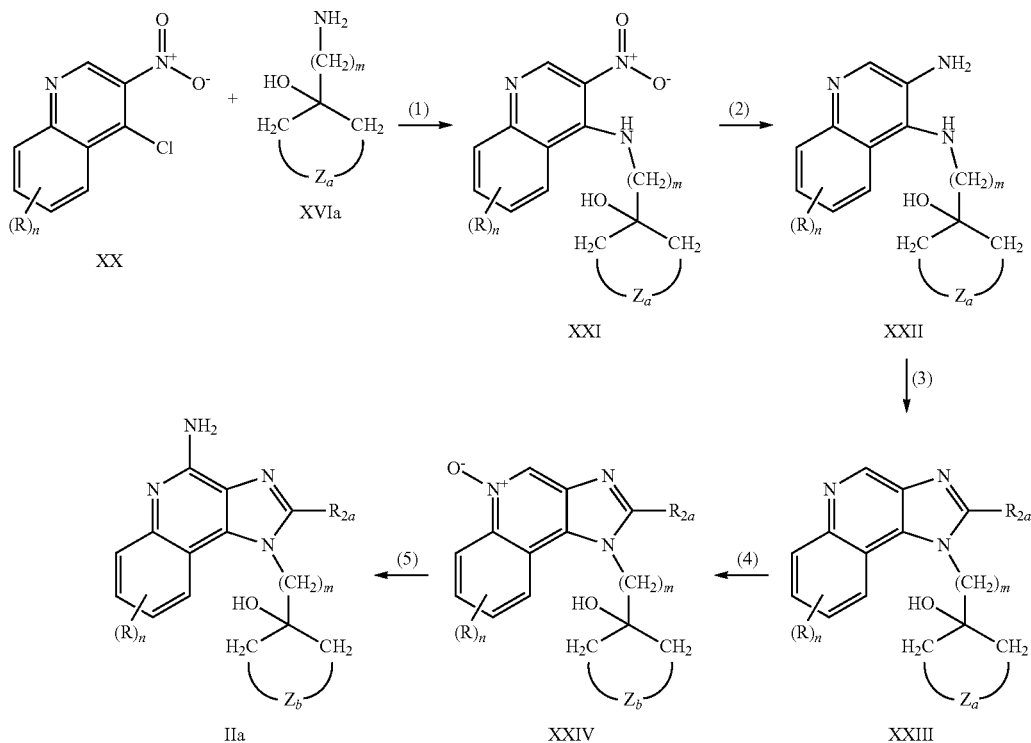

The amine of the Formula XVI where m is 1, R is —OH, and Z is —CH$_2$CH$_2$CH$_2$— can be obtained commercially as the hydrochloride salt. Some amines of the Formula XVI can be prepared according to published procedures or modified versions thereof. For example, the amine of Formula XVI where m is 2, R' is —OH, and Z is —CH$_2$CH$_2$CH$_2$— has been prepared previously by J. Bicking et al., *J. Med. Chem.*, 26, 342-348 (1983). The route described by J. Bicking et al.

Step (2) of Reaction Scheme III can be carried out by hydrogenation using a heterogeneous hydrogenation catalyst such as palladium hydroxide on carbon or palladium on carbon or Raney nickel. The hydrogenation is conveniently carried out in a Parr apparatus in a suitable solvent such as ethanol or methanol. The reaction can be carried out at ambient temperature, and the product amino alcohol of Formula XVIb can be isolated using conventional methods.

Alternatively, amino alcohols of Formula XVIb can be prepared by treating a ketone of Formula XXV with a cyanide source, such as trimethylsilylcyanide, in the presence of a catalytic amount of a crown ether, such as 18-crown-6, and a catalytic amount of a cyanide source, such as potassium cyanide. The intermediate cyanohydrin is then reduced with a hydride reducing agent, such as lithium aluminum hydride. The reduction may be carried out at a sub-ambient temperature, such as 0° C., in a suitable solvent such as THF, and the amino alcohol of Formula XVIb can be isolated by conventional methods.

Reaction Scheme III

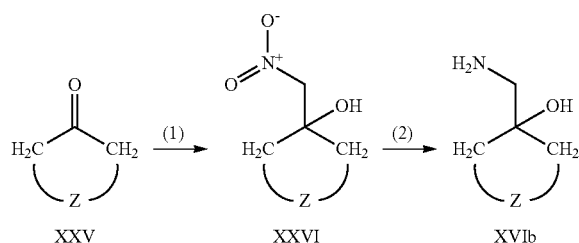

Reaction Scheme IV shows the synthesis of amines of Formula XVIc where m' may equal 0-3, Z is defined as above, and TBS- is a tert-butyldimethylsilyl group. In step (1), a ketone of Formula XXV is treated with an organometallic reagent of the Formula $H_2C=CH_2(CH_2)_{m'}M$ where M is MgCl, MgBr, MgI, ZnBr, ZnI, or Li, or the product of such reagent with $CeCl_3$. The organometallic reagents are commercially available or can be prepared from $H_2C=CH_2(CH_2)_mX$, where X is a chloride or preferably a bromide or iodide. The reaction can be carried out in an appropriate solvent such as tetrahydrofuran or diethyl ether. The resulting tertiary alcohol of Formula XXVII can be isolated using conventional methods.

In step (2) of Reaction Scheme IV, the newly formed tertiary alcohol of Formula XXVII is protected as a tert-butyldimethylsilyl (TBS) ether to yield the product of Formula XXVIII. The tertiary alcohol of Formula XXVII can be reacted with tert-butyldimethylsilyl chloride or tert-butyldimethylsilyl triflate with a base such as pyridine, 2,6-lutidine, triethylamine, or ethyldiisopropylamine in an appropriate solvent such as acetonitrile or dichloromethane optionally with a catalytic amount of dimethylaminopyridine. The resulting compound of Formula XXVIII can be isolated using conventional methods.

In step (3) of Reaction Scheme IV, the terminal olefin of Formula XXVIII undergoes hydroboration and subsequent oxidation to provide a primary alcohol of Formula XXIX. The two step procedure is carried out by first adding a reagent such as borane, catecholborane or 9-borabicyclo (3.3.1)nonane with or without $(PPh_3)_3RhCl$ present in an appropriate solvent such as tetrahydrofuran to generate an alkyl borane intermediate. Sodium hydroxide and an aqueous solution of hydrogen peroxide are added to convert the intermediate to the product of Formula XXIX, which can be isolated using conventional methods.

In step (4) of Reaction Scheme IV, the primary alcohol of Formula XXIX is reacted with methanesulfonyl chloride to yield a compound of Formula XXX. The reaction is conveniently carried out in a solvent such as dichloromethane in the presence of a base such as triethylamine. The reaction may be carried out starting at a sub-ambient temperature, such as 0° C., with warming to ambient temperature. The resulting compound of Formula XXX can be isolated using conventional methods.

In step (5) of Reaction Scheme IV, the compound of Formula XXX may be reacted with sodium azide in a suitable solvent such as dimethylformamide. The reaction may be carried out at ambient temperature or at elevated temperature. The resulting compound of Formula XXXI can be isolated using conventional methods.

In step (6) of Reaction Scheme IV, the tert-butyldimethylsilyl (TBS) group is removed from the compound of Formula XXXI to generate the alcohol in a compound of Formula XXXII. Typically, a compound of Formula XXXI is treated with a fluoride source such as tetrabutylammonium fluoride in a suitable solvent such as tetrahydrofuran with or without acetic acid added. Alternatively, hydrogen fluoride-pyridine may be used in a suitable solvent such as tetrahydrofuran optionally with pyridine added to the reaction. The reaction can be carried out at ambient temperature. The resulting compound of Formula XXXII can be isolated using conventional methods.

In step (7) of Reaction Scheme IV, a compound of Formula XXXII can be reduced to provide a amino alcohol of Formula XVIc. The reaction can be carried out by hydrogenation using a heterogeneous hydrogenation catalyst such as palladium on carbon.

The hydrogenation is conveniently carried out in a Parr apparatus in a suitable solvent such as ethanol. The reaction can be carried out at ambient temperature, and the product of Formula XVIc where $R'_a$ is —OH can be isolated using conventional methods.

In step (7a) of Reaction Scheme IV, an azide of Formula XXXI may be reduced using the conditions described in step (7) of Reaction Scheme IV to yield the corresponding amine of Formula XVIc where $R'_a$ is -OTBS, which may be used in place of an amine of Formula XVIa in Reaction Scheme II. Subsequent removal of the tert-butyldimethylsilyl protecting group after completion of step (4) of Reaction Scheme II using aqueous hydrogen chloride in a suitable solvent such as methanol or using the conditions described for step (6) in Reaction Scheme IV ultimately provides a compound of Formula XXIII, which can be converted to a compound of Formula IIa.

Reaction Scheme IV

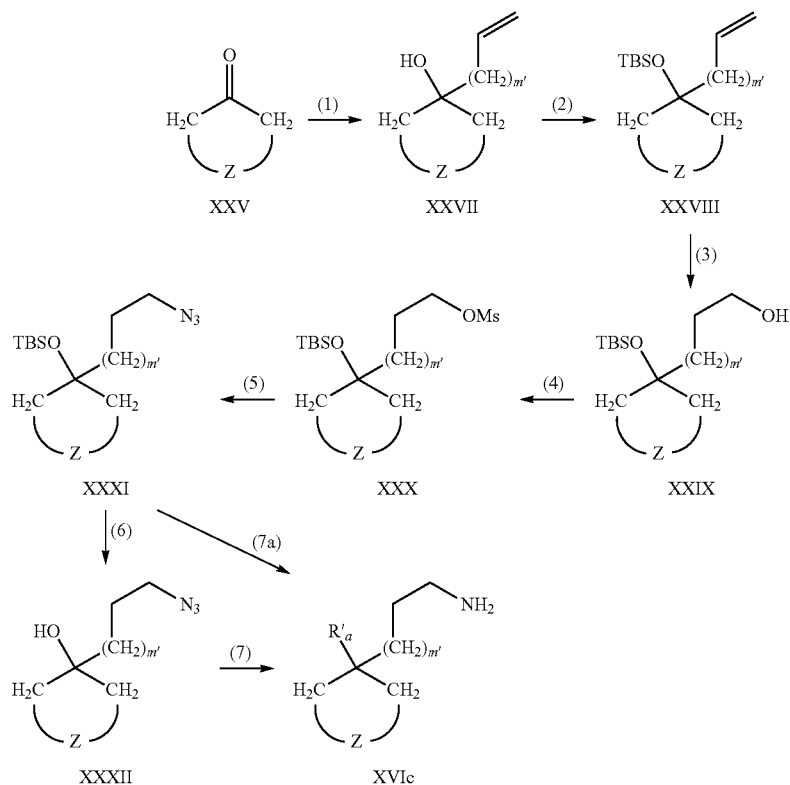

Reaction Scheme V shows a general synthesis of amines of Formula XVId where m equals 1-5 and Bz is a benzyl group. Compounds of the Formula XXXIII are used as the starting material and can be obtained from commercial sources or can be readily synthesized as described by R. K. Olsen et al., *J. Org. Chem.*, 47, 4605-4611 (1982), S. Kobayashi et al., *Syn. Lett.*, 909-912 (1999), and C. F. Garcia et al., *J. Chem. Soc. Chem. Commun.*, 12, 1465-1466 (1996). In step (1) of Reaction Scheme V, a cyclopropane of Formula XXXIV is formed upon treatment of the starting material of Formula XXXIII with ethylmagnesium bromide in the presence of titanium(IV) isopropoxide in a suitable solvent such as tetrahydrofuran at sub-ambient temperature. The product of Formula XXXIV can be isolated using conventional methods.

In step (2) of reaction Scheme V, a compound of Formula XVId is prepared by the reduction of compound of Formula XXXIV. The reaction can be carried out by hydrogenation using a heterogeneous hydrogenation catalyst such as palladium on carbon. The hydrogenation is conveniently carried out in a Parr apparatus using a suitable solvent such as ethanol, methanol, or ethyl acetate. The reaction can be performed at ambient temperature, and the product of Formula XVId can be isolated using conventional methods.

Reaction Scheme V

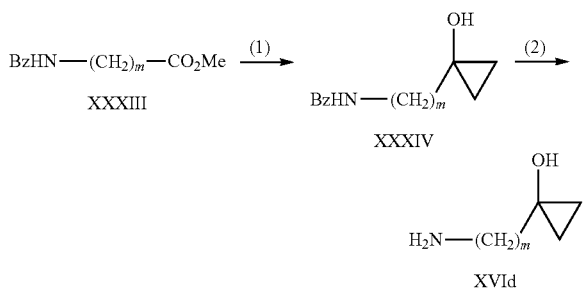

Functional group transformations in a compound of Formula XXIII are possible using known synthetic methods. For example, as shown in step (1) of Reaction Scheme VI, a compound of Formula XXIII where $Z_a$=—$(CH_2)_{0-3}$—NBoc-$(CH_2)_{0-3}$— (Boc is defined as tert-butyloxycarbonyl) can be treated with acid to remove the Boc group to yield an amine of Formula XXXV. In step (2) of Reaction Scheme VI, an amine of Formula XXXV can react with an acid chloride of Formula $R_4C(O)Cl$, an alkyl chloroformate of Formula $R_4OC(O)Cl$, a sulfonyl chloride of Formula $R_4S(O)_2Cl$, a sulfonic anydride of Formula $(R_4S(O)_2)_2O$, or an acid anhydride of the Formula $(R_4C(O))_2O$ to provide compound of Formula XXIII in which $Z_a$ is —$CH_2$-A'-$CH_2$— and A' is —$N(Q-R_4)$ where $R_4$ is defined as above and Q is —C(O)—, —C(O)O—, —$S(O)_2$—. Numerous acid chlorides, alkyl chloroformates, sulfonyl chlorides, and sulfonic anhydrides are commercially available; others can be prepared readily using known synthetic methods. The reaction can be conveniently carried out by adding the acid chloride, alkyl chloroformate, sulfonyl chloride, sulfonic anhydride, or acid anhydride to a solution of amine of Formula XXXV in a suitable solvent such as pyridine. The reaction can be carried out at ambient temperature and the product can be isolated using conventional methods. In step (3) of Reaction Scheme VI, the tertiary hydroxy group of a 1H-imidazo[4,5-c]quinoline of Formula XXIII can be alkylated to produce an ether of Formula XXXVI. The reaction is conventionally carried out in a suitable solvent such as tetrahydrofuran using a base such as sodium hydride or potassium hydride to first deprotonate the alcohol, followed by addition of an alkyl iodide or alkyl triflate. The reaction can be carried out at elevated temperature. Alternatively, the hydroxy group can be reacted with methyl vinyl sulfone after treatment with a sub-stoichiometric amount of sodium hydride in a suitable solvent such as tetrahydrofuran at ambient temperature. The product of Formula XXXVI can be isolated using conventional methods. Steps (4) and (5) can be carried out as described for steps (4) and (5) of Reaction Scheme II to provide a compound of Formula IIb.

—C(O)—, —C(O)O—, —S(O)$_2$—, —C(O)NH—, or —C(S)NH—. Alternatively, a compound of Formula XXIII in Reaction Scheme II, where $Z_a$=—(CH$_2$)$_{0-3}$—NBoc-(CH$_2$)$_{0-3}$— for example, can be treated with acid to remove the Boc group. The resulting amine can react further with an acid chloride of Formula R$_4$C(O)Cl, an alkyl chloroformate of Formula R$_4$OC(O)Cl, a sulfonyl chloride of Formula R$_4$S(O)$_2$Cl, a sulfonic anydride of Formula (R$_4$S(O)$_2$)$_2$O, or an isocyanate of formula R$_4$NCO before step (4) of Reaction Scheme II. The product can then be treated according to steps (4) and (5) of Reaction Scheme II to provide compound of Formula IId in which Z is —(CH$_2$)$_{0-3}$-A'—(CH$_2$)$_{0-3}$- and A' is —N(Q-R$_4$) where R$_4$ is defined as above and Q is —C(O)—, —C(O)O—, —S(O)$_2$—, or —C(O)NH—. Numerous acid chlorides, alkyl chloroformates, sulfonyl chlorides, sulfonic anhydrides, isocyanates, and isothiocyanates are commercially available; others can be prepared readily using known synthetic methods. The reaction can be conveniently carried out by adding the acid chloride, alkyl chloroformate, sulfonyl chloride, sulfonic anhydride, isocyanate, or isothiocyanate to a solution of

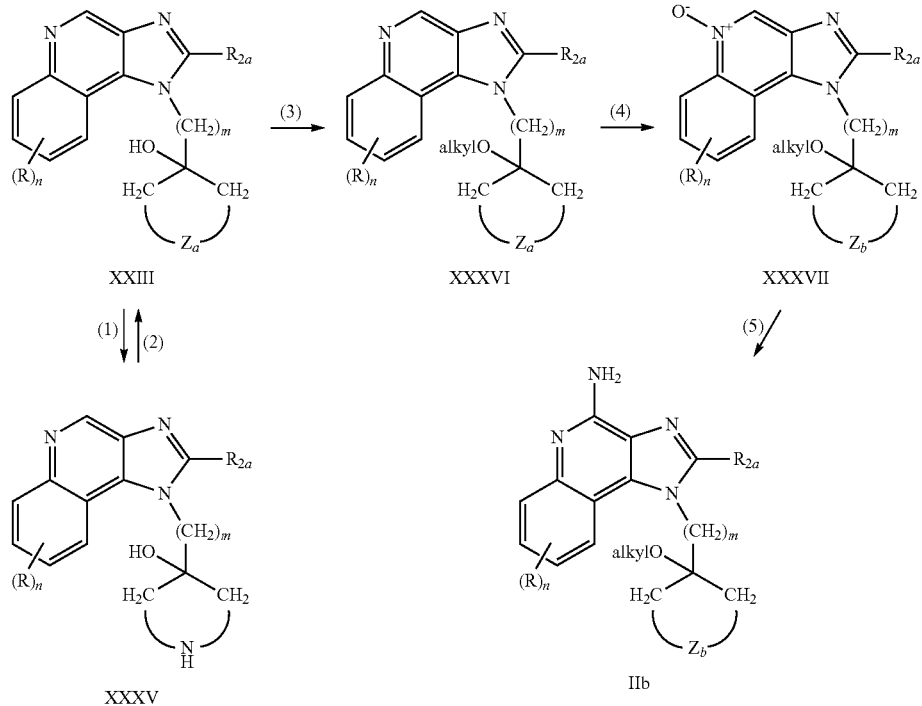

amine of Formula IIc or XXIII, in which Z or $Z_a$ contains a secondary amine in a suitable solvent such as pyridine. The reaction can be carried out at ambient temperature.

In addition, a compound of Formula IIc in Reaction Scheme VII can undergo alkylation of the secondary amine. In step (3) the compound of Formula IIc may react with aldehydes, alkyl halides or triflates to provide a compound Formula IIe in which R$_8$ is defined as above. For example, treatment of a compound of Formula IIc with aqueous formaldehyde and a reducing agent such as sodium cyanoborohydride in an appropriate solvent such as methanol yields a compound of Formula IIe, where R$_8$ is a methyl group.

For some embodiments, compounds shown in Reaction Schemes I and II can be further elaborated using conventional synthetic methods. For example, as shown in Scheme VII, a compound of Formula IIa, where Z is —(CH$_2$)$_{0-3}$—NBoc-(CH$_2$)$_{0-3}$- and Boc is defined as tert-butyloxycarbonyl, can undergo acid mediated cleavage of the Boc group in step (1) to give a secondary amine that can be functionalized in step (2) with an acid chloride of Formula R$_4$C(O)Cl, an alkyl chloroformate of Formula R$_4$OC(O)Cl, a sulfonyl chloride of Formula R$_4$S(O)$_2$Cl, a sulfonic anydride of Formula (R$_4$S(O)$_2$)$_2$O, an isocyanate of formula R$_4$NCO, or an isothiocyanate of formula R$_4$NCS to provide a compound of Formula IId in which Z is —(CH$_2$)$_{0-3}$-A'—(CH$_2$)$_{0-3}$— and A' is —N(Q-R$_4$) where R$_4$ is defined as above and Q is Reaction Scheme VII

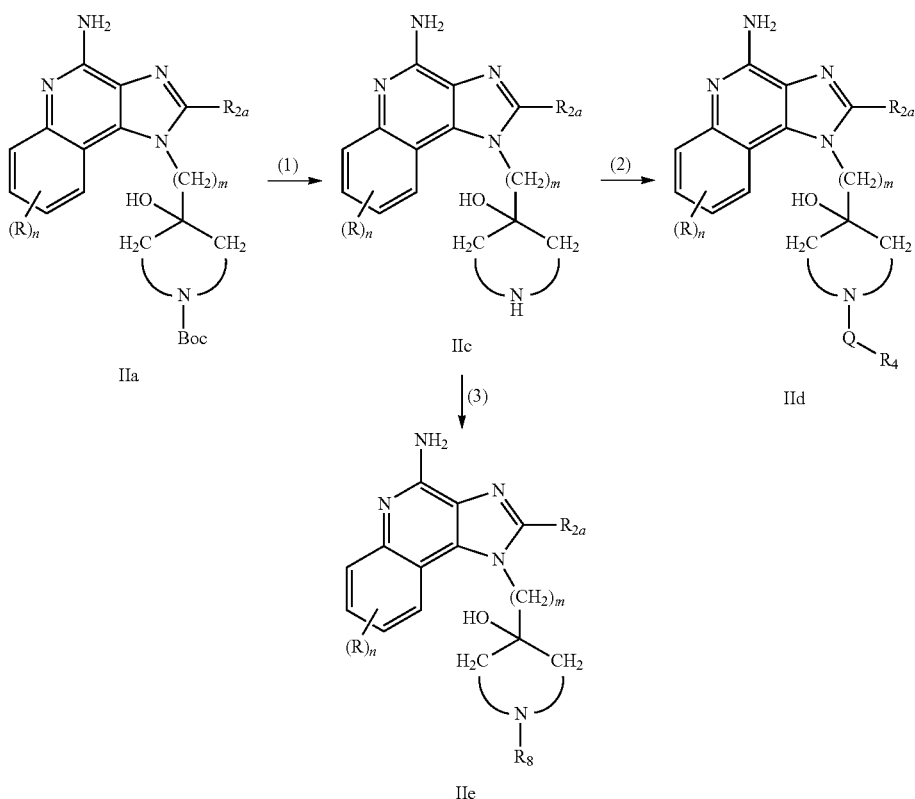

Compounds of the invention of Formula IIf and IIg can be prepared according to Reaction Scheme VIII, wherein R, n, $Z_a$, $Z_b$, and $R_{2a}$ are defined as above. In step (1) of Reaction Scheme VIII, a 4-chloro-3-nitroquinoline of Formula XX is reacted with an amine of the Formula XVIe or a salt thereof to form a compound of Formula XXXVIII. This reaction is carried out as described for step (1) in Reaction Scheme I. Amines of the Formula XVIe and salts thereof can be prepared according to published procedures or modified versions thereof, or by using conventional synthetic methods. For example, the synthesis of amines of the Formula XVI where m is one, R'=$NH_2$ and Z is —$(CH_2)_{2-4}$—, and —$CH_2(NCH_3)CH_2$— has been published by M. A. Fernandez et al., *Anales de la Real Academia de Farmacia*, 54, 502-510 (1988). The starting materials used by M. A. Fernandez et al. were ketones of Formula XXV. A wide variety of ketones of Formula XXV can be obtained from commercial sources or can be synthesized. Those ketones of Formula XXV may be used in the synthesis of amines of Formula XVI where m is one, R'=$NH_2$ and Z is as described above. Similar chemistry to that published by Fernandez et al. that is also relevant has been published by S. L. Deng et al., *Synthesis*, 2445-2449 (2001), A. A. Cordi et al., J. Med. Chem., 44, 787-805 (2001), and M. Freifelder et al., *J. Amer. Chem. Soc.*, 82, 696-698 (1960). In addition, the amine of Formula XVIe wherein m is one and $Z_a$ is a bond has been synthesized previously by F. Vergne et al., *J. Org. Chem.*, 57, 6071-6075 (1992). Many compounds of Formula XX are known or can be prepared using known synthetic methods, see for example, U.S. Pat. Nos. 4,689,338; 5,175,296; 5,367,076; and 5,389,640; and the documents cited therein.

In step (2) of Reaction Scheme VIII, the primary amine in a compound of Formula XXXVIII is converted into a tert-butyl carbamate to provide a compound of Formula XXXIX. The reaction is conveniently carried out using di-tert-butyldicarbonate in the presence of a base such as aqueous sodium hydroxide in a solvent such as tetrahydrofuran. The compound of Formula XXXIX can be isolated using conventional methods.

Steps (3), (4), (5), and (6) of Reaction Scheme VIII can be carried out as described for steps (2), (3), (4), and (5), respectively, of Reaction Scheme II to provide a compound of Formula IIf.

In step (7) of Reaction Scheme VIII, the tert-butyl carbamate in a compound of Formula IIf is converted to a primary amine of Formula IIg. The reaction is conveniently performed in the presence of an acid such as hydrogen chloride in a suitable solvent such as ethanol. The reaction is performed at elevated temperature and the product of Formula IIg or a pharmaceutically acceptable salt thereof is isolated using conventional methods.

Reaction Scheme VIII

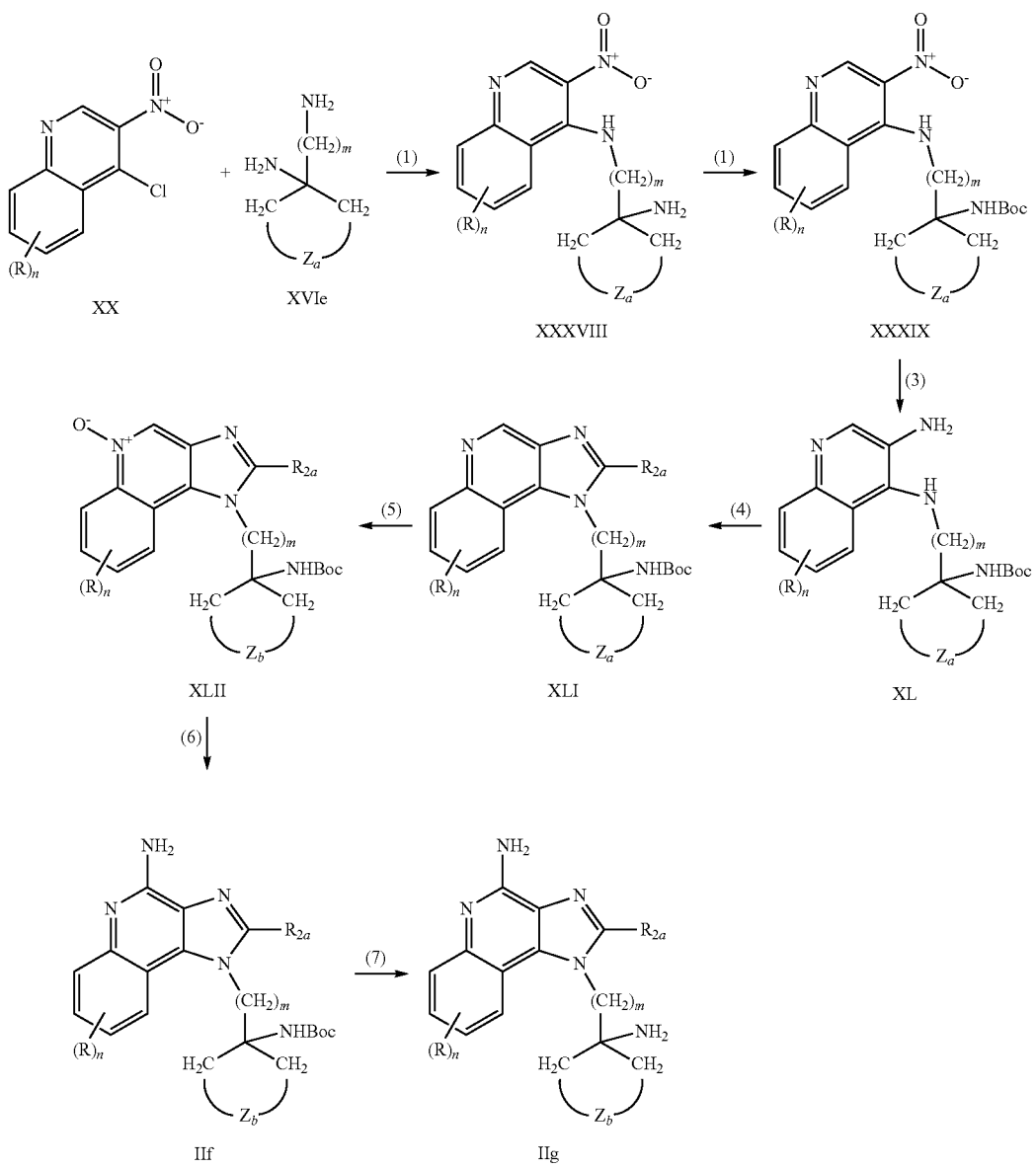

For some embodiments, compounds shown in Reaction Scheme VIII can be further elaborated using conventional synthetic methods. For example, as shown in Scheme IX, a compound of Formula XLI can undergo acid mediated cleavage of the Boc group in step (1) to give a primary amine of Formula XLIII that can be functionalized with the reagents described in step (2) of Reaction Scheme VII to provide a compound of Formula XLIV in which where $R_4$ is defined as above and Q is —C(O)—, —C(O)O—, —S(O)$_2$—, —C(O)NH—, or —C(S)NH—. The reaction can be carried out in an appropriate solvent such as dichloromethane in the presence of a tertiary amine such as triethylamine, or can be performed in pyridine. Optionally, dimethylaminopyridine may be used in the reaction. The reaction is carried out at ambient temperature. Steps (3) and (4) of Reaction Scheme IX can be carried out as described for steps (4) and (5) in Reaction Scheme II to yield a compound of Formula IIh. If $Z_b$ in a compound of Formula IIh contains an appropriately protected amine, deprotection will provide a free amine that may be functionalized with the reagents described in step (2) of Reaction Scheme VII.

Reaction Scheme IX

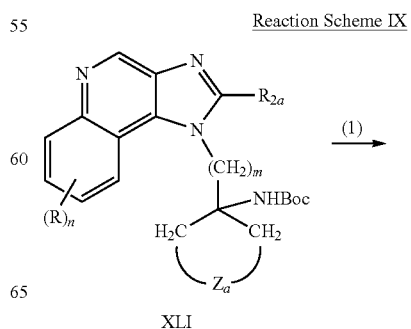

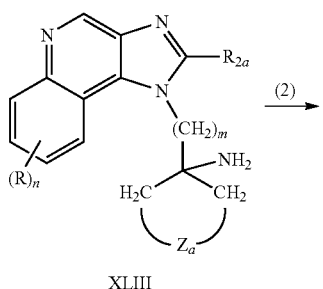

XLIII

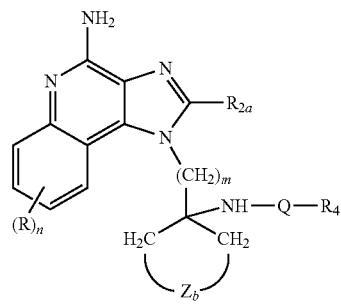

IIh

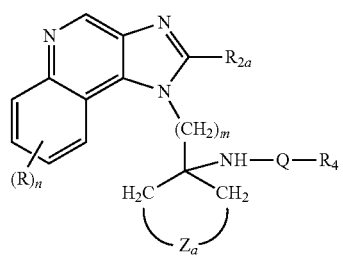

XLIV

Compounds of the Formula IIi can be prepared according to Reaction Scheme X, wherein R, n, and m are as defined above, and $Z_a$, $Z_b$, and $R_{2a}$ are subsets of Z and $R_2$ as defined above. In step (1) of Reaction Scheme X, 4-chloro-3-nitroquinoline of Formula XX is reacted with an amine of the Formula XVIf or hydrochloride salt thereof to form a compound of Formula XLV. Step (1) of Reaction Scheme X is carried out as described for step (1) in Reaction Scheme II. Steps (2), (3), (4), and (5) of Reaction Scheme X can be carried out as described for steps (2), (3), (4), and (5), respectively, of Reaction Scheme II to provide a compound of Formula IIi or a pharmaceutically active salt thereof.

Reaction Scheme X

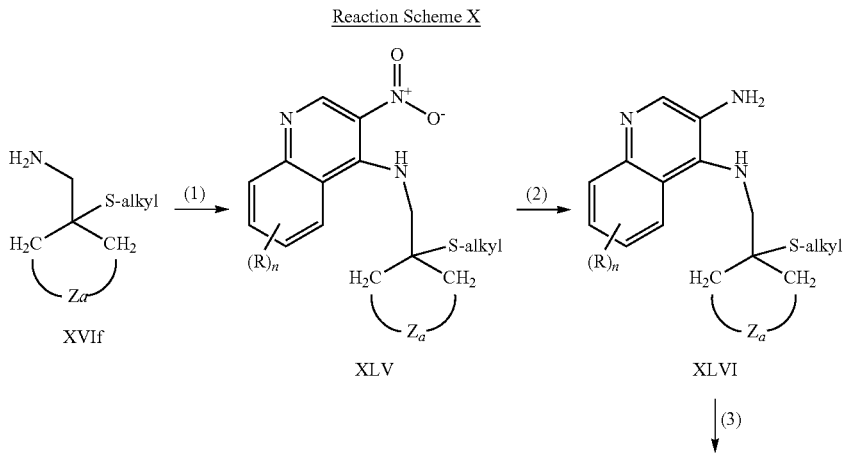

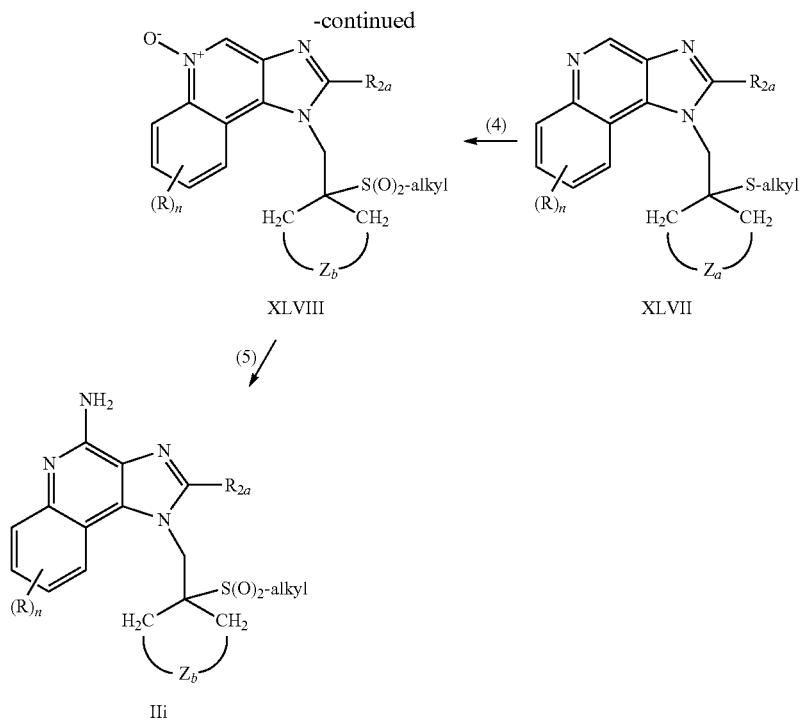

Some amines of the Formula XVIf and hydrochloride salts thereof can be prepared according to Reaction Scheme XI and by conventional synthetic methods. In step (1) of Reaction Scheme XI, a ketone of Formula XXV is treated nitromethane and an alkyl thiol in the presence of a base in an appropriate solvent by modifying the procedure of W. W. Lin et al., *J. Org. Chem.*, 66, 1984-1991 (2001) to yield a compound of Formula XLIX.

In step (2) of Reaction Scheme XI, a compound of Formula XLIX is reduced using lithium aluminum hydride or hydrogenated using a heterogeneous hydrogenation catalyst palladium on carbon. The product of Formula XVIf or salt thereof can be isolated using conventional methods.

Compounds of Formula II where R' is a sulfide and R, $R_2$, n, m, and Z are as defined above can be prepared according to the route shown in Reaction Scheme I using an amine of Formula XVIf as the starting material.

As shown in Reaction Scheme XII, an 1H-imidazo[4,5-c]quinoline of Formula IIj can be reduced to a 6,7,8,9-tetrahydro-1H-imidazo[4,5-c]quinolin-4-amine of Formula IIIa where Z and R' are as defined above and $R_{2b}$ and $R_b$ are subsets of $R_2$ and R as defined above that do not include substituents that one skilled in the art would recognize as being susceptible to reduction under the acidic hydrogenation conditions of step (1). Those susceptible groups include, for example, alkenyl, alkynyl, aryl groups, and groups bearing nitro substituents. The reaction is conveniently carried out under heterogeneous hydrogenation conditions by adding platinum (IV) oxide to a solution of the compound of Formula IIj in trifluoroacetic acid and placing the reaction under hydrogen pressure. The reaction can be carried out on a Parr apparatus at ambient temperature. The product or pharmaceutically acceptable salt thereof can be isolated by conventional methods.

Reaction Scheme XI

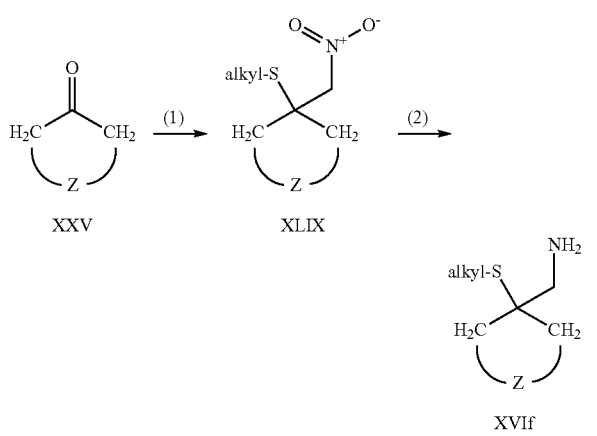

Reaction Scheme XII

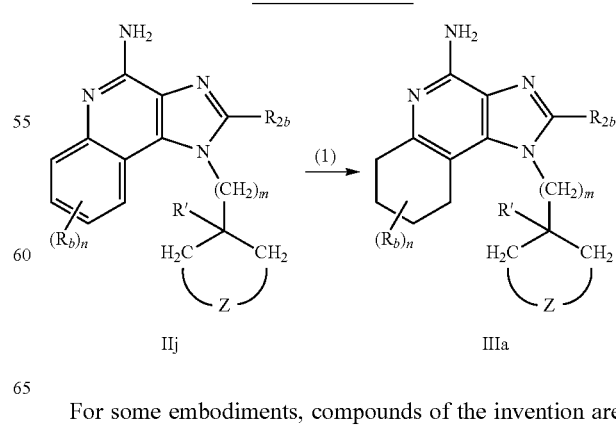

For some embodiments, compounds of the invention are prepared according to Reaction Scheme XIII, where Z, R', $R_2$, $R_A$, and $R_B$ are as defined above. In step (1) of Reaction Scheme XIII, a 2,4-dichloro-3-nitropyridine of Formula LI is reacted with an amine of Formula XVI or a hydrochloride salt thereof to form a 2-chloro-3-nitropyridine of Formula LII. The reaction is conveniently carried out by combining an amine of Formula XVI or a hydrochloride salt thereof and 2,4-dichloro-3-nitropyridine of Formula LI in the presence of a base such as triethylamine in a solvent such as N,N-dimethylformamide (DMF). The reaction can be carried out at ambient temperature or above, and the product can be isolated from the reaction mixture using conventional methods. Many 2,4-dichloro-3-nitropyridines of Formula LI are known and can be readily prepared using known synthetic methods. (See, for example, U.S. Pat. No. 6,525,064 (Dellaria et al.) and the references cited therein.)

In step (2) of Reaction Scheme XIII, a 2-chloro-3-nitropyridine of Formula LII is reacted with dibenzylamine to provide a compound of Formula LIII. The reaction can be carried out by combining the compound of Formula LII with dibenzylamine and a tertiary amine such as triethylamine in a suitable solvent such as toluene. The reaction can be carried out at elevated temperature and the product of Formula LIII is isolated from the reaction mixture using conventional methods.

In step (3) of Reaction Scheme XIII, a compound of formula LIII is reduced to provide a compound of Formula LIV. The reduction can be carried out by hydrogenation using a conventional heterogeneous catalyst, for example, platinum on carbon or palladium on carbon. The reaction can conveniently be carried out on a Parr apparatus in a suitable solvent such as acetonitrile or ethyl acetate. The product of Formula LIV can be isolated from the reaction mixture using conventional methods.

In step (4) of reaction Scheme XIII, a compound of Formula LIV is reacted with a carboxylic acid equivalent to provide a compound of Formula LV. The reaction can be carried out as described in step (3) of Reaction Scheme I, and the product can be isolated from the reaction mixture using conventional methods.

A compound of Formula LV may also be prepared by subjecting a compound of Formula LII to the reaction conditions in described in steps (3) and (4) to provide a 4-chloroimidazopyridine which may then be treated with dibenzylamine in a microwave to provide a compound of Formula LV.

In step (5) of reaction Scheme XIII, the benzyl groups of a compound of Formula LV are cleaved to provide a compound of Formula III. The reaction can be carried out by transfer hydrogenation in the presence of a suitable hydrogenation catalyst. The transfer hydrogenation is conveniently carried out by adding ammonium formate to a solution of a compound of Formula LV in a suitable solvent such as ethanol or methanol in the presence of a catalyst such as palladium on carbon. The reaction is carried out at an elevated temperature, for example, the reflux temperature of the solvent. The product of Formula III or pharmaceutically acceptable salt thereof can be isolated using conventional methods.

Reaction Scheme XIII

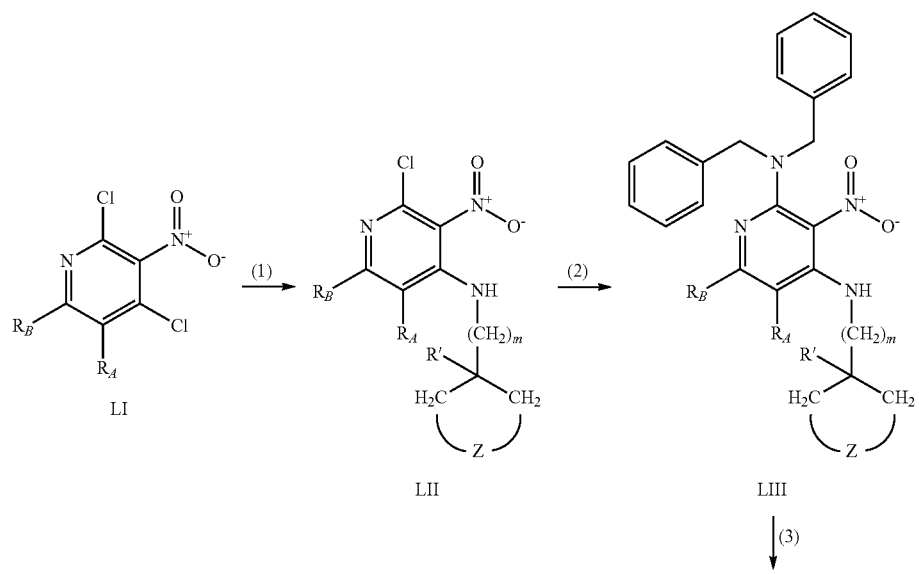

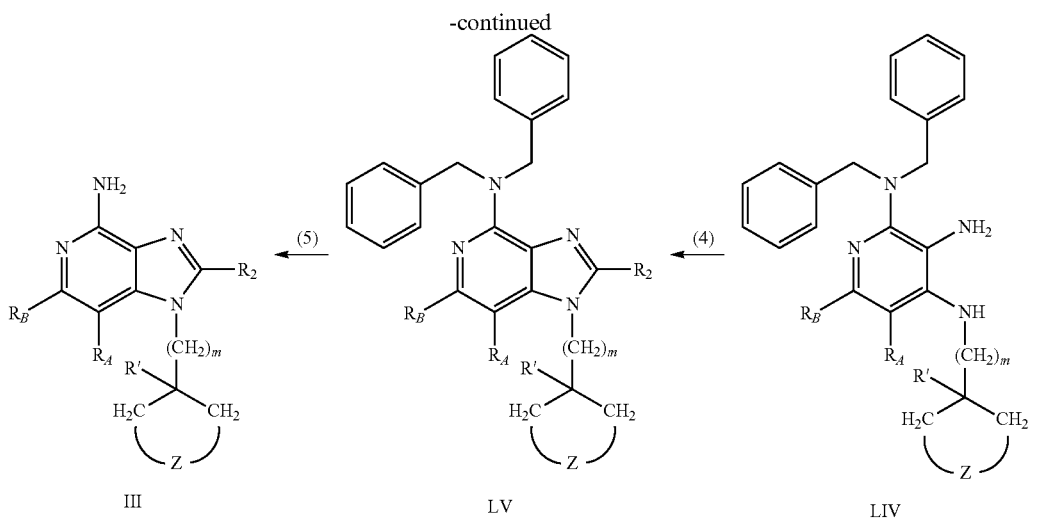

Compounds of the invention can be prepared according to Reaction Scheme XIV, wherein R, $Z_a$, $Z_b$, $R_{2a}$ and m are as defined above. Reaction Scheme XIV begins with a 4-chloro-3-nitro[1,5]naphthyridine of Formula LVI. Compounds of Formula LVI and their preparation are known; see, for example, U.S. Pat. No. 6,194,425 (Gerster) and U.S. Pat. No. 6,518,280 (Gerster). Steps (1) through (5) of Reaction Scheme XIV can be carried out as described for the corresponding steps (1) through (5) of Reaction Scheme II to provide a substituted 1H-imidazo[4,5-c]-1,5-naphthyridin-4-amine of Formula IVa. The product or pharmaceutically acceptable salt thereof can be isolated by conventional methods.

Reaction Scheme XIV

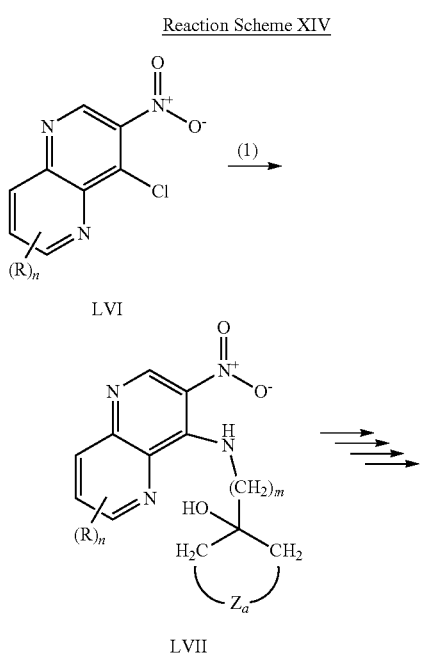

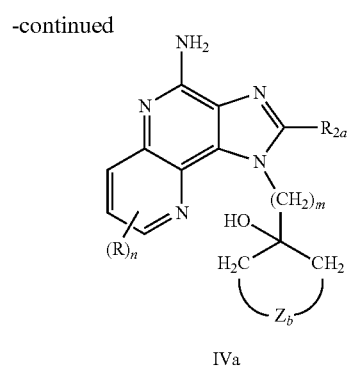

IVa

For some embodiments, naphthyridines of the invention are prepared from tetrazolo compounds of Formulas LVIII and LXI according to Reaction Scheme XV, wherein R, R', $R_2$, m, and Z are as defined above and -OTf is a trifluoromethanesulfonate group. Compounds of Formula LVIII and LXI and synthetic routes to these compounds are known; see, for example, U.S. Pat. No. 6,194,425 (Gerster) and U.S. Pat. No. 6,518,280 (Gerster).

In steps (1) and (1a) of Reaction Scheme XV, a tetrazolonaphthyridine of Formula LVIII or LXI is reacted with an amine of Formula XVI or a hydrochloride salt thereof to form a compound of Formula LIX or LXII. The reaction can be carried out as described in step (1) of Reaction Scheme I. A compound of Formula LIX or LXII is converted to a compound of Formula LX or LXIII according to the methods of steps (2) and (3) of Reaction Scheme I. The tetrazolo group of a compound of Formula LX or LXIII can then be removed to provide a 1H-imidazo[4,5-c]naphthyridin-4-amine of Formula VII or VIII. The removal of the tetrazolo group can be carried out by methods described in U.S. Pat. No. 6,194,425 (Gerster) and U.S. Pat. No. 6,518,280 (Gerster). The product or pharmaceutically acceptable salt thereof can be isolated by conventional methods.

Reaction Scheme XV

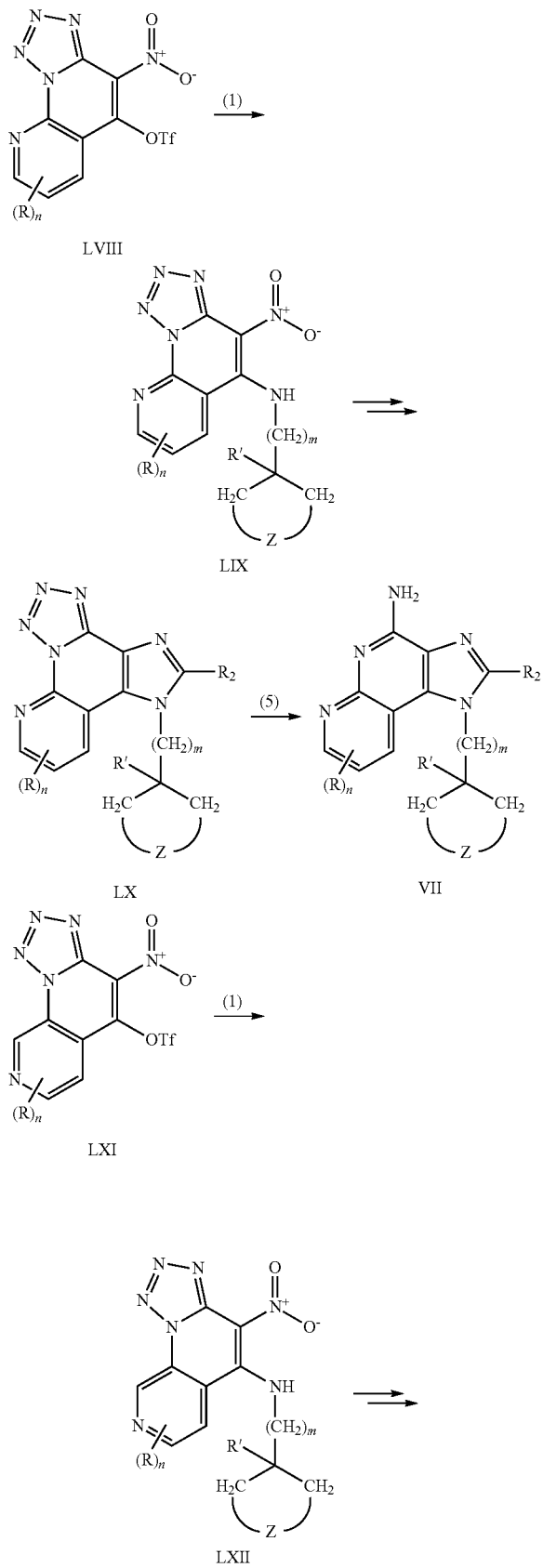

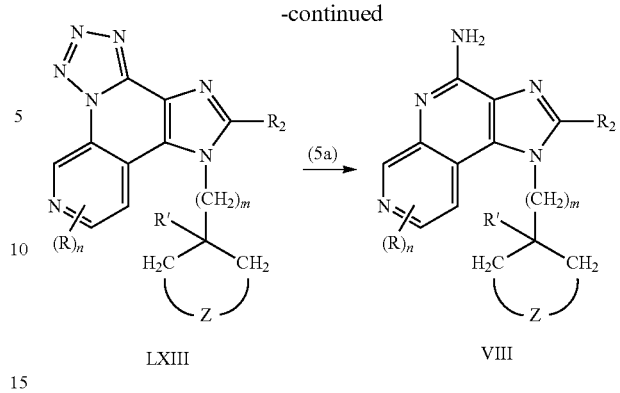

Compounds of the invention can also be prepared using variations of the synthetic routes shown in Reaction Schemes I through XV. For example, tetrahydronapthyridines can be prepared using the method described in Reaction Scheme XII for the preparation of tetrahydroquinolines. Compounds of the invention can also be prepared using the synthetic routes described in the EXAMPLES below.

Prodrugs can be prepared in a variety of ways. For example, a compound wherein $R_2$ is —X—OH can be converted into a prodrug wherein $R_2$ is, for example, —X—O—C($R_6$)—$R_4$, —X—O—C($R_6$)—O—$R_4$, or —X—O—C($R_6$)—N($R_6$)—$R_4$, wherein $R_4$, $R_6$, and $R_8$ are as defined above, using methods known to one skilled in the art. In addition, a compound wherein R' or R is hydroxy may also be converted to an ester, an ether, a carbonate, or a carbamate. For any of these compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D-, and L-amino acids. For compounds containing an alcohol functional group, particularly useful prodrugs are esters made from carboxylic acids containing one to six carbon atoms, unsubstituted or substituted benzoic acid esters, or esters made from racemic, D-, or L-amino acids.

Prodrugs can also be made from a compound containing an amino group by conversion of the amino group to a functional group such as an amide, carbamate, urea, amidine, or another hydrolysable group using conventional methods. A prodrug of this type can be made by the replacement of a hydrogen atom in an amino group, particularly the amino group at the 4-position, with a group such as —C(O)—R'', α-aminoacyl, α-aminoacyl-α-aminoacyl, —C(O)—O—R'', —C(O)—N(R''')—R'', —C(=NY')—R'', —CH(OH)—C(O)—OY', —CH(OC$_{1-4}$ alkyl)Y$_0$, —CH$_2$Y$_1$, or —CH(CH$_3$)Y$_1$; wherein R'' and R''' are each independently $C_{1-10}$ alkyl, $C_{3-7}$ cycloalkyl, or benzyl, each of which may be unsubstituted or substituted by one or more substituents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R''' can also be hydrogen; each α-aminoacyl group is independently selected from racemic, D-, and L-amino acids; Y' is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and $Y_1$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such *chlamydia*, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245, 776, and U.S. Publication Nos. 2003/0139364, 2003/ 185835, 2004/0258698, 2004/0265351, 2004/076633, and 2005/0009858.

EXAMPLES

Objects and advantages of this invention are further illustrated by the following examples, but the particular materials and amounts thereof recited in these examples, as well as other conditions and details, should not be construed to unduly limit this invention.

Example 1

1-{[4-Amino-2-(ethoxymethyl)-1H-imidazo[4,5-c]quinolin-1-yl]methyl}cyclohexanol

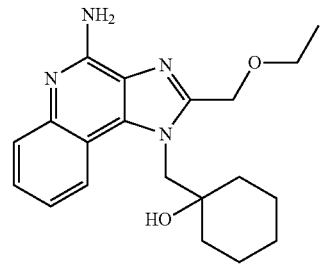 [SMILES: CCOCc1nc2c(N)nc3ccccc3c2n1CC1(O)CCCCC1]

Part A

To a mixture of 4-chloro-3-nitroquinoline (6.30 g, 30.2 mmol) in dichloromethane (100 mL) at 0° C. was added triethylamine (0.1 mL). To the resulting solution was added 1-aminomethyl-1-cyclohexanol hydrochloride (5.00 g, 30.2 mmol), then triethylamine (4.1 mL) and tetrahydrofuran (THF, 20 mL). The mixture was allowed to warm to room temperature (rt) and more triethylamine (4.2 mL) was added. The yellow mixture was stirred overnight, then was concentrated to about half the volume and heated at reflux for 1 hour (h). The mixture was concentrated and the solid was partitioned between 1 M aqueous NaOH (100 mL) and $CH_2Cl_2$ (200 mL). The organic layer was washed with water (2×50 mL) and brine (50 mL), dried over $MgSO_4$, filtered, and concentrated to a yellow solid that was crystallized from hot isopropanol to yield yellow crystals (9.04 g). $^1$H NMR analysis of the yellow crystals showed a 1:1.4 mixture of isopropyl alcohol to 1-{[(3-nitroquinolin-4-yl)amino]methyl}cyclohexanol. Based on the $^1$H NMR result, the mass of the 1-{[(3-nitroquinolin-4-yl)amino]methyl}cyclohexanol in the mixture was calculated (7.88 g, 87%). The product was used without further purification in the next step.

Part B

A mixture of the 1-{[(3-nitroquinolin-4-yl)amino]methyl}cyclohexanol prepared above (87%, 7.00 g, 20.3 mmol) and 5% platinum on carbon (0.60 g) in toluene (160 mL) and ethanol (20 mL) was hydrogenated at 20-30 psi ($1.4×10^5$ to $2.1×10^5$ Pa) on a Parr apparatus for 2 h. The mixture was filtered through CELITE filter agent, which was rinsed with toluene. The filtrate was concentrated to a golden oil. The oil was concentrated twice from toluene. To the oil was added CH$_2$Cl$_2$ (200 mL) and the resulting solution was cooled in an ice bath. Triethylamine (3.11 mL, 22.3 mmol) was added followed by dropwise addition of ethoxyacetyl chloride (88%, 2.96 g, 21.3 mmol). The solution was allowed to warm to rt and stir for 1 h, during which time a precipitate formed. The reaction mixture was concentrated to a yellow foam to which ethanol (200 mL) and triethylamine (11 mL) were added. The resulting solution was heated at reflux for 13 h. The solution was concentrated to a yellow solid, which was dissolved in CH$_2$Cl$_2$ (150 mL) and washed with water (50 mL) and brine (75 mL). The organic layer was dried over MgSO$_4$, filtered, and concentrated to a solid that was crystallized from CDCl$_3$/CH$_2$Cl$_2$ to yield 1-{[2-(ethoxymethyl)-1H-imidazo[4,5-c]quinolin-1-yl]methyl}cyclohexanol as pale orange crystals after drying (1.94 g, 28%).

Part C

To a solution of 1-{[2-(ethoxymethyl)-1H-imidazo[4,5-c]quinolin-1-yl]methyl}cyclohexanol (1.90 g, 5.60 mmol) in CHCl$_3$ (43 mL) was added m-chloroperoxybenzoic acid (m-CPBA, 77% w/w, 1.26 g, 5.60 mmol) over 15 min. The reaction was monitored by thin layer chromatography (TLC) and more m-CPBA was added over 1 h until the starting material was consumed. Water (40 mL) and solid K$_2$CO$_3$ were added to the reaction mixture until the pH=10. The mixture was poured into a separatory funnel and extracted with chloroform, resulting in an emulsion. The aqueous layer was extracted with chloroform three times. The combined organic layers were washed with water and brine, dried over MgSO$_4$, filtered, and concentrated to yield a crude white solid (1.51 g). The white solid (1.51 g, 4.24 mmol) was dissolved in dichloromethane (25 mL) at rt and concentrated ammonium hydroxide (16 mL) was added, followed by p-toluenesulfonyl chloride (TsCl, 0.81 g, 4.24 mmol). The mixture was stirred 1 day (d). Water (25 mL) was added and the aqueous layer was extracted with dichloromethane (2×30 mL). The combined organic layers were washed with brine (25 mL) and were dried over MgSO$_4$, filtered, and concentrated. The crude product was purified by flash chromatography (silica gel, gradient elution with 98:1:1 CH$_2$Cl$_2$/MeOH/NH$_4$OH to 94:5:1 CH$_2$Cl$_2$/MeOH/NH$_4$OH) then crystallized from acetonitrile to yield 1-{[4-amino-2-(ethoxymethyl)-1H-imidazo[4,5-c]quinolin-1-yl]methyl}cyclohexanol as pale orange crystals that were dried under high vacuum (0.32 g, 16% over two steps), mp 186-188° C. $^1$H NMR (300 MHz, CDCl$_3$) δ 8.15 (dm, J=8.4 Hz, 1H), 7.81 (dm, J=8.4 Hz, 1H), 7.52 (m, 1H), 7.32 (m, 1H), 5.38 (br s, 2H), 4.90 (br s, 2H), 4.74 (br s, 2H), 3.66 (q, J=7.0 Hz, 2H), 3.00 (s, 1H), 1.71-1.52 (m, 10), 1.25 (t, J=7.0 Hz, 3H). MS (APCI) m/z 355 (M+H$^+$). Anal. calcd for C$_{20}$H$_{26}$O$_2$N$_4$: C, 67.77; H, 7.39; N, 15.81. Found: C, 67.52; H, 7.57; N, 15.78.

Example 2

Ethyl 4-{[4-amino-2-(ethoxymethyl)-1H-imidazo[4,5-c]quinolin-1-yl]methyl}-4-hydroxypiperidine-1-carboxylate

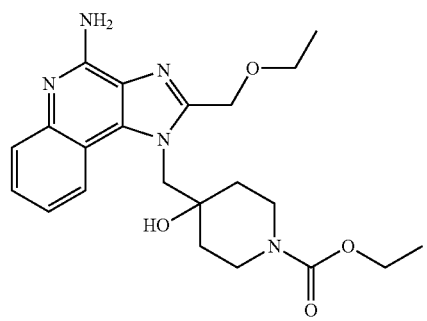 [SMILES: CCOCc1nc2c(N)nc3ccccc3c2n1CC1(O)CCN(C(=O)OCC)CC1]

Part A

To a solution of N-carbethoxy-4-piperidone (11.34 g, 66.24 mmol) in nitromethane (5.3 mL) and ethanol (2 mL) was added a solution of sodium ethoxide in ethanol (2.67 M, 1.24 mL, 3.31 mmol). The mixture was stirred for 5 min and a solution formed from which a solid precipitated. After 1.5 h, water (100 mL) was added and the solid was isolated by filtration, washed with water (100 mL), and dried under vacuum with heat to yield the product ethyl 4-hydroxy-4-(nitromethyl)piperidine-1-carboxylate as an off white solid, 9.58 g (62%).

Part B

A mixture of ethyl 4-hydroxy-4-(nitromethyl)piperidine-1-carboxylate (5.2 g, 22.4 mmol) and 20% palladium hydroxide on carbon (0.50 g) in ethanol (190 mL) was hydrogenated at 35 psi (2.4×10$^5$ Pa) on a Parr apparatus for 5 h. The mixture was filtered through CELITE filter agent and the filtrate was concentrated. By $^1$H NMR analysis, the reaction was incomplete and the crude material was subjected to the reaction conditions again with fresh 20% palladium hydroxide on carbon (0.50 g) for another 24 h. The mixture was filtered through CELITE filter agent and the filtrate was concentrated to provide ethyl 4-(aminomethyl)-4-hydroxypiperidine-1-carboxylate, which was concentrated from chloroform to remove residual ethanol before using in the next reaction.

Part C

To a solution of ethyl 4-(aminomethyl)-4-hydroxypiperidine-1-carboxylate (22.4 mmol, prepared as described above) in dichloromethane (90 mL) was added triethylamine (3.12 mL, 22.4 mmol) and 4-chloro-3-nitroquinoline (3.71 g, 17.8 mmol). The mixture was sonicated and more dichloromethane (10 mL) was added in order to dissolve the 4-chloro-3-nitroquinoline. The solution was allowed to stand at rt for 18 h, then was poured into a separatory funnel and washed with 1 M NaOH (25 mL), water (2×30 mL), and brine (30 mL). The organic layer was dried over MgSO$_4$, filtered, and concentrated to yield a yellow foam that was crystallized from isopropanol. The solid was isolated by filtration and dried to afford ethyl 4-hydroxy-4-{[(3-nitroquinolin-4-yl)amino]methyl}piperidine-1-carboxylate as yellow crystals (4.53 g, 54%).

Part D

A mixture of ethyl 4-hydroxy-4-{[(3-nitroquinolin-4-yl)amino]methyl}piperidine-1-carboxylate (4.53 g, 12.1 mmol) and 5% platinum on carbon (0.50 g) in ethanol was hydrogenated on a Parr apparatus at 40 psi (2.8×10⁵ Pa) for 2.5 h. The mixture was filtered through CELITE filter agent and the filtrate was concentrated. The residue was concentrated twice from toluene and once from chloroform to remove the ethanol, then was dissolved in dichloromethane (100 mL). To the solution at 0° C. was added triethylamine (1.86 mL, 13.3 mmol) and ethoxyacetyl chloride (88%, 1.77 g, 12.7 mmol). After 1 h at rt, the solution was concentrated to a yellow foam and ethanol (120 mL) and triethylamine (6 mL) were added. The resulting solution was heated at reflux for 16 h and then concentrated in vacuo. The residue was partitioned between dichloromethane and water. The organic layer was washed twice with brine, dried over MgSO$_4$, filtered, and concentrated to a crude yellow oil. The oil was purified by flash chromatography (silica gel, gradient elution with 2-7% methanol/dichloromethane) to provide ethyl 4-{[2-(ethoxymethyl)-1H-imidazo[4,5-c]quinolin-1-yl]methyl}-4-hydroxypiperidine-1-carboxylate as a yellow foam (3.04 g, 61%).

Part E

To a solution of ethyl 4-{[2-(ethoxymethyl)-1H-imidazo[4,5-c]quinolin-1-yl]methyl}-4-hydroxypiperidine-1-carboxylate (2.43 g, 5.90 mmol) in dichloromethane (40 mL) at rt was added m-CPBA (55%, 1.85 g, 5.90 mmol). After 1 h, concentrated ammonium hydroxide (40 mL) was added, followed by TsCl (1.18 g, 6.20). The reaction was stirred rapidly overnight. Water (40 mL) was added and the mixture was extracted three times with dichloromethane. The combined organic phases were washed with brine and dried over MgSO$_4$, filtered, and concentrated. The crude product was purified by flash chromatography (silica gel, 4% methanol/dichloromethane with 0.1% conc. NH$_4$OH). The appropriate fractions were concentrated to afford a yellow oil that was concentrated twice from toluene to yield the product as a yellow foam, which crystallized from acetonitrile. The fine off-white crystals were dried under vacuum at 65° C. to yield 0.71 g (28%) of ethyl 4-{[4-amino-2-(ethoxymethyl)-1H-imidazo[4,5-c]quinolin-1-yl]methyl}-4-hydroxypiperidine-1-carboxylate, mp 165-167° C. ¹H NMR (CDCl$_3$, 300 MHz) δ 8.03 (dd, J=8.3, 0.8 Hz, 1H), 7.80 (dm, J=8.3 Hz, 1H), 7.52 (m, 1H), 7.32 (m, 1H), 5.42 (br s, 2H), 4.84 (s, 2H), 4.74 (br s, 2H), 4.10 (q, J=7.1 Hz, 2H), 4.00 (br s, 3H), 3.71 (q, J=7.0 Hz, 2H), 3.08 (m, 2H), 1.85-1.30 (m, 4H), 1.26 (t, J=7.0 Hz, 3H), 1.22 (t, J=7.2 Hz, 3H); MS (APCI) m/z 428 (M+H⁺); Anal. calcd for C$_{22}$H$_{29}$N$_5$O$_4$: C, 61.81; H, 6.84; N, 16.38. Found: C, 61.77; H, 6.99; N, 16.44.

Example 3

1-{[4-Amino-2-(ethoxymethyl)-1H-imidazo[4,5-c]quinolin-1-yl]methyl}cyclopentanol

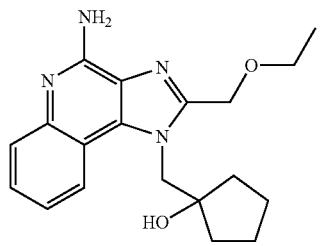 [SMILES: CCOCc1nc2c(N)nc3ccccc3c2n1CC1(O)CCCC1]

Part A

To a solution of cyclopentanone (40.0 mL, 452 mmol) in nitromethane (36 mL) and ethanol (14 mL) was added a solution of sodium ethoxide in ethanol (2.67 M, 8.5 mL, 23 mmol). The solution was stirred for 5 d at rt. Water (400 mL) was added and the mixture was extracted with ethyl acetate (2×350 mL). The combined organic extracts were washed with water (2×200) and brine (200 mL), dried over MgSO$_4$, filtered, and concentrated. The starting materials and solvent were removed from the product by distillation under reduced pressure to yield 1-(nitromethyl)cyclopentanol as a yellow liquid, 8.3 g (13%).

Part B

A mixture of 1-(nitromethyl)cyclopentanol (8.3 g, 57.2 mmol) and 20% palladium hydroxide on carbon (0.6 g) in ethanol (150 mL) was hydrogenated at 35 psi (2.4×10⁵ Pa) on a Parr apparatus for 1 d. After workup, the reaction was not complete and was subjected to the reaction conditions again for 8 d with fresh catalyst. The mixture was filtered through CELITE filter agent and the filtrate was concentrated to yield an oil that contained a 13:1 ratio of the desired amine product, 1-(aminomethyl)cyclopentanol, to the corresponding hydroxylamine. The oil was concentrated from toluene to remove the ethanol and used in the next experiment without further purification.

Part C

To a solution of 1-(aminomethyl)cyclopentanol (approximately 55.2 mmol, prepared as described above) in dichloromethane (280 mL) was added triethylamine (7.76 mL, 55.7 mmol) and 4-chloro-3-nitroquinoline (9.22 g, 44.3 mmol). The mixture was allowed to stand at rt over the weekend. A solid formed that was isolated by filtration. Two more crops of solid were isolated from the mother liquor. The yellow solid was stirred in water and filtered. The solid was washed with water multiple times and was dried under vacuum with heat to give 1-{[(3-nitroquinolin-4-yl)amino]methyl}cyclopentanol as yellow crystals (8.29 g, 52%).

Part D

A mixture of 1-{[(3-nitroquinolin-4-yl)amino]methyl}cyclopentanol (8.26 g, 28.8 mmol) and 5% platinum on carbon (0.9 g) in ethanol (200 mL) was hydrogenated on a Parr apparatus overnight. The mixture was filtered through CELITE filter agent and the filtrate was concentrated. The product 1-{[(3-aminoquinolin-4-yl)amino]methyl}-1-cyclopentanol was concentrated from toluene and dichloromethane 1-{[(3-aminoquinolin-4-yl)amino]methyl}cyclopentanol to remove ethanol, then used immediately in the next step.

Part E

To a solution of 1-{[(3-aminoquinolin-4-yl)amino]methyl}cyclopentanol (approximately 28.8 mmol, prepared as described above) in dichloromethane (200 mL) at 0° C. was added triethylamine (4.41 mL, 31.6 mmol) and ethoxyacetyl chloride (88%, 3.96 g, 30.2 mmol). After 3 h at rt, the solution was concentrated and ethanol (260 mL) and triethylamine (14 mL) were added. The resulting solution was heated at reflux for 18 h and then concentrated in vacuo. The residue was partitioned between dichloromethane and water. The organic layer was washed with brine twice and dried over MgSO$_4$, filtered, and concentrated to an oil that formed a white solid when acetonitrile was added. The mixture was sonicated briefly and filtered. The white powder was dried under vacuum to provide pure 1-{[2-(ethoxymethyl)-1H-imidazo[4,5-c]quinolin-1-yl]methyl}cyclopentanol (4.55 g, 49% for three steps).

Part F

To a solution of 1-{[2-(ethoxymethyl)-1H-imidazo[4,5-c]quinolin-1-yl]methyl}cyclopentanol (3.00 g, 9.22 mmol) in dichloromethane (60 mL) at rt was added m-CPBA (2.89 g, 9.22 mmol). After 1 h, concentrated ammonium hydroxide (60 mL) was added and the mixture was cooled in an ice bath. To the mixture was added TsCl (1.85 g, 9.68 mmol). The reaction was stirred rapidly overnight at rt. Additional TsCl (0.21 g) was added in the morning and the mixture was stirred 45 min. Water (75 mL) was added and the mixture was extracted with dichloromethane (3×100 mL). The combined organic phases were washed with brine and dried over MgSO$_4$, filtered, and concentrated. The resulting foam was treated with acetonitrile and a white solid formed. The solid was recrystallized from acetonitrile and dried under vacuum to yield 1-{[4-amino-2-(ethoxymethyl)-1H-imidazo[4,5-c]quinolin-1-yl]methyl}cyclopentanol as fine tan crystals (1.57 g, 50%), mp 156.5-158.0° C. $^1$H NMR (300 MHz, d$_6$-DMSO) δ 8.27 (dm, J=8.4 Hz, 1H), 7.59 (dd, J=8.4, 1.2 Hz, 1H), 7.40 (m, 1H), 7.20 (m, 1H), 6.54 (br s, 2H), 4.89 (br s, 2H), 4.82 (br s, 2H), 4.78 (s, 1H), 3.52 (q, J=7.0 Hz, 2H), 1.75-1.43 (m, 8H), 1.14 (t, J=7.0 Hz, 3H). MS (APCI) m/z 341 (M+H$^+$). Anal. calcd for C$_{19}$H$_{24}$N$_4$O$_2$: C, 67.04; H, 7.11; N, 16.46. Found: C, 67.12; H, 6.94; N, 16.36.

Example 4 tert-Butyl 4-{[4-amino-2-(ethoxymethyl)-1H-imidazo[4,5-c]quinolin-1-yl]methyl}-4-hydroxypiperidine-1-carboxylate

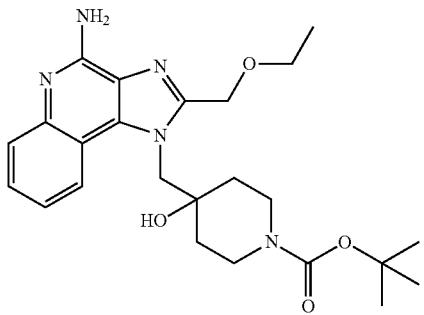 [SMILES: CCOCc1nc2c(N)nc3ccccc3c2n1CC1(O)CCN(C(=O)OC(C)(C)C)CC1]

Part A

To a solution of tert-butyl 4-oxopiperidine-1-carboxylate (52.65 g, 264 mmol) in nitromethane (21 mL) and ethanol (8 mL) was added a solution of sodium ethoxide in ethanol (2.67 M, 5.0 mL, 13.4 mmol). The mixture was stirred at rt and more ethanol (30 mL) was added. The mixture was sonicated for 15 min, stirred overnight, then sonicated again. To the mixture was added water (400 mL). The solid was isolated by filtration, washed with water (300 mL), and dried to yield tert-butyl 4-hydroxy-4-(nitromethyl)piperidine-1-carboxylate as a white solid, 67.60 g (98%).

Part B

A mixture of tert-butyl 4-hydroxy-4-(nitromethyl)piperidine-1-carboxylate (20.42 g, 78.4 mmol) and 20% palladium hydroxide on carbon (1.21 g) in ethanol (250 mL) was hydrogenated at 40 psi (2.8×10$^5$ Pa) for 3 d on a Parr apparatus. More 20% palladium hydroxide on carbon (1.0 g) was added and the hydrogenation was continued for 2 more days. The mixture was filtered through CELITE filter agent and the filtrate was concentrated to provide tert-butyl 4-(aminomethyl)-4-hydroxypiperidine-1-carboxylate, which was concentrated from toluene (200 mL) to remove residual ethanol before use in the next reaction.

Part C

To a solution of tert-butyl 4-(aminomethyl)-4-hydroxypiperidine-1-carboxylate (78.4 mmol, prepared as described above) in dichloromethane (300 mL) was added triethylamine (11 mL, 79 mmol) and 4-chloro-3-nitroquinoline (12.7 g, 61.2 mmol). The mixture was stirred at rt for 1 h, then heated at reflux for 1 h. The solution was transferred to a separatory funnel and extracted with water (100 mL). The organic layer was isolated and upon standing a precipitate formed. The solid was isolated by filtration and washed with dichloromethane and water and dried. Additional solid precipitated from the mother liquor and was isolated. The two yellow solids were combined and dried to yield tert-butyl 4-hydroxy-4-{[(3-nitroquinolin-4-yl)amino]methyl}piperidine-1-carboxylate (20.23 g, 82%).

Part D

The starting material tert-butyl 4-hydroxy-4-{[(3-nitroquinolin-4-yl)amino]methyl}piperidine-1-carboxylate (20.23 g, 50.3 mmol) was divided into two portions. To each portion was added ethanol (220 mL) and 5% platinum on carbon (1.1 g). Both portions were hydrogenated on a Parr apparatus at 40 psi (2.8×10$^5$ Pa) overnight. The mixtures were filtered through CELITE filter agent. The filtrates were combined and concentrated to provide the product tert-butyl 4-{[(3-aminoquinolin-4-yl)amino]methyl}-4-hydroxypiperidine-1-carboxylate as a brown oil. The product was concentrated twice from toluene and once from chloroform and used in the subsequent experiment.

Part E

To a solution of tert-butyl 4-{[(3-aminoquinolin-4-yl)amino]methyl}-4-hydroxypiperidine-1-carboxylate (50.3 mmol, prepared as described above) in dichloromethane (330 mL) at 0° C. was added triethylamine (8 mL, 57.4 mmol) followed by dropwise addition of ethoxyacetyl chloride (88%, 6.59 g, 50.3 mmol). After 3 h at rt, more triethylamine (4 mL) and acid chloride (1.70 g) were added. The solution was stirred 1 h, then concentrated in vacuo to a foam and ethanol (400 mL) and triethylamine (24 mL) were added. The resulting solution was heated at reflux for 20 h and then concentrated in vacuo. The residue was dissolved in dichloromethane (600 mL) and washed with water (2×200 mL) and brine (2×250 mL). The organic layer was dried twice over MgSO$_4$, filtered, and concentrated to an oil. The oil was purified twice by flash chromatography (silica gel, gradient elution with 3-5% methanol/dichloromethane) to provide tert-butyl 4-{[2-(ethoxymethyl)-1H-imidazo[4,5-c]quinolin-1-yl]methyl}-4-hydroxypiperidine-1-carboxylate as a yellow foam containing dichloromethane (13.13 g). Based on $^1$H NMR integration, the calculated amount of product was 12.59 g (57%).

Part F

To a solution of tert-butyl 4-{[2-(ethoxymethyl)-1H-imidazo[4,5-c]quinolin-1-yl]methyl}-4-hydroxypiperidine-1-carboxylate (96%, 10.0 g, 22.7 mmol) in dichloromethane (150 mL) at rt was added m-CPBA (55%, 7.12 g, 22.7 mmol). After 1.5 h, the mixture was cooled to 0° C. and concentrated ammonium hydroxide (150 mL) was added, followed by TsCl (4.54 g, 23.8 mmol). The reaction was stirred rapidly overnight. More TsCl (1.00 g and 0.47 g) was added as the mixture was stirred an additional 6 h. Water (200 mL) was added and the mixture was extracted with dichloromethane (3×200 mL). The combined organic phases were washed with brine (3×250 mL) and dried over MgSO$_4$, filtered, and concentrated to a foam, which was crystallized from acetonitrile twice. The fine yellow crystals were dried under vacuum to yield 1.60 g (15%) of tert-butyl 4-{[4-amino-2-(ethoxymethyl)-1H-imidazo[4,5-c]quinolin-1-yl]methyl}-4-hydroxypiperidine-1-carboxylate, mp 195-197°

C. $^1$H NMR (CDCl$_3$, 300 MHz) δ 8.04 (dm, J=8.3 Hz, 1H), 7.82 (dm, J=8.3 Hz, 1H), 7.53 (m, 1H), 7.31 (m, 1H), 5.40 (br s, 2H), 4.85 (s, 2H), 4.75 (br s, 2H), 3.93 (br s, 3H), 3.72 (q, J=7.0 Hz, 2H), 3.03 (m, 2H), 1.76 (m, 2H), 1.49-1.40 (m, 2H), 1.42 (s, 9H), 1.27 (t, J=7.0 Hz, 3H); MS (APCI) m/z 456 (M+H$^+$); Anal. calcd for C$_{24}$H$_{33}$N$_5$O$_4$: C, 63.28; H, 7.30; N, 15.37. Found: C, 63.32; H, 7.53; N, 15.39.

Example 5

4-{[4-Amino-2-(ethoxymethyl)-1H-imidazo[4,5-c]quinolin-1-yl]methyl}piperidin-4-ol dihydrochloride

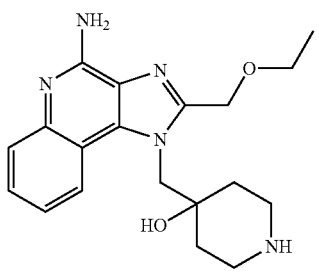 [SMILES: CCOCc1nc2c(N)nc3ccccc3c2n1CC1(O)CCNCC1]

To a solution of tert-butyl 4-{[4-amino-2-(ethoxymethyl)-1H-imidazo[4,5-c]quinolin-1-yl]methyl}-4-hydroxypiperidine-1-carboxylate (0.720 g, 1.62 mmol, prepared as described in Example 4) in ethanol (10 mL) was added 4.3 M HCl in ethanol (2 mL). The solution was heated at 65° C. for 1.5 h. After the mixture cooled to rt, a solid was isolated by filtration. The solid was washed with diethyl ether and dried under reduced pressure at 100° C. to afford 4-{[4-amino-2-(ethoxymethyl)-1H-imidazo[4,5-c]quinolin-1-yl]methyl}piperidin-4-ol dihydrochloride as a 0.5 hydrate and as a white solid, mp>260° C. MS (APCI) m/z 356 (M+H)$^+$; Anal. calcd for C$_{19}$H$_{25}$N$_5$O$_2$.2HCl.0.5H$_2$O: C, 52.18; H, 6.45; N, 16.01. Found: C, 52.32; H, 6.40; N, 15.90.

Example 6

4-{[4-Amino-2-(ethoxymethyl)-1H-imidazo[4,5-c]quinolin-1-yl]methyl}-1-(methyl sulfonyl)piperidin-4-ol

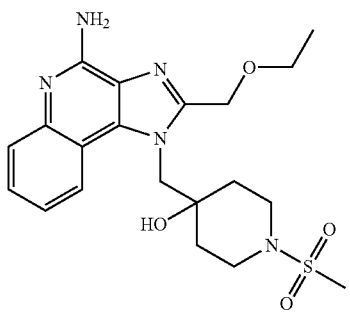 [SMILES: CCOCc1nc2c(N)nc3ccccc3c2n1CC1(O)CCN(S(C)(=O)=O)CC1]

To the 1.5 hydrate of 4-{[4-amino-2-(ethoxymethyl)-1H-imidazo[4,5-c]quinolin-1-yl]methyl}piperidin-4-ol dihydrochloride (1.00 g, 2.20 mmol, prepared in a similar manner as described in Example 5) was added chloroform (150 mL) and triethylamine (1.1 mL, 7.7 mmol). The starting material did not completely dissolve. To the mixture was added methanesulfonyl chloride (MeSO$_2$Cl, 0.19 mL, 2.42 mmol) and more triethylamine (0.3 mL). After 4 h at rt, more MeSO$_2$Cl (0.06 mL) and triethylamine (0.3 mL) were added and the mixture was stirred overnight. Pyridine (20 mL) and dimethylformamide (DMF, 20 mL) were added, followed by MeSO$_2$Cl (0.06 mL). To the mixture was added methanesulfonyl anhydride (115 mg) and the mixture was allowed to stand for 2 d. The mixture was filtered, and the filtrate was concentrated to approximately 25 mL, which was diluted with chloroform (400 mL) and extracted with 1 M NaOH (2×150 mL), water (150 mL), and brine (200 mL). The organic phase was dried over Na$_2$SO$_4$, filtered, and concentrated to a yellow oil. The crude product was purified by flash chromatography (silica gel, eluted with 1% CMA/CHCl$_3$ where CMA is a solution comprised of 80:18:2 chloroform/methanol/concentrated ammonium hydroxide) to afford 4-{[4-amino-2-(ethoxymethyl)-1H-imidazo[4,5-c]quinolin-1-yl]methyl}-1-(methylsulfonyl)piperidin-4-ol as a white solid (0.34 g, 36%) after drying at 60° C. under reduced pressure, mp 254-256° C. $^1$H NMR (300 MHz, DMSO-d$_6$) δ 8.35 (dm, J=8.4 Hz, 1H), 7.59 (dd, J=8.4, 1.4 Hz, 1H), 7.41 (m, 1H), 7.23 (m, 1H), 6.57 (br s, 2H), 5.16-4.60 (br m, 4H), 5.05 (s, 1H), 3.53 (q, J=7.0 Hz, 2H), 3.37-3.27 (br s, 2H), 2.89-2.79 (m, 2H), 2.81 (s, 3H), 1.93-1.78 (m, 2H), 1.62-1.29 (br s, 2H), 1.14 (t, J=7.0 Hz, 3H); MS (APCI) m/z 434 (M+H)$^+$; Anal. calcd for C$_{20}$H$_{27}$N$_5$O$_4$S: C, 55.41; H, 6.28; N, 16.15; S, 7.40. Found: C, 55.21; H, 6.11; N, 16.35; S, 7.37.

Example 7

2-(Ethoxymethyl)-1-[(1-methoxycyclopentyl)methyl]-1H-imidazo[4,5-c]quinolin-4-amine

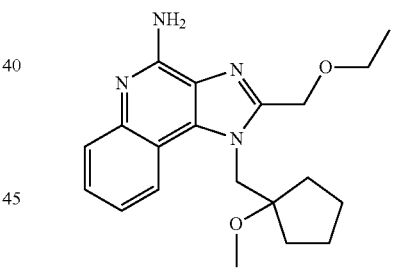

Part A

To a solution of 1-{[4-amino-2-(ethoxymethyl)-1H-imidazo[4,5-c]quinolin-1-yl]methyl}cyclopentanol (1.19 g, 3.66 mmol, prepared as described in Example 3) in THF (18 mL) at rt was added sodium hydride (60% dispersion in oil, 161 mg, 4.03 mmol). The mixture was stirred for 1 h and iodomethane (0.25 mL, 4.03 mmol) was added. The mixture was heated to 50° C. for 3 h and then was left to stand at rt overnight. More sodium hydride (60% dispersion in oil, 80 mg) and iodomethane (0.13 mL) were added. The mixture was heated for 2 h, then water was added and the mixture was extracted three times with ethyl acetate. The combined organic extracts were washed with brine and dried over Na$_2$SO$_4$, filtered and concentrated to an oil. The crude product was purified by flash chromatography (silica gel, eluted with ethyl acetate) to yield 2-(ethoxymethyl)-1-[(1-methoxycyclopentyl)methyl]-1H-imidazo[4,5-c]quinoline as a yellow oil (0.30 g, 24%).

Part B

To a solution of 2-(ethoxymethyl)-1-[(1-methoxycyclopentyl)methyl]-1H-imidazo[4,5-c]quinoline (0.30 g, 0.88 mmol) in dichloromethane at rt was added m-CPBA (278 mg, 0.88 mmol). The solution was stirred for 1.5 h and concentrated ammonium hydroxide (5.73 mL) was added and the mixture was cooled in an ice bath. To the mixture was added TsCl (176 mg, 0.924 mmol). The mixture was stirred 3 h at rt. Water (10 mL) was added and the mixture was extracted with dichloromethane (3×20 mL). The combined organics were washed twice with brine, dried over $Na_2SO_4$, filtered, and concentrated to a yellow oil. The crude product was purified by flash chromatography (silica gel, gradient elution with 1-10% CMA/CHCl$_3$). The purified product was crystallized from acetonitrile to provide 2-(ethoxymethyl)-1-[(1-methoxycyclopentyl)methyl]-1H-imidazo[4,5-c]quinolin-4-amine as off white crystals (0.122 g, 39%) after vacuum drying at 80° C., mp 148.0-150.0° C. $^1$H NMR (300 MHz, CDCl$_3$) δ 8.13 (dd, J=8.4, 1.4 Hz, 1H), 7.81 (dd, J=8.4, 1.4 Hz, 1H), 7.51 (ddd, J=8.4, 7.0, 1.4 Hz, 1H), 7.30 (ddd, J=8.4, 7.0, 1.4 Hz, 1H), 5.39 (br s, 2H), 4.94 (s, 2H), 4.92 (s, 2H), 3.57 (q, J=7.0 Hz, 2H), 3.17 (s, 3H), 1.92-1.56 (m, 8H), 1.23 (t, J=7.0 Hz, 3H); MS (APCI) m/z 355 (M+H$^+$); Anal. calcd for $C_{20}H_{26}N_4O_2$: C, 67.77; H, 7.39; N, 15.81. Found: C, 67.76; H, 7.45; N, 15.76.

Example 8

1-{[4-Amino-2-(ethoxymethyl)-1H-imidazo[4,5-c]quinolin-1-yl]methyl}cyclobutanol

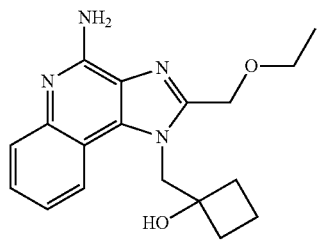 [SMILES: CCOCc1nc2c(N)nc3ccccc3c2n1CC1(O)CCC1]

Part A

To a solution of cyclobutanone (10.0 g, 143 mmol) and nitromethane (12 mL) in ethanol (10 mL) was added sodium ethoxide in ethanol (2.67 M, 2.7 mL, 7.2 mmol). The mixture was stirred for 6 d at rt. Water was added and the mixture was extracted thrice with ethyl acetate. The organic phases were combined, washed with water and brine, dried over $Na_2SO_4$, filtered, and concentrated. The volatiles were removed by distillation under vacuum to provide 1-(nitromethyl)cyclobutanol as a yellow liquid (8.51 g, 45%).

Part B

A mixture of 1-(nitromethyl)cyclobutanol (8.2 g, 62.5 mmol) and 20% palladium hydroxide on carbon (1.0 g) in ethanol (200 mL) was hydrogenated at 40 psi (2.8×10$^5$ Pa) on a Parr apparatus for 6 d. More 20% palladium hydroxide on carbon (1.2 g) was added and the mixture was hydrogenated at 40 psi (2.8×10$^5$ Pa) for an additional 5 d. The mixture was filtered through CELITE filter agent, which was rinsed with ethanol. The filtrate was concentrated to an oil that was concentrated from dichloromethane and chloroform to remove residual ethanol. 1-(Aminomethyl)cyclobutanol was obtained as an off white solid (6.15 g) that was used without further purification in the next step.

Part C

To a solution of 1-(aminomethyl)cyclobutanol (62.5 mmol) in dichloromethane (312 mL) was added triethylamine (8.71 mL, 62.5 mmol) and 4-chloro-3-nitroquinoline (13.04 g, 62.5 mmol). More triethylamine (3 mL) was added almost immediately. The reaction was stirred under $N_2$ for 10 d at rt, then was diluted with dichloromethane and washed with 1 M aqueous NaOH. A solid formed and was isolated by filtration. The organic layer was washed with water and brine, dried over $Na_2SO_4$, filtered, and concentrated to a solid that was crystallized from isopropanol. The resulting crystals were combined with the solid that was isolated from the extraction and the mixture was triturated with hot isopropanol. The solid was isolated by filtration, washed with diethyl ether, and air dried to yield 1-{[(3-nitroquinolin-4-yl)amino]methyl}cyclobutanol as yellow crystals. (12.83 g, 75%).

Part D

A mixture of 1-{[(3-nitroquinolin-4-yl)amino]methyl}cyclobutanol (6.32 g, 23.1 mmol) and 20% palladium hydroxide on carbon (0.60 g) in EtOH (100 mL) was hydrogenated overnight on a Parr apparatus at 40 psi (2.8×10$^5$ Pa). The mixture was filtered through CELITE filter agent, which was rinsed several times with EtOH, and the filtrate was concentrated to provide 1-{[(3-aminoquinolin-4-yl)amino]methyl}cyclobutanol as a pale yellow solid (5.66 g). The solid was concentrated from toluene and chloroform to remove ethanol before using directly in the next reaction.

Part E

To a mixture of 1-{[(3-aminoquinolin-4-yl)amino]methyl}cyclobutanol (23.1 mmol, prepared as described in Part D) in dichloromethane (154 mL) and triethylamine (3.54 mL, 25.4 mmol) at 0° C. was added chloroform (100 mL). The mixture was allowed to warm to rt and approximately two thirds of the starting material dissolved. To the mixture was slowly added ethoxyacetyl chloride (88%, 3.1 g, 24.3 mmol). The solution was stirred at rt for 2 h. More triethylamine (2 mL) and ethoxyacetyl chloride (88%, 1.0 g) were added. After an additional 16 h, the reaction solution was concentrated in vacuo. To the residue was added ethanol (190 mL) and triethylamine (13 mL). The resulting solution was heated at reflux for 20 h and then concentrated in vacuo to a yellow solid. The solid was partitioned between dichloromethane (400 mL) and water (100 mL). The organic layer was washed with water (100 mL) and brine (100 mL). The organic layer was dried over MgSO$_4$, filtered, and concentrated. The crude product was crystallized from acetonitrile and the crystals were isolated by filtration to provide 1-{[2-(ethoxymethyl)-1H-imidazo[4,5-c]quinolin-1-yl]methyl}cyclobutanol (4.52 g, 63%).

Part F

To a solution of 1-{[2-(ethoxymethyl)-1H-imidazo[4,5-c]quinolin-1-yl]methyl}cyclobutanol (4.05 g, 13.0 mmol) in dichloromethane (85 mL) at rt was added m-CPBA (55%, 4.08 g, 13.0 mmol). After 1 h, concentrated ammonium hydroxide (85 mL) was added, followed by TsCl (2.73 g, 14.3 mmol). The reaction was stirred rapidly for 2 d. More TsCl (0.25 g) was added and the mixture was stirred one day more. The layers were separated. Water was added to the aqueous layer, which was extracted twice with dichloromethane. The combined organic layers were washed with water and brine, dried over $Na_2SO_4$, filtered, and concentrated to a pale yellow foam. Acetonitrile was added to the foam, causing a solid to form. The solid was triturated with hot acetonitrile to yield an off white solid that was crystallized from acetonitrile/dichloromethane. Pale yellow crystals were isolated by filtration and dried under vacuum 80° C. to yield 1.81 g (43%) of 1-{[4-amino-2-(ethoxymethyl)-1H-imidazo[4,5-c]quinolin-1-yl]methyl}cyclobutanol, mp 174-175° C. $^1$H NMR (CDCl$_3$, 300 MHz) δ 8.23 (dd, J=8.3, 1.4 Hz, 1H), 7.78 (dd, J=8.4, 1.4 Hz, 1H), 7.50 (ddd, J=8.4, 7.0, 1.4 Hz, 1H), 7.31 (ddd, J=8.4, 7.0, 1.4 Hz, 1H), 5.41 (br s, 2H), 4.893 (s, 2H), 4.886 (s, 2H), 3.64 (q, J=7.0 Hz, 2H), 3.50 (br s, 1H), 2.35-2.27 (m, 2H), 2.10-1.78 (m, 4H), 1.25 (t, J=7.0 Hz, 3H); MS (APCI) m/z 327 (M+H$^+$); Anal. calcd for C$_{18}$H$_{22}$N$_4$O$_2$: C, 66.24; H, 6.79; N, 17.16. Found: C, 66.02; H, 6.87; N, 17.09.

Example 9

8-{[4-Amino-2-(ethoxymethyl)-1H-imidazo[4,5-c]quinolin-1-yl]methyl}-1,4-dioxaspiro[4.5]decan-8-ol

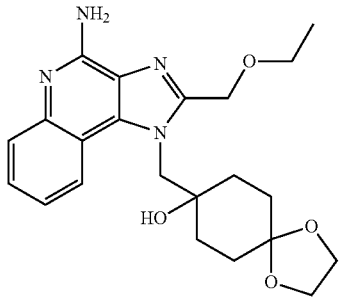 [SMILES: CCOCc1nc2c(N)nc3ccccc3c2n1CC1(O)CCC2(CC1)OCCO2]

Part A

To a solution of 1,4-cyclohexanedione mono-ethylene ketal (30.0 g, 192 mmol) and nitromethane (15.6 mL, 288 mmol) in ethanol (18 mL) was added a solution of sodium ethoxide in ethanol (2.67 M, 3.4 mL, 9.6 mmol). The solution was stirred at room temperature (rt) for 5 days (d), then was concentrated under reduced pressure to a brown oil that was partitioned between water (100 mL) and dichloromethane (100 mL). The aqueous layer was extracted with dichloromethane (3×100 mL). The organic layers were combined, dried over Na$_2$SO$_4$, filtered, and concentrated to a light brown oil. Purification by flash chromatography (silica gel, 40% ethyl acetate/hexanes) provided the product 8-(nitromethyl)-1,4-dioxaspiro[4.5]decan-8-ol as a clear oil (16.7 g, 40%) that slowly formed clear crystals overnight.

Part B

A mixture of 8-(nitromethyl)-1,4-dioxaspiro[4.5]decan-8-ol (16.0 g, 13.8 mmol) and 20% palladium hydroxide on carbon (3.2 g) in ethanol (160 mL) was hydrogenated at 50 psi (3.5×10$^5$ Pa) for 5 d on a Parr apparatus. The reaction mixture was filtered through CELITE filter agent and the filtrate was concentrated to give 8-(aminomethyl)-1,4-dioxaspiro[4.5]decan-8-ol as a clear oil (13.7 g, 99%) that solidified upon standing overnight.

Part C

To a 0° C. solution of 4-chloro-3-nitroquinoline (7.50 g, 36.0 mmol) and triethylamine (7.5 mL, 54 mmol) in dichloromethane (150 mL) was added 8-(aminomethyl)-1,4-dioxaspiro[4.5]decan-8-ol (8.10 g, 43.1 mmol). The reaction was allowed to warm to rt and stir overnight, then was concentrated under reduced pressure to yield a yellow solid. The solid was stirred in water (500 mL) and was isolated by filtration, dried under vacuum, and recrystallized from toluene (280 mL) to yield 8-{[(3-nitroquinolin-4-yl)amino]methyl}-1,4-dioxaspiro[4.5]decan-8-ol as bright yellow crystals (12.3 g, 72%).

Part D

A mixture of 8-{[(3-nitroquinolin-4-yl)amino]methyl}-1,4-dioxaspiro[4.5]decan-8-ol (12.0 g, 33.4 mmol) and 5% platinum on carbon (1.2 g) in acetonitrile (120 mL) was hydrogenated at 50 psi (3.5×10$^5$ Pa) for 4 hours (h) on a Parr apparatus. The reaction mixture was filtered through CELITE filter agent with dichloromethane and ethanol. The filtrate was concentrated to give 8-{[(3-aminoquinolin-4-yl)amino]methyl}-1,4-dioxaspiro[4.5]decan-8-ol as a orange solid (10.9 g, 99%).

Part E

A solution of ethoxyacetyl chloride (4.38 g, 35.7 mmol) in dichloromethane (50 mL) was added to a 0 OC solution of 8-{[(3-aminoquinolin-4-yl)amino]methyl}-1,4-dioxaspiro[4.5]decan-8-ol (10.7 g, 32.5 mmol) and triethylamine (4.98 mL, 35.7 mmol) in dichloromethane (250 mL). After one hour, the solution was allowed to warm to rt and stir for 2 d. More ethoxyacetyl chloride (0.15 equivalent) was added. After two hours, the solution was transferred to a separatory funnel and washed with water (200 mL). The organic layer was dried with Na$_2$SO$_4$, filtered, and concentrated under reduced pressure to yield an orange solid. The solid was dissolved in ethanol (150 mL) and triethylamine (13.6 mL, 97.4 mmol) was added. The solution was heated at reflux for 16 h. The volatiles were removed under reduced pressure to yield a brown oil that was crystallized from isopropanol to yield 8-{[2-(ethoxymethyl)-1H-imidazo[4,5-c]quinolin-1-yl]methyl}-1,4-dioxaspiro[4.5]decan-8-ol as off-white crystals (2.50 g) and a second crop (1.50 g) of crystals. A third crop (4.91 g) was isolated after recrystallization of the mother liquor from ethyl acetate. A total of 8.91 g (69%) of 8-{[2-(ethoxymethyl)-1H-imidazo[4,5-c]quinolin-1-yl]methyl}-1,4-dioxaspiro[4.5]decan-8-ol was isolated.

Part F

To a solution of 8-{[2-(ethoxymethyl)-1H-imidazo[4,5-c]quinolin-1-yl]methyl}-1,4-dioxaspiro[4.5]decan-8-ol (3.0 g, 10.1 mmol) in chloroform at rt was added m-chloroperbenzoic acid (m-CPBA, 3.6 g, 12.1 mmol). After 2 h, the solution was transferred to a separatory funnel and washed with 10% Na$_2$CO$_3$ (100 mL). The aqueous layer was back-extracted with chloroform. The organic layers were combined, dried over MgSO$_4$, filtered, and concentrated under reduced pressure to an off-white solid. To the solid was added dichloromethane (30 mL) and concentrated ammonium hydroxide (10 mL). p-Toluenesulfonyl chloride (TsCl, 1.69 g, 8.85 mmol) was added over 5 minutes (min). After 3 h, the reaction mixture was diluted with water (100 mL) and extracted with dichlormethane (3×100 mL). The organic layers were combined, dried over MgSO$_4$, filtered, and concentrated under reduced pressure. The crude product was purified by flash chromatography (silica gel, 20% methanol in ethyl acetate) and was recrystallized from isopropanol (20 mL). The crystals were dissolved in methanol and concentrated under reduced pressure and dried in a vacuum oven at 80° C. to provide 8-{[4-amino-2-(ethoxymethyl)-1H-imidazo[4,5-c]quinolin-1-yl]methyl}-1,4-dioxaspiro[4.5]decan-8-ol (1.03 g, 33%) as a light tan frothy solid, mp 207-209° C. $^1$H NMR (300 MHz, CDCl$_3$) δ 8.12 (m, 1H), 7.79 (m, 1H), 7.49 (m, 1H), 7.31 (m, 1H), 5.39 (br s, 2H), 4.85 (s, 2H), 4.74 (s, 2H), 3.90 (m, 4H), 3.65 (q, J=7.0 Hz, 2H), 3.21 (br s, 1H), 2.01-1.45 (m, 8H), 1.24 (t, J=6.9 Hz, 3H); MS (APCI) m/z 413 (M+H)$^+$; Anal. Calcd for C$_{22}$H$_{28}$N$_4$O$_4$.0.25H$_2$O: C, 63.37; H, 6.89; N, 13.44. Found: C, 63.32; H, 6.85; N, 13.41.

Example 10

4-{[4-Amino-2-(ethoxymethyl)-1H-imidazo[4,5-c]quinolin-1-yl]methyl}tetrahydro-2H-pyran-4-ol

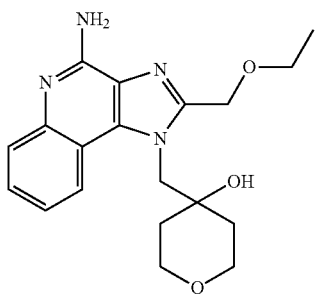

Part A

A solution of tetrahydro-4H-pyran-4-one (45.0 g, 449 mmol) and nitromethane (36.5 mL, 674 mmol) in ethanol (27 mL) was treated with a solution of sodium ethoxide in ethanol (2.67 M, 8.40 mL, 22.5 mmol) using the method described in Part A of Example 9. The reaction mixture was transferred to a separatory funnel and water (450 mL) was added. The mixture was extracted with ethyl acetate (3×900 mL). The organic layers were combined, dried over MgSO$_4$, filtered, and concentrated to a light brown oil. Ethyl acetate/hexanes was added and pale brown crystals formed that were isolated by filtration and dried to provide 4-(nitromethyl)tetrahydro-2H-pyran-4-ol (24.4 g, 34%).

Part B 4-(Nitromethyl)tetrahydro-2H-pyran-4-ol (23.3 g, 145 mmol) was hydrogenated according to the method described in Part B of Example 9 to provide 4-(aminomethyl)tetrahydro-2H-pyran-4-ol as a clear oil (19.0 g, 100%).

Part C

4-Chloro-3-nitroquinoline (12.0 g, 57.5 mmol) and was reacted with 4-(aminomethyl)tetrahydro-2H-pyran-4-ol (11.3 g, 86.3 mmol) according to the method described in Part C of Example 9. The crude yellow solid was stirred in water (100 mL) and was isolated by filtration, dried under vacuum, and recrystallized from 1,2-dichloroethane to yield 4-{[(3-nitroquinolin-4-yl)amino]methyl}tetrahydro-2H-pyran-4-ol as bright yellow crystals (15.6 g, 90%).

Part D

A mixture of 4-{[(3-nitroquinolin-4-yl)amino]methyl}tetrahydro-2H-pyran-4-ol (9.00 g, 29.7 mmol) and 5% platinum on carbon (0.90 g) in acetonitrle (180 mL) was hydrogenated according to the method described in Part D of Example 9 to yield 4-{[(3-aminoquinolin-4-yl)amino]methyl}tetrahydro-2H-pyran-4-ol as a brown solid (7.60 g, 94%).

Part E

4-{[(3-Aminoquinolin-4-yl)amino]methyl}tetrahydro-2H-pyran-4-ol (7.50 g, 27.4 mmol) was reacted with ethoxyacetyl chloride (3.70 g, 30.1 mmol) and the resulting product was cyclized according to the method described in Part E of Example 9 to provide 4-{[2-(ethoxymethyl)-1H-imidazo[4,5-c]quinolin-1-yl]methyl}tetrahydro-2H-pyran-4-ol as pale tan crystals (7.50 g, 76%) after crystallization from ethanol.

Part F

To a solution of 4-{[2-(ethoxymethyl)-1H-imidazo[4,5-c]quinolin-1-yl]methyl}tetrahydro-2H-pyran-4-ol (3.0 g, 8.79 mmol) in chloroform (60 mL) at rt was added m-chloroperbenzoic acid (m-CPBA, 3.2 g, 10.5 mmol). After 2 h, the solution was transferred to a separatory funnel and washed with 10% Na$_2$CO$_3$ (100 mL). The aqueous layer was back-extracted with chloroform. The organic layers were combined, dried over MgSO$_4$, filtered, and concentrated under reduced pressure to yield a light orange solid. To the solid was added dichloromethane (30 mL). Trichloroacetyl isocyanate (1.05 mL, 8.79 mL) was added dropwise. After 1 h, additional trichloroacetyl isocyanate (0.3 equivalent) was added. After 1 h, the volatiles were removed under reduced pressure and the residue was dissolved in methanol (30 mL). A solution of sodium methoxide in methanol (25%, 5.0 mL) was added and the solution stirred overnight at rt and concentrated under reduced pressure. The residue was partitioned between dichloromethane (100 mL) and water (100 mL). The aqueous layer was extracted with dichlormethane (2×100 mL). The organic layers were combined, dried over MgSO$_4$, filtered, and concentrated under reduced pressure. The crude product was purified by flash chromatography (silica gel, eluted with 10% methanol/dichloromethane) to afford a clear oil that was triturated with isopropanol (50 mL) to afford white crystals. The crystals were dissolved in methanol, concentrated under reduced pressure, and dried in a vacuum oven at 80° C. to provide 4-{[4-amino-2-(ethoxymethyl)-1H-imidazo[4,5-c]quinolin-1-yl]methyl}tetrahydro-2H-pyran-4-ol (1.27 g, 41%) as a white frothy solid, mp 212-214° C. $^1$H NMR (300 MHz, DMSO-d$_6$) δ 8.33 (dd, J=8.3, 1.1 Hz, 1H), 7.60 (dd, J=8.3, 1.2 Hz, 1H), 7.40 (ddd, J=8.3, 7.0, 1.4 Hz, 1H), 7.22 (ddd, J=8.3, 7.0, 1.4 Hz, 1H), 6.37 (br s, 2H), 4.90 (br s, 2H), 4.88 (s, 1H), 4.70 (br s, 2H), 3.62-3.47 (m, 6H), 1.87-1.74 (m, 2H), 1.28 (m, 2H), 1.14 (t, J=7.0 Hz, 3H); MS (APCI) m/z 357 (M+H)$^+$; Anal. Calcd for C$_{19}$H$_{24}$N$_4$O$_3$: C, 64.03; H, 6.79; N, 15.72. Found: C, 63.75; H, 7.06; N, 15.71.

Example 11

4-[(4-Amino-2-methyl-1H-imidazo[4,5-c]quinolin-1-yl)methyl]tetrahydro-2H-pyran-4-ol

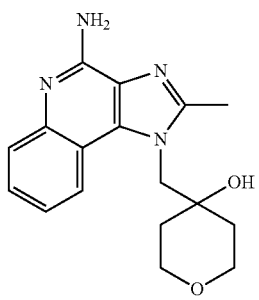 [SMILES: Cc1nc2c(N)nc3ccccc3c2n1CC1(O)CCOCC1]

Part A

A solution of 4-{[(3-aminoquinolin-4-yl)amino]methyl}tetrahydro-2H-pyran-4-ol (prepared as described in Part D of Example 10, 8.0 g, 29.3 mmol), triethylorthoacetate (5.6 mL, 30.7 mmol), and pyridine hydrochloride (1.0 g) in toluene (160 mL) was heated at reflux for 2 h, then was stirred at rt for 2 d. More triethylorthoacetate was added and the solution was heated at reflux. The solution was allowed to cool to rt and was washed with 10% aqueous Na$_2$CO$_3$ (100 mL). The aqueous layer was back-extracted with a solution of 10% methanol in dichloromethane (10×100 mL). The organic layers were combined, dried with MgSO$_4$, filtered, and concentrated under reduced pressure to afford a brown solid (8.7 g). The solid was dissolved in dichloromethane (50 mL). To the solution was added triethylamine (4.00 mL, 28.5 mmol). The solution was cooled to 0° C. and acetyl chloride (0.68 mL, 9.5 mmol) was added dropwise. After three days at rt, the reaction was concentrated under reduced pressure. The residue was dissolved in pyridine (80 mL) and pyridine hydrochloride (5.0 g) was added. The reaction was heated to reflux for 4 h and concentrated under reduced pressure. The resulting brown oil was dissolved in 10% $Na_2CO_3$ (200 mL) and was extracted overnight with chloroform in a continuous extractor. The chloroform layer was reduced to a light brown solid that was purified by flash chromatography (silica gel, eluted with 15% methanol in dichloromethane) to afford 4-[(2-methyl-1H-imidazo[4,5-c]quinolin-1-yl)methyl]tetrahydro-2H-pyran-4-ol (6.2 g, 71%) as a tan solid.

Part B

4-[(2-Methyl-1H-imidazo[4,5-c]quinolin-1-yl)methyl]tetrahydro-2H-pyran-4-ol (3.0 g, 10.1 mmol) was converted to 4-[(4-amino-2-methyl-1H-imidazo[4,5-c]quinolin-1-yl)methyl]tetrahydro-2H-pyran-4-ol (0.28 g, 9%) according to the method described in Part F of Example 10. The product 4-[(4-amino-2-methyl-1H-imidazo[4,5-c]quinolin-1-yl)methyl]tetrahydro-2H-pyran-4-ol was purified by flash chromatography (silica gel, eluted with 30% methanol/ethyl acetate) and crystallized from methanol/water to afford white crystals, mp>250° C. $^1$H NMR (300 MHz, DMSO-$d_6$) δ 8.32 (m, 1H), 7.58 (dd, J=8.3, 1.2 Hz, 1H), 7.37 (ddd, J=8.3, 7.0, 1.2 Hz, 1H), 7.20 (ddd, J=8.3, 7.0, 1.3 Hz, 1H), 6.44 (br s, 2H), 4.90 (s, 1H), 4.55 (br s, 2H), 3.65-3.46 (m, 4H), 2.66 (s, 3H), 1.88-1.74 (m, 2H), 1.40-1.24 (m, 2H); MS (APCI) m/z 313 (M+H)$^+$; Anal. Calcd for $C_{17}H_{20}N_4O_2 \cdot 0.40H_2O$: C, 63.89; H, 6.56; N, 17.53. Found: C, 63.96; H, 6.69; N, 17.61.

Example 12

1-{3-[4-Amino-2-(ethoxymethyl)-1H-imidazo[4,5-c]quinolin-1-yl]propyl}cyclohexanol

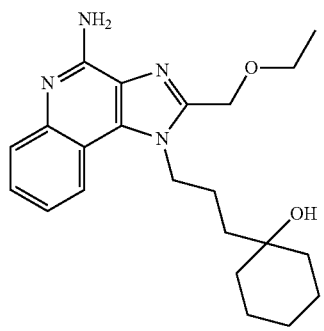 [SMILES: CCOCc1nc2c(N)nc3ccccc3c2n1CCCC1(O)CCCCC1]

Part A

A solution of allyl magnesium bromide in diethyl ether (1 M, 53 mL, 53 mmol) was added dropwise to a solution of cyclohexanone (5.00 mL, 48.2 mmol) in diethyl ether at 0° C. The cloudy white reaction mixture was allowed to stir at rt overnight. The reaction was quenched with saturated aqueous $NH_4Cl$ (100 mL) and diluted with water (20 mL) and diethyl ether (50 mL). The mixture was transferred to a separatory funnel and the layers were separated. The aqueous layer was extracted with diethyl ether (2×50 mL). The combined organic layers were washed with brine (100 mL), dried over $MgSO_4$, filtered, and concentrated to afford a 1-allylcyclohexanol as a colorless oil (6.97, 103%) that contained a small amount of diethyl ether.

Part B

Pyridine (11.7 mL, 145 mmol), 4-dimethylaminopyridine (DMAP, 0.59 g, 4.82 mmol) and tert-butyldimethylsilyl chloride (8.71 g, 57.8 mmol) were added to a solution of 1-allylcyclohexanol (48.2 mmol) in acetonitrile (120 mL). The reaction was heated at reflux overnight, then cooled to rt and concentrated to about 50 mL under reduced pressure. The solution was cooled to 0° C. and tert-butyldimethylsilyl triflate (13.3 mL, 57.8 mmol) was added. After the solution had stirred overnight at rt, additional tert-butyldimethylsilyl triflate (5.00 mL) was added and the solution was stirred for 6 h longer. The reaction was quenched with saturated aqueous sodium bicarbonate (120 mL) and extracted with dichloromethane (100 mL, then 2×75 mL). The combined organic layers were dried over $MgSO_4$, filtered, and concentrated to give a colorless oil that was purified on a on a HORIZON High-Performance Flash Chromatography (HPFC) instrument (available from Biotage, Inc, Charlottesville, Va., USA) (silica gel, gradient elution with 0-5% ethyl acetate/hexanes) to afford [(1-allylcyclohexyl)oxy](tert-butyl)dimethylsilane as a colorless oil (11.96 g, 97%).

Part C

A solution of borane in tetrahydrofuran (1 M, 15.7 mL, 15.7 mmol) was added to a solution of [(1-allylcyclohexyl)oxy](tert-butyl)dimethylsilane (8.00 g, 31.4 mmol) in tetrahydrofuran. After 2 h, water (5 mL) was added dropwise, followed by 3 M NaOH (6 mL), followed by dropwise addition of 30% aqueous hydrogen peroxide (6 mL). The mixture was stirred at rt for 1 h, then was diluted with diethyl ether (100 mL) and water (70 mL). The layers were separated and the aqueous layer was extracted with diethyl ether (2×35 mL). The combined organic layers were washed with brine (90 mL), dried over $MgSO_4$, filtered, and concentrated to yield a colorless oil that was purified using HPFC (silica gel, gradient elution with 2-30% ethyl acetate/hexanes) to afford pure 3-(1-{[tert-butyl(dimethyl)silyl]oxy}cyclohexyl)propan-1-ol (6.80 g, 79%).

Part D

Methanesulfonyl chloride (2.1 mL, 27.4 mmol) was added dropwise to a solution of 3-(1-{[tert-butyl(dimethyl)silyl]oxy}cyclohexyl)propan-1-ol (6.80 g, 24.9 mmol) and triethylamine (4.20 mL, 29.9 mmol) in dichloromethane (100 mL) at 0° C. The solution was stirred for 2 h at 0° C., then was diluted with dichloromethane (20-25 mL) and saturated aqueous sodium bicarbonate (70 mL). The layers were separated and the aqueous layer was extracted with dichloromethane (40 mL). The combined organic layers were dried over $MgSO_4$, filtered, and concentrated to afford 3-(1-{[tert-butyl(dimethyl)silyl]oxy}cyclohexyl)propyl methanesulfonate as a pale oil that was used directly in the next step.

Part E

Sodium azide (1.78 g, 27.4 mmol) was added to a solution of 3-(1-{[tert-butyl(dimethyl)silyl]oxy}cyclohexyl)propyl methanesulfonate (prepared as described in Part D, 24.9 mmol) in dimethylformamide (100 mL). The reaction mixture was stirred for 2.5 d and additional sodium azide (160 mg) was added. The mixture was stirred an additional 1 d, then was diluted with diethyl ether (250 mL) and washed with water (3×75 mL). The combined aqueous layers were back-extracted with diethyl ether (50 mL). The combined organic layers were washed with brine (100 mL), dried over $MgSO_4$, filtered, and concentrated to afford {[1-(3-azidopropyl)cyclohexyl]oxy}(tert-butyl)dimethylsilane (7.05 g, 95% over two steps) as a pale yellow oil. A mixture of the {[1-(3-azidopropyl)cyclohexyl]oxy}(tert-butyl)dimethylsilane (7.05 g, 23.7 mmol) and 5% palladium on carbon (0.71 g) in ethanol (100 mL) was hydrogenated at 30 psi ($2.1 \times 10^5$ Pa) for 4 h on a Parr apparatus. The reaction mixture was filtered through CELITE filter agent, which was rinsed afterwards with dichloromethane, and the filtrate was concentrated to give 3-(1-{[tert-butyl(dimethyl)silyl]oxy}cyclohexyl)propan-1-amine as a pale yellow oil (6.57 g, 102%) that contained a trace amount of solvent.

Part F

4-Chloro-3-nitroquinoline (0.700 g, 3.37 mmol) was added in two portions to a solution of 3-(1-{[tert-butyl(dimethyl)silyl]oxy}cyclohexyl)propan-1-amine (0.960 g, 3.54 mmol) and triethylamine (0.610 mL, 4.38 mmol) in dichloromethane (15 mL) at 0° C. After 30 min, the reaction was allowed to warm to rt and stir overnight. The mixture was diluted with dichloromethane (40 mL) and was washed with saturated aqueous sodium bicarbonate (30 mL). The aqueous layer was extracted with dichloromethane (20 mL). The combined organic layers were dried over $MgSO_4$, filtered, and concentrated to afford a yellow solid. The crude product was purified using HPFC (silica gel, gradient elution with 0-2% ethyl acetate/hexanes) to yield N-[3-(1-{[tert-butyl(dimethyl)silyl]oxy}cyclohexyl)propyl]-3-nitroquinolin-4-amine as a bright yellow solid (1.40 g, 93%).

Part G

A mixture of N-[3-(1-{[tert-butyl(dimethyl)silyl]oxy}cyclohexyl)propyl]-3-nitroquinolin-4-amine (1.40 g, 3.16 mmol) and 5% platinum on carbon (0.14 g) in ethyl acetate (15 mL) was hydrogenated at 30 psi ($2.1 \times 10^5$ Pa) for 2 h on a Parr apparatus. The reaction mixture was filtered through CELITE filter agent, which was rinsed with ethyl acetate afterwards, and the filtrate was concentrated to give $N^4$-[3-(1-{[tert-butyl(dimethyl)silyl]oxy}cyclohexyl)propyl]quinoline-3,4-diamine as an orange colored gum. The gum was dissolved in dichloromethane (15 mL) and the solution was cooled to 0° C. Ethoxyacetyl chloride (0.350 mL, 3.48 mmol) was added dropwise over 2 min. The reaction was allowed to stir at 0° C. for 1 h, then was concentrated in vacuo to yield N-(4-{[3-(1-{[tert-butyl(dimethyl)silyl]oxy}cyclohexyl)propyl]amino}quinolin-3-yl)-2-ethoxyacetamide hydrochloride as a yellow solid. The yellow solid was dissolved in ethanol (12 mL) and 2 M NaOH (2.4 mL, 4.8 mmol) was added. The reaction was heated at 60° C. for 1 h. The reaction was cooled to rt and the solvent was removed in vacuo. The residue was partitioned between dichloromethane (50 mL) and water (30 mL), and 1 M HCl was added to the mixture until the pH=7-8. The aqueous layer was extracted with dichloromethane (2×15 mL). The combined organic layers were dried over $MgSO_4$, filtered, and concentrated to afford 1-[3-(1-{[tert-butyl(dimethyl)silyl]oxy}cyclohexyl)propyl]-2-(ethoxymethyl)-1H-imidazo[4,5-c]quinoline as a brown oil (1.57 g, 96%) that contained some dichloromethane.

Part H

An aqueous solution of 3 M HCl (3.0 mL) was added to a solution of 1-[3-(1-{[tert-butyl(dimethyl)silyl]oxy}cyclohexyl)propyl]-2-(ethoxymethyl)-1H-imidazo[4,5-c]quinoline (prepared as described in part G, 3.16 mmol) in methanol (10 mL). A solid formed and additional methanol (10 mL) was added. The reaction was stirred at rt for 3 d and the solvent was removed in vacuo. The residue was dissolved in dichloromethane (40 mL) and saturated aqueous sodium bicarbonate (30 mL) was added so that the pH=8. The aqueous layer was extracted with dichloromethane (20 mL). The combined organic layers were dried over $MgSO_4$, filtered, and concentrated to yield 1-{3-[2-(ethoxymethyl)-1H-imidazo[4,5-c]quinolin-1-yl]propyl}cyclohexanol (1.14 g, 98%) as a brown gum.

Part I

To a solution of 1-({3-[2-(ethoxymethyl)-1H-imidazo[4,5-c]quinolin-1-yl]propyl}cyclohexanol (1.10 g, 2.99 mmol) in chloroform (15 mL) at rt was added m-CPBA (0.96 g, 3.89 mmol) in portions. The reaction was stirred for 1.5 h, then was cooled to 0° C. and concentrated ammonium hydroxide (5 mL) was added followed by portionwise addition of p-toluenesulfonyl chloride (0.630 g, 3.29 mmol). The mixture was stirred at 0° C. for 1 h, then was filtered. The filtrate was diluted with dichloromethane (30 mL) and saturated aqueous sodium bicarbonate (30 mL). The layers were separated and the aqueous layer was extracted with dichloromethane (20 mL). The organic layers were combined, dried over $MgSO_4$, filtered, and concentrated to afford an orange solid, which was purified by HPFC (silica gel, eluted with 0-35% CMA/chloroform). The appropriate fractions were concentrated to afford a tan solid that was crystallized from chloroform/hexanes and dried at 75° C. under vacuum to afford 1-{3-[4-amino-2-(ethoxymethyl)-1H-imidazo[4,5-c]quinolin-1-yl]propyl}cyclohexanol as white crystals (600 mg, 53%), mp 175-176° C. Anal. calcd for $C_{22}H_{30}N_4O_2$: C, 69.08; H, 7.91; N, 14.65. Found: C, 68.94; H, 8.21; N, 14.53.

Example 13

2-(Ethoxymethyl)-1-({4-[2-(methylsulfonyl)ethoxy]piperidin-4-yl}methyl)-1H-imidazo[4,5-c]quinolin-4-amine

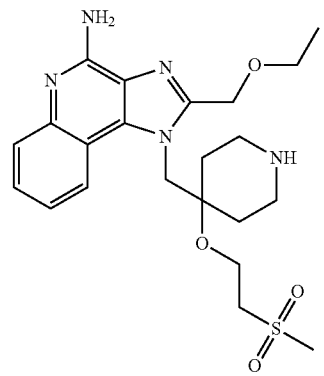 [SMILES: CCOCc1nc2c(N)nc3ccccc3c2n1CC1(OCCS(C)(=O)=O)CCNCC1]

Part A

To a solution of tert-butyl 4-{[2-(ethoxymethyl)-1H-imidazo[4,5-c]quinolin-1-yl]methyl}-4-hydroxypiperidine-1-carboxylate (prepared as described in Part E of Example 4, 1.9 g, 4.3 mmol) in tetrahydrofuran (17 mL) at rt was added solid NaH (60%, 17 mg, 0.43 mmol). After 10 min, methyl vinyl sulfone (0.92 g, 8.6 mmol) was added dropwise. After 1 h, the reaction was quenched with water (50 mL) and extracted with ethyl acetate (50 mL). The organic layer was concentrated under reduced pressure to afford a yellow oil. Purification by flash chromatography (silica gel, eluted with 5% methanol/dichloromethane) yielded tert-butyl 4-{[2-(ethoxymethyl)-1H-imidazo[4,5-c]quinolin-1-yl]methyl}-4-[2-(methylsulfonyl)ethoxy]piperidine-1-carboxylate (0.40 g, 19%).

Part B

To a solution of 4-{[2-(ethoxymethyl)-1H-imidazo[4,5-c]quinolin-1-yl]methyl}-4-[2-(methylsulfonyl)ethoxy]piperidine-1-carboxylate (0.7 g, 1.28 mmol) in chloroform (13 mL) at rt was added m-chloroperbenzoic acid (m-CPBA, 0.37 g, 1.28 mmol). After 30 min, the solution was transferred to a separatory funnel, diluted with chloroform (50 mL), and washed with saturated aqueous $Na_2CO_3$ (50 mL). The organic layer was washed with saturated aqueous $Na_2CO_3$ (50 mL) and brine (50 mL), dried over $Na_2SO_4$, filtered, and concentrated under reduced pressure to an orange colored oil. To the oil was added dichloromethane (6 mL) and concentrated ammonium hydroxide (2 mL). p-Toluenesulfonyl chloride (TsCl, 0.270 g, 1.41 mmol) was added in portions. After 10 min, the reaction mixture was partitioned between chloroform (50 mL) and saturated aqueous $Na_2CO_3$. The organic layer was washed with brine (50 mL), dried over $Na_2SO_4$, filtered, and concentrated under reduced pressure. The crude product was purified by flash chromatography (silica gel, eluted with 5% methanol/dichloromethane) to provide tert-butyl 4-{[4-amino-2-(ethoxymethyl)-1H-imidazo[4,5-c]quinolin-1-yl]methyl}-4-[2-(methylsulfonyl)ethoxy]piperidine-1-carboxylate as a white foam (0.40 g, 56%).

Part C

A solution of HCl in ethanol (4.2 M, 0.8 mL, 3.56 mmol) was added to a suspension of tert-butyl 4-{[4-amino-2-(ethoxymethyl)-1H-imidazo[4,5-c]quinolin-1-yl]methyl}-4-[2-(methylsulfonyl)ethoxy]piperidine-1-carboxylate (0.40 g, 0.71 mmol) in ethanol (4 mL) at rt. The resulting yellow solution was heated at reflux for 1.5 h. The reaction was stirred at rt for 16 h, then was concentrated under reduced pressure. The resulting solid was dissolved in water (20 mL) and 20% aqueous NaOH was added until the pH=13. The solution was extracted with dichloromethane (3×50 mL). The organic layers were combined, washed with brine (50 mL), dried over $Na_2SO_4$, filtered, and concentrated under reduced pressure to provide a solid that was crystallized from acetonitrile. The crystals were dried under vacuum at 65° C. to provide 2-(ethoxymethyl)-1-({4-[2-(methylsulfonyl)ethoxy]piperidin-4-yl}methyl)-1H-imidazo[4,5-c]quinolin-4-amine (0.25 g, 76%) as crystalline plates, mp 212-214° C. $^1$H NMR (300 MHz, DMSO-$d_6$) δ 8.26 (d, J=8.1 Hz, 1H), 7.61 (d, J=8.1 Hz, 1H), 7.44 (t, J=8.1 Hz, 1H), 7.26 (t, J=8.1 Hz, 1H), 6.61 (bs, 2H), 4.85 (s, 2H), 4.81 (s, 2H), 3.70 (t, J=5.6 Hz, 2H), 3.55 (q, J=7.5 Hz, 2H), 3.19 (t, J=5.6 Hz, 2H), 2.92 (s, 3H) 2.66-2.58 (m, 4H), 1.84 (bs, 1H), 1.70-1.66 (m, 2H), 1.48-1.38 (m, 2H), 1.16 (t, J=7.5 Hz, 3H); MS (APCI) m/z 462 (M+H)$^+$; Anal. Cacld for $C_{22}H_{31}N_5O_4S$: C, 57.25; H, 6.77: N, 15.17. Found: C, 57.48; H, 7.05; N, 15.57.

Example 14

1-({1-Acetyl-4-[2-(methyl sulfonyl)ethoxy]piperidin-4-yl}methyl)-2-(ethoxymethyl)-1H-imidazo[4,5-c]quinolin-4-amine

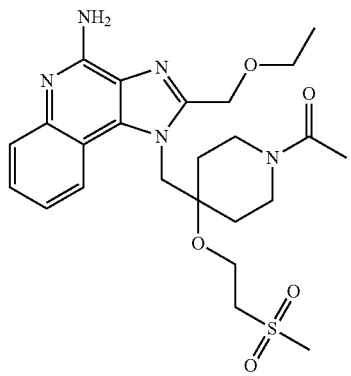 [SMILES: CCOCc1nc2c(N)nc3ccccc3c2n1CC1(OCCS(C)(=O)=O)CCN(C(C)=O)CC1]

Part A

To a solution of tert-butyl 4-{[2-(ethoxymethyl)-1H-imidazo[4,5-c]quinolin-1-yl]methyl}-4-hydroxypiperidine-1-carboxylate (prepared as described in Part E of Example 4, 14.94 g, 33.91 mmol) in ethanol (170 mL) was added a solution of HCl in ethanol (2.7 M, 31 mL, 84.7 mmol). The solution was heated at reflux for 1 h, during which time a precipitate formed. The mixture was allowed to cool to rt and the volatiles were removed under reduced pressure. To the residue was added water (400 mL) followed by 50% aqueous NaOH until the pH=10. The solution was extracted with dichloromethane (3×100 mL). The aqueous layer was treated with 50% aqueous NaOH until the pH=12, then was extracted with dichloroemethane (2×100 mL). The organic layers were combined, dried over $Na_2SO_4$, filtered, and concentrated under reduced pressure. The resulting solid was triturated with hot ethyl acetate and the remaining solid was isolated by filtration to afford 4-{[2-(ethoxymethyl)-1H-imidazo[4,5-c]quinolin-1-yl]methyl}piperidin-4-ol (7.0 g, 61%) as an off-white powder.

Part B

Acetyl chloride (0.57 mL, 8.1 mmol) was added to a suspension of 4-{[2-(ethoxymethyl)-1H-imidazo[4,5-c]quinolin-1-yl]methyl}piperidin-4-ol (2.50 g, 7.34 mmol) and triethylamine (1.50 mL, 11.0 mmol) in dichloromethane (37 mL) at rt. The resulting solution was stirred for 1 h. The solution was diluted with dichloromethane (100 mL) and washed with water (50 mL) and saturated aqueous sodium bicarbonate (50 mL). The combined aqueous layers were back-extracted with dichloromethane (50 mL). The combined organic layers were washed with brine (50 mL), dried over $Na_2SO_4$, filtered, and concentrated under reduced pressure to a brown foam. Purification by flash chromatography (silica gel, eluted with 10% methanol/dichloromethane) provided 1-acetyl-4-{[2-(ethoxymethyl)-1H-imidazo[4,5-c]quinolin-1-yl]methyl}piperidin-4-ol as a white foam (1.8 g, 64%).

Part C

1-Acetyl-4-{[2-(ethoxymethyl)-1H-imidazo[4,5-c]quinolin-1-yl]methyl}piperidin-4-ol (1.80 g, 4.68 mmol) was converted into 1-({1-acetyl-4-[2-(methylsulfonyl)ethoxy]piperidin-4-yl}methyl)-2-(ethoxymethyl)-1H-imidazo[4,5-c]quinoline according to the method described in Part A of Example 13. Purification by flash chromatography (silica gel, eluted with 10% methanol/dichloromethane) yielded 1-({1-acetyl-4-[2-(methyl sulfonyl)ethoxy]piperidin-4-yl}methyl)-2-(ethoxymethyl)-1H-imidazo[4,5-c]quinoline (0.30 g, 13%) and recovered starting material, 1-acetyl-4-{[2-(ethoxymethyl)-1H-imidazo[4,5-c]quinolin-1-yl]methyl}piperidin-4-ol (1.20 g).

Part D 1-({1-Acetyl-4-[2-(methylsulfonyl)ethoxy]piperidin-4-yl}methyl)-2-(ethoxymethyl)-1H-imidazo[4,5-c]quinoline (0.28 g, 0.57 mmol) was converted into 1-({1-acetyl-4-[2-(methyl sulfonyl)ethoxy]piperidin-4-yl}methyl)-2-(ethoxymethyl)-1H-imidazo[4,5-c]quinolin-4-amine according to the method described in Part B of Example 13. Purification by flash chromatography twice (silica gel, eluted with 10% methanol/dichloromethane) followed by crystallization from acetonitrile yielded 1-({1-acetyl-4-[2-(methyl sulfonyl)ethoxy]piperidin-4-yl}methyl)-2-(ethoxymethyl)-1H-imidazo[4,5-c]quinolin-4-amine (0.10 g, 34%) as crystalline plates, mp 208-210° C. $^1$H NMR (300 MHz, DMSO-$d_6$) δ 8.27 (d, J=8.1 Hz, 1H), 7.61 (d, J=8.1 Hz, 1H), 7.45 (t, J=8.1 Hz, 1H), 7.27 (t, J=8.1 Hz, 1H), 6.62 (bs, 2H), 4.89 (s, 2H), 4.80 (s, 2H), 4.12 (d, J=13.8 Hz, 1H), 3.74 (t, J=5.6 Hz, 2H), 3.55 (q, J=6.8 Hz, 2H), 3.31 (t, J=5.6 Hz, 2H), 3.24-3.16 (m, 2H), 2.97 (s, 3H) 2.72 (t, J=11.8 Hz, 1H), 1.90 (s, 3H), 1.83-1.76 (m, 2H), 1.60-1.44 (m, 2H), 1.14 (t, J=6.8 Hz, 3H); MS (APCI) m/z 504 (M+H)$^+$; Anal. Cacld for $C_{24}H_{33}N_5O_5S$: C, 57.24; H, 6.60: N, 13.91. Found: C, 57.08; H, 6.83; N, 13.90.

Example 15

1-{[4-Amino-2-(ethoxymethyl)-6,7,8,9-tetrahydro-1H-imidazo[4,5-c]quinolin-1-yl]methyl}cyclopentanol

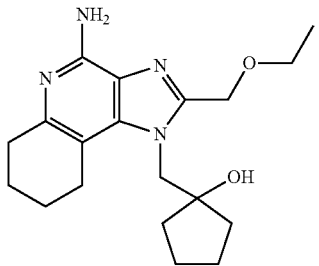 [SMILES: CCOCc1nc2c(N)nc3c(c2n1CC1(O)CCCC1)CCCC3]

A mixture of 1-{[4-amino-2-(ethoxymethyl)-1H-imidazo[4,5-c]quinolin-1-yl]methyl}cyclopentanol (prepared as described in Example 3, 0.50 g, 1.47 mmol) and platinum (IV) oxide (0.25 g) in trifluoroacetic acid (20 mL) was hydrogenated at 50 psi (3.5×10$^5$ Pa) for 5 d on a Parr apparatus. The reaction mixture was filtered through CELITE filter agent and the filtrate was treated with saturated aqueous NaOH until the pH=14, then was extracted with dichloromethane (3×100 mL). The organic layers were combined, dried over MgSO$_4$, filtered, and concentrated to an oil that was purified by flash chromatography (silica gel, 10% methanol in dichloromethane). The appropriate fractions were combined and concentrated to yield a colorless oil. The oil was dissolved in ethanol and 2.7 M HCl in ethanol (1 mL) was added and the mixture was concentrated under reduced pressure. The resulting oil was dissolved in water and Na$_2$CO$_3$ was added until the pH=12. A gummy white solid formed and the mixture was heated at 60° C. for 20 min until a free flowing precipitate formed. The mixture was allowed to cool to rt and the precipitate was isolated by filtration and dried in a vacuum oven at 80° C. to provide 1-{[4-amino-2-(ethoxymethyl)-6,7,8,9-tetrahydro-1H-imidazo[4,5-c]quinolin-1-yl]methyl}cyclopentanol as a white solid, mp 171-173° C. $^1$H NMR (300 MHz, DMSO-$d_6$) δ 5.78 (br s, 2H), 4.77 (br s, 2H), 4.66 (s, 1H), 4.45 (br s, 2H), 3.46 (q, J=7.0 Hz, 2H), 2.95 (m, 2H), 2.66 (m, 2H), 1.82-1.36 (m, 12H), 1.11 (t, J=7.0 Hz, 3H); MS (ESI) m/z 345 (M+H)$^+$; Anal. Calcd for $C_{19}H_{28}N_4O_2 \cdot 0.2H_2O$: C, 65.57; H, 8.22; N, 16.10. Found: C, 65.78; H, 8.27; N, 15.70.

Examples 16-53

A mixture (50 mL) of the 1.5 hydrate of the dihydrochloride salt of 4-[(4-amino-2-ethoxymethyl-1H-imidazo[4,5-c]quinolin-1-yl)methyl]-4-hydroxypiperidine (2.26 g, 5 mmol, prepared in a similar manner as described in Example 5) and anhydrous pyridine was heated until a solution formed. The solution was allowed to cool and aliquots (1 mL, 0.1 mmol) were transferred to 50 test tubes. Appropriate amounts of the reagents (1.1 equivalents) listed below were added to the solutions in the test tubes. The test tubes were shaken overnight. The solvent was removed from the test tubes by vacuum centrifugation.

The compounds were purified by preparative high performance liquid chromatography (prep HPLC) using a Waters Fraction Lynx automated purification system. The prep HPLC fractions were analyzed using a Micromass LC/TOF-MS, and the appropriate fractions were centrifuge evaporated to provide the trifluoroacetate salt of the desired compound. Column: Zorbax BonusRP, 21.2×50 millimeters (mm), 5 micron particle size; non-linear gradient elution from 5-95% B where A is 0.05% trifluoroacetic acid/water and B is 0.05% trifluoroacetic acid/acetonitrile; fraction collection by mass-selective triggering. The table below shows the reagent used for each example, the structure of the resulting compound, and the observed accurate mass for the isolated trifluoroacetate salt.

| Example | Reagent | R | Measured Mass (M + H) |
|---|---|---|---|
| 16 | Acetyl chloride | -C(=O)CH$_3$ | 398.2201 |
| 17 | Methyl chloroformate | -C(=O)OCH$_3$ | 414.2140 |

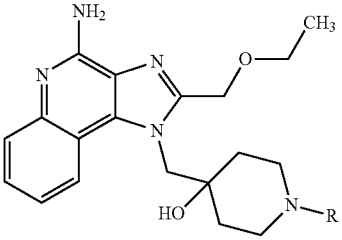

| Example | Reagent | R | Measured Mass (M + H) |
|---|---|---|---|
| 18 | Cyclopropanecarbonyl chloride | 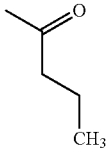 | 424.2343 |
| 19 | Butyryl chloride |  | 426.2506 |
| 20 | Cyclobutanecarbonyl chloride | 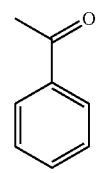 | 438.2492 |
| 21 | Benzoyl chloride | 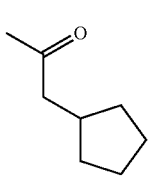 | 460.2353 |
| 22 | Cyclopentylacetyl chloride | 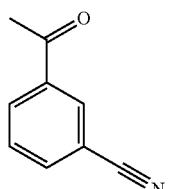 | 466.2838 |
| 23 | 3-Cyanobenzoyl chloride | 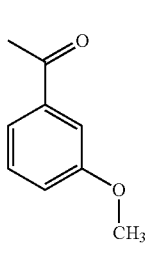 | 485.2313 |
| 24 | 3-Methoxybenzoyl chloride | 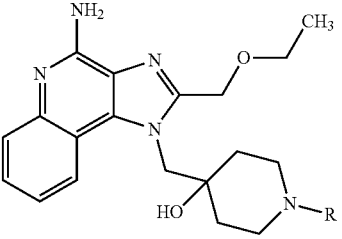 | 490.2451 |
| 25 | 3-Chlorobenzoyl chloride | 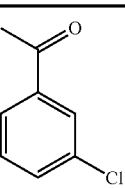 | 494.1923 |
| 26 | Nicotinoyl chloride hydrochloride | 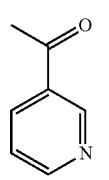 | 461.2328 |
| 27 | trans-2-Phenyl-1-cyclopropanecarbonyl chloride | 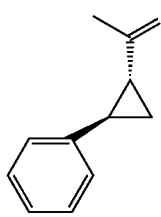 | 500.2654 |
| 28 | 4-Acetamidobenzoyl chloride | 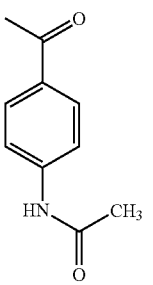 | 517.2612 |
| 29 | Methanesulfonyl chloride | 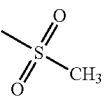 | 434.1852 |
| 30 | Ethanesulfonyl chloride | 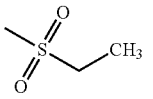 | 448.2020 |
| 31 | 1-Propanesulfonyl chloride | 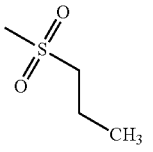 | 462.2150 |

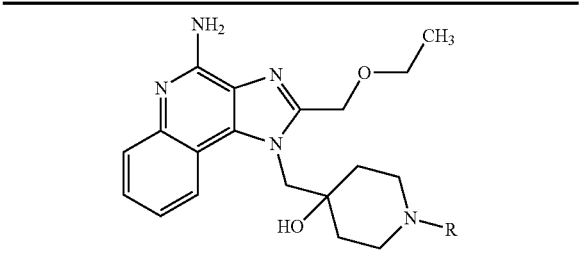

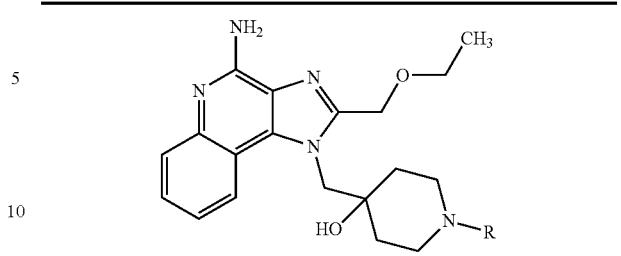

| Example | Reagent | R | Measured Mass (M + H) |
|---|---|---|---|
| 32 | Benzenesulfonyl chloride | -SO2-C6H5 | 496.2027 |
| 33 | 1-Methylimidazole-4-sulphonyl chloride | -SO2-(1-methylimidazol-4-yl) | 500.2097 |
| 34 | 2-Fluorobenzenesulfonyl chloride | -SO2-(2-F-C6H4) | 514.1899 |
| 35 | 3-Fluorobenzenesulfonyl chloride | -SO2-(3-F-C6H4) | 514.1904 |
| 36 | 4-Fluorobenzenesulfonyl chloride | -SO2-(4-F-C6H4) | 514.1935 |
| 37 | 2-Cyanobenzenesulfonyl chloride | -SO2-(2-CN-C6H4) | 521.1967 |
| 38 | 3-Cyanobenzenesulfonyl chloride | -SO2-(3-CN-C6H4) | 521.1950 |
| 39 | 4-Cyanobenzenesulfonyl chloride | -SO2-(4-CN-C6H4) | 521.2000 |
| 40 | Methyl isocyanate | -C(O)NH-CH3 | 413.2282 |
| 41 | Ethyl isocyanate | -C(O)NH-CH2CH3 | 427.2455 |
| 42 | Isopropyl isocyanate | -C(O)NH-CH(CH3)2 | 441.2593 |
| 43 | Isopropyl isothiocyante | -C(S)NH-CH(CH3)2 | 457.2386 |
| 44 | Phenyl isocyanate | -C(O)NH-C6H5 | 475.2425 |
| 45 | Cyclohexyl isocyanate | -C(O)NH-C6H11 | 481.2922 |
| 46 | Benzyl isocyanate | -C(O)NH-CH2-C6H5 | 489.2624 |

Example 54

N-(1-{[4-Amino-2-(ethoxymethyl)-1H-imidazo[4,5-c]quinolin-1-yl]methyl}cyclohexyl)acetamide

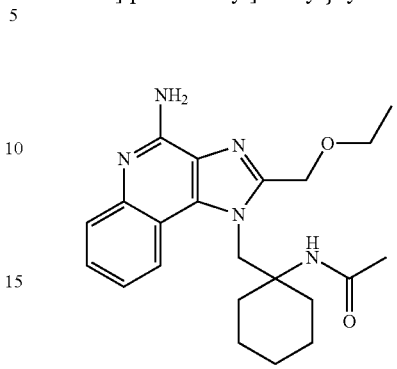

Part A

Sodium cyanide (23.7 g, 482 mmol) was added to a solution of ammonium hydroxide (28%, 122 mL, 965 mmol) and ammonium chloride (28.4 mL, 531 mmol) in water (100 mL). Cyclohexanone (50 mL, 482 mmol) was added over 5 min. The reaction was heated at 60° C. for 6 h, then was allowed to cool to rt and stir overnight. The mixture was transferred to a separatory funnel and was washed with dichloromethane (3×200 mL). The organic layers were combined, dried over MgSO$_4$, filtered, and concentrated under reduced pressure. Purification by flash chromatography (silica gel, eluted with 20% hexanes/ethyl acetate) provided 1-aminocyclohexanecarbonitrile as a clear oil (49.5 g, 83%).

Part B

A mixture of 1-aminocyclohexanecarbonitrile (48.5 g, 391 mmol) and platinum oxide (5.0 g) in 4.2 M HCl in ethanol (200 mL) and 2.7 M HCl in ethanol (300 mL) was hydrogenated at 50 psi (3.4×10$^5$ Pa) for 20 h on a Parr apparatus. The reaction mixture was filtered through CELITE filter agent and the filtrate was concentrated to yield a clear oil. The oil was triturated with isopropanol to yield a white solid that was isolated by filtration, washed with ether, and dried to provide 1-(aminomethyl)cyclohexanamine dihydrochloride (70.0 g, 89%).

Part C

To a 0° C. solution of 4-chloro-3-nitroquinoline (25.0 g, 120 mmol) and triethylamine (84 mL, 599 mmol) in dichloromethane (500 mL) was added 1-(aminomethyl)cyclohexanamine dihydrochloride (36.2 g, 180 mmol). The reaction was allowed to warm to rt and stirred for 20 h. The reaction was transferred to a separatory funnel and washed with water (200 mL). The water was back-extracted with dichloromethane (2×500 mL). The organic layers were combined, dried over Na$_2$SO$_4$, filtered, and concentrated under reduced pressure to yield N-[(1-aminocyclohexyl)methyl]-3-nitroquinolin-4-amine as a yellow solid (35.5 g, 99%).

Part D

To a 0° C. solution of N-[(1-aminocyclohexyl)methyl]-3-nitroquinolin-4-amine (38.0 g, 127 mmol) in tetrahydrofuran (250 mL) was added dropwise 2 M aqueous NaOH (64 mL, 128 mmol). A solution of di-tert-butyl dicarbonate (27.6 g, 127 mmol) in tetrahydrofuran (150 mL) was added to the reaction mixture over 60 min. The reaction was allowed to warm to rt. After 3 d, additional di-tert-butyl dicarbonate (10 g) was added to the reaction. The solvent was removed under reduced pressure and the resulting orange oil was dissolved in dichloromethane (1 L) and washed with water (3×500 mL). The combined aqueous layers were back-extracted with dichloromethane (500 mL). The organic layers were combined, dried over MgSO$_4$, filtered, and concentrated under reduced pressure to yield an orange oil. Purification by flash chromatography (silica gel, eluted with 30% ethyl acetate/hexanes) provided tert-butyl 1-{[(3-nitroquinolin-4-yl)amino]methyl}cyclohexylcarbamate as a yellow solid (29.8 g, 59%).

Part E

A mixture of tert-butyl 1-{[(3-nitroquinolin-4-yl)amino]methyl}cyclohexylcarbamate (29.5 g, 73.7 mmol) and 5% platinum on carbon (0.30 g) in toluene (300 mL) was hydrogenated at 50 psi (3.5×10$^5$ Pa) for 4 hours (h) on a Parr apparatus. The reaction mixture was diluted with ethanol (200 mL) and was filtered through CELITE filter agent. The filtrate was concentrated to give tert-butyl 1-{[(3-aminoquinolin-4-yl)amino]methyl}cyclohexylcarbamate as a brown solid (27.3 g, 100%).

Part F

Ethoxyacetyl chloride (9.00 g, 73.4 mmol) was reacted with tert-butyl 1-{[(3-aminoquinolin-4-yl)amino]methyl}cyclohexylcarbamate (27.2 g, 73.4 mmol) according to the method described in Part E of Example 9 and the resulting product was treated according to the method described in Part E of Example 9. After the solvent was removed to yield an oil, the oil was dissolved in ethanol (300 mL) and water (30 mL). Sodium hydroxide (4.3 g, 108 mmol) was added and the solution was heated at reflux for 6 h. The volatiles were removed under reduced pressure and the resulting brown oil was partitioned between dichloromethane (500 mL) and water. The organic layer was dried over Na$_2$SO$_4$, filtered, and concentrated under reduced pressure to yield a brown oil. Purification by flash chromatography (silica gel, 30% ethyl acetate/hexanes) provided tert-butyl 1-{[2-(ethoxymethyl)-1H-imidazo[4,5-c]quinolin-1-yl]methyl}cyclohexylcarbamate as a brown solid (11.9 g, 38%).

Part G

To a solution of tert-butyl 1-{[2-(ethoxymethyl)-1H-imidazo[4,5-c]quinolin-1-yl]methyl}cyclohexylcarbamate (24.6 g, 56.1 mmol) in ethanol (100 mL) was added 2.7 M HCl in ethanol (150 mL). The solution was heated at 65° C. for 4 h, the was allowed to cool to rt overnight. A light brown precipitate was isolated by filtration and washed with ethanol. The precipitate was dissolved in water (100 mL) and NaOH was added until the pH=14. The mixture was extracted with dichloromethane (3×200 mL). The organic layers were combined, dried over Na$_2$SO$_4$, filtered, and concentrated to an oil that was dissolved in ethanol (100 mL). To the ethanol solution was added 2.7 M HCl in ethanol (18.7 mL). A pale tan solid crashed out of solution and was isolated by filtration and dried. The solid was dissolved in water (100 mL) and NaOH was added until the pH=14. The mixture was extracted with dichloromethane (3×200 mL). The organic layers were combined, dried over Na$_2$SO$_4$, filtered, and concentrated to yield 1-{[2-(ethoxymethyl)-1H-imidazo[4,5-c]quinolin-1-yl]methyl}cyclohexanamine as a light yellow oil (15.1 g, 79%).

Part H

Acetyl chloride (0.036 mL, 0.50 mmol) was added to a 0 OC solution of 1-{[2-(ethoxymethyl)-1H-imidazo[4,5-c]quinolin-1-yl]methyl}cyclohexanamine (0.17 g, 0.50 mmol) and triethylamine (0.11 mL, 0.75 mmol) in dichloromethane (5 mL). The solution was stirred at 0 C for 2 h, then at rt for 1 h. The reaction was repeated on a larger scale with 1-{[2-(ethoxymethyl)-1H-imidazo[4,5-c]quinolin-1-yl]methyl}cyclohexanamine (2.00 g, 5.91 mmol). The reactions were combined and washed with water (100 mL). The organic phase was dried over Na$_2$SO$_4$, filtered, and concentrated under reduced pressure to yield a light yellow oil. Purification by flash chromatography (silica gel, 15% methanol/ethyl acetate) afforded N-(1-{[2-(ethoxymethyl)-1H-imidazo[4,5-c]quinolin-1-yl]methyl}cyclohexyl)acetamide as a white oil (2.20 g, 90%).

Part I

N-(1-{[2-(Ethoxymethyl)-1H-imidazo[4,5-c]quinolin-1-yl]methyl}cyclohexyl)acetamide (2.0 g, 5.26 mmol) was converted to N-(1-{[4-amino-2-(ethoxymethyl)-1H-imidazo[4,5-c]quinolin-1-yl]methyl}cyclohexyl)acetamide following the method described in part F of Example 9. The final product was crystallized from ethyl acetate/hexanes to afford N-(1-{[4-amino-2-(ethoxymethyl)-1H-imidazo[4,5-c]quinolin-1-yl]methyl}cyclohexyl)acetamide (0.52 g, 25%) as light tan crystals, mp 178-180° C. $^1$H NMR (300 MHz, CDCl$_3$) δ 8.29 (dd, J=8.3, 1.0 Hz, 1H), 7.80 (dd, J=8.4, 0.9 Hz, 1H), 7.51 (ddd, J=8.3, 7.0, 1.3 Hz, 1H), 7.32 (ddd, J=8.3, 6.9, 1.4 Hz, 1H), 5.46 (br s, 2H), 5.19 (br s, 1H), 5.07 (br s, 2H), 4.83 (br s, 2H), 3.62 (m, 2H), 2.39 (br s, 2H), 1.94 (s, 3H), 1.65-1.44 (m, 3H), 1.39-0.95 (m, 8H); MS (ESI) m/z 396 (M+H)$^+$; Anal. Calcd for C$_{22}$H$_{29}$N$_5$O$_2$.0.25H$_2$O: C, 66.06; H, 7.43; N, 17.51. Found: C, 65.73; H, 7.61; N, 17.48.

Example 55

N-(1-{[4-Amino-2-(ethoxymethyl)-1H-imidazo[4,5-c]quinolin-1-yl]methyl}cyclohexyl)methanesulfonamide

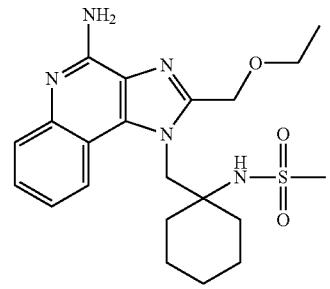 [SMILES: CCOCc1nc2c(N)nc3ccccc3c2n1CC1(NS(C)(=O)=O)CCCCC1]

Part A

Methanesulfonyl chloride (0.75 mL, 9.75 mmol) was added to a 0 OC solution of 1-{[2-(ethoxymethyl)-1H-imidazo[4,5-c]quinolin-1-yl]methyl}cyclohexanamine (2.75 g, 8.13 mmol), 4-dimethylaminopyridine (DMAP, 2.75 g) and pyridine (11 mL) in dichloromethane (28 mL). The solution was stirred at 0° C. for 2 h, then at rt for 1 h. The reaction was washed with water (100 mL). The organic phase was dried over Na$_2$SO$_4$, filtered, and concentrated under reduced pressure to yield a light yellow oil. Purification by flash chromatography (silica gel, 20% methanol/ethyl acetate) afforded N-(1-{[2-(ethoxymethyl)-1H-imidazo[4,5-c]quinolin-1-yl]methyl}cyclohexyl)methanesulfonamide as a white solid (2.72 g, 80%).

Part B

N-(1-{[2-(Ethoxymethyl)-1H-imidazo[4,5-c]quinolin-1-yl]methyl}cyclohexyl)methanesulfonamide (2.60 g, 6.24 mmol) was converted into N-(1-{[4-amino-2-(ethoxymethyl)-1H-imidazo[4,5-c]quinolin-1-yl]methyl}cyclohexyl)methanesulfonamide using the method described in Part F of Example 10. The crude N-(1-{[4-amino-2-(ethoxymethyl)-1H-imidazo[4,5-c]quinolin-1-yl]methyl}cyclohexyl)methanesulfonamide was purified by flash chromatography twice (silica gel, eluted with 20% methanol/ethyl acetate for the first column, and 15% methanol/dichloromethane for the second column) then crystallized from acetonitrile to afford white crystals (1.3 g, 48%), mp 186-188° C. $^1$H NMR (300 MHz, DMSO-$d_6$) δ 8.39 (m, 1H), 7.61 (dd, J=8.3, 1.4 Hz, 1H), 7.42 (ddd, J=8.3, 7.0, 1.3 Hz, 1H), 7.21 (ddd, J=8.3, 7.1, 1.4 Hz, 1H), 7.03 (br s, 1H), 6.45 (br s, 2H), 5.05 (br s, 2H), 4.84 (br s, 2H), 3.56 (q, J=7.0 Hz, 2H), 3.14 (s, 3H), 2.22-2.07 (m, 2H), 1.64-1.26 (m, 5H), 1.18-1.00 (m, 2H), 1.15 (t, J=7.0 Hz, 3H), 0.90-0.69 (m, 1H); MS (APCI) m/z 432 (M+H)$^+$; Anal. Calcd for $C_{21}H_{29}N_5O_3S$: C, 58.45; H, 6.77; N, 16.23. Found: C, 58.34; H, 6.80; N, 16.19.

Example 56

N-(1-{[4-amino-2-(ethoxymethyl)-1H-imidazo[4,5-c]quinolin-1-yl]methyl}cyclohexyl)-N-isopropylurea

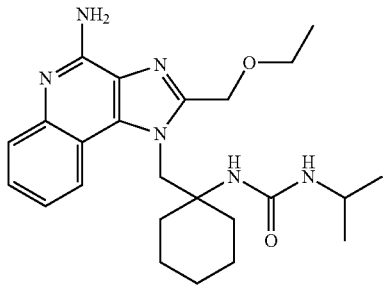 [SMILES: CCOCc1nc2c(N)nc3ccccc3c2n1CC1(NC(=O)NC(C)C)CCCCC1]

Part A

Isopropyl isocyanate (0.15 mL, 1.45 mmol) was added to a solution of 1-{[2-(ethoxymethyl)-1H-imidazo[4,5-c]quinolin-1-yl]methyl)}cyclohexanamine (0.50 g, 1.45 mmol) dichloromethane (5 mL) at rt. After 4 h, the reaction was set up on a larger scale with 1-{[2-(ethoxymethyl)-1H-imidazo[4,5-c]quinolin-1-yl]methyl)}cyclohexanamine (1.50 g, 4.43 mmol). Both reactions were allowed to stir overnight and additional isopropyl isocyanate (0.5 equivalent) was added to each reaction. After stirring another day, the reactions were combined and concentrated under reduced pressure to yield an oil. The oil was triturated with hexane and N-(1-{[2-(ethoxymethyl)-1H-imidazo[4,5-c]quinolin-1-yl]methyl}cyclohexyl)-N'-isopropylurea was isolated as a white solid (2.23 g, 89%).

Part B

N-(1-{[2-(Ethoxymethyl)-1H-imidazo[4,5-c]quinolin-1-yl]methyl}cyclohexyl)-N-isopropylurea (2.20 g, 5.19 mmol) was converted to N-(1-{[4-amino-2-(ethoxymethyl)-1H-imidazo[4,5-c]quinolin-1-yl]methyl}cyclohexyl)-N'-isopropylurea following the method described in part F of Example 9. The crude final product was purified by flash chromatography (silica gel, eluted with 20% methanol/ethyl acetate) to provide a tan oil. The oil was triturated with ethyl acetate/hexanes to provide a white powder that was isolated by filtration. The white powder was purified by flash chromatography again (silica gel, 10% methanol/dichloromethane). The resulting oil was dissolved in ethanol (20 mL) and 1 M HCl in ethanol (1 mL) was added. After thirty minutes, the volatiles were removed under reduced pressure and the residue was dissolved in water (100 mL). Solid $Na_2CO_3$ was added to the solution until a precipitate formed. The solid was isolated by filtration, washed with water, and dried in a vacuum oven at 80° C. to provide N-(1-{[4-amino-2-(ethoxymethyl)-1H-imidazo[4,5-c]quinolin-1-yl]methyl}cyclohexyl)-N-isopropylurea as a white solid (0.40 g, 18%), mp 135-160° C. $^1$H NMR (300 MHz, CDCl$_3$) δ 8.24 (m, 1H), 7.78 (m, 1H), 7.47 (m, 1H), 7.29 (m, 1H), 5.37 (br s, 2H), 5.03 (s, 2H), 4.83 (br s, 2H), 4.24 (br d, J=6.9 Hz, 1H), 4.00 (s, 1H), 3.85-3.74 (m, 1H), 3.64 (q, J=7.0 Hz, 2H), 1.72-0.96 (m, 10H), 1.23 (t, J=7.0 Hz, 3H), 1.14 (d, J=6.6 Hz, 6H); MS (APCI) m/z 439 (M+H)$^+$; Anal. Calcd for $C_{24}H_{34}N_6O_2 \cdot 0.60H_2O$: C, 64.15; H, 7.90; N, 18.70. Found: C, 64.05; H, 7.77; N, 18.63.

Example 57

1-[(4-Amino-2-propyl-1H-imidazo[4,5-c][1,5]naphthyridin-1-yl)methyl]cyclohexanol

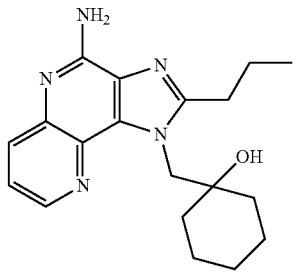 [SMILES: CCCc1nc2c(N)nc3cccnc3c2n1CC1(O)CCCCC1]

Part A

Triethylamine (8.38 mL, 60.1 mmol) was added over 10 min to a stirred mixture of 4-chloro-3-nitro-1,5-naphthyridine (6.00 g, 28.6 mmol) and 1-aminomethyl-1-cyclohexanol hydrochloride (5.00 g, 30.1 mmol) in dichloromethane (115 mL) at 0° C. The solution was allowed to warm to rt and more 1-aminomethyl-1-cyclohexanol hydrochloride (0.2 g) was added. The solution was stirred overnight and more triethylamine (0.5 mL) was added. After 30 min, the solution was partitioned between saturated aqueous sodium bicarbonate (100 mL) and chloroform (200 mL). The aqueous layer was extracted with chloroform (3×200 mL). The combined organic extracts were washed with saturated aqueous sodium bicarbonate (2×100 mL) and brine (80 mL), dried over $MgSO_4$, filtered, concentrated under reduced pressure, and dried under vacuum to afford 1-{[(3-nitro[1,5]naphthyridin-4-yl)amino]methyl}cyclohexanol as a yellow solid (8.65 g, 100%).

Part B

A mixture of 1-{[(3-nitro[1,5]naphthyridin-4-yl)amino]methyl}cyclohexanol (4.55 g, 15.1 mmol) and 5% platinum on carbon (0.50 g) in acetonitrile (100 mL) was hydrogenated at 50 psi (3.5×10$^5$ Pa) overnight on a Parr apparatus. The reaction mixture was filtered through CELITE filter agent, which was rinsed with methanol afterwards. The filtrate was concentrated to give 1-{[(3-amino[1,5]naphthyridin-4-yl)amino]methyl}cyclohexanol. The 1-{[(3-amino[1,5]naphthyridin-4-yl)amino]methyl}cyclohexanol was concentrated from chloroform several times to remove residual methanol and was used directly onto the next step.

Part C

A solution of 1-{[(3-amino[1,5]naphthyridin-4-yl)amino]methyl)}cyclohexanol (prepared as described in Part B, 15.1 mmol), trimethyl orthobutyrate (2.63 mL, 16.6 mmol), and pyridine hydrochloride (0.650 g, 5.64 mmol) in toluene (100 mL) was heated at reflux overnight. The solution was allowed to cool to rt, then was concentrated under reduced pressure. The residue was partitioned between chloroform (200 mL) and saturated aqueous sodium bicarbonate (75 mL). The aqueous layer was extracted with chloroform (2×50 mL). The combined organic layers were washed with brine (50 mL), dried over MgSO$_4$, filtered, and concentrated under reduced pressure. The resulting solid was triturated with ethyl acetate and isolated by filtration. The filtrate was concentrated and the solid was again triturated with ethyl acetate; this procedure was repeated two more times. The white solids were combined and dried under vacuum to yield 1-[(2-propyl-1H-imidazo[4,5-c][1,5]naphthyridin-1-yl)methyl]cyclohexanol (3.40 g, 70% over two steps).

Part D

To a solution of 1-[(2-propyl-1H-imidazo[4,5-c][1,5]naphthyridin-1-yl)methyl]cyclohexanol (1.43 g, 4.41 mmol) in chloroform (20 mL) at rt was added m-chloroperbenzoic acid (m-CPBA, 70%, 2.17 g, 8.82 mmol). After 1.5 h, the solution was was cooled to 0° C. and concentrated ammonium hydroxide (5 mL) was added. After 3 min, p-toluenesulfonyl chloride (TsCl, 0.920 g, 4.85 mmol) was added in portions. After 1 h, the reaction mixture was filtered and the filter cake was washed with chloroform. The filtrate was washed with saturated aqueous sodium bicarbonate (50 mL) and dried over Na$_2$SO$_4$, filtered, and concentrated under reduced pressure to yield an orange foam which was purified twice by HPFC (silica gel, gradient elution with 0-25% CMA/CHCl$_3$ where CMA is a solution comprised of 80% CHCl$_3$, 18% MeOH, and 2% conc. NH$_4$OH; followed by 0-30% CMA/CHCl$_3$). The appropriate fractions were concentrated and triturated with acetonitrile. The solid was isolated by filtration and dried at 100° C. under vacuum to yield 1-[(4-amino-2-propyl-1H-imidazo[4,5-c][1,5]naphthyridin-1-yl)methyl]cyclohexanol (567 mg, 38%) as a white powder, mp 209.0-211.0° C. Anal. Calcd for C$_{19}$H$_{25}$N$_5$O$_5$O.0.2H$_2$O C, 66.35; H, 7.47; N, 20.36; Found: C, 66.62; H, 7.34; N, 20.05.

Example 58

1-{[4-Amino-2-(ethoxymethyl)-1H-imidazo[4,5-c][1,5]naphthyridin-1-yl]methyl}cyclohexanol

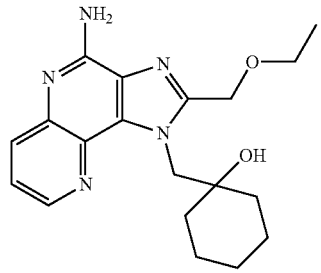 [SMILES: CCOCc1nc2c(N)nc3cccnc3c2n1CC1(O)CCCCC1]

Part A

Ethoxyacetyl chloride (1.78 g, 14.6 mmol) was added dropwise to a 0° C. solution of 1-{[(3-amino[1,5]naphthyridin-4-yl)amino]methyl}cyclohexanol (prepared as described in Part B of Example 57, 13.2 mmol) in dichloromethane (90 mL). After 1.5 h, more ethoxyacetyl chloride (0.3 mL) was added and stirring was continued for another 30 min. More ethoxyacetyl chloride (0.4 mL) was added and stirring was continued overnight. The solvent was removed under reduced pressure and the residue was dissolved in ethanol (90 mL). Sodium hydroxide (1.06 g, 26.5 mmol) was added and the reaction was heated at reflux for about 1 d. The solvent was removed under reduced pressure and the residue was partitioned between dichloromethane (200 mL) and water (100 mL). The aqueous phase was extracted with dichloromethane (2×100 mL). The combined organic layers were washed with brine (50 mL), dried over MgSO$_4$, filtered, and concentrated under reduced pressure to yield a brown foam. The foam was triturated with ethyl acetate and sonicated briefly. A white solid was isolated by filtration. The filtrate was concentrated and the trituration process was repeated two more times. The off white solids were combined and dried to yield 1-{[2-(ethoxymethyl)-1H-imidazo[4,5-c][1,5]naphthyridin-1-yl]methyl}cyclohexanol (3.40 g, 76% over three steps).

Part B

1-{[2-(Ethoxymethyl)-1H-imidazo[4,5-c][1,5]naphthyridin-1-yl]methyl}cyclohexanol (1.50 g, 4.41 mmol) was converted to 1-{[4-amino-2-(ethoxymethyl)-1H-imidazo[4,5-c]-1,5-naphthyridin-1-yl]methyl}cyclohexanol according to the method described in Part D of Example 57. The final product was purified by HPFC twice (silica gel, gradient elution with 0-30% CMA/CHCl$_3$). The appropriate fractions were concentrated and triturated with acetonitrile. The solid was isolated by filtration, recrystallized twice from dichloromethane/hexanes and dried at 100° C. under vacuum to yield 1-{[4-amino-2-(ethoxymethyl)-1H-imidazo[4,5-c][1,5]naphthyridin-1-yl]methyl}cyclohexanol (350 mg, 22%) as a white powder, mp 171.0-173.0° C. Anal. Calcd for C$_{19}$H$_{25}$N$_5$O$_2$ C, 64.20; H, 7.09; N, 19.70; Found: C, 63.91; H, 7.40; N, 19.67.

Example 59

1-[(4-Amino-6,7-dimethyl-2-propyl-1H-imidazo[4,5-c]pyridin-1-yl)methyl]cyclohexanol

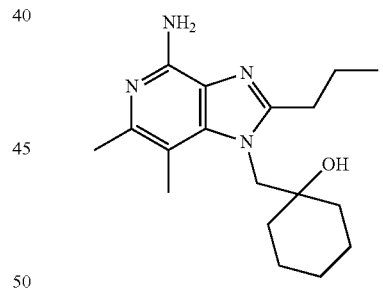

Part A

A 500 mL round bottom flask was charged with 2,4-dichloro-5,6-dimethyl-3-nitropyridine (6.00 g, 27.1 mmol), 1-aminomethyl-1-cyclohexanol hydrochloride (4.94 g, 29.8 mmol), and N,N-dimethylformamide (200 mL). The solution was cooled to 0° C. and triethylamine (8.31 mL, 59.6 mmol) was added dropwise. The solution was heated to 35° C. for 3 d. The volatiles were removed under reduced pressure and the resulting oil was partitioned between dichloromethane (300 mL) and water (50 mL). The organic layer was washed with water (50 mL) and brine (30 mL), dried over MgSO$_4$, filtered, concentrated under reduced pressure, and dried under vacuum to yield 1-{[(2-chloro-5,6-dimethyl-3-nitropyridin-4-yl)amino]methyl}cyclohexanol that was used without further manipulation in the next step.

Part B

A solution of 1-{[(2-chloro-5,6-dimethyl-3-nitropyridin-4-yl)amino]methyl}cyclohexanol (prepared as described in Part A, 27.1 mmol), dibenzylamine (15.6 mL, 81.3 mmol), and triethylamine (5.67 mL, 40.7 mmol) in toluene (100 mL) was heated at reflux for 7 d. The volatiles were removed under reduced pressure and the residue was partitioned between chloroform (300 mL) and water (100 mL). The aqueous layer was extracted with chloroform (2×75 mL). The combined organic layers were washed with brine (50 mL), dried over MgSO$_4$, filtered, and concentrated to give a semi-solid. The semi-solid was triturated with 1:2 ethyl acetate/hexanes and filtered. The filtrate was concentrated to an orange oil that was purified on a Biotage (gradient elution, 0-30% ethyl acetate/hexanes) to yield an oil contained both product and dibenzylamine. The oil was dissolved in ethyl acetate (100 mL) and 1 M HCl in diethyl ether (50 mL) and methanol (100 mL) were added. The solution was stirred for 10 minutes and the solvent was removed in vacuo. The residue was triturated with 1:2 ethyl acetate/hexanes and filtered. The filtrate was concentrated, and the resulting oil was dissolved in chloroform (300 mL), washed with saturated aqueous sodium bicarbonate (50 mL), dried over MgSO$_4$, filtered, and concentrated. The material was dissolved in ethyl acetate (400 mL) and washed with 10% aqueous citric acid (2×100 mL), saturated aqueous sodium bicarbonate (50 mL) and brine (50 mL), dried over MgSO$_4$, filtered, and concentrated in vacuo to yield 1-({[2-(dibenzylamino)-5,6-dimethyl-3-nitropyridin-4-yl]amino}methyl)cyclohexanol (10.14 g, 79% yield over two steps).

Part C

A mixture of 1-({[2-(dibenzylamino)-5,6-dimethyl-3-nitropyridin-4-yl]amino}methyl)cyclohexanol (4.00 g, 8.43 mmol) and 5% platinum on carbon (0.40 g) in ethyl acetate (84 mL) was hydrogenated at 50 psi (3.4×10$^5$ Pa) for 3 h on a Parr apparatus. The reaction mixture was filtered through CELITE filter agent, which was rinsed with ethyl acetate afterwards. The filtrate was concentrated to give 1-({[3-amino-2-(dibenzylamino)-5,6-dimethylpyridin-4-yl]amino}methyl)cyclohexanol and was used directly in the next step.

Part D 1-({[3-amino-2-(dibenzylamino)-5,6-dimethylpyridin-4-yl]amino}methyl)cyclohexanol (prepared as described in Part C, 8.43 mmol) was converted to 1-{[4-(dibenzylamino)-6,7-dimethyl-2-propyl-1H-imidazo[4,5-c]pyridin-1-yl]methyl}cyclohexanol (4.08 g, 97%) according to the method described in Part C of Example 57.

Part E

A mixture of 1-{[4-(dibenzylamino)-6,7-dimethyl-2-propyl-1H-imidazo[4,5-c]pyridin-1-yl]methyl}cyclohexanol (1.50 g, 3.02 mmol), ammonium formate (2.84 g, 45.0 mmol), and 10% palladium on carbon (1.50 g) in methanol (60 mL) and ethanol (120 mL) was heated at 85° C. for 2 h. More ammonium formate (1.00 g) was added and heating was continued of 3 h, then the reaction mixture was stirred overnight at rt. The mixture was filtered through CELITE filter agent and the filtrate was concentrated in vacuo. The crude product was purified using HPFC (gradient elution with 10-40% CMA/chloroform). The appropriate fractions were concentrated and the resulting solid was triturated with acetonitrile. A solid was isolated by filtration and dried at 100° C. under vacuum to provide 1-[(4-amino-6,7-dimethyl-2-propyl-1H-imidazo[4,5-c]pyridin-1-yl)methyl]cyclohexanol as a white powder (0.61 g, 64%), mp 214.0-216.0° C.

Anal. Calcd for C$_{18}$H$_{28}$N$_4$O C, 68.32; H, 8.92; N, 17.71; Found: C, 68.06; H, 8.65; N, 17.45.

Example 60

4-{[4-Amino-2-(2-methoxyethyl)-1H-imidazo[4,5-c]quinolin-1-yl]methyl}tetrahydro-2H-pyran-4-ol

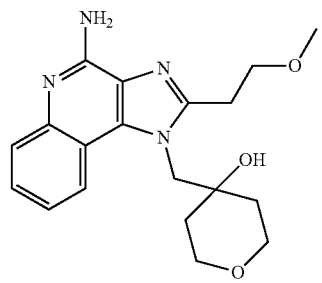 [SMILES: COCCc1nc2c(N)nc3ccccc3c2n1CC1(O)CCOCC1]

Part A

4-{[2-(2-Methoxyethyl)-1H-imidazo[4,5-c]quinolin-1-yl]methyl}tetrahydro-2H-pyran-4-ol was prepared according to the general methods of Example 10 using methoxypropionyl chloride in lieu of ethoxyacetyl chloride in Part E.

Part B

4-{[2-(2-Methoxyethyl)-1H-imidazo[4,5-c]quinolin-1-yl]methyl}tetrahydro-2H-pyran-4-ol (2.97 g) was oxidized and then aminated according to the method of Part I of Example 12 except that the amination was run at ambient temperature. The crude product was purified by HPFC eluting with a gradient of 0 to 45% CMA in chloroform to provide a yellow solid. The solid was triturated with acetonitrile, isolated by filtration, and dried in a vacuum oven at 85° C. to provide 4-{[4-amino-2-(2-methoxyethyl)-1H-imidazo[4,5-c]quinolin-1-yl]methyl}tetrahydro-2H-pyran-4-ol as a tan solid, mp 205-206° C. MS (ESI) m/z 357 (M+H)$^+$; Anal. calcd for C$_{19}$H$_{24}$N$_4$O$_3$: C, 64.03; H, 6.79; N, 15.72. Found: C, 63.93; H, 6.79; N, 15.61.

Example 61

4-{[4-Amino-2-(2-hydroxyethyl)-1H-imidazo[4,5-c]quinolin-1-yl]methyl}tetrahydro-2H-pyran-4-ol

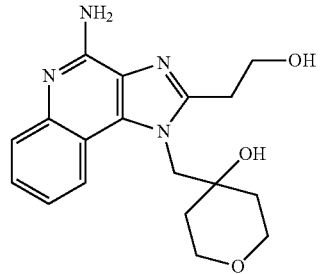 [SMILES: Nc1nc2ccccc2c2c1nc(CCO)n2CC1(O)CCOCC1]

A suspension of 4-{[4-amino-2-(2-methoxyethyl)-1H-imidazo[4,5-c]quinolin-1-yl]methyl}tetrahydro-2H-pyran-4-ol (0.95 g, 2.67 mmol) in dichloromethane (15 mL) was cooled to 0° C. Boron tribromide (8 mL, 8.00 mmol) was added and the reaction mixture was allowed to stir overnight while slowly warming to ambient temperature. The reaction mixture was concentrated. The residue was taken up in a mixture of methanol (15 mL) and 6M hydrochloric acid (10 mL) and refluxed for 2.5 hours. The reaction mixture was cooled to ambient temperature and the pH was adjusted to 8 with 2M sodium hydroxide. The mixture was extracted with chloroform (12×20 mL). The combined extracts were dried over magnesium sulfate, filtered, and then concentrated under reduced pressure to provide a yellow solid. This material purified by HPFC eluting with a gradient of 0 to 45% CMA in chloroform to provide an off white solid. The solid was triturated with acetonitrile, isolated by filtration, and dried in a vacuum oven at 140° C. to provide 0.536 g of 4-{[4-amino-2-(2-hydroxyethyl)-1H-imidazo[4,5-c]quinolin-1-yl]methyl}tetrahydro-2H-pyran-4-ol as a white solid, mp 237-238° C. MS (ESI) m/z 343 (M+H)$^+$; Anal. calcd for $C_{18}H_{22}N_4O_3$: C, 63.14; H, 6.48; N, 16.36. Found: C, 63.04; H, 6.57; N, 16.19.

Example 62

4-{[4-Amino-2-(hydroxymethyl)-1H-imidazo[4,5-c]quinolin-1-yl]methyl}tetrahydro-2H-pyran-4-ol

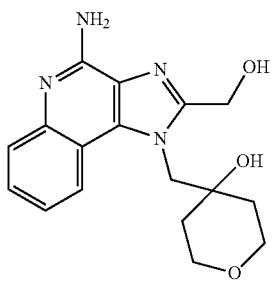 [SMILES: Nc1nc2ccccc2c2c1nc(CO)n2CC1(O)CCOCC1]

Part A

4-[(2-Chloromethyl-1H-imidazo[4,5-c]quinolin-1-yl)methyl]tetrahydro-2H-pyran-4-ol was prepared according to the general methods of Example 10 using chloroacetyl chloride in lieu of ethoxyacetyl chloride in Part E.

Part B

3-Chloroperbenzoic acid (0.46 g) was added to a solution of 4-[(2-chloromethyl-1H-imidazo[4,5-c]quinolin-1-yl)methyl]tetrahydro-2H-pyran-4-ol (0.44 g) in chloroform (8 mL) and the reaction mixture was stirred at ambient temperature for 2 hours. The reaction mixture was diluted with aqueous saturated sodium bicarbonate (30 mL) and stirred for 20 minutes. 4-[(2-chloromethyl-5-oxy-1H-imidazo[4,5-c]quinolin-1-yl)methyl]tetrahydro-2H-pyran-4-ol was isolated by filtration as a white solid.

Part C

Benzenesulfonyl chloride (0.36 mL) was added dropwise to a suspension of the material from Part B in methanol (8 mL) and ammonium hydroxide (0.44 mL). The reaction mixture was stirred at ambient temperature and then filtered to provide 4-[(4-amino-2-chloromethyl-1H-imidazo[4,5-c]quinolin-1-yl)methyl]tetrahydro-2H-pyran-4-ol hydrochloride as a white solid.

Part D

Potassium acetate (0.08 g) was added to a solution of material from Part C (0.25 g) in N,N-dimethylformamide (4 mL). The reaction mixture was stirred overnight. Additional potassium acetate (0.08 g) was added and the reaction mixture was stirred overnight. The solvent was removed under vacuum to provide 4-[(4-amino-2-hydroxymethyl-H-imidazo[4,5-c]quinolin-1-yl)methyl]tetrahydro-2H-pyran-4-ol acetate hydrochloride.

Part E

Potassium carbonate (0.36 g) was added to a solution of the material from Part D in methanol (8 mL). The reaction mixture was stirred for 1 hour and then concentrated under reduced pressure. The residue was diluted with water and then extracted with chloroform (20×10 mL). The combined extracts were dried over magnesium sulfate, filtered, and then concentrated under reduced pressure to provide a white solid. The solid was triturated with acetonitrile, isolated by filtration, and dried in a vacuum oven at 85° C. to provide 71 mg of 4-{[4-amino-2-(hydroxymethyl)-1H-imidazo[4,5-c]quinolin-1-yl]methyl}tetrahydro-2H-pyran-4-ol as a white solid, mp greater than 250° C. MS (ESI) m/z 329 (M+H)$^+$; Anal. calcd for $C_{17}H_{20}N_4O_3$: C, 62.18; H, 6.14; N, 17.06. Found: C, 61.97; H, 6.02; N, 17.00.

Example 63

4-[(4-Amino-2-butyl-1H-imidazo[4,5-c]quinolin-1-yl)methyl]tetrahydro-2H-pyran-4-ol

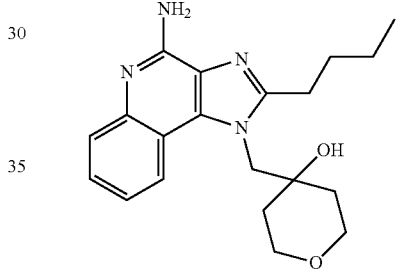

Part A

Trimethylorthovalerate (1.8 mL, 10.4 mmol) and pyridine hydrochloride (92 mg, 0.8 mmol) were added to a suspension of 4-[(3-aminoquinolin-4-ylamino)methyl]tetrahydro-pyran-4-ol (8.0 mmol) in toluene (40 mL). The reaction mixture was heated at reflux for 2.5 hours and then cooled to ambient temperature. A precipitate was isolated by filtration and dried to provide 4-[(2-butyl-1H-imidazo[4,5-c]quinolin-1-yl)methyl]tetrahydro-2H-pyran-4-ol as a white solid, mp 180-181° C. MS (ESI) m/z 340 (M+H)$^+$; Anal. calcd for $C_{20}H_{25}N_3O_2$: C, 70.77; H, 7.42; N, 12.38. Found: C, 70.58; H, 7.53; N, 12.40.

Part B

The material from Part A was oxidized and then aminated according to the method of Part I of Example 12 except that the amination was run at ambient temperature. The crude product was triturated with hot ethanol to provide 0.822 g of 4-[(4-amino-2-butyl-1H-imidazo[4,5-c]quinolin-1-yl)methyl]tetrahydro-2H-pyran-4-ol as a white solid, mp 235-236° C. MS (ESI) m/z 355 (M+H)$^+$; Anal. calcd for $C_{20}H_{26}N_4O_2$: C, 67.77; H, 7.39; N, 15.81. Found: C, 67.57; H, 7.49; N, 15.84.

Example 64

4-[(4-Amino-2-propyl-1H-imidazo[4,5-c]quinolin-1-yl)methyl]tetrahydro-2H-pyran-4-ol

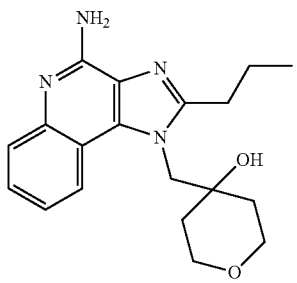 [SMILES: CCCc1nc2c(N)nc3ccccc3c2n1CC1(O)CCOCC1]

Part A

Trimethylorthobutyrate (1.9 mL, 12.0 mmol) and pyridine hydrochloride (58 mg, 0.5 mmol) were added to a suspension of 4-[(3-aminoquinolin-4-ylamino)methyl]tetrahydropyran-4-ol (10.0 mmol) in toluene (50 mL). The reaction mixture was heated at reflux for 4 hours and then concentrated under reduced pressure. The residue was triturated with acetonitrile and the filtered to provide 4-[(2-propyl-1H-imidazo[4,5-c]quinolin-1-yl)methyl]tetrahydro-2H-pyran-4-ol as a tan solid.

Part B

The material from Part A was oxidized and then aminated according to the method of Part I of Example 12 except that the amination was run at ambient temperature. The crude product was triturated with hot ethanol to provide 0.758 g of 4-[(4-amino-2-propyl-1H-imidazo[4,5-c]quinolin-1-yl)methyl]tetrahydro-2H-pyran-4-ol as a white solid, mp 231-233° C. MS (ESI) m/z 341 (M+H)$^+$; Anal. calcd for $C_{19}H_{24}N_4O_2$: C, 67.04; H, 7.11; N, 16.46. Found: C, 66.85; H, 7.39; N, 16.42.

Example 65

4-[(4-Amino-2-ethyl-1H-imidazo[4,5-c]quinolin-1-yl)methyl]tetrahydro-2H-pyran-4-ol

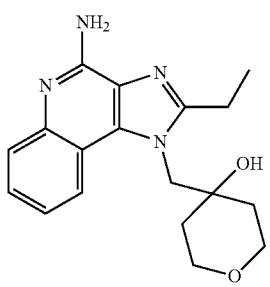 [SMILES: CCc1nc2c(N)nc3ccccc3c2n1CC1(O)CCOCC1]

Part A

Triethylorthopropionate (2.4 mL, 12.0 mmol) and pyridine hydrochloride (60 mg, 0.5 mmol) were added to a suspension of 4-[(3-aminoquinolin-4-ylamino)methyl]tetrahydropyran-4-ol (10.0 mmol) in toluene (50 mL). The reaction mixture was heated at reflux for 2.5 hours and then concentrated under reduced pressure. The residue was triturated with acetonitrile and the filtered to provide 4-[(2-ethyl-1H-imidazo[4,5-c]quinolin-1-yl)methyl]tetrahydro-2H-pyran-4-ol as a tan solid.

Part B

The material from Part A was oxidized and then aminated according to the method of Part I of Example 12 except that the amination was run at ambient temperature. The crude product was triturated with 1M sodium hydroxide, isolated by filtration, washed with water, and dried under vacuum at 85° C. to provide 1.6 g of 4-[(4-amino-2-ethyl-1H-imidazo[4,5-c]quinolin-1-yl)methyl]tetrahydro-2H-pyran-4-ol as a tan solid, mp greater than 250° C. MS (ESI) m/z 327 (M+H)$^+$; Anal. calcd for $C_{18}H_{22}N_4O_2$: C, 66.24; H, 6.79; N, 17.17. Found: C, 65.99; H, 7.08; N, 17.23.

Example 66

4-[(4-Amino-2-ethoxymethyl-1H-imidazo[4,5-c][1,5]naphthyridin-1-yl)methyl]tetrahydro-2H-pyran-4-ol

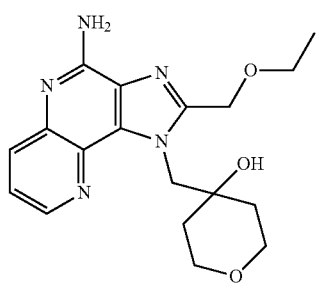 [SMILES: CCOCc1nc2c(N)nc3cccnc3c2n1CC1(O)CCOCC1]

Part A

A solution of 4-chloro-3-nitro[1,5]naphthyridine (16.6 g, 79.0 mmol) in dichloromethane (250 mL) and triethylamine (14.3 mL, 102.7 mmol) was cooled to 4° C. A solution of 4-aminomethyltetrahydropyran-4-ol (11.4 g, 86.9 mmol) in dichloromethane (70 mL) was added dropwise over a period of 30 minutes. The reaction mixture was allowed to stir at ambient temperature over the weekend and then it was concentrated under reduced pressure. The residue was stirred with water (300 mL). The resulting solid was isolated by filtration, rinsed with water, and dried in a vacuum oven at 50° C. for 4 hours to provide 22.53 g of 4-[(3-nitro[1,5]naphthyridin-4-ylamino)methyl]tetrahydropyran-4-ol.

Part B

A mixture of 4-[(3-nitro[1,5]naphthyridin-4-ylamino)methyl]tetrahydropyran-4-ol (12.2 g), 5% platinum on carbon (1.22 g), and ethyl acetate (160 mL) was placed under hydrogen pressure (40 psi, 2.8×10$^5$ Pa) for 3 hours. The reaction mixture was filtered through a layer of CELITE filter aid and the filter cake was rinsed with 1:1 ethyl acetate:methanol (150 mL). The filtrate was concentrated under reduced pressure to provide 12.66 g of 4-[(3-amino[1,5]naphthyridin-4-ylamino)methyl]tetrahydropyran-4-ol as a thick semi-solid.

Part C

Ethoxyacetyl chloride (1.1 mL, 11.0 mmol) was added dropwise over a period of 5 minutes to a chilled (0° C.) suspension of material from Part B (10.0 mmol) in dichloromethane (50 mL). The reaction mixture was allowed to warm to ambient temperature and then stirred for two hours. The reaction mixture was concentrated under reduced pressure to provide 2-ethoxy-N-{4-[(4-hydroxytetrahydropyran-4-ylmethyl)amino][1,5]napthyridin-3-yl}acetamide hydrochloride as an orange solid.

Part D

Triethylamine (4.2 mL, 30.0 mmol) was added to a solution of the material from Part C in ethanol (40 mL). The reaction mixture was heated at 60° C. overnight and then concentrated under reduced pressure. The residue was dissolved in dichloromethane (50 mL) and washed with aqueous saturated sodium bicarbonate (50 mL). The aqueous layer was back extracted with dichloromethane (2×25 mL). The combined organics were dried over magnesium sulfate, filtered, and then concentrated under reduced pressure to provide a dark yellow oil. This material was crystallized from acetonitrile to provide 2.96 g of an off white solid. A portion (375 mg) was recrystallized from acetonitrile to provide 281 mg of 4-{[2-(ethoxymethyl)-1H-imidazo[4,5-c][1,5]naphthyridin-1-yl]methyl}tetrahydro-2H-pyran-4-ol as white needles, mp 168-169° C. MS (ESI) m/z 343 (M+H)$^+$; Anal. calcd for $C_{18}H_{22}N_4O_3$: C, 63.14; H, 6.48; N, 16.36. Found: C, 63.06; H, 6.32; N, 16.28.

Part E

Material from Part D (2.92 g) was oxidized and then aminated according to the method of Part I of Example 12. The crude product was purified by HPFC eluting with a gradient of 0 to 30% CMA in chloroform to provide a tan solid. This material was recrystallized from methanol to provide 0.404 g of 4-[(4-amino-2-ethoxymethyl-1H-imidazo[4,5-c][1,5]naphthyridin-1-yl)methyl]tetrahydro-2H-pyran-4-ol as off-white needles, mp 166-167° C. MS (ESI) m/z 358 (M+H)$^+$; Anal. calcd for $C_{18}H_{23}N_5O_3$: C, 60.49; H, 6.49; N, 19.59. Found: C, 60.43; H, 6.45; N, 19.94.

Example 67

4-[(4-Amino-2-hydroxymethyl-1H-imidazo[4,5-c][1,5]naphthyridin-1-yl)methyl]tetrahydro-2H-pyran-4-ol

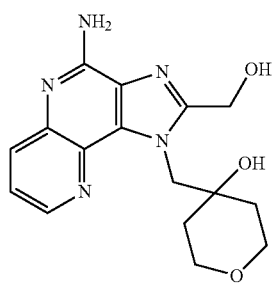 [SMILES: Nc1nc2cccnc2c2c1nc(CO)n2CC1(O)CCOCC1]

Boron tribromide (8.4 mL of 1M in dichloromethane) was added dropwise over a period of 10 minutes to a chilled (0° C.) suspension of 4-[(4-amino-2-ethoxymethyl-1H-imidazo[4,5-c]-1,5-naphthyridin-1-yl)methyl]tetrahydro-2H-pyran-4-ol (1.00 g, 2.81 mmol) in dichloromethane (15 mL). The reaction mixture was allowed to slowly warm to ambient temperature overnight, quenched with methanol (5 mL), and then concentrated under reduced pressure. The residue was dissolved in methanol (15 mL) and 6M hydrochloric acid (10 mL). The reaction mixture was heated at reflux for 6 hours, cooled to ambient temperature, neutralized with solid sodium bicarbonate and water (15 mL), and then extracted with chloroform (6×15 mL). The combined organics were dried over magnesium sulfate, filtered, and then concentrated under reduced pressure to provide 0.72 g of a tan solid. This material was purified by HPFC eluting with a gradient of 0 to 50% CMA in chloroform to provide a white solid which was dried under vacuum at 140° C. for 20 hours to provide 0.39 g of 4-[(4-amino-2-hydroxymethyl-1H-imidazo[4,5-c]-1,5-naphthyridin-1-yl)methyl]tetrahydro-2H-pyran-4-ol as off-white needles, mp greater than 250° C. MS (ESI) m/z 330 (M+H)$^+$; Anal. calcd for $C_{16}H_{19}N_5O_3$: C, 58.35; H, 5.81; N, 21.26. Found: C, 58.32; H, 5.81; N, 21.21.

Example 68

4-{[4-Amino-2-(2-hydroxyethyl)-1H-imidazo[4,5-c][1,5]naphthyridin-1-yl]methyl}tetrahydro-2H-pyran-4-ol

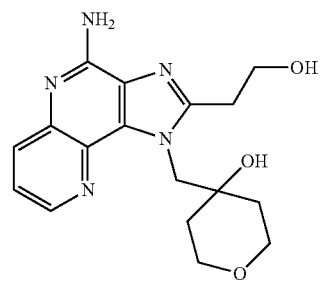 [SMILES: Nc1nc2cccnc2c2c1nc(CCO)n2CC1(O)CCOCC1]

Part A

4-{[2-(2-Methoxyethyl)-1H-imidazo[4,5-c][1,5]naphthyridin-1-yl]methyl}tetrahydro-2H-pyran-4-ol was prepared according to the method of Parts A through D of Example 66 using 3-methoxypropionyl chloride in lieu of ethoxyacetyl chloride in Part C. The product was provided as white needles, mp 156-157° C. MS (ESI) m/z 343 (M+H)$^+$; Anal. calcd for $C_{18}H_{22}N_4O_3$: C, 63.14; H, 6.48; N, 16.36. Found: C, 62.91; H, 6.52; N, 16.53.

Part B

Material from Part A (2.1 g) was oxidized and then aminated according to the method of Part I of Example 12. The crude product was purified by HPFC eluting with a gradient of 0 to 50% CMA in chloroform to provide a pale yellow oil. The oil was triturated with acetonitrile to provide 0.83 g of 4-{[4-amino-2-(2-methoxyethyl)-1H-imidazo[4,5-c][1,5]naphthyridin-1-yl]methyl}tetrahydro-2H-pyran-4-ol as a tan solid.

Part C

The ether linkage was cleaved according to the method of Example 67. The crude product was purified by HPFC eluting with a gradient of 0 to 50% CMA in chloroform to provide a white solid which was dried under vacuum at 140° C. for 20 hours to provide 0.43 g of 4-{[4-amino-2-(2-hydroxyethyl)-1H-imidazo[4,5-c][1,5]naphthyridin-1-yl]methyl}tetrahydro-2H-pyran-4-ol as off-white needles, mp 226-227° C. MS (ESI) m/z 344 (M+H)$^+$; Anal. calcd for $C_{17}H_{21}N_5O_3$: C, 59.46; H, 6.16; N, 20.40. Found: C, 59.40; H, 6.17; N, 20.35.

Example 69

4-{[4-Amino-2-(3-hydroxypropyl)-1H-imidazo[4,5-c][1,5]naphthyridin-1-yl]methyl}tetrahydro-2H-pyran-4-ol

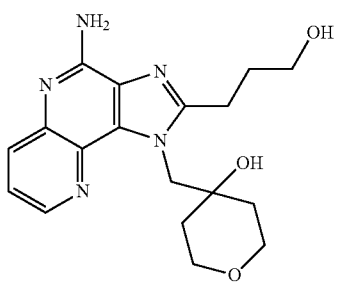 [SMILES: Nc1nc2cccnc2c2c1nc(CCCO)n2CC1(O)CCOCC1]

Part A

4-Benzyloxybutyric acid (0.87 mL, 4.93 mmol), 1-hydroxybenzotriazole (0.79 g, 5.83 mmol), and N-(3-dimethylaminopropyl)-N'-ethylcarbodiimide (1.12 g, 5.83 mmol) were added to a solution of 4-[(3-amino[1,5]naphthyridin-4-ylamino)methyl]tetrahydropyran-4-ol (1.23 g, 4.48 mmol) in DMF (20 mL). The reaction mixture was stirred at ambient temperature for 5.5 hours. An additional 0.5 eq of N-(3-dimethylaminopropyl)-N'-ethylcarbodiimide and 1-hydroxybenzotriazole were added and the reaction mixture was stirred overnight. An additional 0.3 eq of the acid was added and the reaction mixture was stirred for an hour. The reaction mixture was combined with that from another run, diluted with water (100 mL), and extracted with dichloromethane (3×50 mL). The combined organics were washed with brine (75 mL), dried over magnesium sulfate, and then concentrated under reduced pressure to provide 8.03 g of a brown oil. This material was purified by HPFC eluting with a gradient of 0 to 35% CMA in chloroform to provide 2.67 g of 4-benzyloxy-N-4-[(4-hydroxytetrahydropyran-4-ylmethyl)amino][1,5]napthyridin-3-yl}butyramide as a yellow oil.

Part B

The material from Part A was combined with a solution of ammonia in methanol (25 mL of 7M) and placed in a pressure vessel. The vessel was sealed and then heated at 150° C. for 18 hours. The reaction mixture was cooled and then concentrated under reduced pressure. The residue was purified by HPFC eluting with a gradient of 0 to 40% CMA in chloroform to provide 1.77 g of 4-{[2-(3-benzyloxypropyl)-1H-imidazo[4,5-c][1,5]naphthyridin-1-yl]methyl}tetrahydro-2H-pyran-4-ol as an off white solid.

Part C

The material from Part B was oxidized and then aminated according to the method of Part I of Example 12. The crude product was purified by HPFC eluting with a gradient of 0 to 40% CMA in chloroform to provide a yellow oil. This material was triturated with acetonitrile to provide 0.70 g of 4-{[4-amino-2-(3-benzyloxypropyl)-1H-imidazo[4,5-c][1,5]naphthyridin-1-yl]methyl}tetrahydro-2H-pyran-4-ol as a tan solid.

Part D

Acetyl chloride (0.12 mL, 1.64 mmol) and ethanol (10 mL) were combined at 0° C. and then stirred at ambient temperature for 30 minutes. The material from Part C (1.56 mmol) and 10% palladium on carbon (0.14 g) were added and the mixture was placed under hydrogen pressure (45 psi, $3.1\times10^5$ Pa) over the weekend. The reaction mixture was filtered through a layer of CELITE filter aid and the filter cake was rinsed with methanol (30 mL). The filtrate was concentrated under reduced pressure. The residue was combined with aqueous saturated sodium bicarbonate (30 mL) and then extracted with chloroform (9×15 mL). The combined organics were dried over magnesium sulfate, filtered, and then concentrated under reduced pressure to provide a yellow solid. This material was purified by HPFC eluting with a gradient of 0 to 50% CMA in chloroform to provide 0.36 g of a white solid. This material was triturated with hot methanol and then dried under vacuum at 140° C. to provide 140 mg of 4-{[4-amino-2-(3-hydroxypropyl)-1H-imidazo[4,5-c][1,5]naphthyridin-1-yl]methyl}tetrahydro-2H-pyran-4-ol as off-white needles, mp 237-238° C. MS (ESI) m/z 358 $(M+H)^+$; Anal. calcd for $C_{18}H_{23}N_5O_3$: C, 60.49; H, 6.49; N, 19.59. Found: C, 60.56; H, 6.48; N, 19.64.

Example 70

4-[(4-Amino-2-propyl-1H-imidazo[4,5-c][1,5]naphthyridin-1-yl)methyl]tetrahydro-2H-pyran-4-ol

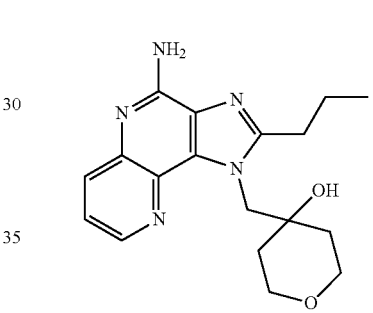

Part A

Trimethylorthobutyrate (1.9 mL, 12.0 mmol) and pyridine hydrochloride (23 mg, 0.2 mmol) were added to a suspension of 4-[(3-amino[1,5]naphthyridin-4-ylamino)methyl]tetrahydropyran-4-ol (10.0 mmol) in toluene (50 mL). The reaction mixture was heated at reflux overnight and then concentrated under reduced pressure. The residue was triturated with acetonitrile and the resulting solid was isolated by filtration to provide 2.26 g of 4-[(2-propyl-1H-imidazo[4,5-c][1,5]naphthyridin-1-yl)methyl]tetrahydro-2H-pyran-4-ol as a tan solid.

Part B

The material from Part A was oxidized and aminated according to the method of Part I of Example 12 except that the amination was run at ambient temperature. The crude product was triturated with acetonitrile to provide a yellow solid. This material was recrystallized from hot ethanol to provide pale yellow crystals which were triturated with hot acetonitrile and then dried under vacuum at 85° C. to provide 0.546 g of 4-[(4-amino-2-propyl-1H-imidazo[4,5-c][1,5]naphthyridin-1-yl)methyl]tetrahydro-2H-pyran-4-ol as off-white needles, mp 209-210° C. MS (ESI) m/z 342 $(M+H)^+$; Anal. calcd for $C_{18}H_{23}N_5O_2$: C, 63.32; H, 6.79; N, 20.51. Found: C, 63.44; H, 6.92; N, 20.65.

Example 71

4-[(4-Amino-1H-imidazo[4,5-c][1,5]naphthyridin-1-yl)methyl]tetrahydro-2H-pyran-4-ol

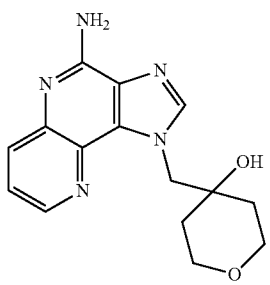 [SMILES: Nc1nc2cccnc2c2c1ncn2CC1(O)CCOCC1]

Part A

4-[(1H-imidazo[4,5-c][1,5]naphthyridin-1-yl)methyl]tetrahydro-2H-pyran-4-ol was prepared according to the method of Part A of Example 70 using trimethylorthoformate in lieu of trimethylorthobutyrate.

Part B

The material from Part A was oxidized and aminated according to the method of Part I of Example 12 except that the amination was run at 5° C. The crude product was purified by HPFC eluting with a gradient of 0 to 35% CMA in chloroform to provide an off white solid. This material was triturated with acetonitrile and then dried in a vacuum oven at 85° C. to provide 0.154 g of 4-[(4-amino-1H-imidazo[4,5-c][1,5]naphthyridin-1-yl)methyl]tetrahydro-2H-pyran-4-ol as a beige solid, mp 225-226° C. MS (ESI) m/z 300 (M+H)$^+$; Anal. calcd for $C_{15}H_{17}N_5O_2$: C, 60.19; H, 5.72; N, 23.40. Found: C, 59.97; H, 5.71; N, 23.39.

Example 72

4-[(4-Amino-2-ethyl-1H-imidazo[4,5-c][1,5]naphthyridin-1-yl)methyl]tetrahydro-2H-pyran-4-ol

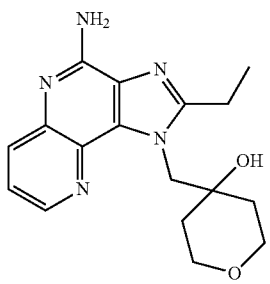 [SMILES: CCc1nc2c(N)nc3cccnc3c2n1CC1(O)CCOCC1]

Part A

4-[(2-ethyl-1H-imidazo[4,5-c][1,5]naphthyridin-1-yl)methyl]tetrahydro-2H-pyran-4-ol was prepared according to the method of Part A of Example 70 using triethylorthopropionate in lieu of trimethylorthobutyrate.

Part B

The material from Part A was oxidized and aminated according to the method of Part I of Example 12 except that the amination was run at 5° C. The crude product was triturated sequentially with hot acetonitrile and hot ethanol and then purified by HPFC eluting with a gradient of 0 to 30% CMA in chloroform to provide an off white solid. This material was triturated with acetonitrile and then dried in a vacuum oven at 85° C. to provide 0.543 g of 4-[(4-amino-2-ethyl-1H-imidazo[4,5-c][1,5]naphthyridin-1-yl)methyl]tetrahydro-2H-pyran-4-ol as off-white needles, mp greater than 250° C. MS (ESI) m/z 328 (M+H)$^+$; Anal. calcd for $C_{17}H_{21}N_5O_2$: C, 62.37; H, 6.47; N, 21.39. Found: C, 62.38; H, 6.39; N, 21.53.

Example 73

1-[3-(4-Amino-2-propyl-1H-imidazo[4,5-c]quinolin-1-yl)propyl]cyclohexanol

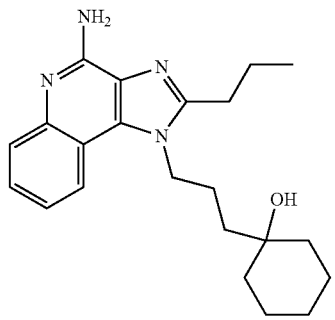 [SMILES: CCCc1nc2c(N)nc3ccccc3c2n1CCCC1(O)CCCCC1]

Part A

Trimethylorthobutyrate (0.86 mL, 5.41 mmol) and pyridine hydrochloride (0.03 g, 0.23 mmol) were added to a solution of N$^4$-{3-[1-tert-butyldimethylsilanyloxy)cyclohexyl]propyl}quinoline-3,4-diamine (4.51 mmol) in toluene (20 mL). The reaction mixture was refluxed for 2 hours, cooled to ambient temperature, and then concentrated under reduced pressure. The residue was dissolved in dichloromethane (100 mL) and washed with aqueous saturated sodium bicarbonate (50 mL). The aqueous was extracted with dichloromethane (2×20 mL). The combined organics were dried over magnesium sulfate, filtered, and then concentrated under reduced pressure to provide 2.23 g of crude 1-{3-[1-tert-butyldimethylsilanyloxy)cyclohexyl]propyl}-2-propyl-1H-imidazo[4,5-c]quinoline as an orange goo.

Part B

The tert-butyldimethylsilyl group was removed according to the method of Part H of Example 12 to provide 1-[3-(2-propyl-1H-imidazo[4,5-c]quinolin-1-yl)propyl]cyclohexanol as a brown solid.

Part C

The material from Part B was oxidized and then aminated according to the method of Part I of Example 12. The crude product was purified by HPFC eluting with a gradient of 0 to 35% CMA in chloroform to provide a tan solid. This material was recrystallized 3 times from chloroform/hexanes and then dried in a vacuum oven at 75° C. to provide 239 mg of 1-[3-(4-amino-2-propyl-1H-imidazo[4,5-c]quinolin-1-yl)propyl]cyclohexanol as off-white needles, mp 200.5-201.5° C. MS (ESI) m/z 367 (M+H)$^+$; Anal. calcd for $C_{22}H_{30}N_4O$: C, 72.10; H, 8.25; N, 15.29. Found: C, 72.00; H, 8.50; N, 15.42.

Example 74

1-[2-(4-Amino-2-methyl-1H-imidazo[4,5-c]quinolin-1-yl)ethyl]cyclohexanol

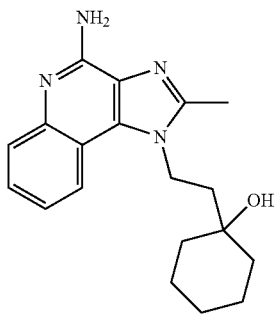 [SMILES: Cc1nc2c(N)nc3ccccc3c2n1CCC1(O)CCCCC1]

Part A $N^4$-{2-[1-tert-butyldimethylsilanyloxy)cyclohexyl]ethyl}quinoline-3,4-diamine was prepared according to the general methods of Parts A through G of Example 12 except that vinyl magnesium bromide was used in lieu of allyl magnesium bromide in Part A and the tert-butyldimethylsilanyl protecting group was installed by treating a solution of the cyclohexanol in dichloromethane with tert-butyldimethylsilyl trifluoromethanesulfonate in the presence of 2,6-lutidine.

Part B

Trimethylorthoacetate (1.1 mL) and pyridine hydrochloride (42 mg, 0.37 mmol) were added to a suspension of $N^4$-{2-[1-tert-butyldimethylsilanyloxy)cyclohexyl]ethyl}quinoline-3,4-diamine (2.95 g, 7.38 mmol) in toluene (30 mL). The reaction mixture was refluxed for 2.5 hours, cooled to ambient temperature, and then concentrated under reduced pressure. The residue was dissolved in dichloromethane (80 mL) and washed with aqueous saturated sodium bicarbonate (50 mL). The aqueous was extracted with dichloromethane (30 mL). The combined organics were dried over magnesium sulfate, filtered, and then concentrated under reduced pressure to provide 1-{2-[1-tert-butyldimethylsilanyloxy)cyclohexyl]ethyl}-2-methyl-1H-imidazo[4,5-c]quinoline as a brown solid.

Part C

The tert-butyldimethylsilyl group was removed according to the method of Part H of Example 12. The crude product was purified by HPFC eluting with a gradient of 0 to 40% CMA in chloroform to provide 1.70 g of 1-[2-(2-methyl-1H-imidazo[4,5-c]quinolin-1-yl)ethyl]cyclohexanol as a tan solid.

Part D

The material from Part C was oxidized and then aminated according to the method of Part I of Example 12. The crude product was triturated sequentially with hot methanol and hot ethanol and then dried in a vacuum oven at 85° C. to provide 0.549 g of 1-[2-(4-amino-2-methyl-1H-imidazo[4,5-c]quinolin-1-yl)ethyl]cyclohexanol as beige needles, mp>252° C. MS (ESI) m/z 325 (M+H)$^+$; Anal. calcd for $C_{19}H_{24}N_4O \cdot 0.02$ $CHCl_3$: C, 69.90; H, 7.41; N, 17.14. Found: C, 69.69; H, 7.41; N, 16.95.

Example 75

1-[2-(4-Amino-2-propyl-1H-imidazo[4,5-c]quinolin-1-yl)ethyl]cyclohexanol

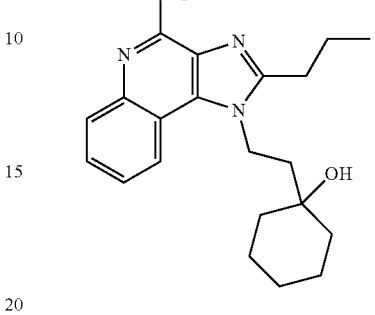

1-[2-(4-Amino-2-propyl-1H-imidazo[4,5-c]quinolin-1-yl)ethyl]cyclohexanol was prepared according to the method of Parts A through D of Example 74 using trimethylorthobutyrate in lieu of trimethylorthoacetate in Part B. The crude product was purified by HPFC eluting with a gradient of 0 to 40% CMA in chloroform to provide a tan solid. This material was recrystallized from hot chloroform and then triturated with hot acetonitrile to provide 0.444 g of pure product as beige needles, mp 181-182° C. MS (ESI) m/z 353 (M+H)$^+$; Anal. calcd for $C_{21}H_{28}N_4O$: C, 71.56; H, 8.01; N, 15.90. Found: C, 71.37; H, 8.15; N, 15.82.

Example 76

1-{2-[4-Amino-2-(ethoxymethyl)-1H-imidazo[4,5-c]quinolin-1-yl]ethyl}cyclohexanol

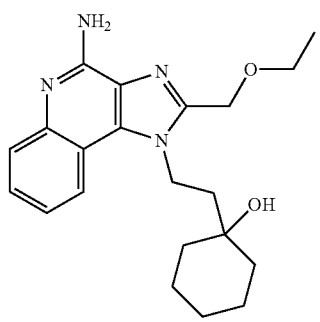 [SMILES: CCOCc1nc2c(N)nc3ccccc3c2n1CCC1(O)CCCCC1]

1-{2-[4-Amino-2-(ethoxymethyl)-1H-imidazo[4,5-c]quinolin-1-yl]ethyl}cyclohexanol was prepared according to the general methods of Parts G through I of Example 12 using N-{2-[1-tert-butyldimethylsilanyloxy)cyclohexyl]ethyl}-3-nitroquinolin-4-amine in lieu of $N^4$-{3-[1-tert-butyldimethylsilanyloxy)cyclohexyl]propyl}-3-nitroquinolin-4-amine in Part G. The crude product was purified by HPFC eluting with a gradient of 0 to 25% CMA in chloroform to provide a tan solid. This material was recrystallized from hot chloroform to provide 0.346 g of pure product as off-white needles, mp 205-206° C. MS (ESI) m/z 369 (M+H)$^+$; Anal. calcd for $C_{21}H_{28}N_4O_2$: C, 68.45; H, 7.66; N, 15.20. Found: C, 68.38; H, 7.74; N, 15.13.

Example 77

N-({4-Amino-1-[(1-hydroxycyclohexyl)methyl]-1H-imidazo[4,5-c]quinolin-2-yl}methyl)cyclopropanecarboxamide

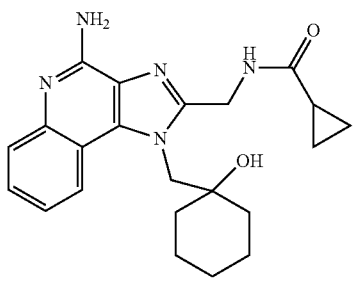 [SMILES: Nc1nc2ccccc2c2c1nc(CNC(=O)C1CC1)n2CC1(O)CCCCC1]

Part A
Potassium phthalimide (2.59 g, 14.0 mmol) was added to a solution of 1-[(4-amino-2-chloromethyl-1H-imidazo[4,5-c]quinolin-1-yl)methyl]cyclohexanol (13.3 mmol) in DMF (50 mL). The reaction mixture was stirred at ambient temperature overnight. Additional potassium phthalimide (1.0 g) was added. The reaction mixture was stirred for 5 hours and then concentrated under reduced pressure. The residue was triturated with methanol to provide 6.91 g of crude 2-({4-amino-1-[(1-hydroxycyclohexyl)methyl]-1H-imidazo[4,5-c]quinolin-2-yl}methyl)isoindole-1,3-dione as a white solid.

Part B
Hydrazine (2.1 mL, 66.5 mmol) was added to a suspension of the material from Part A in ethanol (50 mL). The reaction mixture was stirred at ambient temperature for 24 hours and then concentrated under reduced pressure. The residue was sonicated with 1M hydrochloric acid (50 mL) and then filtered. The filtrate was adjusted to pH 8 with solid sodium bicarbonate. The resulting precipitate was isolated by filtration and dried in a vacuum oven at 50° C. to provide 2.99 g of 1-[(4-amino-2-aminomethyl-1H-imidazo[4,5-c]quinolin-1-yl)methyl]cyclohexanol as a white powder.

Part C
Triethylamine (0.28 mL, 2.01 mmol) was added to a suspension of material from Part B (0.503 g, 1.55 mmol) in dichloromethane (12 mL). The mixture was cooled to 0° C. and cyclopropylcarbonyl chloride (0.15 mL, 1.62 mmol) was added. The reaction mixture was stirred overnight at ambient temperature and then diluted with dichloromethane (50 mL) and aqueous saturated sodium bicarbonate (40 mL). The layers were separated and the aqueous layer was extracted with dichloromethane (2×20 mL). The combined organics were dried over magnesium sulfate, filtered, and then concentrated under reduced pressure to provide 0.70 g of a white solid. This material was purified by HPFC eluting with a gradient of 0 to 45% CMA in chloroform to provide 0.56 g of a white powder. This material was triturated with hot acetonitrile, isolated by filtration, and dried under high vacuum at 100° C. to provide 0.440 g of N-({4-amino-1-[(1-hydroxycyclohexyl)methyl]-1H-imidazo[4,5-c]quinolin-2-yl}methyl)cyclopropanecarboxamide as white needles, mp is greater than 250° C. MS (ESI) m/z 394 (M+H)$^+$; Anal. calcd for $C_{22}H_{27}N_5O_2$: C, 67.15; H, 6.92; N, 17.80. Found: C, 66.93; H, 7.07; N, 17.92.

Example 78

1-[(4-Amino-2-methyl-1H-imidazo[4,5-c]quinolin-1-yl)methyl]cyclohexanol

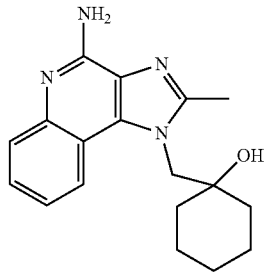 [SMILES: Cc1nc2c(N)nc3ccccc3c2n1CC1(O)CCCCC1]

Part A
A mixture of 1-[(3-nitroquinolin-4-ylamino)methyl]cyclohexanol (10.0 g, 33.2 mmol), 5% platinum on carbon (1.0 g), and ethyl acetate (140 mL) was placed under hydrogen pressure (40 psi, $2.8 \times 10^5$ Pa) for 2.5 hours. The reaction mixture was filtered through a layer of CELITE filter aid and the filter cake was rinsed with ethyl acetate (100 mL). The filtrate was concentrated under reduced pressure to provide 1-[(3-aminoquinolin-4-ylamino)methyl]cyclohexanol as an orange gooey solid.

Part B
Trimethylorthoacetate (1.7 mL, 13.2 mmol) was added to a suspension of material from Part A (11.0 mmol) in toluene (45 mL). The reaction mixture was heated at reflux for 6 hours, allowed to cool to ambient temperature, and then concentrated under reduced pressure. The residue was triturated with acetonitrile to provide 2.61 g of 1-[(2-methyl-1H-imidazo[4,5-c]quinolin-1-yl)methyl]cyclohexanol as a tan solid.

Part C
The material from Part B was oxidized and then aminated using the method of Part I of Example 12 except that the amination was run at ambient temperature. The crude product was triturated sequentially with 2M sodium hydroxide and hot ethanol to provide 1.00 g of 1-[(4-amino-2-methyl-1H-imidazo[4,5-c]quinolin-1-yl)methyl]cyclohexanol as beige needles, mp is greater than 250° C. MS (ESI) m/z 311 (M+H)$^+$; Anal. calcd for $C_{18}H_{22}N_4O$: C, 69.65; H, 7.14; N, 18.05. Found: C, 69.64; H, 7.40; N, 18.35.

Example 79

1-[(4-Amino-1H-imidazo[4,5-c]quinolin-1-yl)methyl]cyclohexanol

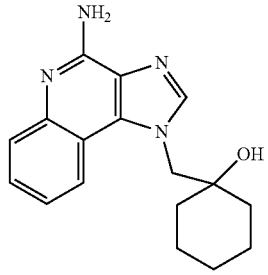 [SMILES: Nc1nc2ccccc2c2c1ncn2CC1(O)CCCCC1]

1-[(4-Amino-1H-imidazo[4,5-c]quinolin-1-yl)methyl]cy-clohexanol was prepared according to the general methods of Example 78 except that trimethylorthoformate was used in lieu of trimethylorthoacetate in Part B. The crude product was triturated sequentially with 1M sodium hydroxide and hot ethanol and then further purified by HPFC eluting with a gradient of 0 to 50% CMA in chloroform to provide an off-white solid. This material was triturated with boiling methanol and then dried in a vacuum oven at 130° C. to provide product as off-white needles, mp greater than 250° C. MS (ESI) m/z 297 (M+H)$^+$; Anal. calcd for $C_{17}H_{20}N_4O$: C, 68.90; H, 6.80; N, 18.90. Found: C, 68.57; H, 6.62; N, 18.75.

Example 80

1-{[4-Amino-2-(hydroxymethyl-1H-imidazo[4,5-c]quinolin-1-yl]methyl}cyclohexanol

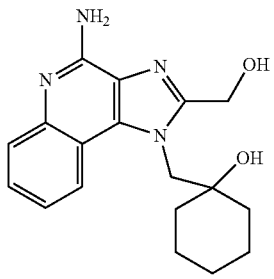 [SMILES: Nc1nc2ccccc2c2c1nc(CO)n2CC1(O)CCCCC1]

Part A

Ethyl chloroacetimidate hydrochloride (1.90 g, 12.0 mmol) was added to a solution of 1-[(3-aminoquinolin-4-ylamino)methyl]cyclohexanol (10.0 mmol) in 1,2-dichloroethane (70 mL) and the reaction mixture was heated at 65° C. for 8 hours. Additional imidate (1.2 eq) was added and the reaction mixture was heated at 65° C. overnight. Additional imidate (2 eq) was added in portions over a period of 6 hours. The reaction mixture was cooled to ambient temperature. A solid was isolated by filtration and rinsed with dichloromethane. The solid was stirred with water for 30 minutes, isolated by filtration, and then dried to provide 2.77 g of 1-(2-chloromethyl)-1H-imidazo[4,5-c]quinolin-1-yl]methyl}cyclohexanol.

Part B

A portion (2.34 g, 7.09 mmol) of the material from Part A was oxidized and then animated using the method of Part I of Example 12 except that the amination was run at ambient temperature. The crude product was triturated with acetonitrile to provide 0.57 g of 1-{[4-amino-2-(chloromethyl)-1H-imidazo[4,5-c]quinolin-1-yl]methyl}cyclohexanol as a tan solid.

Part C

Potassium acetate (0.28 g, 2.89 mmol) was added to a solution of 1-{[4-amino-2-(chloromethyl)-1H-imidazo[4,5-c]quinolin-1-yl]methyl}cyclohexanol (0.83 g, 2.41 mmol) in DMF (10 mL). The reaction mixture was stirred at ambient temperature overnight and then concentrated under reduced pressure to provide crude [4-amino-1-(1-hydroxycyclohex-ylmethyl)-1H-imidazo[4,5-c]quinolin-2-yl]methyl acetate.

Part D

Potassium carbonate (0.67 g, 4.82 mmol) was added to a solution of the material from Part C in methanol (10 mL). The reaction mixture was stirred at ambient temperature for 1 hour and then concentrated under reduced pressure. The residue was triturated sequentially with water and hot acetonitrile and then dried in a vacuum oven at 85° C. to provide 0.458 g of 1-{[4-amino-2-(hydroxymethyl)-1H-imidazo[4,5-c]quinolin-1-yl]methyl}cyclohexanol as tan needles, mp 244-248° C. MS (ESI) m/z 327 (M+H)$^+$; Anal. calcd for $C_{18}H_{22}N_4O_2$: C, 66.24; H, 6.79; N, 17.17. Found: C, 66.23; H, 6.57; N, 17.04.

Example 81

4-[2-(4-Amino-2-propyl-1H-imidazo[4,5-c]quinolin-1-yl)ethyl]tetrahydro-2H-pyran-4-ol

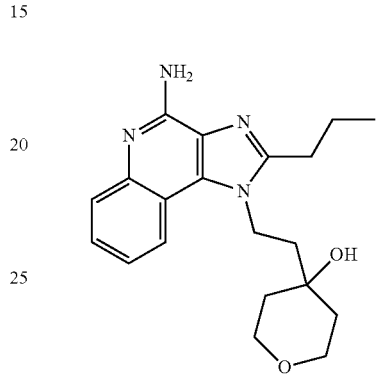

Part A

N-{2-[4-tert-butyldimethylsilanyloxy)tetrahydropyran-4-yl]ethyl}-3-nitroquinolin-4-amine was prepared according to the general method of Part A of Example 74 except that tetrahydropyran-4-one was used in lieu of cyclohexanone.

Part B

Acetic acid (27 mL) and water (9 mL) were added to a solution of N-{2-[4-tert-butyldimethylsilanyloxy)tetrahydropyran-4-yl]ethyl}-3-nitroquinolin-4-amine in tetrahydrofuran (THF, 9 mL). The reaction mixture was heated at 50° C. for 2 hours. Analysis indicated that the protecting group was still in place. 6M hydrochloric acid (5 mL) was added, the reaction mixture was heated at 50° C. for 48 hours, and then concentrated under reduced pressure. The residue was slurried with aqueous saturated sodium bicarbonate (50 mL) and the pH was adjusted to 8 with solid sodium bicarbonate. A solid was isolated by filtration and then triturated with dichloromethane to provide 3.43 g of 4-[2-(3-nitroquinolin-4-ylamino)ethyl]tetrahydropyran-4-ol as a yellow solid.

Part C

A mixture of the material from Part B (3.43 g, 10.8 mmol), 5% platinum on carbon (0.34 g), and ethyl acetate (50 mL) was placed under hydrogen pressure (40 psi, 2.8×10$^5$ Pa) for 3 hours. The reaction mixture was filtered through a layer of CELITE filter aid and the filter cake was rinsed with ethyl acetate (100 mL). The filtrate was concentrated under reduced pressure to provide 2.92 g of 4-[2-(3-aminoquinolin-4-ylamino)ethyl]tetrahydropyran-4-ol as a yellow solid.

Part D

Trimethylorthobutyrate (0.93 mL, 5.88 mmol) and pyridine hydrochloride (27 mg, 0.23 mmol) were added to a suspension of a portion (1.30 g, 4.52 mmol) of the material from Part C in toluene (20 mL). The reaction mixture was heated at reflux for 3 hours, allowed to cool to ambient temperature, and then concentrated under reduced pressure.

The residue was dissolved in dichloromethane (20 mL), decolorized with charcoal, and then concentrated under reduced pressure to provide a yellow solid. This material was recrystallized from acetonitrile to provide 0.491 g of 4-[2-(2-propyl-1H-imidazo[4,5-c]quinolin-1-yl)ethyl]tetrahydro-2H-pyran-4-ol as white needles, mp 186-188° C. MS (ESI) m/z 340 (M+H)$^+$; Anal. calcd for $C_{20}H_{25}N_3O_2$: C, 70.77; H, 7.42; N, 12.38. Found: C, 70.63; H, 7.31; N, 12.43.

Part E

The material from Part D was oxidized and then animated using the method of Part I of Example 12. The crude product was triturated with 2M sodium hydroxide. The resulting solid was recrystallized from chloroform/hexanes and dried under vacuum at 85° C. to provide 0.322 g of 4-[2-(4-amino-2-propyl-1H-imidazo[4,5-c]quinolin-1-yl)ethyl]tetrahydro-2H-pyran-4-ol as beige needles, mp 181-183° C. MS (ESI) m/z 355 (M+H)$^+$; Anal. calcd for $C_{20}H_{26}N_4O_2$: C, 67.77; H, 7.39; N, 15.81. Found: C, 67.62; H, 7.59; N, 15.84.

Example 82

4-[2-(4-Amino-2-methyl-1H-imidazo[4,5-c]quinolin-1-yl)ethyl]tetrahydro-2H-pyran-4-ol

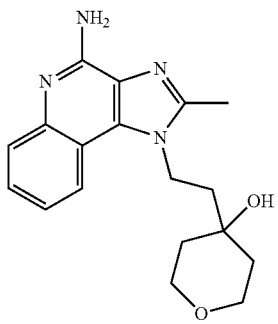 [SMILES: Cc1nc2c(N)nc3ccccc3c2n1CCC1(O)CCOCC1]

Part A

4-[2-(2-Methyl-1H-imidazo[4,5-c]quinolin-1-yl)ethyl]tetrahydro-2H-pyran-4-ol was prepared according to the methods of Parts A through D of Example 81 except that trimethylorthoacetate was used in lieu of trimethylorthobutyrate in Part D. The crude product was triturated with acetonitrile to provide 0.69 g of product as a grey solid.

Part B

The material from Part A was oxidized and then animated using the method of Part I of Example 12. The crude product was triturated with 2M sodium hydroxide. The resulting solid was recrystallized from chloroform/hexanes and dried under vacuum at 120° C. to provide 0.363 g of 4-[2-(4-amino-2-methyl-1H-imidazo[4,5-c]quinolin-1-yl)ethyl]tetrahydro-2H-pyran-4-ol as beige needles, mp greater than 253° C. MS (ESI) m/z 327 (M+H)$^+$; Anal. calcd for $C_{18}H_{22}N_4O_2$: C, 66.24; H, 6.79; N, 17.17. Found: C, 65.98; H, 6.80; N, 16.97.

Example 83

4-[2-(4-Amino-2-ethyl-1H-imidazo[4,5-c]quinolin-1-yl)ethyl]tetrahydro-2H-pyran-4-ol

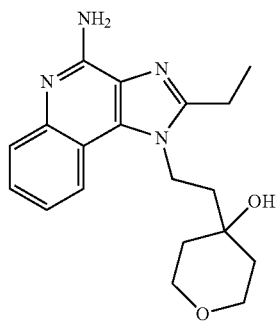 [SMILES: CCc1nc2c(N)nc3ccccc3c2n1CCC1(O)CCOCC1]

Part A

4-[2-(2-Ethyl-1H-imidazo[4,5-c]quinolin-1-yl)ethyl]tetrahydro-2H-pyran-4-ol was prepared according to the methods of Parts A through D of Example 81 except that triethylorthopropionate was used in lieu of trimethylorthobutyrate in Part D. The crude product was triturated with acetonitrile to provide 0.78 g of product as a grey solid.

Part B

The material from Part A was oxidized and then animated using the method of Part I of Example 12. The crude product was triturated with 2M sodium hydroxide. The resulting solid was recrystallized from chloroform/hexanes and dried under vacuum at 120° C. to provide 0.405 g of 4-[2-(4-amino-2-ethyl-1H-imidazo[4,5-c]quinolin-1-yl)ethyl]tetrahydro-2H-pyran-4-ol as yellow needles, mp 243-244° C. MS (ESI) m/z 341 (M+H)$^+$; Anal. calcd for $C_{19}H_{24}N_4O_2$: C, 67.04; H, 7.11; N, 16.46. Found: C, 66.81; H, 7.28; N, 16.29.

Example 84

1-[2-(4-Amino-2-ethyl-1H-imidazo[4,5-c]quinolin-1-yl)ethyl]cyclopropanol

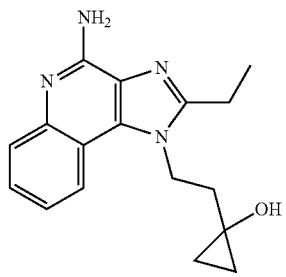 [SMILES: CCc1nc2c(N)nc3ccccc3c2n1CCC1(O)CC1]

Part A

Sodium carbonate (21.1 g, 199 mmol) was added to a suspension of fl-alanine ethyl ester hydrochloride (10.2 g, 66.4 mmol) and benzyl bromide (16.2 mL, 136 mmol) in acetonitrile (265 mL). The reaction mixture was stirred at ambient temperature overnight and then filtered through a layer of CELITE filter aid. The filter cake was rinsed with acetonitrile (100 mL). The filtrate was concentrated under reduced pressure to provide 20.28 g of ethyl 3-dibenzylaminopropionate as a pale yellow oil.

Part B

Titanium(IV) isopropoxide (3.9 mL, 13.28 mmol) was added to a solution of the material from Part A in diethyl ether. The mixture was cooled to 4° C. and ethylmagnesium bromide (63 mL of 3.16 M in diethyl ether) was added dropwise over a period of 90 minutes while maintaining the temperature at 1.5-4° C. The reaction mixture was stirred at ambient temperature overnight. Hydrochloric acid (75 mL of 3 M) was added and the reaction mixture was stirred at ambient temperature for 2 hours. The reaction mixture was made basic with solid sodium bicarbonate and diluted with water (200 mL). The layers were separated. The aqueous layer was extracted with diethyl ether (4×100 mL). The combined organics were dried over magnesium sulfate, filtered, and then concentrated under reduced pressure to provide a yellow oil. This material was purified by HPFC eluting with a gradient of 0 to 40% ethyl acetate in hexanes to provide 6.73 g of 1-[2-(dibenzylamino)ethyl]cyclopropanol as a pale yellow oil.

Part C

Ammonium formate (6.03 g, 95.7 mmol) and 10% palladium on carbon (1.10 g) were added to a solution of the material from Part B in methanol (95 mL). The reaction mixture was stirred at 65° C. for 2 hours and then filtered through a layer of CELITE filter aid. The filter cake was rinsed with methanol (70 mL). The filtrate was concentrated under reduced pressure to provide 2.78 g of crude 1-(2-aminoethyl)cyclopropanol.

Part D

The material from Part C was dissolved in a mixture of dichloromethane (65 mL) and triethylamine (6.0 mL, 43.4 mmol). The solution was cooled to 0° C. and then 4-chloro-3-nitroquinoline (4.53 g, 21.7 mmol) was added in portions over a period of 5 minutes. The reaction mixture was stirred over the weekend while slowly warming to ambient temperature. The reaction mixture was diluted with dichloromethane (20 mL) and aqueous saturated sodium bicarbonate (40 mL). The layers were separated and the aqueous layer was extracted with dichloromethane (2×15 mL). The combined organics were dried over magnesium sulfate, filtered, and then concentrated under reduced pressure. The residue was triturated with acetonitrile to provide 3.16 g of 1-[2-(3-nitroquinolin-4-ylamino)ethyl]cyclopropanol as a yellow solid.

Part E

A mixture of the material from Part D, 5% platinum on carbon (0.32 g), and ethyl acetate (50 mL) was placed under hydrogen pressure (40 psi, $2.8 \times 10^5$ Pa) for 3 hours.

The reaction mixture was filtered through a layer of CELITE filter aid and the filter cake was rinsed with ethyl acetate (75 mL). The filtrate was concentrated under reduced pressure to provide crude 1-[2-(3-aminoquinolin-4-ylamino)ethyl]cyclopropanol.

Part F

Triethylorthopropionate (1.2 mL, 5.78 mmol) and pyridine hydrochloride (45 mg, 0.39 mmol) were added to a suspension of the material from Part E in toluene (16 mL). The reaction mixture was heated at reflux for 2.5 hours, allowed to cool to ambient temperature, and the precipitate was isolated by filtration to provide 0.68 g of 1-[2-(2-ethyl-1H-imidazo[4,5-c]quinolin-1-yl)ethyl]cyclopropanol as a white solid.

Part G

The material from Part F was oxidized and then aminated according to the general method of Part I of Example 12. The crude product was triturated with 2M sodium hydroxide, recrystallized from chloroform/methanol 99/1 and hexanes, and then dried in a vacuum oven at 85° C. to provide 300 mg of 1-[2-(4-amino-2-ethyl-1H-imidazo[4,5-c]quinolin-1-yl)ethyl]cyclopropanol as white needles, mp 199-200° C. MS (ESI) m/z 297 (M+H)$^+$; Anal. calcd for $C_{17}H_{20}N_4O$: C, 68.90; H, 6.80; N, 18.90. Found: C, 68.72; H, 7.04; N, 18.83.

Example 85

1-[2-(4-Amino-2-methyl-1H-imidazo[4,5-c]quinolin-1-yl)ethyl]cyclopropanol

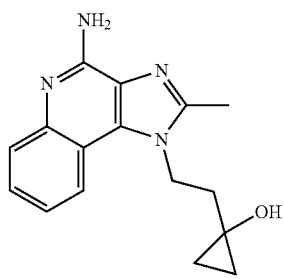 [SMILES: Cc1nc2c(N)nc3ccccc3c2n1CCC1(O)CC1]

1-[2-(4-Amino-2-methyl-1H-imidazo[4,5-c]quinolin-1-yl)ethyl]cyclopropanol was prepared and purified according to the methods of Parts A through G of Example 84 using trimethylorthoacetate in lieu of triethylorthopropionate in Part F. The product was provided as white needles, mp decomposed at 203° C. MS (ESI) m/z 283 (M+H)$^+$; Anal. calcd for $C_{16}H_{18}N_4O$: C, 68.06; H, 6.43; N, 19.84. Found: C, 67.86; H, 6.33; N, 19.87.

Example 86

1-[2-(4-Amino-2-(ethoxymethyl)-1H-imidazo[4,5-c]quinolin-1-yl)ethyl]cyclopropanol

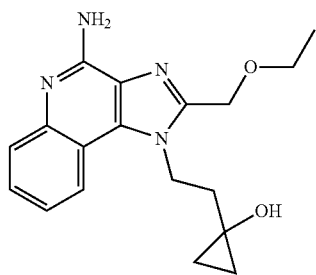 [SMILES: CCOCc1nc2c(N)nc3ccccc3c2n1CCC1(O)CC1]

Part A

Ethoxyacetyl chloride (0.43 mL) was added to a cooled (0° C.) solution of 1-[2-(3-aminoquinolin-4-ylamino)ethyl]cyclopropanol (3.85 mmol) in dichloromethane (16 mL). The reaction mixture was stirred at 0-5° C. for 60 minutes and then concentrated under reduced pressure to provide crude 2-ethoxy-N-{4-[2-(1-hydroxycyclopropyl)ethylamino]quinolin-3-yl}acetamide hydrochloride.

Part B

Triethylamine (1.6 mL) was added to a solution of the material from Part A in ethanol (16 mL). The reaction mixture was stirred at ambient temperature overnight and then at 60° C. for 2 hours. The reaction mixture was concentrated under reduced pressure and the residue was partitioned between dichloromethane (50 mL) and aqueous saturated sodium bicarbonate (40 mL). The aqueous layer was separated and extracted with dichloromethane (2×20 mL). The combined organics were dried over magnesium sulfate, filtered, and then concentrated under reduced pressure to provide a green solid. This material was triturated with acetonitrile to provide 0.77 g of 1-[2-(2-(ethoxymethyl)-1H-imidazo[4,5-c]quinolin-1-yl)ethyl]cyclopropanol as a white solid.

Part C

The material from Part F was oxidized and then aminated according to the general method of Part I of Example 12. The crude product was triturated with 2M sodium hydroxide, recrystallized from chloroform/methanol 99/1 and hexanes, and then dried in a vacuum oven at 85° C. to provide 0.333 g of 1-[2-(4-amino-2-(ethoxymethyl)-1H-imidazo[4,5-c]quinolin-1-yl)ethyl]cyclopropanol as white needles, mp 210-211° C. MS (ESI) m/z 327 (M+H)$^+$; Anal. calcd for $C_{18}H_{22}N_4O_2$: C, 66.24; H, 6.79; N, 17.17. Found: C, 65.98; H, 6.82; N, 17.08.

Example 87

1-[3-(4-Amino-2-methyl-1H-imidazo[4,5-c]quinolin-1-yl)propyl]cyclopropanol

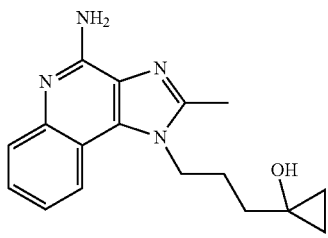 [SMILES: Cc1nc2c(N)nc3ccccc3c2n1CCCC1(O)CC1]

1-[3-(4-amino-2-methyl-1H-imidazo[4,5-c]quinolin-1-yl)propyl]cyclopropanol was prepared according to the general methods of Parts A through G of Example 84 except that ethyl 4-aminobutyrate hydrochloride was used in lieu of β-alanine ethyl ester hydrochloride in Part A and trimethylorthoacetate was used in lieu of triethylorthopropionate in Part F. The crude product was triturated with 2M sodium hydroxide and the resulting tan solid was purified by HPFC eluting with a gradient of 0 to 60% CMA in chloroform to provide 0.57 g of an off white solid. This material was triturated with hot acetonitrile and then dried in a vacuum oven at 85° C. to provide 0.34 g of product as off-white needles, mp 210-212° C. MS (ESI) m/z 297 (M+H)$^+$; Anal. calcd for $C_{17}H_{20}N_4O$: C, 68.90; H, 6.80; N, 18.90. Found: C, 68.69; H, 7.06; N, 19.07.

Example 88

1-[(4-Amino-2-ethyl-1H-imidazo[4,5-c][1,5]naphthyridin-1-yl)methyl]cyclopropanol

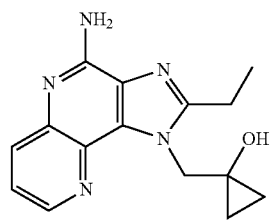 [SMILES: CCc1nc2c(N)nc3cccnc3c2n1CC1(O)CC1]

Part A

Ethyl bromoacetate (19.52 mL, 176 mol) was added in a single portion to a chilled (0° C.) solution of dibenzylamine (33.84 mL, 176 mmol) and triethylamine (27 mL, 193.6 mmol) in THF. The reaction mixture was stirred overnight at ambient temperature. Additional triethylamine (30 mL) and THF (100 mL) were added and the reaction mixture was heated at 50° C. for 1.5 hours. Additional ethyl bromoacetate (13 mL) was added and the reaction mixture was heated for 1 hour and then stirred at ambient temperature overnight. About half of the THF was removed under reduced pressure. The mixture was diluted with water (300 mL) and then extracted with ethyl acetate (2×400 mL). The combined extracts were washed sequentially with water and with brine, dried over sodium sulfate, filtered, and then concentrated under reduced pressure. The residue was purified by flash chromatography (700 g of silica gel, eluting with 20% ethyl acetate in hexanes) to provide 37.12 g of ethyl dibenzylaminoacetate as a colorless oil.

Part B

1-[(4-Amino-2-ethyl-1H-imidazo[4,5-c][1,5]naphthyridin-1-yl)methyl]cyclopropanol was prepared according to the general methods of Parts B through G of Example 84 using ethyl dibenzylaminoacetate in lieu of ethyl 3-dibenzylaminopropionate in Part B and 4-chloro-3-nitronaphthyridine in lieu of 4-chloro-3-nitroquinoline in Part D. The crude product was triturated with acetonitrile to provide a tan solid. This material was purified by HPFC eluting with a gradient of 0-35% CMA in chloroform to provide an off white solid. This material was triturated with hot acetonitrile and then dried in a vacuum oven at 85° C. to provide 0.515 g of product as an off-white solid, mp 210-212° C. MS (APCI) m/z 284 (M+H)$^+$; Anal. calcd for $C_{15}H_{17}N_5O$: C, 63.59; H, 6.05; N, 24.72. Found: C, 63.27; H, 5.99; N, 25.06.

Example 89

1-{[4-Amino-2-(ethoxymethyl)-1H-imidazo[4,5-c]quinolin-1-yl]methyl}cyclopropanol

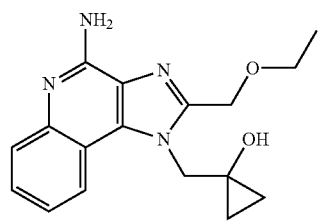 [SMILES: CCOCc1nc2c(N)nc3ccccc3c2n1CC1(O)CC1]

Part A

1-[(3-Aminoquinolin-4-ylamino)methyl]cyclopropanol was prepared according to the methods of Parts B through E of Example 84 using ethyl dibenzylaminoacetate in lieu of ethyl 3-dibenzylaminopropionate in Part B.

Part B

1-{[4-Amino-2-(ethoxymethyl)-1H-imidazo[4,5-c]quinolin-1-yl]methyl)}cyclopropanol was prepared according to the methods of Parts A through C of Example 86 using 1-[(3-aminoquinolin-4-ylamino)methyl]cyclopropanol in lieu of 1-[2-(3-aminoquinolin-4-ylamino)ethyl]cyclopropanol in Part A. The crude was purified by HPFC eluting with a gradient of 0-50% CMA in chloroform to provide a tan solid. This material was recrystallized from chloroform and hexanes and dried in a vacuum oven at 85° C. to provide product as tan crystals, mp 185-186° C. MS (ESI) m/z 313 (M+H)$^+$; Anal. calcd for $C_{17}H_{20}N_4O_2$: C, 65.37; H, 6.45; N, 17.94. Found: C, 65.14; H, 6.43; N, 17.92.

Example 90

1-[(4-Amino-2-propyl-1H-imidazo[4,5-c][1,5]naphthyridin-1-yl)methyl]cyclopropanol

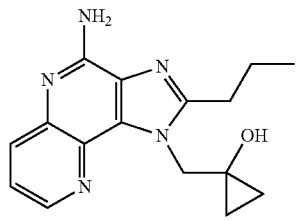 [SMILES: CCCc1nc2c(N)nc3cccnc3c2n1CC1(O)CC1]

1-[(4-Amino-2-propyl-1H-imidazo[4,5-c][1,5]naphthyridin-1-yl)methyl]cyclopropanol was prepared according to the general methods of Parts D through G of Example 84 using 1-(aminomethyl)cyclopropanol in lieu of 1-(2-aminoethyl)cyclopropanol in Part D, 4-chloro-3-nitronaphthyridine in lieu of 4-chloro-3-nitroquinoline in Part D, and trimethyl orthobutyrate in lieu of triethyl orthopropionate in Part F. The crude product was triturated with hot acetonitrile to provide a tan solid. Which was recrystallized from chloroform and hexanes and dried at 140° C. under vacuum to provide product as an off-white solid, mp 199-200° C. MS (ESI) m/z 298 (M+H)$^+$; Anal. calcd for $C_{16}H_{19}N_5O$: C, 64.63; H, 6.44; N, 23.55. Found: C, 64.32; H, 6.62; N, 23.67.

Example 91

1-[(4-Amino-2-(ethoxymethyl)-1H-imidazo[4,5-c][1,5]naphthyridin-1-yl)methyl]cyclopropanol

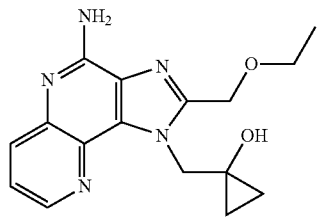 [SMILES: CCOCc1nc2c(N)nc3cccnc3c2n1CC1(O)CC1]

1-[(4-Amino-2-(ethoxymethyl)-1H-imidazo[4,5-c][1,5]naphthyridin-1-yl)methyl]cyclopropanol was prepared according to the general methods of Example 89 using 4-chloro-3-nitronaphthyridine in lieu of 4-chloro-3-nitroquinoline in Part A. The crude product was purified by HPFC eluting with a gradient of 0-35% CMA in chloroform followed by recrystallization from hot acetonitrile to provide product as an off-white solid, mp 178-179° C. MS (APCI) m/z 314 (M+H)$^+$; Anal. calcd for $C_{16}H_{19}N_5O_2$: C, 61.33; H, 6.11; N, 22.35. Found: C, 60.99; H, 6.09; N, 22.52.

Example 92

N-(1-{[4-Amino-2-(ethoxymethyl)-1H-imidazo[4,5-c]quinolin-1-yl]methyl}cyclopropyl)methanesulfonamide

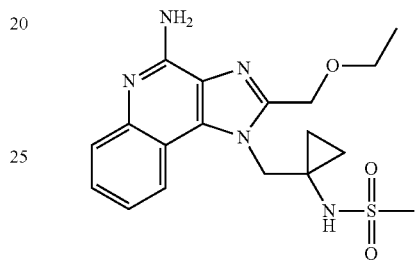

Part A

Ethyl cyanoacetate (15 mL, 141 mmol) was added to a mixture of potassium carbonate (48.7 g, 353 mmol) and acetone (200 mL). 1,2-Dibromoethane (13.4 mL, 155 mmol) was added dropwise over a period of 8 minutes. The reaction mixture was refluxed overnight. More 1,2-dibromoethane (1.8 mL) was added and the reaction mixture was refluxed for 4 hours. The reaction mixture was filtered through a layer of CELITE filter aid. The filter cake was rinsed with acetone (200 mL). The filtrate was concentrated under reduced pressure to provide ethyl 1-cyanocyclopropionate as a pale orange oil.

Part B

Concentrated hydrochloric acid (25 mL) and platinum oxide (0.98 g) were added to a solution of the material from Part A in ethanol (225 mL). The mixture was placed under hydrogen pressure (40 psi, $2.8 \times 10^5$ Pa) on a Parr apparatus for 20 hours. The reaction mixture was filtered through a layer of CELITE filter aid. The filter cake was rinsed with methanol (200 mL). The filtrate was concentrated under reduced pressure. The residue was reconcentrated under reduced pressure three times from methanol and twice from toluene to provide 31.7 g of ethyl 1-aminomethylcyclopropionate hydrochloride.

Part C

Triethylamine (41 mL, 294 mmol) was added to a suspension of 4-chloro-3-nitroquinoline (24.5 g, 118 mmol) in dichloromethane (250 mL). The mixture was cooled to 5° C. A solution of the material from Part B in dichloromethane (200 mL) was added over a period of 15 minutes. The reaction mixture was stirred at 5° C. for 1 hour and then at ambient temperature overnight. The reaction mixture was washed with aqueous saturated sodium bicarbonate (250 mL). The aqueous layer was back extracted with dichloromethane (2×50 mL). The combined organics were dried over magnesium sulfate, filtered, and then concentrated under reduced pressure to provide an orange oil. This material was recrystallized from acetonitrile to provide 21.47 g of ethyl 1-[(3-nitroquinolin-4-ylamino)methyl]cyclopropionate as a bright yellow solid.

Part D

A mixture of material from Part C (8.0 g, 25.4 mmol), 5% platinum on carbon (0.80 g), and ethyl acetate (100 mL) was placed under hydrogen pressure (30 psi, $2.1 \times 10^5$ Pa) on a Parr apparatus for 3 hours. The reaction mixture was filtered through a layer of CELITE filter aid. The filter cake was rinsed with ethyl acetate (50 mL). The filtrate was concentrated under reduced pressure to provide ethyl 1-[(3-aminoquinolin-4-ylamino)methyl]cyclopropionate as a yellow solid.

Part E

Ethoxyacetyl chloride (2.9 mL, 28 mmol) was added dropwise over a period of 5 minutes to a chilled (0° C.) solution of the material from Part D in dichloromethane (100 mL). The reaction mixture was allowed to slowly warm to ambient temperature overnight and then concentrated under reduced pressure to provide crude ethyl 1-{[3-(2-ethoxyacetylamino)quinolin-4-ylamino]methyl]cyclopropionate hydrochloride.

Part F

Triethylamine (10.6 mL, 76.2 mmol) was added to a solution of the material from Part E in ethanol (100 mL). The reaction mixture was heated at 60° C. overnight and then concentrated under reduced pressure. The residue was dissolved in dichloromethane (100 mL) and washed with aqueous saturated sodium bicarbonate (75 mL). The aqueous layer was back extracted with dichloromethane (2×35 mL). The combined organics were dried over magnesium sulfate, filtered, and then concentrated under reduced pressure to provide 9.5 g of ethyl 1-[(2-ethoxymethyl-1H-imidazo[4,5-c]quinolin-1-yl)methyl]cyclopropionate as a brown semisolid.

Part G

Sodium hydroxide (8.5 mL of 6 M) was added to a solution of the material from Part F in ethanol (80 mL). The reaction mixture was stirred at ambient temperature for 3 hours and then concentrated under reduced pressure. The residue was slurried with water (60 mL). The pH of the mixture was adjusted to 12 and then it was extracted with diethyl ether (3×20 mL). The pH of the aqueous was adjusted to 4 and a precipitate formed. The precipitate was isolated by filtration to provide 4.36 g of 1-[(2-ethoxymethyl-1H-imidazo[4,5-c]quinolin-1-yl)methyl]cyclopropanecarboxylic acid.

Part H

Triethylamine (3.9 mL, 27.7 mol) and diphenylphosphoryl azide (2.2 mL, 10.1 mmol) were added to a chilled (0° C.) suspension of material from Part G (3.00 g, 9.2 mmol) in toluene (45 mL). The reaction mixture was stirred at 0° C. for 2 hours, warmed to ambient temperature, and then stirred for an additional 4 hours. Tert-butanol was added and the reaction mixture was refluxed overnight. The reaction mixture was diluted with dichloromethane (50 mL) and aqueous saturated sodium bicarbonate (75 mL). The aqueous was back extracted with dichloromethane (2×30 mL). The combined organics were dried over magnesium sulfate, filtered, and then concentrated under reduced pressure to provide 3.41 g of tert-butyl {1-[(2-ethoxymethyl-1H-imidazo[4,5-c]quinolin-1-yl)methyl]cyclopropyl]}carbamate as an off white foam.

Part I

Hydrochloric acid (2 mL of 6M) was added to a solution of material from Part H (0.49 g, 1.24 mmol) in ethanol (4 mL). The reaction mixture was heated at 50° C. for 4 hours, cooled to ambient temperature, and then concentrated under reduced pressure. The residue was concentrated under reduced pressure from methanol 3 times. The resulting solid was triturated with acetonitrile to provide 0.43 g of 1-[(2-ethoxymethyl-1H-imidazo[4,5-c]quinolin-1-yl)methyl]cyclopropylamine hydrochloride.

Part J

Methanesulfonyl chloride (0.12 mL, 1.6 mmol) was added dropwise to a chilled (0° C. solution of the material from Part I in dichloromethane (8 mL) and triethylamine (0.52 mL, 3.7 mmol). The reaction mixture was allowed to stir at 0-5° C. for 2.5 hours. The reaction mixture was diluted with dichloromethane (25 mL) and aqueous saturated sodium bicarbonate (25 mL). The aqueous was back extracted with dichloromethane (2×10 mL). The combined organics were dried over magnesium sulfate, filtered, and then concentrated under reduced pressure to provide 0.48 g of N-(1-{[2-(ethoxymethyl)-1H-imidazo[4,5-c]quinolin-1-yl]methyl}cyclopropyl)methanesulfonamide as a white solid.

Part K

The material from Part J was oxidized and then aminated according to the methods of Part I of Example 12. The crude product was purified by HPFC eluting with a gradient of 0-35% CMA in chloroform to provide a yellow gooey solid. This material was combined with 2M hydrochloric acid and stirred for 1 hour. The mixture was made basic (pH 8) with solid sodium bicarbonate. The resulting solid was isolated by filtration, washed with water, and then dried in a vacuum oven at 85° C. to provide 201 mg of N-(1-{[4-amino-2-(ethoxymethyl)-1H-imidazo[4,5-c]quinolin-1-yl]methyl}cyclopropyl)methanesulfonamide as white needles, mp dehydrates at 98 C, no discernible melting point ° C. MS (ESI) m/z 390 (M+H)⁺; Anal. calcd for $C_{18}H_{23}N_5O_3S*1.8H_2O$: C, 51.24; H, 6.35; N, 16.60. Found: C, 51.19; H, 6.36; N, 16.38.

Example 93

1-[(4-Amino-2-ethoxymethyl-6,7-dimethyl-1H-imidazo[4,5-c]pyridin-1-yl)methyl]cyclohexanol

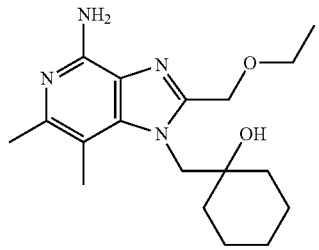 [SMILES: CCOCc1nc2c(N)nc(C)c(C)c2n1CC1(O)CCCCC1]

Part A

1-[(3-Amino-2-dibenzylamino-5,6-dimethylpyridin-4-ylamino)methyl]cyclohexanol (0.94 g, 2.1 mmol, prepared as described in Parts A through C of Example 59 was reacted with ethoxyacetyl chloride (0.31 g, 2.52 mmol) according to the general method of Part A of Example 58. The resulting amide was cyclized according to the general method of Part A of Example 58 to provide 0.67 g of 1-[(4-dibenzylamino-2-ethoxymethyl-6,7-dimethyl-1H-imidazo[4,5-c]pyridin-1-yl)methyl]cyclohexanol as a white solid.

Part B

The benzyl groups were removed from the material from Part A using the general method of Part E of Example 59. The crude product was recrystallized from acetonitrile to provide 321 mg of 1-[(4-amino-2-ethoxymethyl-6,7-dimethyl-1H-imidazo[4,5-c]pyridin-1-yl)methyl]cyclohexanol as white needles, mp 194.0-195.0° C. Anal. Calcd for $C_{18}H_{28}N_4O_2$ C, 65.03; H, 8.49; N, 16.85; Found: C, 64.92; H, 8.42; N, 17.11.

Example 94

2-Ethoxymethyl-1-(1-methoxycyclohexyl)-6,7-dimethyl-1H-imidazo[4,5-c]pyridin-4-amine

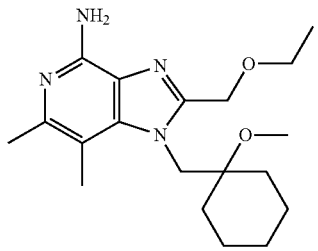 [SMILES: CCOCc1nc2c(N)nc(C)c(C)c2n1CC1(OC)CCCCC1]

Part A

Under a nitrogen atmosphere iodomethane (0.58 mL, 9.3 mmol) and 1-[(4-dibenzylamino-2-ethoxymethyl-6,7-dimethyl-1H-imidazo[4,5-c]pyridin-1-yl)methyl]cyclohexanol (1.59 g, 3.10 mmol) were added to a mixture of potassium hydride (0.87 g of 30 wt %, 6.5 mmol) and tetrahydrofuran (31 mL). The reaction mixture was stirred at ambient temperature for 1 hour and then quenched with methanol. Water and a few drops of acetic acid were added until the reaction mixture was slightly acidic. The volume of the reaction mixture was reduced under vacuum and then it was diluted with water (20 mL) and hexanes (20 mL). A solid was isolated by filtration, rinsed with water and hexanes, and then dried in a vacuum oven at 70° C. to provide 1.50 g of dibenzyl[2-ethoxymethyl-1-(1-methoxycyclohexyl)-6,7-dimethyl-1H-imidazo[4,5-c]pyridin-4-yl]amine.

Part B

The benzyl groups were removed from the material from Part A using the general method of Part E of Example 59. The crude product was recrystallized from acetonitrile. The resulting solid was dissolved in dichloromethane (150 mL), washed with saturated aqueous sodium bicarbonate (50 mL) and brine (30 mL), dried over sodium sulfate, filtered, and concentrated under reduced pressure. The residue was recrystallized from acetonitrile to provide 2-ethoxymethyl-1-(1-methoxycyclohexyl)-6,7-dimethyl-1H-imidazo[4,5-c]pyridin-4-amine as white needles, mp 172.0-173.0° C. Anal. Calcd for $C_{19}H_{30}N_4O_2$ C, 65.87; H, 8.73; N, 16.17; Found: C, 65.64; H, 8.93; N, 16.32.

Example 95

1-(1-Methoxycyclohexyl)-6,7-dimethyl-2-propyl-1H-imidazo[4,5-c]pyridin-4-amine

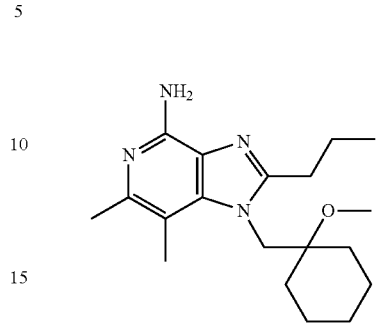

1-(1-Methoxycyclohexyl)-6,7-dimethyl-2-propyl-1H-imidazo[4,5-c]pyridin-4-amine was prepared according to the general methods of Example 94 using 1-[(4-dibenzylamino-6,7-dimethyl-2-propyl-1H-imidazo[4,5-]pyridin-1-yl)methyl]cyclohexanol (Example 59, Parts A through D) in lieu of 1-[(4-dibenzylamino-2-ethoxymethyl-6,7-dimethyl-1H-imidazo[4,5-c]pyridin-1-yl)methyl]cyclohexanol in Part A. The crude product was recrystallized from acetonitrile to provide pure product as white needles, mp 192.0-193.0° C. Anal. Calcd for $C_{19}H_{30}N_4O$ C, 69.06; H, 9.15; N, 16.95; Found: C, 68.79; H, 9.27; N, 16.88.

Example 96

2-Ethoxymethyl-1-(1-methoxycyclohexyl)-1H-imidazo[4,5-c][1,5]naphthyridin-4-amine

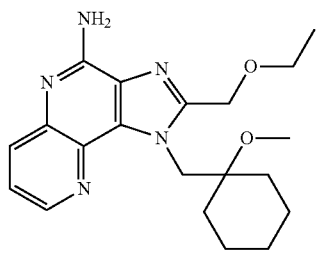 [SMILES: CCOCc1nc2c(N)nc3cccnc3c2n1CC1(OC)CCCCC1]

Part A

1-[(2-Ethoxymethyl-1H-imidazo[4,5-c][1,5]napthyridin-1-yl)methyl]cyclohexanol (1.87 g, 5.49 mmol, Example 58 Part A) was treated with iodomethane according to the general method of Part A of Example 94 to provide 1.75 g of 2-ethoxymethyl-1-(1-methoxycyclohexyl)-1H-imidazo[4,5-c][1,5]naphthyridine.

Part B

The material from Part A was oxidized and then aminated according to the general method of Part D of Example 57. The crude product was purified twice by HPFC eluting the first time with a gradient of 0-35% CMA in chloroform and the second time with a gradient of 0-30% CMA in chloroform and then recrystallized from acetonitrile to provide 304 mg of 2-ethoxymethyl-1-(1-methoxycyclohexyl)-1H-imidazo[4,5-c][1,5]naphthyridin-4-amine as an off-white powder, mp 160.0-161.0° C. Anal. Calcd for $C_{20}H_{27}N_5O_2$ C, 65.02; H, 7.37; N, 18.96; Found: C, 65.03; H, 7.43; N, 18.94.

Example 97

1-(1-Methoxycyclohexyl)-2-propyl-1H-imidazo[4,5-c][1,5]naphthyridin-4-amine

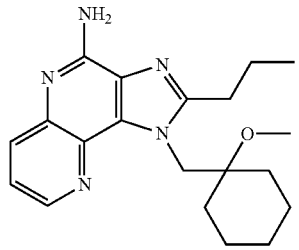 [SMILES: CCCc1nc2c(N)nc3cccnc3c2n1CC1(OC)CCCCC1]

1-(1-Methoxycyclohexyl)-2-propyl-1H-imidazo[4,5-c][1,5]naphthyridin-4-amine was prepared according to the general methods of Example 96 using 1-[(2-propyl-1H-imidazo[4,5-c][1,5]napthyridin-1-yl)methyl]cyclohexanol in lieu of 1-[(2-ethoxymethyl-1H-imidazo[4,5-c][1,5]napthyridin-1-yl)methyl]cyclohexanol. The crude product was purified twice by HPFC eluting with a gradient of 0-30% CMA in chloroform and then triturated twice with acetonitrile to provide pure product as an off-white powder, mp 187.0-188.0° C. Anal. Calcd for $C_{20}H_{27}N_5O$ C, 67.96; H, 7.70; N, 19.81; Found: C, 67.63; H, 7.84; N, 19.96.

Example 98

1-[(4-Amino-2-propyl-1H-imidazo[4,5-c][1,5]napthyridin-1-yl)methyl]cyclopentanol

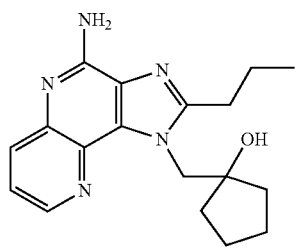 [SMILES: CCCc1nc2c(N)nc3cccnc3c2n1CC1(O)CCCC1]

1-[(4-Amino-2-propyl-1H-imidazo[4,5-c][1,5]napthyridin-1-yl)methyl]cyclopentanol was prepared according to the general methods of Example 57 Parts A through D using 1-(aminomethyl)cyclopentanol in lieu of 1-(aminomethyl)cyclohexanol in Part A. The crude product was purified by HPFC eluting with a gradient of 0-30% CMA in chloroform and then triturated sequentially with acetonitrile and ethyl acetate to provide pure product as a white powder, mp 184.0-186.0° C. Anal. Calcd for $C_{18}H_{23}N_5O$ C, 66.44; H, 7.12; N, 21.52; Found: C, 66.18; H, 7.31; N, 21.45.

Example 99

1-[(4-Amino-2-propyl-6,7,8,9-tetrahydro-1H-imidazo[4,5-c][1,5]napthyridin-1-yl)methyl]cyclopentanol

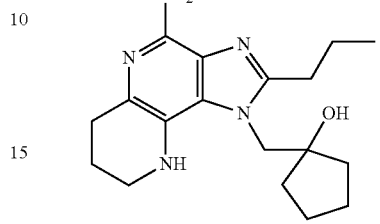

A mixture of 1-[(4-amino-2-propyl-1H-imidazo[4,5-c][1,5]napthyridin-1-yl)methyl]cyclopentanol (511 mg), platinum oxide (511 mg), and trifluoroacetic acid was placed under hydrogen pressure (50 psi, $3.4 \times 10^5$ Pa) overnight on a Parr apparatus. The mixture was filtered through a layer of CELITE filter aid and the filter cake was rinsed with methanol. The filtrate was concentrated under reduced pressure. The residue was combined with concentrated hydrochloric acid (2 mL) and stirred at ambient temperature for 2 hours. The mixture was diluted with water (10 mL) and then cooled to 0° C. The pH was adjusted to 12 with 6N sodium hydroxide and then the mixture was extracted with dichloromethane (3×50 mL). The combined organics were washed with brine (20 mL), dried over sodium sulfate, filtered, and then concentrated under reduced pressure. The residue was triturated with acetonitrile, purified by HPFC eluting with a gradient of 0-35% CMA in chloroform, and then triturated with acetonitrile to provide 167 mg of 1-[(4-amino-2-propyl-6,7,8,9-tetrahydro-1H-imidazo[4,5-c][1,5]napthyridin-1-yl)methyl]cyclopentanol as a white powder, mp 207.0-208.0° C. Anal. Calcd for $C_{18}H_{27}N_5O \cdot 0.25H_2O$ C, 64.74; H, 8.30; N, 20.97; Found: C, 64.71; H, 8.29; N, 20.98.

Example 100

1-[(4-Amino-2-ethoxymethyl-1H-imidazo[4,5-c][1,5]napthyridin-1-yl)methyl]cyclopentanol

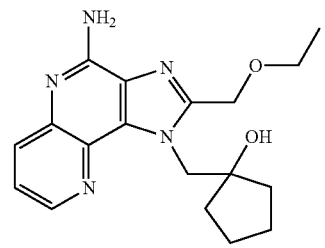 [SMILES: CCOCc1nc2c(N)nc3cccnc3c2n1CC1(O)CCCC1]

1-[(4-Amino-2-ethoxymethyl-1H-imidazo[4,5-c][1,5]napthyridin-1-yl)methyl]cyclopentanol was prepared according to the general methods of Example 58 using 1-(aminomethyl)cyclopentanol in lieu of 1-(aminomethyl)cyclohexanol. The crude product was purified by HPFC eluting with a gradient of 0-30% CMA in chloroform, triturated with acetonitrile, and then recrystallized from ethyl acetate/hexanes to provide pure product as an off-white powder, mp 165.0-166.0° C. Anal. Calcd for $C_{18}H_{23}N_5O_2$ C, 63.32; H, 6.79; N, 20.51; Found: C, 63.07; H, 7.01; N, 20.35.

Example 101

1-[(4-Amino-2-ethoxymethyl-6,7,8,9-tetrahydro-1H-imidazo[4,5-c][1,5]napthyridin-1-yl)methyl]cyclopentanol

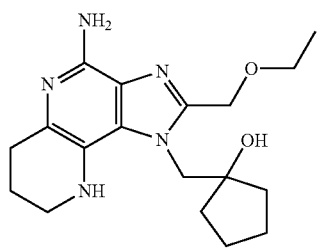 [SMILES: CCOCc1nc2c(N)nc3c(c2n1CC1(O)CCCC1)NCCC3]

1-[(4-Amino-2-ethoxymethyl-1H-imidazo[4,5-c][1,5]napthyridin-1-yl)methyl]cyclopentanol (503 mg) was reduced according to the method of Example 100. The crude product was triturated twice with acetonitrile to provide 329 mg of pure product as a white powder, mp 207.0-208.0° C. Anal. Calcd for $C_{18}H_{27}N_5O_2$ C, 62.59; H, 7.88; N, 20.27; Found: C, 62.36; H, 7.82; N, 20.42.

Example 102

1-[(4-Amino-2-propyl-1H-imidazo[4,5-c][1,5]napthyridin-1-yl)methyl]cyclobutanol

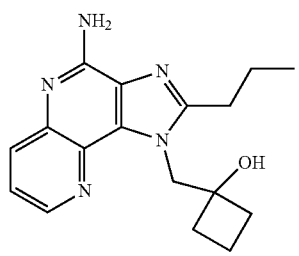

1-[(4-Amino-2-propyl-1H-imidazo[4,5-c][1,5]napthyridin-1-yl)methyl]cyclobutanol was prepared according to the general methods of Example 57 Parts A through D using 1-(aminomethyl)cyclobutanol in lieu of 1-(aminomethyl)cyclohexanol in Part A. The crude product was triturated sequentially with acetonitrile and ethyl acetate and then recrystallized from chloroform/hexanes to provide pure product as a white powder, mp 226.0-227.0° C. Anal. Calcd for $C_{17}H_{21}N_5O.0.1H_2O$ C, 65.20; H, 6.82; N, 22.36; Found: C, 64.95; H, 6.94; N, 22.40.

Example 103

1-[(4-Amino-2-ethoxymethyl-1H-imidazo[4,5-c][1,5]napthyridin-1-yl)methyl]cyclobutanol

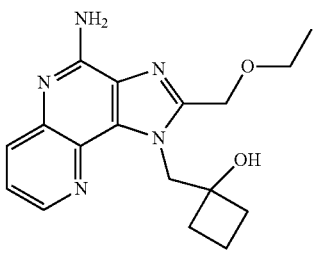 [SMILES: CCOCc1nc2c(N)nc3cccnc3c2n1CC1(O)CCC1]

1-[(4-Amino-2-ethoxymethyl-1H-imidazo[4,5-c][1,5]napthyridin-1-yl)methyl]cyclobutanol was prepared according to the general methods of Example 58 using 1-(aminomethyl)cyclobutanol in lieu of 1-(aminomethyl)cyclohexanol. The crude product was triturated sequentially with acetonitrile and ethyl acetate, recrystallized twice from chloroform/hexanes, purified by HPFC eluting with a gradient of 0-25% CMA in chloroform, and then triturated with acetonitrile to provide pure product as a white powder, mp 162.0-163.0° C. Anal. Calcd for $C_{17}H_{21}N_5O_2.0.2H_2O$ C, 61.69; H, 6.52; N, 21.16; Found: C, 61.51; H, 6.47; N, 21.13.

Example 104

1-[(4-Amino-2-hydroxymethyl-1H-imidazo[4,5-c][1,5]napthyridin-1-yl)methyl]cyclobutanol

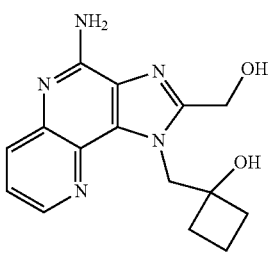 [SMILES: Nc1nc2cccnc2c2c1nc(CO)n2CC1(O)CCC1]

Under a nitrogen atmosphere boron tribromide (6.15 mL of 1M in dichloromethane) was added dropwise over a period of 10 minutes to a chilled (0° C.) solution of 1-[(4-amino-2-ethoxymethyl-1H-imidazo[4,5-c][1,5]napthyridin-1-yl)methyl]cyclobutanol (0.67 g, 2.0 mmol) in dichloromethane (20 mL). The reaction mixture was allowed to warm to ambient temperature and was stirred overnight. The reaction mixture was cooled to 0° C. and then more boron tribromide (1.0 mL) was added. The reaction mixture was stirred at ambient temperature for 4 hours. Methanol (10 mL) and hydrochloric acid (10 mL of 6N) were added and the reaction mixture was heated at reflux for 1 hour. The reaction mixture was allowed to cool to ambient temperature and was then made basic with 6N sodium hydroxide. A portion of the solvent was removed under vacuum, water (10 mL) was added, and the mixture was sonicated. A solid was isolated by filtration and rinsed with water. The aqueous filtrate was extracted with chloroform (3×80 mL). The combined organics were washed with brine (20 mL), dried over sodium sulfate, filtered, and then concentrated under reduced pressure. The residue was combined with the isolated solid and then purified by HPFC eluting with a gradient of 0-30% CMA in chloroform, triturated with acetonitrile, and dried. The resulting material was suspended in water (70 mL) and heated to 90° C. Concentrated hydrochloric acid (about 0.8 mL) was added until a solution was obtained. The hot solution was made basic with solid sodium bicarbonate and then allowed to cool. A precipitate was isolated by filtration, washed well with water, and then dried to provide 1-[(4-amino-2-hydroxymethyl-1H-imidazo[4,5-c][1,5]napthyridin-1-yl)methyl]cyclobutanol as a white powder, mp 244.0-246.0° C. Anal. Calcd for $C_{15}H_{17}N_5O_2$ C, 60.19; H, 5.72; N, 23.40; Found: C, 59.97; H, 5.81; N, 23.31.

Example 105

1-[(4-Amino-2-propyl-6,7-dimethyl-1H-imidazo[4,5-c]pyridin-1-yl)methyl]cyclobutanol

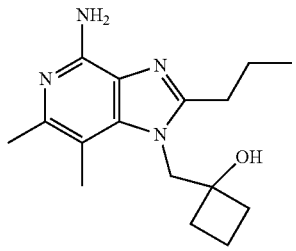 [SMILES: CCCc1nc2c(N)nc(C)c(C)c2n1CC1(O)CCC1]

1-[(4-Amino-2-propyl-6,7-dimethyl-1H-imidazo[4,5-c]pyridin-1-yl)methyl]cyclobutanol was prepared according to the general methods of Example 59 using 1-(aminomethyl)cyclobutanol in lieu of 1-(aminomethyl)cyclohexanol in Part A. The crude product was triturated with acetonitrile, purified by HPFC eluting with a gradient of 0-50% CMA in chloroform, triturated with 1N sodium hydroxide, washed with water, dried, triturated with hot ethyl acetate, and then dried to provide pure product as a white powder, mp 180.0-181.0° C. Anal. Calcd for $C_{16}H_{24}N_4O$ C, 66.64; H, 8.39; N, 19.43; Found: C, 66.49; H, 8.74; N, 19.60.

Example 106

1-[(4-Amino-2,6,7-trimethyl-1H-imidazo[4,5-c]pyridin-1-yl)methyl]cyclobutanol

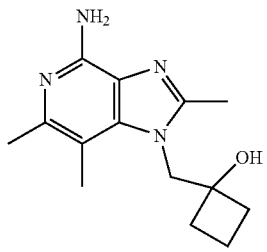 [SMILES: Cc1nc(N)c2nc(C)n(CC3(O)CCC3)c2c1C]

1-[(4-amino-2,6,7-trimethyl-1H-imidazo[4,5-c]pyridin-1-yl)methyl]cyclobutanol was prepared according to the general methods of Example 59 using 1-(aminomethyl)cyclobutanol in lieu of 1-(aminomethyl)cyclohexanol in Part A and trimethylorthoacetate in lieu of trimethylorthobutyrate in Part D. The crude product was purified by HPFC eluting with a gradient of 0-50% CMA in chloroform, triturated with 1N sodium hydroxide, and then it was suspended in water (70 mL). Concentrated hydrochloric acid (1.0 mL) was added and the mixture was heated to 90° C. The hot solution was made basic with solid sodium bicarbonate and then allowed to cool. A precipitate was isolated by filtration, washed well with water, and then dried to provide pure product as a white powder, mp>250.0° C. Anal. Calcd for $C_{14}H_{20}N_4O$ C, 64.59; H, 7.74; N, 21.52; Found: C, 64.57; H, 7.81; N, 21.61.

Example 107

1-[(4-Amino-2-ethoxymethyl-6,7-dimethyl-1H-imidazo[4,5-c]pyridin-1-yl)methyl]cyclobutanol

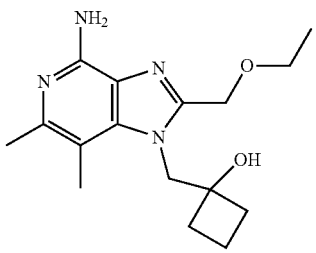 [SMILES: CCOCc1nc2c(N)nc(C)c(C)c2n1CC1(O)CCC1]

1-[(4-Amino-2-ethoxymethyl-6,7-dimethyl-1H-imidazo[4,5-c]pyridin-1-yl)methyl]cyclobutanol was prepared according to the general methods of Example 93 using 1-[(3-amino-2-dibenzylamino-5,6-dimethylpyridin-4-ylamino)methyl]cyclobutanol in lieu of 1-[(3-amino-2-dibenzylamino-5,6-dimethylpyridin-4-ylamino)methyl]cyclohexanol in Part A. The crude product was purified by HPFC eluting with a gradient of 0-50% CMA in chloroform and then suspended in water (70 mL). Concentrated hydrochloric acid (2 mL) was added and the mixture was heated to 90° C. The hot solution was made basic (pH 8) with solid sodium bicarbonate. Sodium hydroxide (1N) was added until the solution became cloudy. The solution was allowed to cool to ambient temperature. A precipitate was isolated by filtration, washed well with water, and then dried to provide pure product as a white powder, mp 190.0-191.0° C. Anal. Calcd for $C_{16}H_{24}N_4O_2$ C, 63.13; H, 7.95; N, 18.41; Found: C, 63.01; H, 8.04; N, 18.48.

Example 108

1-[(4-Amino-2-methyl-1H-imidazo[4,5-c]quinolin-1-yl)methyl]cyclobutanol

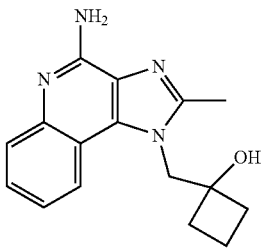 [SMILES: Cc1nc2c(N)nc3ccccc3c2n1CC1(O)CCC1]

1-[(4-Amino-2-methyl-1H-imidazo[4,5-c]quinolin-1-yl)methyl]cyclobutanol was prepared according to the general methods of Example 57 using 4-chloro-3-nitroquinoline in lieu of 4-chloro-3-nitronaphthyridine and 1-(aminomethyl)cyclobutanol in lieu of 1-(aminomethyl)cyclohexanol in Part A and trimethylorthoacetate in lieu of trimethylorthobutyrate in Part C. The crude product was triturated sequentially with ethyl acetate, hot chloroform, and acetonitrile, purified by HPFC eluting with a gradient of 0-40% CMA in chloroform, and then suspended in water (100 mL). Concentrated hydrochloric acid (2 mL) was added and the mixture was heated to 90° C. The hot solution was made basic (pH 10) with solid sodium bicarbonate. The solution was allowed to cool to ambient temperature. A precipitate was isolated by filtration, washed well with water, and then dried to provide pure product as a white powder, mp>250.0° C. Anal. Calcd for $C_{16}H_{18}N_4O$ C, 68.06; H, 6.43; N, 19.84; Found: C, 67.99; H, 6.54; N, 19.81.

Example 109

1-[(4-Amino-2-propyl-1H-imidazo[4,5-c]quinolin-1-yl)methyl]cyclobutanol

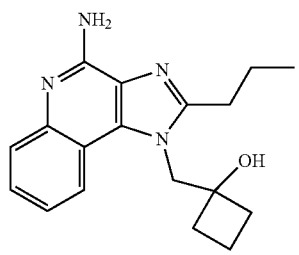 [SMILES: CCCc1nc2c(N)nc3ccccc3c2n1CC1(O)CCC1]

Part A

1-[(4-Chloro-2-propyl-1H-imidazo[4,5-c]quinolin-1-yl)methyl]cyclobutanol was prepared according to the general methods of Example 57 using 2,4-dichloro-3-nitroquinoline in lieu of 4-chloro-3-nitronaphthyridine and 1-(aminomethyl)cyclobutanol in lieu of 1-(aminomethyl)cyclohexanol in Part A.

Part B

1-[(4-Chloro-2-propyl-1H-imidazo[4,5-c]quinolin-1-yl)methyl]cyclobutanol (1.56 g) was combined with a solution of ammonia in methanol (23 mL). The mixture was heated at 150° C. in a pressure vessel for 2 days. A portion of the solvent was removed under vacuum and then the mixture was diluted with additional methanol. A solid was isolated by filtration, washed with methanol, triturated with acetonitrile, and then dried. The material was suspended in water (70 mL). Concentrated hydrochloric acid (1.4 mL) was added and the mixture was heated at 90° C. for 30 minutes. The hot solution was neutralized with solid sodium bicarbonate. The solution was allowed to cool to ambient temperature. A precipitate was isolated by filtration, washed well with water, and then dried to provide 1-[(4-amino-2-propyl-1H-imidazo[4,5-c]quinolin-1-yl)methyl]cyclobutanol as a white powder, mp 228.0-229.0° C. Anal. Calcd for $C_{18}H_{22}N_4O$ C, 69.65; H, 7.14; N, 18.05; Found: C, 69.36; H, 7.24; N, 18.03.

Example 110

1-[(4-Amino-1H-imidazo[4,5-c]quinolin-1-yl)methyl]cyclobutanol

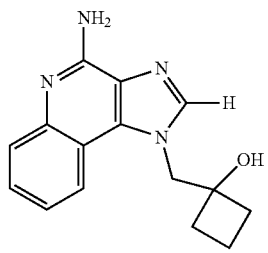 [SMILES: Nc1nc2ccccc2c2c1ncn2CC1(O)CCC1]

1-[(4-Amino-1H-imidazo[4,5-c]quinolin-1-yl)methyl]cyclobutanol was prepared according to the general methods of Example 109 using trimethylorthoformate in lieu of trimethylorthobutyrate. The crude product was triturated with refluxing 1:1 ethyl acetate:acetonitrile, purified by HPFC eluting with a gradient of 0-45% CMA in chloroform, triturated with 1:1 water:acetonitrile, and then suspended in water (80 mL). Concentrated hydrochloric acid (1.5 mL) was added and the mixture was heated at 90° C. for 10 minutes. The hot solution was made basic (pH 9) with solid sodium bicarbonate. The solution was allowed to cool to ambient temperature. A precipitate was isolated by filtration, washed well with water, and then dried. This material was triturated with sodium hydroxide (15 mL of 1N), isolated by filtration, washed well with water, and then dried to provide pure product as a white powder, mp>250.0° C. Anal. Calcd for $C_{15}H_{16}N_4O$ C, 67.15; H, 6.01; N, 20.88; Found: C, 67.06; H, 6.01; N, 21.09.

Example 111

1-[(4-Amino-2-hydroxymethyl-1H-imidazo[4,5-c]quinolin-1-yl)methyl]cyclobutanol

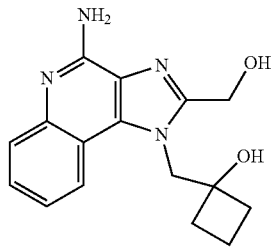 [SMILES: Nc1nc2ccccc2c2c1nc(CO)n2CC1(O)CCC1]

Part A

1-[(4-Amino-2-chloromethyl-1H-imidazo[4,5-c]quinolin-1-yl)methyl]cyclobutanol was prepared according to the general methods of Example 103 except that chloroacetyl chloride was used in lieu of ethoxyacetyl chloride and triethylamine was used in lieu of sodium hydroxide.

Part B

1-[(4-Amino-2-chloromethyl-1H-imidazo[4,5-c]quinolin-1-yl)methyl]cyclobutanol was converted to 1-[(4-amino-2-hydroxymethyl-1H-imidazo[4,5-c]quinolin-1-yl)methyl]cyclobutanol according to the general methods of Parts D and E of Example 62. The crude product was triturated with 1:1 ethyl acetate:methanol, dried, and then suspended in water (90 mL). Concentrated hydrochloric acid (1.5 mL) was added and the mixture was heated at 90° C. for 3 minutes. The mixture was allowed to cool to ambient temperature and was then made basic with solid sodium bicarbonate. A solid was isolated by filtration, rinsed well with water, dried, and then purified by HPFC eluting with a gradient of 0-60% CMA in chloroform. The resulting solid was triturated with acetonitrile, dried, and then suspended in water (80 mL). Concentrated hydrochloric acid (1.5 mL) was added and the mixture was heated at 90° C. for 10 minutes. The hot solution was made basic (pH 9) with solid sodium bicarbonate. The solution was allowed to cool to ambient temperature. A precipitate was isolated by filtration, washed well with water, and then dried to provide pure product as a white powder, mp>250.0° C. Anal. Calcd for $C_{16}H_{18}N_4O_2$ C, 64.41; H, 6.08; N, 18.78; Found: C, 64.30; H, 6.10; N, 18.54.

Example 112

1-[(4-Amino-2,6,7-trimethyl-1H-imidazo[4,5-c]pyridin-1-yl)methyl]tetrahydro-2H-pyran-4-ol

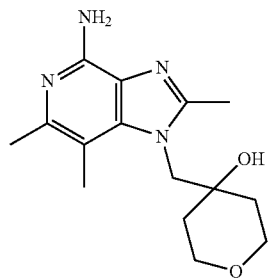 [SMILES: Cc1nc(N)c2nc(C)n(CC3(O)CCOCC3)c2c1C]

Part A

Under a nitrogen atmosphere 2,4-dichloro-5,6-dimethyl-3-nitropyridine (25 g, 113 mmol) was added to a solution of 4-(aminomethyl)tetrahydro-2H-pyran-4-ol (17 g, 130 mmol) in DMF (375 mL). Triethylamine (18 mL, 130 mmol) was added slowly and the reaction mixture was stirred at ambient temperature over the weekend. The reaction mixture was concentrated under reduced pressure and the residue was partitioned between ethyl acetate (700 mL) and saturated aqueous sodium bicarbonate (100 mL). The organic layer was washed with water (3×100 mL) and brine (50 mL), dried over magnesium sulfate, filtered, and then concentrated under reduced pressure to provide an orange solid. This material was triturated with ethyl acetate to provide 6.38 g of 4-{[(2-chloro-5,6-dimethyl-3-nitropyridin-4-yl)amino]methyl}tetrahydro-2H-pyran-4-ol as a yellow solid. An additional 4.36 g of product was recovered from the mother liquor.

Part B

4-{[(2-Chloro-5,6-dimethyl-3-nitropyridin-4-yl)amino]methyl}tetrahydro-2H-pyran-4-ol (8.74 g, 27.7 mmol), 10% platinum on carbon (874 mg), and ethyl acetate (185 mL) were combined and placed under hydrogen pressure (50 psi, $3.4 \times 10^5$ Pa) on a Parr apparatus for 4 hours. The reaction mixture was filtered through a layer of CELITE filter aid and the filter cake was washed with 1:1 ethyl acetate:methanol. The filtrate was concentrated under reduced pressure to provide crude 4-{[(3-amino-2-chloro-5,6-dimethylpyridin-4-yl)amino]methyl}tetrahydro-2H-pyran-4-ol.

Part C

Under a nitrogen atmosphere a mixture of the material from Part B, trimethylorthoacetate (1.94 mL, 15.2 mmol), pyridine hydrochloride (240 mg), and toluene was heated at reflux overnight. The reaction mixture was allowed to cool to ambient temperature. A precipitate was isolated by filtration to provide 2.35 g of 1-[(4-chloro-2,6,7-trimethyl-1H-imidazo[4,5-c]pyridin-1-yl)methyl]tetrahydro-2H-pyran-4-ol as a white solid. An additional 1.15 g was isolated from the mother liquor. A portion was recrystallized from ethyl acetate hexanes to provide pure product as a white powder, mp 217.0-218.0° C. Anal. Calcd for $C_{15}H_{20}ClN_3O_2$ C, 58.16; H, 6.51; N, 13.56; Cl, 11.44; Found: C, 58.14; H, 6.37; N, 13.31; Cl, 11.30.

Part D

1-[(4-Chloro-2,6,7-trimethyl-1H-imidazo[4,5-c]pyridin-1-yl)methyl]tetrahydro-2H-pyran-4-ol (1.00 g, 3.23 mmol), benzylamine (3.53 mL, 32.3 mmol), pyridine hydrochloride (2.52 g, 16.2 mmol) and 2,2,2-trifluoroethanol (10 mL) were combined in a process vial and heated in a microwave at 160° for 2.5 hours. The reaction mixture was concentrated under reduced pressure. The residue was dissolved in chloroform (200 mL), washed with saturated aqueous sodium bicarbonate (3×50 mL) and brine (30 mL), dried over magnesium sulfate, filtered, and then concentrated under reduced pressure to provide a yellow solid. This material was triturated with acetonitrile to provide 1.14 g of 1-{[4-(benzylamino)-2,6,7-trimethyl-1H-imidazo[4,5-c]pyridin-1-yl]methyl}tetrahydro-2H-pyran-4-ol as a white solid.

Part E

The benzyl group was removed from the material from Part D according to the general method of Part E of Example 59. The crude product was triturated with acetonitrile and dried to provide a white solid. This material was dissolved in chloroform (200 mL), washed with saturated aqueous sodium bicarbonate (2×40 mL) and brine (30 mL), dried over sodium sulfate, filtered, and then concentrated under reduced pressure. The residue was triturated with acetonitrile and dried to provide 1-[(4-amino-2,6,7-trimethyl-1H-imidazo[4,5-c]pyridin-1-yl)methyl]tetrahydro-2H-pyran-4-ol as a white powder, mp>250.0° C. Anal. Calcd for $C_{15}H_{22}N_4O_2$ C, 62.05; H, 7.64; N, 19.30; Found: C, 61.89; H, 7.77; N, 19.34.

Example 113

1-[(2,6,7-Trimethyl-1H-imidazo[4,5-c]pyridin-1-yl)methyl]tetrahydro-2H-pyran-4-ol

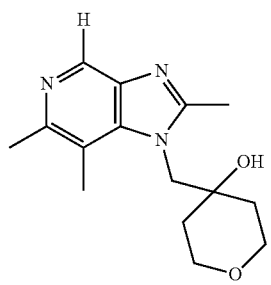 [SMILES: Cc1ncc2nc(C)n(CC3(O)CCOCC3)c2c1C]

A mixture of 1-[(4-chloro-2,6,7-trimethyl-1H-imidazo[4,5-c]pyridin-1-yl)methyl]tetrahydro-2H-pyran-4-ol (1.0 g), 10% palladium on carbon (200 mg), and ethanol (16 mL) were combined and placed under hydrogen pressure (50 psi, 3.4×10⁵ Pa) on a Parr apparatus for 6 days. The reaction mixture was filtered through a layer of CELITE filter aid and the filter cake was washed with methanol. The filtrate was concentrated under reduced pressure. The residue was triturated with acetonitrile to provide a solid. This material was dissolved in dichloromethane (100 mL) and washed with sodium hydroxide (1N, 2×30 mL) and brine, dried over sodium sulfate, filtered, and then concentrated under reduced pressure. The residue was triturated with acetonitrile to provide 1-[(2,6,7-trimethyl-1H-imidazo[4,5-c]pyridin-1-yl)methyl]tetrahydro-2H-pyran-4-ol as a white powder, mp 246.0-248.0° C. Anal. Calcd for $C_{15}H_{21}N_3O_2$ C, 65.43; H, 7.69; N, 15.26; Found: C, 65.53; H, 7.79; N, 15.42.

Example 114

1-[(4-Amino-2-ethoxymethyl-6,7-dimethyl-1H-imidazo[4,5-c]pyridin-1-yl)methyl]tetrahydro-2H-pyran-4-ol

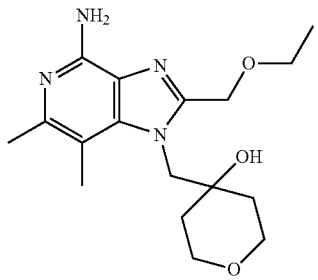 [SMILES: CCOCc1nc2c(N)nc(C)c(C)c2n1CC1(O)CCOCC1]

Part A

Under a nitrogen atmosphere ethoxyacetyl chloride (2.26 g, 16.6 mmol) was added dropwise to a chilled (0° C.) suspension of 4-{[(3-amino-2-chloro-5,6-dimethylpyridin-4-yl)amino]methyl}tetrahydro-2H-pyran-4-ol (3.96 g) in dichloromethane (140 mL). The reaction mixture was stirred at ambient temperature overnight. The reaction mixture was cooled to 0° C., more ethoxyacetyl chloride (0.3 mL) was added, and the reaction mixture was stirred at ambient temperature for an additional 4 hours. The reaction mixture was concentrated under reduced pressure to provide crude N-(2-chloro-4-{[(4-hydroxytetrahydro-2H-pyran-4-yl)methyl]amino}-5,6-dimethylpyridin-3-yl)-2-ethoxyacetamide.

Part B

Sodium hydroxide (1.11 g, 27.7 mmol) was added to a suspension of the material from Part A in ethanol (138 mL). The reaction mixture was heated at reflux for 1.5 hours and then concentrated under reduced pressure. The residue was dissolved in dichloromethane (400 mL), washed with water (2×80 mL) and brine (40 mL), dried over magnesium sulfate, filtered, and then concentrated under reduced pressure to provide 4.46 g of a yellow solid. This material was triturated with ethyl acetate and then recrystallized from ethyl acetate/hexanes to provide 1-[(4-chloro-2-ethoxymethyl-6,7-dimethyl-1H-imidazo[4,5-c]pyridin-1-yl)methyl]tetrahydro-2H-pyran-4-ol as a white powder, mp 151.0-152.0° C. Anal. Calcd for $C_{17}H_{24}ClN_3O_3$ C, 57.70; H, 6.84; N, 11.88; Cl, 10.02; Found: C, 57.57; H, 6.87; N, 11.68; Cl, 10.00.

Part C

1-[(4-Chloro-2-ethoxymethyl-6,7-dimethyl-1H-imidazo[4,5-c]pyridin-1-yl)methyl]tetrahydro-2H-pyran-4-ol (1.4 g) was converted to 1-[(4-amino-2-ethoxymethyl-6,7-dimethyl-1H-imidazo[4,5-c]pyridin-1-yl)methyl]tetrahydro-2H-pyran-4-ol according to the general methods of Parts D and E of Example 112. The crude product was dissolved in chloroform (200 mL) and methanol (10 mL), washed with saturated aqueous sodium bicarbonate (2×40 mL) and brine (30 mL), dried over sodium sulfate, filtered, and then concentrated under reduced pressure. The residue was triturated with acetonitrile and dried to provide pure product as a white powder, mp 197.0-198.0° C. Anal. Calcd for $C_{17}H_{26}N_4O_3$ C, 61.06; H, 7.84; N, 16.75; Found: C, 60.91; H, 8.18; N, 16.87.

Example 115

1-[(2-Ethoxymethyl-6,7-dimethyl-1H-imidazo[4,5-c]pyridin-1-yl)methyl]tetrahydro-2H-pyran-4-ol

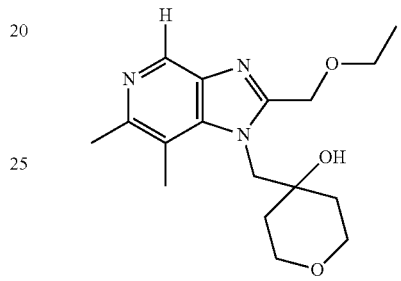

A mixture of 1-[(4-chloro-2-ethoxymethyl-6,7-dimethyl-1H-imidazo[4,5-c]pyridin-1-yl)methyl]tetrahydro-2H-pyran-4-ol (1.0 g), 10% palladium on carbon (200 mg), and ethanol (16 mL) were combined and placed under hydrogen pressure (50 psi, 3.4×10⁵ Pa) on a Parr apparatus for 1 week. The reaction mixture was filtered through a layer of CELITE filter aid and the filter cake was washed with methanol. The filtrate was concentrated under reduced pressure. The residue was dissolved in dichloromethane (150 mL) and washed with sodium hydroxide (1N, 2×20 mL) and brine (20 mL), dried over sodium sulfate, filtered, and then concentrated under reduced pressure. The residue was triturated with acetonitrile and then recrystallized from acetonitrile to provide 1-[(2-ethoxymethyl-6,7-dimethyl-1H-imidazo[4,5-c]pyridin-1-yl)methyl]tetrahydro-2H-pyran-4-ol as a white powder, mp 144.0-145.0° C. Anal. Calcd for $C_{17}H_{25}N_3O_3$ C, 63.93; H, 7.89; N, 13.16; Found: C, 63.68; H, 7.89; N, 13.04.

Example 116

4-[(4-Amino-2-propyl-1H-imidazo[4,5-c]quinolin-1-yl)methyl]tetrahydro-2H-thiopyran-4-ol

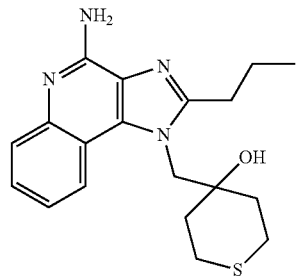

Part A

Under a nitrogen atmosphere sodium methoxide (1.03 mL of 25 wt % in methanol, 4.51 mmol) was added dropwise to a solution of tetrahydro-4H-thiopyran-4-one (10.48 g, 90.20 mol) and nitromethane (7.33 mL, 135.3 mmol) in ethanol (6 mL). The reaction mixture was stirred at ambient temperature for 5 days and then concentrated under reduced pressure. The residue was partitioned between chloroform (400 mL) and water (60 mL). The aqueous was extracted with chloroform (5×100 mL). The combined organics were dried over magnesium sulfate, filtered, and then concentrated under reduced pressure. The residue was purified by HPFC eluting with a gradient of 3-35% ethyl acetate in hexanes to provide 10.23 g of 4-(nitromethyl)tetrahydro-2H-thiopyran-4-ol.

Part B

The material from Part B, 20% palladium hydroxide on carbon (2.0 g), and ethanol (165 mL) were combined and placed under hydrogen pressure (50 psi, 3.4×10$^5$ Pa) on a Parr apparatus for 1 week. The reaction mixture was filtered through a layer of CELITE filter aid and the filter cake was washed with methanol. The filtrate was concentrated under reduced pressure. The residue was dried under high vacuum to provide 8.54 g of 4-(aminomethyl)tetrahydro-2H-thiopyran-4-ol as a white semi-solid.

Part C

Under a nitrogen atmosphere triethylamine (3.91 mL, 28.0 mmol) was added to a chilled (0° C.) solution of 2,4-dichloro-3-nitroquinoline (7.22 g, 26.7 mmol) in dichloromethane (100 mL). A solution of 4-(aminomethyl)tetrahydro-2H-thiopyran-4-ol (4.12 g, 28.0 mmol) in dichloromethane (30 mL) was added dropwise. The reaction mixture was stirred at ambient temperature overnight and then concentrated under reduced pressure. The orange residue was combined with saturated aqueous sodium bicarbonate (50 mL) and ethyl acetate (40 mL), sonicated for 10 minutes, and then filtered. The isolated solid was washed extensively with water and then dried to provide 5.63 g of 4-{[(2-chloro-3-nitroquinolin-4-yl)amino]methyl}tetrahydro-2H-thiopyran-4-ol as a yellow solid.

Part D

A portion (1.00 g) of the material from Part C, 5% platinum on carbon (200 mg g) and ethyl acetate (28 mL) were combined and placed under hydrogen pressure (50 psi, 3.4×10$^5$ Pa) on a Parr apparatus overnight. The reaction mixture was filtered through a layer of CELITE filter aid and the filter cake was washed with methanol. The filtrate was concentrated under reduced pressure to provide 4-{[(3-amino-2-chloroquinolin-4-yl)amino]methyl}tetrahydro-2H-thiopyran-4-ol as an off-white solid.

Part E

Under a nitrogen atmosphere butyryl chloride (322 µL, 3.11 mmol) was added dropwise was added to a suspension of 4-{[(3-amino-2-chloroquinolin-4-yl)amino] methyl}tetrahydro-2H-thiopyran-4-ol (0.92 g, 2.83 mmol) in dichloromethane (28 mL). After 2 hours triethylamine (0.79 mL, 5.66 mol) was added and the reaction mixture was stirred for 2 hours. More butyryl chloride (0.2 mL) and triethylamine (0.30 mL) were added. The reaction mixture was stirred for an additional hour and then diluted with saturated aqueous sodium bicarbonate (50 mL) and extracted with dichloromethane (3×60 mL). The combined organics were washed with saturated aqueous sodium bicarbonate (40 mL) and brine (30 mL), dried over sodium sulfate, filtered, and then concentrated under reduced pressure to provide N-(2-chloro-4-{[(4-hydroxytetrahydro-2Hthiopyran-4-yl)methyl]amino)}quinolin-3-yl)butanamide as an off-white solid.

Part F

The material from Part E was combined with a solution of ammonia in methanol (17 mL of 7N) in a pressure vessel. The vessel was sealed and heated at 150° C. for 24 hours. A solid was isolated by filtration and rinsed with methanol to provide 0.60 g of yellow needles. This material was combined with acetonitrile and sonicated. A white solid was isolated by filtration, rinsed with acetonitrile, and dried under high vacuum at 120° C. to provide 538 mg of 4-[(4-amino-2-propyl-1H-imidazo[4,5-c]quinolin-1-yl) methyl]tetrahydro-2H-thiopyran-4-ol as a white powder, mp 243.0-244.0° C. Anal. Calcd for $C_{19}H_{24}N_4OS$ C, 64.02; H, 6.79; N, 15.72; Found: C, 64.20; H, 6.99; N, 15.52.

Example 117

4-[(4-Amino-2-propyl-1H-imidazo[4,5-c]quinolin-1-yl)methyl]tetrahydro-2H-thiopyran-4-ol 1,1-dioxide

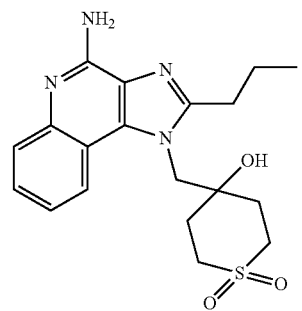 [SMILES: CCCc1nc2c(N)nc3ccccc3c2n1CC1(O)CCS(=O)(=O)CC1]

Under a nitrogen atmosphere 3-chloroperbenzoic acid (1.20 g of 70%, 4.89 mmol) was added to a cooled (0° C.) solution of 4-[(4-amino-2-propyl-1H-imidazo[4,5-c]quinolin-1-yl)methyl]tetrahydro-2H-thiopyran-4-ol (0.79 g, 2.22 mmol) in chloroform (22 mL) and methanol (22 mL). The reaction mixture was warmed to ambient temperature. The reaction mixture was treated with additional 3-chloroperbenzoic acid (0.8 g total) and stirred until analysis by LC-MS (liquid chromatography-mass spectroscopy) indicated that the reaction was complete. The reaction mixture was diluted with saturated aqueous sodium carbonate (50 mL) and then extracted with chloroform (4×50 mL). The combined organics were washed with brine (20 mL), dried over sodium sulfate, filtered, and then concentrated under reduced pressure to provide 1.1 g of a brown solid. This material was purified by HPFC eluting with a gradient of 0-30% CMA in chloroform to give 0.43 g of a solid. This material was triturated with acetonitrile and dried under high vacuum at 130° C. to provide 266 mg of 4-[(4-amino-2-propyl-1H-imidazo[4,5-c]quinolin-1-yl)methyl]tetrahydro-2H-thiopyran-4-ol 1,1-dioxide as a tan powder, mp>250.0° C. Anal. Calcd for $C_{19}H_{24}N_4O_3S$ C, 58.74; H, 6.23; N, 14.42; Found: C, 58.71; H, 6.14; N, 14.42.

Example 118

4-[(4-Amino-2-ethyl-1H-imidazo[4,5-c]quinolin-1-yl)methyl]tetrahydro-2H-thiopyran-4-ol

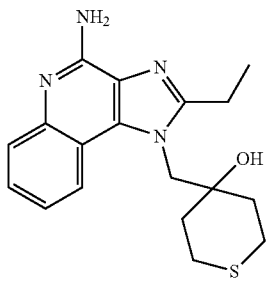 [SMILES: CCc1nc2c(N)nc3ccccc3c2n1CC1(O)CCSCC1]

4-[(4-Amino-2-ethyl-1H-imidazo[4,5-c]quinolin-1-yl) methyl]tetrahydro-2H-thiopyran-4-ol was prepared according to the general methods of Example 116 using propionyl chloride in lieu of butyryl chloride in Part E. The crude product was recrystallized from methanol/chloroform, isolated by filtration, rinsed with chloroform and methanol, and then dried under high vacuum at 130° C. to provide pure product as a white powder, mp>250.0° C. Anal. Calcd for $C_{18}H_{22}N_4OS \cdot 0.2H_2O$ C, 62.47; H, 6.52; N, 16.19; Found: C, 62.47; H, 6.37; N, 16.09.

Example 119

4-[(4-Amino-2-ethyl-1H-imidazo[4,5-c]quinolin-1-yl)methyl]tetrahydro-2H-thiopyran-4-ol 1,1 dioxide

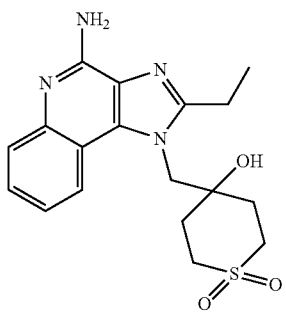 [SMILES: CCc1nc2c(N)nc3ccccc3c2n1CC1(O)CCS(=O)(=O)CC1]

4-[(4-Amino-2-ethyl-1H-imidazo[4,5-c]quinolin-1-yl) methyl]tetrahydro-2H-thiopyran-4-ol (900 mg) was oxidized according to the method of Example 117. The crude product (1.1 g of a brown solid) was triturated with acetonitrile, and then purified by HPFC eluting with a gradient of 0-40% CMA in chloroform to provide 1.1 g of a brown solid. This material was triturated with acetonitrile and dried under high vacuum at 120° C. to provide 330 mg of 4-[(4-amino-2-ethyl-1H-imidazo[4,5-c]quinolin-1-yl)methyl]tetrahydro-2H-thiopyran-4-ol 1,1 dioxide as a white powder, mp>250.0° C. Anal. Calcd for $C_{18}H_{22}N_4O_3S$ C, 57.74; H, 5.92; N, 14.96; Found: C, 57.51; H, 5.97; N, 15.13.

Example 120 tert-Butyl 4-[(4-amino-2-ethyl-1H-imidazo[4,5-c][1,5]naphthyridin-1-yl)methyl]-4-hydroxypiperidine-1-carboxylate

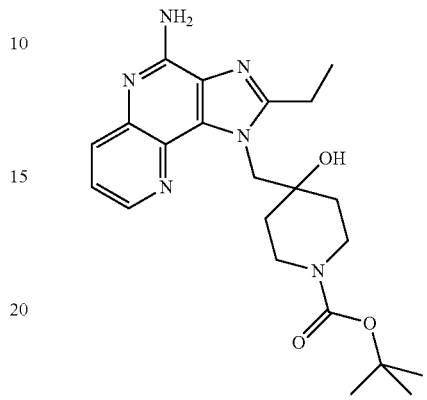

Part A

Under a nitrogen atmosphere a solution of tert-butyl 4-(aminomethyl)-4-hydroxypiperidine-1-carboxylate (38.9 g, 169 mmol, prepared according to Parts A and B of Example 4) in dichloromethane (420 mL) was cooled to 0° C. Triethylamine (23.6 mL, 169 mmol) was added followed by the portionwise addition of 4-chloro-3-nitronaphthyridine (30.8 g, 147 mmol). The reaction mixture was stirred at ambient temperature overnight and then diluted with saturated aqueous sodium bicarbonate (200 mL). The layers were separated and the aqueous was extracted with dichloromethane (3×100 mL). The combined organics were concentrated under reduced pressure to provide a dark yellow solid. This material was triturated with saturated aqueous sodium bicarbonate, isolated by filtration, rinsed well with water, and then dried in a vacuum oven at 70° C. overnight to provide 58.85 g of tert-butyl 4-hydroxy-4-{[(3-nitro[1,5]naphthyridin-4-yl)amino]methyl}piperidine-1-carboxylate as a yellow solid.

Part B

The material from Part A, 5% platinum on carbon (5.89 g), and ethyl acetate (500 mL) were combined and placed under hydrogen pressure (30 psi, $2.1 \times 10^5$ Pa) on a Parr apparatus for 2.5 hours. The reaction mixture was filtered through a layer of CELITE filter aid and the filter cake was washed with ethyl acetate. The filtrate was concentrated under reduced pressure to provide tert-butyl 4-hydroxy-4-{[(3-amino[1,5]naphthyridin-4-yl)amino]methyl}piperidine-1-carboxylate.

Part C

Under a nitrogen atmosphere a portion (27.24 g, 72.9 mmol) of the material from Part B was combined with toluene (300 mL), triethylorthopropionate (16.1 mL, 80.2 mmol), and pyridine hydrochloride (1.3 g, 10.9 mmol). The reaction mixture was stirred at reflux for 3 hours, allowed to cool to ambient temperature, and then concentrated under reduced pressure. The residue was dried under high vacuum, dissolved in chloroform (500 mL), washed with saturated aqueous sodium bicarbonate (2×80 mL) and brine (40 mL), dried over magnesium sulfate, filtered, and then concentrated under reduced pressure to provide 34 g of a yellow solid. This material was triturated with ethyl acetate/ hexanes, isolated by filtration, rinsed with hexanes, and then dried to provide tert-butyl 4-[(2-ethyl-1H-imidazo[4,5-c][1,5]naphthyridin-1-yl)methyl]-4-hydroxypiperidine-1-carboxylate. A portion (2 g) of this material was recrystallized from ethyl acetate/hexanes, isolated by filtration, rinsed with hexanes, and then dried under vacuum at 120° C. to provide 1.1 g of pure product as a white powder, mp 155.0-156.0° C. Anal. Calcd for $C_{22}H_{29}N_5O_3$ C, 64.21; H, 7.10; N, 17.02; Found: C, 63.99; H, 6.88; N, 16.90.

Part D

Under a nitrogen atmosphere, 3-chloroperoxybenzoic acid (13.8 g of 70%, 56.0 mmol) was added to a solution of tert-butyl 4-[(2-ethyl-1H-imidazo[4,5-c][1,5]naphthyridin-1-yl)methyl]-4-hydroxypiperidine-1-carboxylate (16.5 g, 40.0 mmol) in chloroform (160 mL). After 1.5 hours the reaction mixture was concentrated under reduced pressure to provide a yellow foam. Under a nitrogen atmosphere this material was dissolved in methanol (160 mL) and then cooled to 0° C. Ammonium hydroxide (13.3 mL, 200 mmol) was slowly added followed by the dropwise addition of benzenesulfonyl chloride (10.7 mL, 84.0 mmol). The reaction mixture was stirred at 0° C. for 1.5 hours and then concentrated under reduced pressure. The residue was partitioned between chloroform (400 mL) and saturated aqueous sodium bicarbonate (50 mL). The organic was washed with saturated aqueous sodium bicarbonate (50 mL) and brine (30 mL), dried over magnesium sulfate, filtered, and then concentrated under reduced pressure. The residue was triturated with ethyl acetate to provide a yellow solid. This material was triturated with saturated aqueous sodium carbonate to provide 7.2 g of a yellow solid. A portion (1.2 g) of this material was triturated twice with acetonitrile, isolated by filtration, and dried under vacuum at 120° C. to provide 736 mg of tert-butyl 4-[(4-amino-2-ethyl-1H-imidazo[4,5-c][1,5]naphthyridin-1-yl)methyl]-4-hydroxypiperidine-1-carboxylate as a white powder, mp 233.0-235.0° C. Anal. Calcd for $C_{22}H_{30}N_6O_3$ C, 61.95; H, 7.09; N, 19.70; Found: C, 61.78; H, 7.15; N, 19.51.

Example 121

4-[(4-Amino-2-ethyl-1H-imidazo[4,5-c][1,5]naphthyridin-1-yl)methyl]piperidin-4-ol

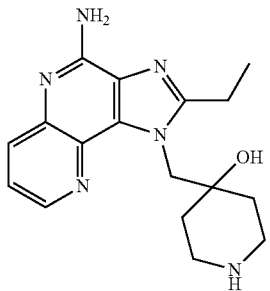 [SMILES: CCc1nc2c(N)nc3cccnc3c2n1CC1(O)CCNCC1]

Part A

Under a nitrogen atmosphere a mixture of tert-butyl 4-[(4-amino-2-ethyl-1H-imidazo[4,5-c][1,5]naphthyridin-1-yl)methyl]-4-hydroxypiperidine-1-carboxylate (6.00 g), aqueous hydrochloric acid (14 mL of 6M), and ethanol (56 mL) was heated at 50° C. overnight. The reaction mixture was concentrated under reduced pressure. The residue was concentrated from methanol 3 times, triturated with acetonitrile, isolated by filtration, washed with acetonitrile, and then dried under high vacuum to provide 5.55 g of 4-[(4-amino-2-ethyl-1H-imidazo[4,5-c][1,5]naphthyridin-1-yl)methyl]piperidin-4-ol dihydrochloride as a tan powder.

Part B

A mixture of 4-[(4-amino-2-ethyl-1H-imidazo[4,5-c][1,5]naphthyridin-1-yl)methyl]piperidin-4-ol dihydrochloride (0.80 g) and 1N sodium hydroxide (8 mL) was sonicated for 2 minutes. A solid was isolated by filtration, washed with water, and dried. This procedure was repeated and the material was dried under high vacuum at 120° C. to provide 0.61 g of 4-[(4-amino-2-ethyl-1H-imidazo[4,5-c][1,5]naphthyridin-1-yl)methyl]piperidin-4-ol as a tan powder, mp 232.0-233.0° C. Anal. Calcd for $C_{17}H_{22}N_6O$ C, 62.56; H, 6.79; N, 25.75; Found: C, 62.43; H, 7.04; N, 25.78.

Example 122

4-[(4-Amino-2-ethyl-1H-imidazo[4,5-c][1,5]naphthyridin-1-yl)methyl]-1-(morpholin-4-ylcarbonyl)piperidin-4-ol

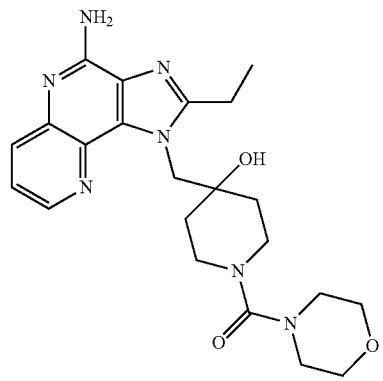 [SMILES: CCc1nc2c(N)nc3cccnc3c2n1CC1(O)CCN(C(=O)N2CCOCC2)CC1]

Under a nitrogen atmosphere triethylamine (1.39 mL, 10.0 mmol) was added to a suspension of 4-[(4-amino-2-ethyl-1H-imidazo[4,5-c][1,5]naphthyridin-1-yl)methyl]piperidin-4-ol dihydrochloride (1.00 g, 2.50 mmol) in dichloromethane (25 mL). The mixture was cooled to −5° C. 4-Morpholinecarbonyl chloride (292 µL, 2.50 mmol) was added and the reaction mixture was allowed to slowly warm to ambient temperature. The reaction mixture was stirred at ambient temperature for 2 days and then at 30° C. for 2 days. More 4-morpholinecarbonyl chloride (30 µL) was added and the reaction mixture was stirred at 30° C. for 5 days. The reaction mixture was concentrated under reduced pressure. The residue was partitioned between chloroform (150 mL) and saturated aqueous sodium carbonate (30 mL). The organic was washed with saturated aqueous sodium carbonate (20 mL) and brine (20 mL), dried over sodium sulfate, filtered, and then concentrated under reduced pressure to provide an off white solid. This material was triturated with acetonitrile, recrystallized from chloroform/hexanes, isolated by filtration, washed with hexanes, and dried under high vacuum at 130° C. to provide 0.97 g of 4-[(4-amino-2-ethyl-1H-imidazo[4,5-c][1,5]naphthyridin-1-yl)methyl]-1-(morpholin-4-ylcarbonyl)piperidin-4-ol as a white powder, mp>255.0° C. Anal. Calcd for $C_{22}H_{29}N_7O_3 \cdot 0.25H_2O$ C, 59.51; H, 6.70; N, 22.08; Found: C, 59.32; H, 6.36; N, 22.00.

Example 123

4-[(4-Amino-2-ethyl-1H-imidazo[4,5-c][1,5]naphthyridin-1-yl)methyl]-1-(methyl sulfonyl)piperidin-4-ol

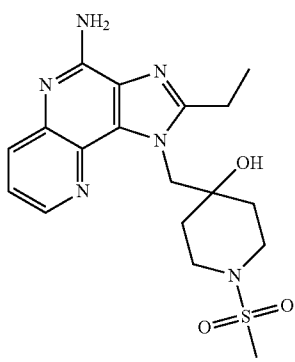 [SMILES: CCc1nc2c(N)nc3cccnc3c2n1CC1(O)CCN(S(C)(=O)=O)CC1]

Under a nitrogen atmosphere triethylamine (1.12 mL, 8.06 mmol) was added to a suspension of 4-[(4-amino-2-ethyl-1H-imidazo[4,5-c][1,5]naphthyridin-1-yl)methyl]piperidin-4-ol dihydrochloride (1.04 g, 2.60 mmol) in chloroform (26 mL). Methanesulfonic anhydride (0.50 g, 2.86 mmol) was added and the reaction mixture was stirred at ambient temperature. After 1.5 hours more methanesulfonic anhydride (0.25 g) was added and a solution was obtained. On two successive days more methanesulfonic anhydride (0.50 g) and triethylamine (360 µL) were added. The reaction mixture was stirred for 2 hours after the second addition and then concentrated under reduced pressure. The residue was triturated with saturated aqueous sodium bicarbonate, isolated by filtration, washed with water, triturated with hot chloroform, isolated by filtration, washed with chloroform and hexanes, dried, triturated with acetonitrile, sonicated, isolated by filtration, and then dried under high vacuum at 130° C. to provide 4-[(4-amino-2-ethyl-1H-imidazo[4,5-c][1,5]naphthyridin-1-yl)methyl]-1-(methylsulfonyl)piperidin-4-ol as a white powder, mp>255.0° C. Anal. Calcd for $C_{18}H_{24}N_6O_3S$ C, 53.45; H, 5.98; N, 20.78; Found: C, 53.55; H, 5.71; N, 20.75.

Example 124 tert-butyl 4-[(4-Amino-2-methyl-1H-imidazo[4,5-c][1,5]naphthyridin-1-yl)methyl]-4-hydroxypiperidine-1-carboxylate

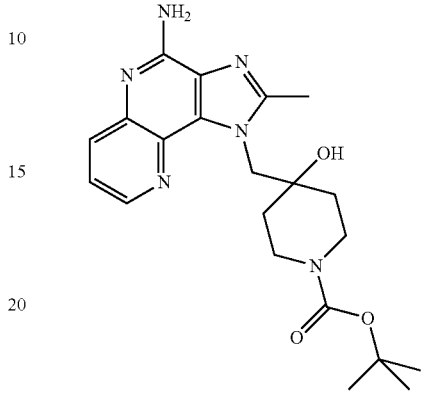

Part A tert-Butyl 4-[(2-methyl-1H-imidazo[4,5-c][1,5]naphthyridin-1-yl)methyl]-4-hydroxypiperidine-1-carboxylate was prepared according to the methods of Parts A through C of Example 120 using trimethylorthoacetate in lieu of triethylorthopropionate in Part C. The product was provided as a white powder, mp 175.0-176.0° C. Anal. Calcd for $C_{21}H_{27}N_5O_3$ C, 63.46; H, 6.85; N, 17.62; Found: C, 63.30; H, 6.77; N, 17.53.

Part B tert-Butyl 4-[(2-methyl-1H-imidazo[4,5-c][1,5]naphthyridin-1-yl)methyl]-4-hydroxypiperidine-1-carboxylate (15.9 g) was oxidized and then aminated according to the methods of Part D of Example 120. The crude product was triturated with ethyl acetate to provide 5.8 g of a yellow solid. A portion (0.8 g) of this material was twice triturated with acetonitrile, isolated by filtration, and dried under high vacuum at 120° C. to provide tert-butyl 4-[(4-amino-2-methyl-1H-imidazo[4,5-c][1,5]naphthyridin-1-yl)methyl]-4-hydroxypiperidine-1-carboxylate as a white powder, mp 233.0-235.0° C. Anal. Calcd for $C_{21}H_{28}N_6O_3 \cdot 0.5H_2O$ C, 59.84; H, 6.93; N, 19.94; Found: C, 59.96; H, 6.78; N, 19.59.

Example 125

4-[(4-Amino-2-methyl-1H-imidazo[4,5-c][1,5]naphthyridin-1-yl)methyl]piperidin-4-ol

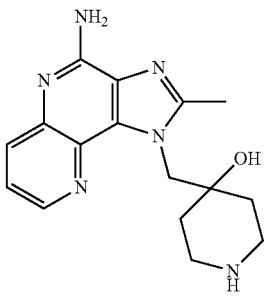 [SMILES: Cc1nc2c(N)nc3cccnc3c2n1CC1(O)CCNCC1]

Part A

Under a nitrogen atmosphere a mixture of tert-butyl 4-[(4-amino-m2-ethyl-1H-imidazo[4,5-c][1,5]naphthyridin-1-yl)methyl]-4-hydroxypiperidine-1-carboxylate (5.00 g), aqueous hydrochloric acid (12 mL of 6M), and ethanol (48 mL) was heated at 50° C. overnight. The reaction mixture was concentrated under reduced pressure. The residue was concentrated from methanol 3 times, triturated with acetonitrile, isolated by filtration, washed with acetonitrile, and then dried under high vacuum to provide 4.67 g of 4-[(4-amino-2-methyl-1H-imidazo[4,5-c][1,5]naphthyridin-1-yl)methyl]piperidin-4-ol dihydrochloride as a pale yellow solid.

Part B

A mixture of 4-[(4-amino-2-methyl-1H-imidazo[4,5-c][1,5]naphthyridin-1-yl)methyl]piperidin-4-ol dihydrochloride (0.80 g) and 1N sodium hydroxide (8 mL) was sonicated for 2 minutes. A solid was isolated by filtration, washed with water, and dried under high vacuum at 100° C. to provide 0.50 g of 4-[(4-amino-2-methyl-1H-imidazo[4,5-c][1,5]naphthyridin-1-yl)methyl]piperidin-4-ol as a yellow powder, mp>260.0° C. Anal. Calcd for $C_{16}H_{20}N_6O$ C, 61.52; H, 6.45; N, 26.90; Found: C, 61.23; H, 6.39; N, 26.92.

Example 126

4-[(4-Amino-2-methyl-1H-imidazo[4,5-c][1,5]naphthyridin-1-yl)methyl]-1-(morpholin-4-ylcarbonyl)piperidin-4-ol

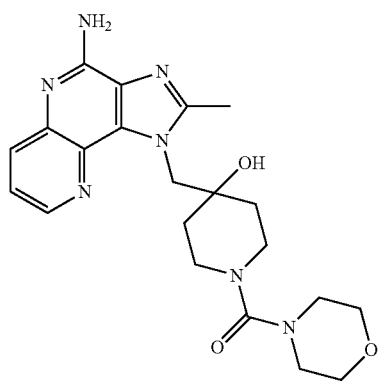 [SMILES: Cc1nc2c(N)nc3cccnc3c2n1CC1(O)CCN(C(=O)N2CCOCC2)CC1]

4-[(4-Amino-2-methyl-1H-imidazo[4,5-c][1,5]naphthyridin-1-yl)methyl]-1-(morpholin-4-ylcarbonyl)piperidin-4-ol was prepared and purified according to the general method of Example 122 using 4-[(4-amino-2-methyl-1H-imidazo[4,5-c][1,5]naphthyridin-1-yl)methyl]piperidin-4-ol dihydrochloride in lieu of 4-[(4-amino-2-ethyl-1H-imidazo[4,5-c][1,5]naphthyridin-1-yl)methyl]piperidin-4-ol dihydrochloride. The product was provided as a white powder, mp 245.0-248.0° C. Anal. Calcd for $C_{21}H_{27}N_7O_3$ C, 59.28; H, 6.40; N, 23.04; Found: C, 58.98; H, 6.67; N, 22.91.

Example 127

4-[(4-Amino-2-methyl-1H-imidazo[4,5-c][1,5]naphthyridin-1-yl)methyl]-1-(methyl sulfonyl)piperidin-4-ol

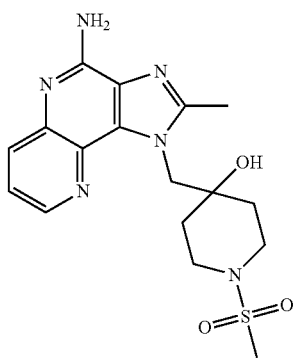 [SMILES: Cc1nc2c(N)nc3cccnc3c2n1CC1(O)CCN(S(C)(=O)=O)CC1]

4-[(4-Amino-2-methyl-1H-imidazo[4,5-c][1,5]naphthyridin-1-yl)methyl]-1-(methylsulfonyl)piperidin-4-ol was prepared and purified according to the general method of Example 123 using 4-[(4-amino-2-methyl-1H-imidazo[4,5-c][1,5]naphthyridin-1-yl)methyl]piperidin-4-ol dihydrochloride in lieu of 4-[(4-amino-2-ethyl-1H-imidazo[4,5-c][1,5]naphthyridin-1-yl)methyl]piperidin-4-ol dihydrochloride. The product was provided as a white powder, mp>255.0° C. Anal. Calcd for $C_{17}H_{22}N_6O_3S$ C, 52.29; H, 5.68; N, 21.52; Found: C, 52.14; H, 5.39; N, 21.38.

Example 128

1-[(1-Aminocyclohexyl)methyl]-2-ethoxymethyl-1H-imidazo[4,5-c]quinolin-4-amine

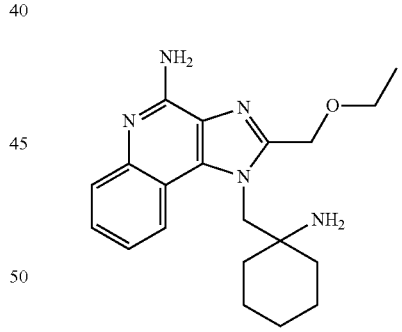

Part A

Tert-butyl 1-[(2-ethoxymethyl-1H-imidazo[4,5-c]quinolin-1-yl)methyl]cyclohexylcarbamate (3.80 g, Example 54 Parts A through F) was oxidized and aminated according to the general methods of Part F of Example 10 to provide 2.46 g of tert-butyl 1-[(4-amino-2-ethoxymethyl-1H-imidazo[4,5-c]quinolin-1-yl)methyl]cyclohexylcarbamate as a light tan frothy solid, mp 82.0-92.0° C.

Part B

Under a nitrogen atmosphere a mixture of the material from Part A, hydrochloric acid (25 mL of 2.7M in ethanol), and ethanol (50 mL) was heated at reflux for 2 hours. The reaction mixture was diluted with isopropanol. A solid was isolated by filtration and then partitioned between dichloromethane (100 mL) and 5% sodium carbonate (100 mL). The aqueous layer was extracted with dichloromethane (2×100 mL). The organics were combined, dried over magnesium sulfate, filtered, and then concentrated under reduced pressure to provide a light yellow oil. This material was purified by column chromatography (silica gel eluting with 90/10 dichloromethane/methanol) to provide a clear oil. The oil was dissolved in methanol and then concentrated under reduced pressure to provide 1.10 g of 1-[(1-aminocyclohexyl)methyl]-2-ethoxymethyl-1H-imidazo[4,5-c]quinolin-4-amine as a white frothy solid, mp 166-168° C. $^1$H NMR (300 MHz, CDCl$_3$) δ 8.26 (m, 1H), 7.80 (m, 1H), 7.49 (ddd, J=8.3, 6.9, 1.4 Hz, 1H), 7.30 (ddd, J=8.3, 6.9, 1.4 Hz, 1H), 5.45 (br s, 2H), 5.02 (br s, 2H), 4.66 (br s, 2H), 3.57 (q, J=7.0 Hz, 2H), 1.70-1.37 (m, 10H), 1.29-0.94 (m, 2H), 1.23 (t, J=7.0 Hz, 3H); MS (APCI) m/z 354 (M+H)$^+$; Anal. Calcd for C$_{20}$H$_{27}$N$_5$O.0.25H$_2$O: C, 67.11; H, 7.74; N, 19.56. Found: C, 67.06; H, 7.74; N, 19.36.

Example 129

Ethyl 1-[(4-amino-2-ethoxymethyl-1H-imidazo[4,5-c]quinolin-1-yl)methyl]cyclohexylcarbamate

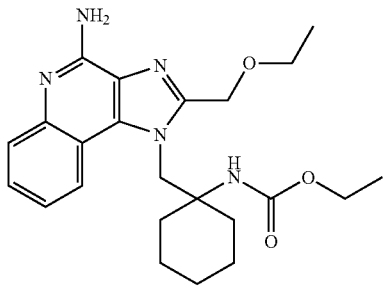 [SMILES: CCOCc1nc2c(N)nc3ccccc3c2n1CC1(NC(=O)OCC)CCCCC1]

Part A

Under a nitrogen atmosphere a mixture of 1-[(2-ethoxymethyl-1H-imidazo[4,5-c]quinolin-1-yl)methyl]cyclohexylamine (2.00 g, 5.91 mmol, Example 54 Parts A through G) and THF (40 mL) was cooled in an ice bath. Sodium hydroxide (0.24 g, 5.97 mmol, in 3 mL of water) was added dropwise followed by diethylpyrocarbonate (0.87 mL, 5.91 mmol). After two days an additional 0.5 eq of both sodium hydroxide and diethylpyrocarbonate were added. After 5 days the reaction mixture was concentrated under reduced pressure. The residue was partitioned between water (100 mL) and dichloromethane (100 mL). The organic was dried over magnesium sulfate, filtered, and then concentrated under reduced pressure to provide an oil. This material was purified by column chromatography (silica gel eluting with 95/5 ethyl acetate/methanol) to provide 1.89 g of ethyl 1-[(2-ethoxymethyl-1H-imidazo[4,5-c]quinolin-1-yl)methyl]cyclohexylcarbamate as a clear oil.

Part B

The material from Part A was oxidized and then aminated according to the general methods of Part F of Example 9. Crude product (0.25 g of an amber oil) was dissolved in hot ethyl acetate/hexanes and the solution was cooled to provide a solid. This material was dissolved in methanol and then concentrated under reduced pressure to provide 67 mg of ethyl 1-[(4-amino-2-ethoxymethyl-1H-imidazo[4,5-c]quinolin-1-yl)methyl]cyclohexylcarbamate as a white frothy solid, mp 95-100° C. $^1$H NMR (300 MHz, CDCl$_3$) δ 8.24 (m, 1H), 7.80 (dd, J=8.3, 1.0 Hz, 1H), 7.50 (ddd, J=8.3, 7.0, 1.3 Hz, 1H), 7.31 (ddd, J=8.3, 7.0, 1.3 Hz, 1H), 5.45 (br s, 2H), 5.00 (s, 2H), 4.83 (br s, 2H), 4.54 (br s, 1H), 4.07 (q, J=7.1 Hz, 2H), 3.59 (q, J=7.0 Hz, 2H), 1.79-0.96 (m, 10H), 1.24 (t, J=7.0 Hz, 3H), 1.21 (t, J=7.2 Hz, 3H); MS (APCI) m/z 426 (M+H)$^+$; Anal. Calcd for C$_{23}$H$_{31}$N$_5$O$_3$.0.25H$_2$O: C, 64.24; H, 7.38; N, 16.29. Found: C, 63.99; H, 7.41; N, 16.31.

Example 130

1-{[4-Amino-2-(2-methoxyethyl)-1H-imidazo[4,5-c]quinolin-1-yl]methyl}cyclobutanol

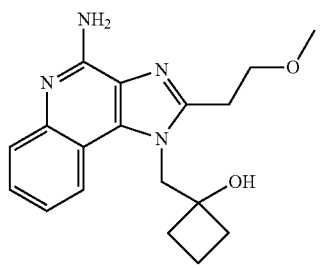 [SMILES: COCCc1nc2c(N)nc3ccccc3c2n1CC1(O)CCC1]

Part A

Under a nitrogen atmosphere a mixture of 1-[(3-aminoquinolin-4-ylamino)methyl]cyclobutanol (6.65 g, 27.3 mmol, Example 8 Parts A through D), triethylamine (3.81 mL, 27.3 mmol), and dichloromethane (200 mL) was cooled in an ice bath. 3-Methoxypropionyl chloride (3.35 g, 27.3 mmol) was added dropwise. The reaction mixture was kept cool for 2 hours and then allowed to warm to ambient temperature overnight. More acid chloride (0.25 eq) was added and the reaction mixture was stirred for 4 hours. The reaction mixture was washed with water. The organic layer was concentrated under reduced pressure to provide crude amide intermediate as an orange foamy solid. This material was purified by column chromatography (silica gel eluting with 80/20 dichloromethane/methanol) to provide 5.2 g of a white foamy solid. This material was dissolved in ethanol (100 mL) and triethylamine (10 mL). The solution was refluxed for 4 days and then concentrated under reduced pressure. The residue was purified by column chromatography (silica gel eluting with 85/15 ethyl acetate/methanol) to provide 3.51 g of 1-{[2-(2-methoxyethyl)-1H-imidazo[4,5-c]quinolin-1-yl]methyl}cyclobutanol as a white foamy solid.

Part B

The material from Part A was oxidized and then aminated according to the general methods of Part F of Example 9. The crude product was purified by column chromatography (silica gel eluting with a gradient of 10-20% methanol in dichloromethane) to provide a light tan oil. This material was triturated with acetonitrile.

The resulting solid was isolated by filtration and dried in a vacuum oven at 80° C. to provide 1.85 g of 1-{[4-amino-2-(2-methoxyethyl)-1H-imidazo[4,5-c]quinolin-1-yl]methyl}cyclobutanol as light tan crystals, mp 169-171° C. $^1$H NMR (300 MHz, DMSO-d$_6$) δ 8.31 (m, 1H), 7.60 (dd, J=8.3, 1.3 Hz, 1H), 7.38 (ddd, J=8.2, 7.1, 1.2 Hz, 1H), 7.21 (ddd, J=8.3, 6.9, 1.3 Hz, 1H), 6.44 (br s, 2H), 5.53 (s, 1H), 4.70 (br s, 2H), 3.81 (t, J=6.9 Hz, 2H), 3.29 (t, J=6.9 Hz, 2H), 3.28 (s, 3H), 2.08 (m, 2H), 1.90 (m, 2H), 1.73 (m, 2H); MS (APCI) m/z 327 (M+H)$^+$; Anal. Calcd for C$_{18}$H$_{22}$N$_4$O$_2$: C, 66.24; H, 6.79; N, 17.16. Found: C, 66.05; H, 6.64; N, 17.28.

Example 131

1-{[4-Amino-2-(2-hydroxyethyl)-1H-imidazo[4,5-c]quinolin-1-yl]methyl}cyclobutanol

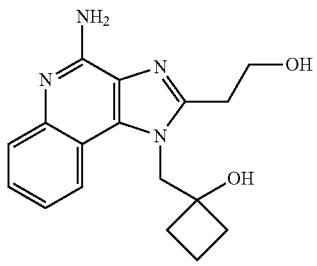 [SMILES: Nc1nc2ccccc2c2c1nc(CCO)n2CC1(O)CCC1]

Under a nitrogen atmosphere a mixture of 1-{[4-amino-2-(2-methoxyethyl)-1H-imidazo[4,5-c]quinolin-1-yl]methyl}cyclobutanol (1.43 g, 4.38 mmol) and dichloromethane (30 mL) was cooled in an ice bath. Boron tribromide (11.0 mL of 1M in dichloromethane) was added dropwise. The reaction mixture was allowed to warm to ambient temperature after 1 hour and then stirred for 6 hours. The reaction mixture was combined with a smaller scale run. Methanol (20 mL) was added and the reaction mixture was stirred for 20 minutes. Hydrochloric acid (20 mL of 6N) was added. The reaction mixture was heated at 40° C. for 2 hours and then allowed to stir at ambient temperature overnight. The reaction mixture was made basic (pH 13) with 50% sodium hydroxide and then extracted with dichloromethane (5×100 mL). The combined organics were concentrated under reduced pressure. The residue was purified by column chromatography (silica gel eluting with a gradient of 10-30% methanol in dichloromethane) to provide 1.2 g of a white frothy solid. This material was triturated with ethyl acetate to provide a white solid which was recrystallized from water (100 mL) to provide 0.83 g of 1-{[4-amino-2-(2-hydroxyethyl)-1H-imidazo[4,5-c]quinolin-1-yl]methyl}cyclobutanol as white needles, mp 132-137° C. $^1$H NMR (300 MHz, DMSO-$d_6$) δ 8.31 (m, 1H), 7.59 (dd, J=8.3, 1.2 Hz, 1H), 7.38 (ddd, J=8.2, 7.1, 1.1 Hz, 1H), 7.20 (ddd, J=8.3, 6.9, 1.2 Hz, 1H), 6.47 (br s, 2H), 5.52 (s, 1H), 4.85 (t, J=5.6 Hz, 1H), 4.71 (br s, 2H), 3.86 (m, 2H), 3.19 (t, J=6.6 Hz, 2H), 2.09 (m, 2H), 1.90 (m, 2H), 1.72 (m, 2H); MS (APCI) m/z 313 (M+H)$^+$; Anal. Calcd for $C_{17}H_{20}N_4O_2 \cdot 0.50H_2O$: C, 63.53; H, 6.59; N, 17.43. Found: C, 63.76; H, 6.19; N, 17.52.

Example 132

1-[4-Amino-2-ethyl-1H-imidazo[4,5-c]quinolin-1-yl)methyl]cyclobutanol

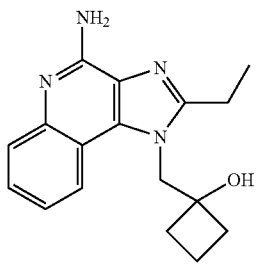 [SMILES: CCc1nc2c(N)nc3ccccc3c2n1CC1(O)CCC1]

1-[4-Chloro-2-ethyl-1H-imidazo[4,5-c]quinolin-1-yl)methyl]cyclobutanol (2.95 g, 9.34 mmol, prepared according to the general methods of Example 8 using 2,4-dichloro-3-nitroquinoline in lieu of 4-chloro-3-nitroquinoline in Part C and propionyl chloride in lieu of ethoxyacetyl chloride in Part E), ammonium chloride (0.50 g, 9.34 mmol), and ammonia in methanol (90 mL of 7.0N) were combined in a bomb reactor. The reactor was sealed and heated at 150° for 48 hours. The reaction mixture was filtered and concentrated under reduced pressure to provide a tan solid. This material was recrystallized from acetonitrile/ethanol and dried under vacuum at 80° C. to provide 1.14 g of 1-[4-amino-2-ethyl-1H-imidazo[4,5-c]quinolin-1-yl)methyl]cyclobutanol as light tan crystals, mp 226-228° C. $^1$H NMR (300 MHz, DMSO-$d_6$) δ 8.30 (m, 1H), 7.59 (dd, J=8.3, 1.2 Hz, 1H), 7.37 (ddd, J=8.3, 7.0, 1.2 Hz, 1H), 7.20 (ddd, J=8.3, 6.9, 1.2 Hz, 1H), 6.40 (br s, 2H), 5.51 (s, 1H), 4.65 (br s, 2H), 3.03 (q, J=7.4 Hz, 2H), 2.08 (m, 2H), 1.90 (m, 2H), 1.71 (m, 2H), 1.35 (t, J=7.4 Hz, 3H); MS (APCI) m/z 297 (M+H)$^+$; Anal. Calcd for $C_{17}H_{20}N_4O$: C, 68.90; H, 6.80; N, 18.90. Found: C, 68.71; H, 7.16; N, 18.94.

Example 133

1-[4-Amino-2-butyl-1H-imidazo[4,5-c]quinolin-1-yl)methyl]cyclobutanol

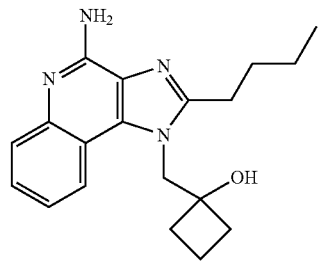 [SMILES: CCCCc1nc2c(N)nc3ccccc3c2n1CC1(O)CCC1]

1-[4-Amino-2-butyl-1H-imidazo[4,5-c]quinolin-1-yl)methyl]cyclobutanol was prepared according to the method of Example 132 using valeryl chloride in lieu of propionyl chloride. The crude product was partitioned between 5% sodium carbonate (100 mL) and dichloromethane (200 mL). The organic was concentrated under reduced pressure to provide a tan solid, which was purified by column chromatography (silica gel eluting with 85/15 dichloromethane/methanol) to provide a white solid. This solid was recrystallized from isopropanol then dissolved in methanol. The solution was concentrated under reduced pressure to provide a white solid, which was dried under vacuum at 80° C. to provide pure product as a white solid, mp 186-188° C. $^1$H NMR (300 MHz, DMSO-$d_6$) δ 8.30 (m, 1H), 7.59 (dd, J=8.4, 1.2 Hz, 1H), 7.37 (ddd, J=8.3, 7.0, 1.2 Hz, 1H), 7.20 (ddd, J=8.3, 6.9, 1.2 Hz, 1H), 6.40 (br s, 2H), 5.50 (s, 1H), 4.65 (br s, 2H), 3.00 (m, 2H), 2.08 (m, 2H), 1.98-1.58 (m, 6H), 1.43 (sextet, J=7.4 Hz, 2H), 0.94 (t, J=7.3 Hz, 3H); MS (APCI) m/z 325 (M+H)$^+$; Anal. Calcd for $C_{19}H_{24}N_4O$: C, 70.34; H, 7.46; N, 17.27. Found: C, 70.26; H, 7.62; N, 17.27.

Example 134

4-[(4-Amino-2-ethoxymethyl-1H-imidazo[4,5-c]quinolin-1-yl)methyl]-4-hydroxy-N-phenylpiperidine-1-carboxamide

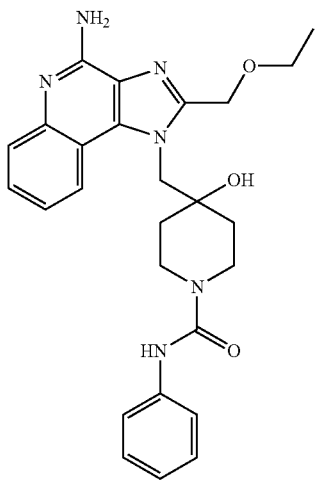 [SMILES: CCOCc1nc2c(N)nc3ccccc3c2n1CC1(O)CCN(C(=O)Nc2ccccc2)CC1]

Part A

Under a nitrogen atmosphere a mixture of trifluoroacetic acid (40 mL) and dichloromethane (200 mL) was chilled in an ice bath. A solution of tert-butyl 4-[(2-ethoxymethyl-1H-imidazo[4,5-c]quinolin-1-yl)methyl]-4-hydroxypiperidine-1-carboxylate (20 g, Example 4 Parts A through E) in dichloromethane (200 mL) was slowly added. The reaction mixture was allowed to warm to ambient temperature, stirred for 6 hours, and then concentrated under reduced pressure to provide a dark amber oil. The oil was dissolved in water (200 mL), the pH was adjusted to 13 with 50% sodium hydroxide, and the mixture was extracted with dichloromethane. The combined extracts were dried over magnesium sulfate, filtered, and concentrated under reduced pressure to provide 15.2 g of 4-[(2-ethoxymethyl-1H-imidazo[4,5-c]quinolin-1-yl)methyl]piperidin-4-ol as a tan frothy solid.

Part B

Under a nitrogen atmosphere phenyl isocyanate (1.00 mL, 9.25 mmol) was added dropwise to a chilled mixture of 4-[(2-ethoxymethyl-1H-imidazo[4,5-c]quinolin-1-yl)methyl]piperidin-4-ol (3.00 g, 8.81 mmol) and dichloromethane (90 mL). The reaction mixture was allowed to warm to ambient temperature. After 2 hours the reaction mixture was concentrated under reduced pressure to provide an orange oil. This material was triturated with diethyl ether to provide 4.1 g of 4-[(2-ethoxymethyl-1H-imidazo[4,5-c]quinolin-1-yl)methyl]-4-hydroxy-N-phenylpiperidine-1-carboxamide as a light orange solid.

Part C

The material from Part B was oxidized and aminated according to the general methods of Part F of Example 10. The crude product was purified by column chromatography (eluting with a gradient of 10-30% methanol in dichloromethane) to provide 1.5 g of a white frothy solid. This material was recrystallized from acetonitrile (12 mL) and dried under vacuum at 80° C. to provide 4-[(4-amino-2-ethoxymethyl-1H-imidazo[4,5-c]quinolin-1-yl)methyl]-4-hydroxy-N-phenylpiperidine-1-carboxamide as white crystals, mp 184-186° C. $^1$H NMR (300 MHz, DMSO-$d_6$) δ 8.40 (s, 1H), 8.34 (m, 1H), 7.59 (dd, J=8.4, 1.2 Hz, 1H), 7.45-7.36 (m, 3H), 7.24-7.16 (m, 3H), 6.90 (ddd, J=8.4, 7.2, 1.1 Hz, 1H), 6.56 (br s, 2H), 5.29-4.34 (m, 4H), 5.02 (s, 1H), 3.90 (m, 2H), 3.53 (q, J=7.0 Hz, 2H), 2.95 (m, 2H), 1.75 (m, 2H), 1.39 (br s, 2H), 1.14 (t, J=7.0 Hz, 3H); MS (APCI) m/z 475 (M+H)$^+$; Anal. Calcd for $C_{26}H_{30}N_6O_3 \cdot 0.25H_2O$: C, 65.19; H, 6.42; N, 17.54. Found: C, 64.80; H, 6.38; N, 17.45.

Example 135

4-[4-Amino-2-ethoxymethyl-1H-imidazo[4,5-c]quinolin-1-yl)methyl]-1-(cyclopropylcarbonyl)piperidin-4-ol

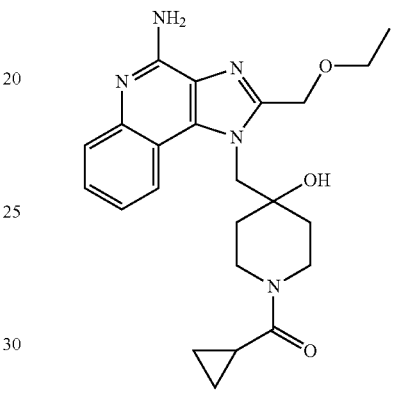

Part A

Under a nitrogen atmosphere cyclopropanecarbonyl chloride (0.84 mL, 9.25 mmol) was added dropwise to a chilled mixture of 4-[(2-ethoxymethyl-1H-imidazo[4,5-c]quinolin-1-yl)methyl]piperidin-4-ol (3.00 g, 8.81 mmol), triethylamine (1.47 mL, 10.6 mmol) and dichloromethane (90 mL). The reaction mixture was allowed to warm to ambient temperature. After 2 hours the reaction mixture was washed with water. The organic layer was concentrated under reduced pressure. The residue was purified by column chromatography (silica gel eluting with 90/10 dichloromethane/methanol) to provide 3.16 g of 4-[2-ethoxymethyl-1H-imidazo[4,5-c]quinolin-1-yl)methyl]-1-(cyclopropylcarbonyl)piperidin-4-ol as a light orange frothy solid.

Part B

The material from Part A was oxidized and aminated according to the general methods of Part F of Example 10. The crude product was purified by column chromatography (silica gel eluting with a gradient of 15-20% methanol in dichloromethane) to provide 1.9 g of a white frothy solid. This material product was purified by column chromatography (silica gel eluting with 80/20 ethyl acetate/methanol) to provide a clear oil. This material was dissolved in hot water (100 mL) and the solution was allowed to cool to ambient temperature. A precipitate was isolated by filtration and dried under vacuum at 60° C. to provide 1.39 g of 4-[4-amino-2-ethoxymethyl-1H-imidazo[4,5-c]quinolin-1-yl)methyl]-1-(cyclopropylcarbonyl)piperidin-4-ol as white crystals, mp 128-131° C. $^1$H NMR (300 MHz, DMSO-$d_6$) δ 8.33 (m, 1H), 7.59 (dd, J=8.3, 1.2 Hz, 1H), 7.40 (m, 1H), 7.21 (ddd, J=8.3, 6.9, 1.3 Hz, 1H), 6.56 (br s, 2H), 5.40-4.40 (m, 4H), 5.07 (s, 1H), 4.10 (m, 2H), 3.53 (q, J=7.0 Hz, 2H), 2.97 (m, 2H), 2.00-1.20 (m, 5H), 1.13 (t, J=7.0 Hz, 3H), 0.79-0.56 (m, 4H); MS (APCI) m/z 424 (M+H)+; Anal. Calcd for $C_{23}H_{29}N_5O_3 \cdot 1.00H_2O$: C, 62.57; H, 7.08; N, 15.86. Found: C, 62.78; H, 7.04; N, 15.92.

Example 136

4-[4-Amino-2-ethoxymethyl-1H-imidazo[4,5-c]quinolin-1-yl)methyl]-4-hydroxy-N,N-dimethylpiperidine-1-carboxamide

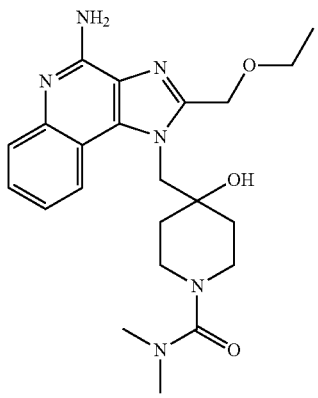 [SMILES: CCOCc1nc2c(N)nc3ccccc3c2n1CC1(O)CCN(C(=O)N(C)C)CC1]

4-[4-Amino-2-ethoxymethyl-1H-imidazo[4,5-c]quinolin-1-yl)methyl]-4-hydroxy-N,N-dimethylpiperidine-1-carboxamide was prepared according to the general methods of Example 135 using dimethylcarbamoyl chloride in lieu of cyclopropanecarbonyl chloride in Part A. The crude product was purified by column chromatography (eluting with a gradient of 15-20% methanol in dichloromethane) to provide a white solid. This material was recrystallized from acetonitrile to provide 1.3 g of a tan solid. The solid was dissolved in methanol and concentrated hydrochloric acid was added. The mixture was stirred for 30 minutes and then concentrated under reduced pressure to provide the hydrochloride salt as an oil. The oil was dissolved in water (100 mL) and then sodium carbonate (5 g) was added. A precipitate was isolated by filtration and dried in a vacuum oven at 50° C. to provide 0.92 g of pure product as a white powder, mp 115-125° C. $^1$H NMR (300 MHz, DMSO-d$_6$) δ 8.32 (m, 1H), 7.59 (dd, J=8.3, 1.2 Hz, 1H), 7.40 (m, 1H), 7.20 (ddd, J=8.2, 6.9, 1.2 Hz, 1H), 6.57 (br s, 2H), 5.50-4.20 (m, 4H), 4.95 (s, 1H), 3.52 (q, J=7.0 Hz, 2H), 3.28 (m, 2H), 2.89 (m, 2H), 2.68 (s, 6H), 1.75 (m, 2H), 1.34 (m, 2H), 1.13 (t, J=6.9 Hz, 3H); MS (APCI) m/z 427 (M+H)+; Anal. Calcd for $C_{22}H_{30}N_6O_3$: C, 61.95; H, 7.09; N, 19.70. Found: C, 61.71; H, 7.18; N, 19.50.

Example 137

4-[4-Amino-2-ethoxymethyl-1H-imidazo[4,5-c]quinolin-1-yl)methyl]-1-(propyl sulfonyl)piperidin-4-ol

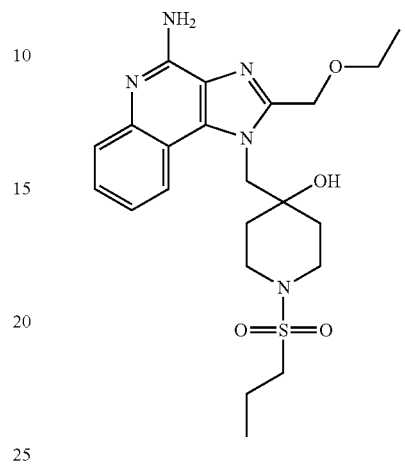

Part A

Under a nitrogen atmosphere, 1-propanesulfonyl chloride (1.04 mL, 9.25 mmol) was added dropwise to a chilled mixture of 4-[(2-ethoxymethyl-1H-imidazo[4,5-c]quinolin-1-yl)methyl]piperidin-4-ol (3.00 g, 8.81 mmol), dimethylaminopyridine (3.00 g), pyridine (10 mL), and dichloromethane (60 mL). The reaction mixture was allowed to warm to ambient temperature. After 2 hours the reaction mixture was concentrated under reduced pressure. The residue was partitioned between water (100 mL) and dichloromethane (100 mL). The aqueous layer was extracted with dichloromethane (2×100 mL). The combined organics were concentrated under reduced pressure to provide an orange oil. The oil was purified by column chromatography (silica gel eluting with 95/5 dichloromethane/methanol) to provide 3.68 g of 4-[(2-ethoxymethyl-1H-imidazo[4,5-c]quinolin-1-yl)methyl]-1-(propylsulfonyl)piperidin-4-o as a light orange frothy solid.

Part B

The material from Part A was oxidized and aminated according to the general methods of Part F of Example 10. The crude product was purified by column chromatography (silica gel eluting with 90/10 dichloromethane/methanol) to provide a white solid. This material was recrystallized for ethyl acetate to provide 1.8 g of a white crystalline solid. This solid was purified by column chromatography (silica gel eluting with 80/20 ethyl acetate/methanol) to provide a clear oil. The oil was triturated with hot water. The resulting solid was isolated by filtration and dried in a vacuum oven at 80° C. to provide 4-[4-amino-2-ethoxymethyl-1H-imidazo[4,5-c]quinolin-1-yl)methyl]-1-(propylsulfonyl)piperidin-4-ol as white crystals, mp 211-213° C. $^1$H NMR (300 MHz, DMSO-d$_6$) δ 8.34 (m, 1H), 7.60 (dd, J=8.3, 1.1 Hz, 1H), 7.41 (m, 1H), 7.23 (m, 1H), 6.57 (br s, 2H), 5.50-4.20 (m, 4H), 5.05 (s, 1H), 3.53 (q, J=6.9 Hz, 2H), 3.35 (m, 2H), 3.05-2.80 (m, 4H), 1.95-1.20 (m, 6H), 1.14 (t, J=7.0 Hz, 3H), 0.96 (t, J=7.3 Hz, 3H); MS (APCI) m/z 462 (M+H)+; Anal. Calcd for $C_{22}H_{31}N_5O_4S$: C, 57.25; H, 6.77; N, 15.17. Found: C, 57.10; H, 6.97; N, 15.24.

Example 138

4-[4-Amino-2-butyl-1H-imidazo[4,5-c]quinolin-1-yl)methyl]-1-(methyl sulfonyl)piperidin-4-ol

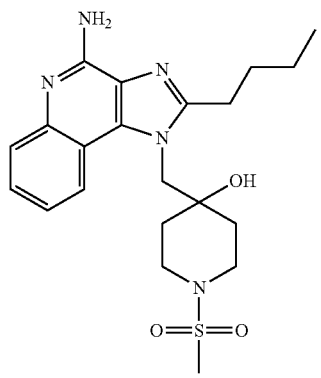 [SMILES: CCCCc1nc2c(N)nc3ccccc3c2n1CC1(O)CCN(S(C)(=O)=O)CC1]

Part A

The BOC protecting group was removed from tert-butyl 4-[(4-chloro-2-butyl-1H-imidazo[4,5-c]quinolin-1-yl) methyl]-4-hydroxypiperidine-1-carboxylate (3.55 g, prepared according to the general methods of Example 4 using 2,4-dichloro-3-nitroquinoline in lieu of 4-chloro-3-nitroquinoline in Part C and valeryl chloride in lieu of ethoxyacetyl chloride in Part E) using the method of Part A of Example 134 to provide 2.60 g of 4-[4-chloro-2-butyl-1H-imidazo[4,5-c]quinolin-1-yl)methyl]piperidin-4-ol as a tan solid.

Part B

Under a nitrogen atmosphere, methanesulfonyl chloride (0.53 mL, 7.18 mmol) was added dropwise to a chilled mixture of the material from Part A (2.55 g, 6.84 mmol), dimethylaminopyridine (1.27 g), pyridine (10 mL), and dichloromethane (75 mL). The reaction was maintained at 0° C. for 2 hours and then allowed to warm to ambient temperature. After 16 hours the reaction mixture was washed with water (100 mL). The aqueous layer was extracted with dichloromethane (2×100 mL). The combined organics were concentrated under reduced pressure. The residue was purified by column chromatography (silica gel eluting with 95/5 dichloromethane/methanol) to provide 2.60 g of 4-[4-chloro-2-butyl-1H-imidazo[4,5-c]quinolin-1-yl)methyl]-1-(methylsulfonyl)piperidin-4-ol as a white foamy solid.

Part C

A portion (2.35 g, 5.21 mmol) of the material from Part B, ammonium chloride (0.28 g, 5.21 mmol), and ammonia in methanol (50 mL of 7.0 N) were combined in a bomb reactor. The reactor was sealed and heated at 150° for 48 hours. The reaction mixture was filtered and then concentrated under reduced pressure. The residue was partitioned between 5% sodium carbonate and dichloromethane. The aqueous layer was extracted with dichloromethane (×2). The combined organics were concentrated under reduced pressure to provide an amber oil. The oil was purified by column chromatography (silica gel eluting with 90/10 dichloromethane/methanol) to provide a clear oil. This material was triturated with acetonitrile to provide a solid. The solid was suspended in water (100 mL), concentrated hydrochloric acid (5 mL) was added, and the mixture was stirred for 2 hours. Sodium carbonate (10 g) was added and the mixture was heated at 45° C. for 1 hour. The mixture was allowed to cool to ambient temperature. A solid was isolated by filtration and dried in a vacuum oven at 80° C. to provide 1.43 g of 4-[4-amino-2-butyl-1H-imidazo[4,5-c]quinolin-1-yl) methyl]-1-(methylsulfonyl)piperidin-4-ol as a white solid, mp 240-242° C. $^1$H NMR (300 MHz, DMSO-$d_6$) δ 8.32 (m, 1H), 7.58 (dd, J=8.3, 1.2 Hz, 1H), 7.37 (m, 1H), 7.21 (ddd, J=8.3, 6.9, 1.3 Hz, 1H), 6.40 (br s, 2H), 5.00-4.20 (m, 2H), 4.94 (s, 1H), 3.34 (m, 2H), 3.32 (br t, J=7.7 Hz, 2H), 2.85 (m, 2H), 2.81 (s, 3H), 2.00-1.10 (m, 6H), 1.43 (sextet, J=7.4 Hz, 2H), 0.95 (t, J=7.3 Hz, 3H); MS (APCI) m/z 432 (M+H)$^+$; Anal. Calcd for $C_{21}H_{29}N_5O_3S \cdot 0.25\ H_2O$: C, 57.84; H, 6.82; N, 16.06. Found: C, 57.71; H, 7.00; N, 16.00.

Example 139

4-[4-Amino-2-propyl-1H-imidazo[4,5-c]quinolin-1-yl)methyl]-1-(methyl sulfonyl)piperidin-4-ol

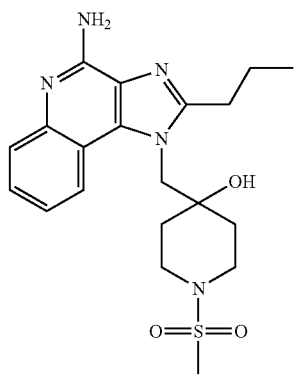 [SMILES: CCCc1nc2c(N)nc3ccccc3c2n1CC1(O)CCN(S(C)(=O)=O)CC1]

4-[4-Amino-2-propyl-1H-imidazo[4,5-c]quinolin-1-yl) methyl]-1-(methylsulfonyl)piperidin-4-ol was prepared according to the general methods of Example 138 using butyryl chloride in lieu of valeryl chloride. The crude product was purified by column chromatography (silica gel eluting with a gradient of 10-20% methanol in dichloromethane) to provide a white solid. This material was recrystallized from acetonitrile and then from methanol. The resulting solid was dissolved in water (100 mL), concentrated hydrochloric acid (10 mL) was added, and the mixture was stirred for 1 hour. Sodium carbonate (10 g) was added and the mixture was heated at 40° C. for 1 hour. A solid was isolated by filtration and dried in a vacuum oven at 80° C. to provide pure product as a white solid, mp>250° C. $^1$H NMR (300 MHz, DMSO-$d_6$, 354 K) δ 8.29 (m, 1H), 7.60 (dd, J=8.3, 1.2 Hz, 1H), 7.36 (ddd, J=8.2, 7.0, 1.2 Hz, 1H), 7.20 (ddd, J=8.2, 7.0, 1.2 Hz, 1H), 6.06 (br s, 2H), 4.72 (br s, 1H), 4.60 (br s, 2H), 3.36 (m, 2H), 3.06-2.84 (m, 4H), 2.78 (s, 3H), 1.94-1.72 (m, 4H), 1.53 (m, 2H), 1.02 (t, J=7.3 Hz, 3H); MS (APCI) m/z 418 (M+H)$^+$; Anal. Calcd for $C_{20}H_{27}N_5O_3S \cdot 0.50\ H_2O$: C, 56.32; H, 6.62; N, 16.42. Found: C, 56.41; H, 6.39; N, 16.49.

Example 140

4-[4-Amino-2-ethyl-1H-imidazo[4,5-c]quinolin-1-yl)methyl]-1-(methyl sulfonyl)piperidin-4-ol

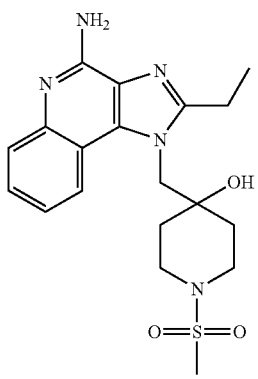 [SMILES: CCc1nc2c(N)nc3ccccc3c2n1CC1(O)CCN(S(C)(=O)=O)CC1]

4-[4-Amino-2-ethyl-1H-imidazo[4,5-c]quinolin-1-yl)methyl]-1-(methylsulfonyl)piperidin-4-ol was prepared according to the general methods of Example 138 using propionyl chloride in lieu of valeryl chloride. The crude product was suspended in water, isolated by filtration, and then dried to provide a white solid. This material was recrystallized twice from acetonitrile to provide 0.95 g of pure product as white needles, mp 260-262° C. $^1$H NMR (300 MHz, DMSO-$d_6$, 354 K) δ 8.29 (dd, J=8.3, 1.0 Hz, 1H), 7.60 (dd, J=8.3, 1.1 Hz, 1H), 7.36 (ddd, J=8.3, 7.0, 1.3 Hz, 1H), 7.20 (ddd, J=8.3, 6.9, 1.4 Hz, 1H), 6.04 (br s, 2H), 4.73 (br s, 1H), 4.60 (s, 2H), 3.37 (m, 2H), 3.03 (q, J=7.5 Hz, 2H), 2.92 (m, 2H), 2.78 (s, 3H), 1.80 (app. td, J=12.8, 4.7 Hz, 2H), 1.53 (m, 2H), 1.37 (t, J=7.5 Hz, 3H); MS (APCI) m/z 404 (M+H)$^+$; Anal. Calcd for $C_{19}H_{25}N_5O_3S$: C, 56.56; H, 6.25; N, 17.36. Found: C, 56.38; H, 6.45; N, 17.53.

Example 141

4-[4-Amino-2-methyl-1H-imidazo[4,5-c]quinolin-1-yl)methyl]-1-(methyl sulfonyl)piperidin-4-ol

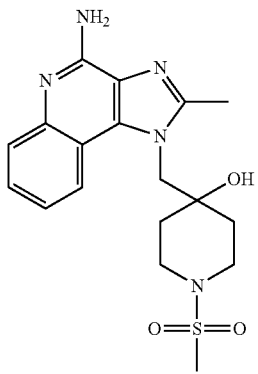 [SMILES: Cc1nc2c(N)nc3ccccc3c2n1CC1(O)CCN(S(C)(=O)=O)CC1]

4-[4-Amino-2-methyl-1H-imidazo[4,5-c]quinolin-1-yl)methyl]-1-(methylsulfonyl)piperidin-4-ol was prepared according to the general methods of Example 138 using acetyl chloride in lieu of valeryl chloride. The crude product was isolated by filtration, washed with methanol, and then dissolved in hot DMF. The solution was allowed to cool to ambient temperature. A solid was isolated by filtration, washed with DMF, and then dissolved in hot water. A precipitate was isolated by filtration and dried under vacuum at 80° C. to provide pure product as a white solid, mp 294-296° C. $^1$H NMR (300 MHz, DMSO-$d_6$) δ 8.33 (m, 1H), 7.58 (dd, J=8.3, 1.2 Hz, 1H), 7.37 (m, 1H), 7.20 (m, 1H), 6.44 (br s, 2H), 4.97 (s, 1H), 4.60 (br s, 2H), 3.34 (m, 2H), 2.87 (m, 2H), 2.82 (s, 3H), 2.66 (s, 3H), 1.85 (m, 2H), 1.54 (m, 2H); MS (APCI) m/z 390 (M+H)$^+$; Anal. Calcd for $C_{18}H_{23}N_5O_3S$: C, 55.51; H, 5.95; N, 17.98. Found: C, 55.29; H, 6.18; N, 17.95.

Example 142

4-[4-Amino-1H-imidazo[4,5-c]quinolin-1-yl)methyl]-1-(methylsulfonyl)piperidin-4-ol

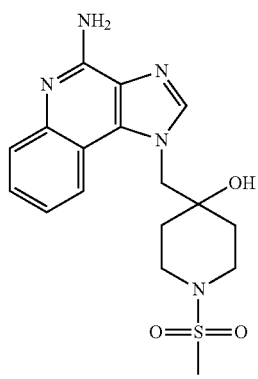 [SMILES: CS(=O)(=O)N1CCC(O)(Cn2cnc3c(N)nc4ccccc4c32)CC1]

Part A

Under a nitrogen atmosphere, tert-butyl 4{[(3-amino-2-chloroquinolin-4-yl)amino]methyl}-4-hydroxypiperidine-1-carboxylate (0.25 g, 0.61 mmol, prepared according to the general methods of Example 4 Parts A through D using 2,4-dichloro-3-nitroquinoline in lieu of 4-chloro-3-nitroquinoline in Part C), toluene (5 mL), pyridine hydrochloride (0.02 g), and triethylorthoformate (0.11 mL, 0.65 mmol) was heated at reflux for 2 hours. More triethylorthoformate (0.5 eq) was added and the reaction mixture was heated for an additional hour. The reaction was rerun in the same manner using 5.25 g of tert-butyl 4 {[(3-amino-2-chloroquinolin-4-yl)amino]methyl}-4-hydroxypiperidine-1-carboxylate. The small and larger scale reaction mixtures were combined and washed with water (50 mL). The aqueous layer was extracted with dichloromethane (2×100 mL). The organic layers were combined and concentrated under reduced pressure. The residue was purified by column chromatography (silica gel eluting with a gradient of 0-10% methanol in ethyl acetate) to provide 4.08 g of tert-butyl 4-[(4-chloro-1H-imidazo[4,5-c]quinolin-1-yl)methyl]-4-hydroxypiperidine-1-carboxylate as a tan frothy solid.

Part B

The material from part A was converted to 4-[4-amino-1H-imidazo[4,5-c]quinolin-1-yl)methyl]-1-(methylsulfonyl)piperidin-4-ol according to the general methods of Example 138. The crude product was isolated by filtration, washed with methanol, recrystallized from methanol/water, and then dried in a vacuum oven at 80° C. to provide 0.84 g of pure product as white needles, mp>250° C. $^1$H NMR (300 MHz, DMSO-$d_6$, 354 K) δ 8.33 (m, 1H), 8.04 (s, 1H), 7.61 (m, 1H), 7.40 (ddd, J=8.3, 7.0, 1.3 Hz, 1H), 7.22 (ddd, J=8.3, 6.9, 1.3 Hz, 1H), 6.18 (br s, 2H), 4.81 (br s, 1H), 4.61 (s, 2H), 3.40 (m, 2H), 2.99 (m, 2H), 2.80 (s, 3H), 1.78 (m, 2H), 1.53 (m, 2H); MS (APCI) m/z 376 (M+H)$^+$; Anal. Calcd for $C_{17}H_{21}N_5O_3S$: C, 54.38; H, 5.64; N, 18.65. Found: C, 54.18; H, 5.68; N, 18.64.

Example 143

1-[(4-Aminotetrahydro-2H-pyran-4-yl)methyl]-2-ethoxymethyl-1H-imidazo[4,5-c]quinolin-4-amine

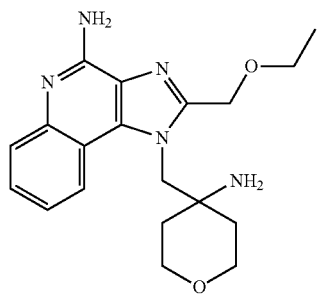 [SMILES: CCOCc1nc2c(N)nc3ccccc3c2n1CC1(N)CCOCC1]

Part A

Tert-Butyl {4-[(2-ethoxymethyl-1H-imidazo[4,5-c]quinolin-1-yl)methyl]tetrahydropyran-4-yl}carbamate (1.70 g, prepared according to the general methods of Parts A through F of Example 54 using tetrahydro-4H-pyran-4-one in lieu of cyclohexanone in Part A) was oxidized and aminated according to the general method of Part F of Example 10 to provide 1.13 g of tert-Butyl {4-[(4-amino-2-ethoxymethyl-1H-imidazo[4,5-c]quinolin-1-yl)methyl]tetrahydropyran-4-yl}carbamate as a light brown solid.

Part B

The material from Part A was combined with hydrochloric acid (20 mL of 2.8 M in ethanol) and heated at reflux for six hours. The reaction mixture was concentrated under reduced pressure and the residue was partitioned between 10% sodium hydroxide (100 mL) and dichloromethane (100 mL). The aqueous layer was extracted with dichloromethane (2×100 mL). The pH of the aqueous was adjusted to pH 11 with hydrochloric acid and sodium carbonate and then extracted with dichloromethane (3×100 mL). The combined organics were dried over sodium sulfate, filtered, and then concentrated under reduced pressure to provide 0.95 g of an amber oil. This material was purified by column chromatography (silica gel eluting with 90/10 dichloromethane/methanol) to provide 0.45 g of a white solid. This material was dissolved in methanol and then dried in a vacuum oven at 40° C. to provide 1-[(4-aminotetrahydro-2H-pyran-4-yl)methyl]-2-ethoxymethyl-1H-imidazo[4,5-c]quinolin-4-amine as a white frothy solid, mp 53-63° C. $^1$H NMR (300 MHz, CDCl$_3$) δ 8.19 (dd, J=8.3, 1.0 Hz, 1H), 7.81 (dd, J=8.4, 0.9 Hz, 1H), 7.51 (ddd, J=8.4, 7.0, 1.4 Hz, 1H), 7.30 (ddd, J=8.3, 7.0, 1.3 Hz, 1H), 5.50 (br s, 2H), 4.97 (br s, 2H), 4.69 (br s, 2H), 3.82-3.63 (m, 4H), 3.59 (q, J=7.0 Hz, 2H), 2.10-1.27 (m, 6H), 1.24 (t, J=7.0 Hz, 3H); MS (ESI) m/z 356 (M+H)$^+$; Anal. Calcd for $C_{19}H_{25}N_5O_2 \cdot 0.50H_2O$: C, 62.62; H, 7.19; N, 19.22. Found: C, 62.61; H, 7.20; N, 19.20.

Example 144

N-{[4-(4-Amino-2-ethoxymethyl-1H-imidazo[4,5-c]quinolin-1-yl)methyl]tetrahydropyran-4-yl}methanesulfonamide

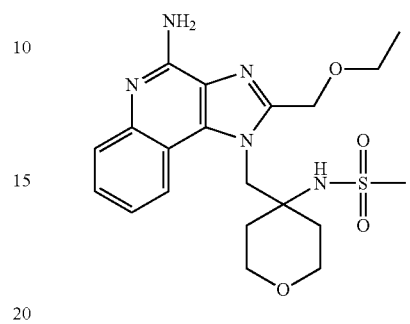

Part A

Under a nitrogen atmosphere, a mixture of tert-Butyl {4-[(2-ethoxymethyl-1H-imidazo[4,5-c]quinolin-1-yl)methyl]tetrahydropyran-4-yl}carbamate (3.0 g, prepared according to the general methods of Parts A through F of Example 54 using tetrahydro-4H-pyran-4-one in lieu of cyclohexanone in Part A), hydrochloric acid (12.2 mL of 2.8 M in ethanol), and ethanol (18 mL) was heated at reflux for 4 hours. The reaction mixture was allowed to cool to ambient temperature and was then concentrated under reduced pressure. The residue was combined with isopropanol (100 mL). A solid was isolated by filtration to provide 2.56 g of 4-[(2-ethoxymethyl-1H-imidazo[4,5-c]quinolin-1-yl)methyl]tetrahydropyran-4-amine as a tan solid.

Part B

Under a nitrogen atmosphere, methanesulfonyl chloride (0.068 mL, 0.88 mmol) was added dropwise to a chilled mixture of the material from Part A (0.25 g, 0.73 mmol), dimethylaminopyridine (0.25 g), pyridine (2 mL), and dichloromethane (2.5 mL). The reaction was maintained at 0° C. for 1 hour, allowed to warm to ambient temperature, and then stirred for 16 hours. The reaction was repeated on a larger scale using the remainder of the material from Part A. The reaction mixtures were combined and concentrated under reduced pressure. The residue was partitioned between water (100 mL) and dichloromethane (100 mL). The aqueous layer was extracted with dichloromethane (100 mL). The combined organics were dried over magnesium sulfate, filtered, and then concentrated under reduced pressure. The residue was purified by column chromatography (silica gel eluting with 80/20 ethyl acetate/methanol) to provide 1.64 g of N-{[4-(2-ethoxymethyl-1H-imidazo[4,5-c]quinolin-1-yl)methyl]tetrahydropyran-4-yl}methanesulfonamide as a light yellow solid.

Part C

The material from Part B was oxidized and aminated according to the general method of Part F of Example 10. The crude product was partitioned between water (100 mL) and dichloromethane (100 mL). The aqueous layer was extracted with dichloromethane (2×100 mL). The pH of the aqueous was adjusted to pH 11 with hydrochloric acid and sodium carbonate and then extracted with dichloromethane (2×100 mL). The combined organics were dried over magnesium sulfate, filtered, and then concentrated under reduced pressure to provide a clear oil. The oil was purified by column chromatography (silica gel eluting with 90/10 dichloromethane/methanol) to provide 0.90 g of a clear oil. This material was dissolved in methanol and then dried in a vacuum oven at 50° C. to provide 0.86 g of N-{[4-(4-amino-2-ethoxymethyl-1H-imidazo[4,5-c]quinolin-1-yl)methyl]tetrahydropyran-4-yl}methanesulfonamide as a white frothy solid, mp 97-110° C. $^1$H NMR (300 MHz, CDCl$_3$) δ 8.20 (dd, J=8.3, 0.9 Hz, 1H), 7.80 (dd, J=8.4, 1.1 Hz, 1H), 7.51 (ddd, J=8.3, 7.0, 1.3 Hz, 1H), 7.29 (ddd, J=8.3, 6.9, 1.3 Hz, 1H), 6.02 (br s, 1H), 5.66 (br s, 2H), 5.25 (br s, 2H), 4.90 (br s, 2H), 3.78-3.58 (m, 4H), 3.68 (q, J=7.0 Hz, 2H), 3.20 (s, 3H), 2.70-1.30 (m, 4H), 1.23 (t, J=7.0 Hz, 3H); MS (APCI) m/z 434 (M+H)$^+$; Anal. Calcd for C$_{20}$H$_{27}$N$_5$O$_4$S.0.75H$_2$O: C, 53.74; H, 6.43; N, 15.67. Found: C, 53.87; H, 6.34; N, 15.70.

Example 145

1-[(4-Amino-2-butyl-1H-imidazo[4,5-c]quinolin-1-yl)methyl]cyclohexanol

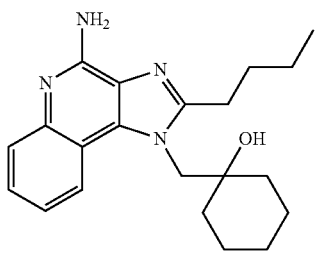 [SMILES: CCCCc1nc2c(N)nc3ccccc3c2n1CC1(O)CCCCC1]

1-[(4-Amino-2-butyl-1H-imidazo[4,5-c]quinolin-1-yl)methyl]cyclohexanol was prepared according to the general methods of Example 1 using valeryl chloride in lieu of ethoxyacetyl chloride in Part B. The crude product was recrystallized from acetonitrile to provide pure product as a brown solid, mp 218-220° C. $^1$H NMR (300 MHz, DMSO-d$_6$) δ 8.30 (d, J=8.1 Hz, 1H), 7.57 (d, J=6.9 Hz, 1H), 7.36 (t, J=6.9 Hz, 1H), 7.19 (t, J=8.1 Hz, 1H), 6.37, (br s, 2H), 4.53 (s, 1H), 4.51 (br s, 1H), 3.01 (t, J=8.1 Hz, 2H), 1.79 (pent, J=7.5 Hz, 2H), 1.46 (hex, J=7.5 Hz, 2H), 1.43 (m, 10H), 1.10 (br s, 1H), 0.94 (t, J=6.9 Hz, 3H); MS (APCI) m/z 353 (M+H)$^+$; Anal. calcd for C$_{21}$H$_{28}$N$_4$O: C, 71.56; H, 8.01; N, 15.89. Found: C, 71.29; H, 8.01; N, 16.02.

Example 146

1-{[4-Amino-2-(2-methoxyethyl)-1H-imidazo[4,5-c]quinolin-1-yl]methyl}cyclohexanol

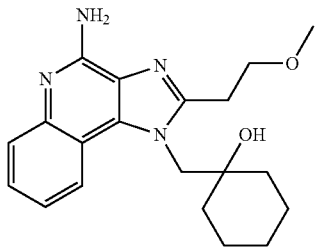 [SMILES: COCCc1nc2c(N)nc3ccccc3c2n1CC1(O)CCCCC1]

1-{[4-Amino-2-(2-methoxyethyl)-1H-imidazo[4,5-c]quinolin-1-yl]methyl}cyclohexanol was prepared according to the general methods of Example 1 using 3-methoxypropionyl chloride in lieu of ethoxyacetyl chloride in Part B. The crude product was purified by column chromatography (silica gel eluting with 5% methanol in chloroform), recrystallized from acetonitrile/water, and then dried in a vacuum oven at 105° C. to provide hydrated product as a light brown solid, mp 189-191° C. $^1$H NMR (300 MHz, DMSO-d$_6$) δ 8.30 (d, J=8.1 Hz, 1H), 7.57 (d, J=8.1 Hz, 1H), 7.37 (t, J=8.1 Hz, 1H), 7.19 (t, J=8.1 Hz, 1H), 6.39, (br s, 2H), 4.56 (s, 1H), 4.54 (br s, 1H), 3.81 (t, J=6.9 Hz, 2H), 3.30 (m, 2H), 3.28 (s, 3H), 1.47 (m, 10H), 1.10 (br s, 1H); MS (APCI) m/z 355 (M+H)$^+$; Anal. calcd for C$_{20}$H$_{26}$N$_4$O$_2$.0.29H$_2$O: C, 66.79; H, 7.45; N, 15.58. Found: C, 66.74; H, 7.54; N, 15.81.

Example 147

1-[(4-Amino-2-propyl-1H-imidazo[4,5-c]quinolin-1-yl)methyl]cyclohexanol

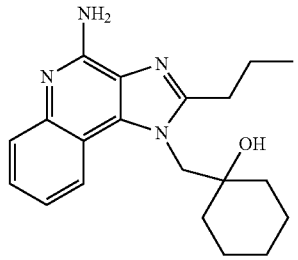 [SMILES: CCCc1nc2c(N)nc3ccccc3c2n1CC1(O)CCCCC1]

1-[(4-Amino-2-propyl-1H-imidazo[4,5-c]quinolin-1-yl)methyl]cyclohexanol was prepared according to the general methods of Example 1 using butyryl chloride in lieu of ethoxyacetyl chloride in Part B. The crude product was purified twice by HPFC eluting the first time with a gradient of 2-40% CMA in chloroform and the second time with a gradient of 8-25% CMA in chloroform to provide pure product as an off-white solid, mp 250-252° C. $^1$H NMR (300 MHz, DMSO-d$_6$) δ 8.30 (d, J=7.5 Hz, 1H), 7.57 (d, J=7.5 Hz, 1H), 7.36 (t, J=7.5 Hz, 1H), 7.19 (t, J=7.5 Hz, 1H), 6.36, (br s, 2H), 4.52 (s, 1H), 4.49 (br s, 1H), 2.99 (t, J=7.5 Hz, 2H), 1.83 (hex, J=7.5 Hz, 2H), 1.46 (m, 10H), 1.10 (br s, 1H), 1.00 (t, J=7.5 Hz, 3H); MS (APCI) m/z 339 (M+H)$^+$; Anal. calcd for C$_{20}$H$_{26}$N$_4$O: C, 70.98; H, 7.74; N, 16.55. Found: C, 70.73; H, 7.73; N, 16.44.

Example 148

1-[(4-Amino-2-ethyl-1H-imidazo[4,5-c]quinolin-1-yl)methyl]cyclohexanol

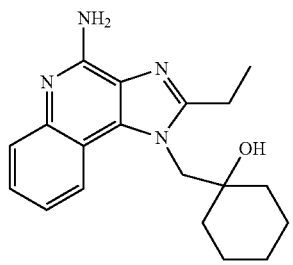 [SMILES: CCc1nc2c(N)nc3ccccc3c2n1CC1(O)CCCCC1]

1-[(4-Amino-2-ethyl-1H-imidazo[4,5-c]quinolin-1-yl)methyl]cyclohexanol was prepared according to the general methods of Example 1 using propionyl chloride in lieu of ethoxyacetyl chloride in Part B. The crude product was recrystallized from acetonitrile/water to provide pure product as a brown solid, mp 217-218° C. $^1$H NMR (300 MHz, DMSO-$d_6$) δ 8.31 (d, J=7.5 Hz, 1H), 7.57 (d, J=7.5 Hz, 1H), 7.36 (t, J=7.5 Hz, 1H), 7.19 (t, J=7.5 Hz, 1H), 6.36, (br s, 2H), 4.53 (s, 1H), 4.49 (br s, 1H), 3.04 (q, J=7.5 Hz, 2H), 1.46 (m, 10H), 1.35 (t, J=7.5 Hz, 3H), 1.10 (br s, 1H); MS (APCI) m/z 325 (M+H)$^+$; Anal. calcd for $C_{19}H_{24}N_4O$: C, 70.34; H, 7.46; N, 17.27. Found: C, 70.06; H, 7.34; N, 17.21.

Example 149

4-[(4-Amino-1H-imidazo[4,5-c]quinolin-1-yl)methyl]tetrahydro-2H-pyran-4-ol

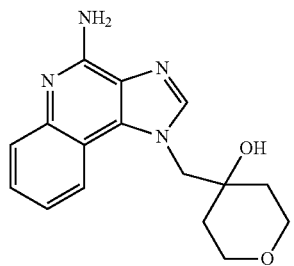 [SMILES: Nc1nc2ccccc2c2c1ncn2CC1(O)CCOCC1]

Part A

4-[(1H-imidazo[4,5-c]quinolin-1-yl)methyl]tetrahydro-2H-pyran-4-ol was prepared according to the general methods of Example 11 using triethyl orthoformate in lieu of triethyl orthoacetate in Part A.

Part B

4-[(1H-imidazo[4,5-c]quinolin-1-yl)methyl]tetrahydro-2H-pyran-4-ol was oxidized and then aminated according to the general methods of Part E of Example 2. The crude product was purified by column chromatography (silica gel eluting with 9% methanol in chloroform) and then by HPFC eluting with a gradient of 8-35% CMA in chloroform. The resulting material was triturated with methanol and then dried in a vacuum oven at 105° C. to provide 4-[(4-amino-1H-imidazo[4,5-c]quinolin-1-yl)methyl]tetrahydro-2H-pyran-4-ol as a brown solid, mp 260-262° C. $^1$H NMR (300 MHz, DMSO-$d_6$) δ 8.37 (d, J=8.1 Hz, 1H), 8.08 (s, 1H), 7.59 (d, J=8.1 Hz, 1H), 7.41 (t, J=8.1 Hz, 1H), 7.21 (t, J=8.1 Hz, 1H), 6.51, (br s, 2H), 4.91 (s, 1H), 4.57 (br s, 2H), 3.58 (m, 4H), 1.76 (dt, J=6.9 Hz, 2H), 1.31 (d, J=6.9 Hz, 2H); MS (APCI) m/z 299 (M+H)$^+$; Anal. calcd for $C_{16}H_{18}N_4O_2$: C, 64.41; H, 6.08; N, 18.78. Found: C, 64.04; H, 5.87; N, 18.83.

Example 150

1-[(4-Amino-2-methyl-1H-imidazo[4,5-c]quinolin-1-yl)methyl]cyclopentanol

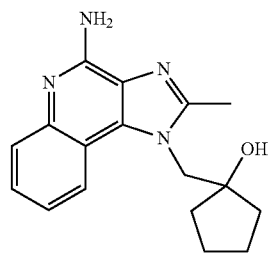 [SMILES: Cc1nc2c(N)nc3ccccc3c2n1CC1(O)CCCC1]

1-[(4-Amino-2-methyl-1H-imidazo[4,5-c]quinolin-1-yl)methyl]cyclopentanol was prepared according to the general methods of Example 3 using acetyl chloride in lieu of ethoxyacetyl chloride in Part E. The crude product was isolated by filtration, rinsed with methanol, and then dried. This material was triturated with hot acetonitrile/water, isolated by filtration without cooling, rinsed with water, and then dried. The resulting material was triturated with 1N aqueous hydrochloric acid (20 mL/g) for 2 hours. A solid was isolated by filtration. This solid was triturated with a minimum amount of water and then the pH was adjusted to pH 14 using 50% aqueous sodium hydroxide. A solid was isolated by filtration, rinsed with water, and then dried in a vacuum oven at 108° C. to provide pure product as an off-white solid, mp 306.5-307.5° C. $^1$H NMR (300 MHz, DMSO-$d_6$) δ 8.26 (d, J=8.1 Hz, 1H), 7.57 (d, J=8.1 Hz, 1H), 7.37 (d, J=7.5 Hz, 1H), 7.19 (t, J=7.5 Hz, 1H), 6.42 (br s, 2H), 4.73 (s, 1H), 4.67 (s, 2H), 2.65 (s, 3H), 1.66 (m, 4H), 1.55 (m, 4H); MS (APCI) m/z 297 (M+H)$^+$; Anal. calcd for $C_{17}H_{20}N_4O$: C, 68.89; H, 6.80; N, 18.90. Found: C, 68.62; H, 6.60; N, 18.76.

Example 151

1-[(4-Amino-2-ethyl-1H-imidazo[4,5-c]quinolin-1-yl)methyl]cyclopentanol

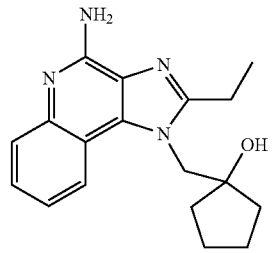 [SMILES: CCc1nc2c(N)nc3ccccc3c2n1CC1(O)CCCC1]

1-[(4-Amino-2-ethyl-1H-imidazo[4,5-c]quinolin-1-yl)methyl]cyclopentanol was prepared according to the general methods of Example 3 using propionyl chloride in lieu of ethoxyacetyl chloride in Part E. The crude product was recrystallized from acetonitrile/water then triturated with 1N aqueous sodium hydroxide, isolated by filtration, rinsed with water, and dried under vacuum at 100° C. to provide pure product as an off-white solid, mp 251.0-252.5° C. $^1$H NMR (300 MHz, DMSO-$d_6$) δ 8.26 (d, J=7.5 Hz, 1H), 7.58 (d, J=8.1 Hz, 1H), 7.37 (d, J=8.1 Hz, 1H), 7.19 (t, J=8.1 Hz, 1H), 6.38 (br s, 2H), 4.71 (s, 1H), 4.68 (s, 2H), 3.03 (q, J=7.5 Hz, 2H), 1.64 (m, 4H), 1.53 (m, 4H), 1.35 (t, J=7.5 Hz, 3H); MS (APCI) m/z 311 (M+H)$^+$; Anal. calcd for C$_{18}$H$_{22}$N$_4$O: C, 69.65; H, 7.14; N, 18.05. Found: C, 69.45; H, 6.88; N, 17.94.

Example 152

1-[(4-Amino-2-propyl-1H-imidazo[4,5-c]quinolin-1-yl)methyl]cyclopentanol

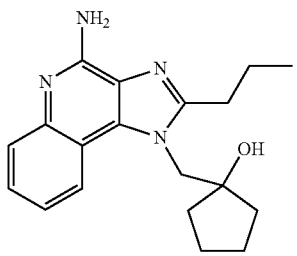 [SMILES: CCCc1nc2c(N)nc3ccccc3c2n1CC1(O)CCCC1]

1-[(4-Amino-2-ethyl-1H-imidazo[4,5-c]quinolin-1-yl)methyl]cyclopentanol was prepared according to the general methods of Example 3 using butyryl chloride in lieu of ethoxyacetyl chloride in Part E. The crude product was isolated by filtration, triturated with a minimum amount of chloroform, isolated by filtration, and dried. The resulting material was triturated with 1N aqueous sodium hydroxide, isolated by filtration, and dried under vacuum at 100° C. to provide pure product as an off-white solid, mp 209.5-210.5° C. $^1$H NMR (300 MHz, DMSO-d$_6$) δ 8.26 (d, J=8.1 Hz, 1H), 7.58 (d, J=7.5 Hz, 1H), 7.37 (d, J=8.1 Hz, 1H), 7.19 (t, J=8.1 Hz, 1H), 6.38 (br s, 2H), 4.71 (s, 1H), 4.69 (s, 2H), 2.98 (t, J=7.5 Hz, 2H), 1.84 (hex, J=7.5 Hz, 2H), 1.63 (m, 4H), 1.53 (m, 4H), 1.00 (t, J=7.5 Hz, 3H); MS (APCI) m/z 325 (M+H)$^+$; Anal. calcd for C$_{19}$H$_{24}$N$_4$O: C, 70.34; H, 7.46; N, 17.27. Found: C, 70.27; H, 7.43; N, 17.30.

Example 153

1-[(4-Amino-7-bromo-2-ethoxymethyl-1H-imidazo[4,5-c]quinolin-1-yl)methyl]cyclopentanol

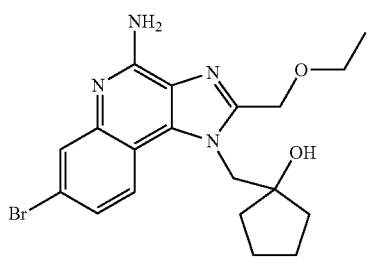 [SMILES: CCOCc1nc2c(N)nc3cc(Br)ccc3c2n1CC1(O)CCCC1]

1-[(4-Amino-7-bromo-2-ethoxymethyl-1H-imidazo[4,5-c]quinolin-1-yl)methyl]cyclopentanol was prepared according to the general methods of Example 3 using 7-bromo-4-chloro-3-nitroquinoline in lieu of 4-chloro-3-nitroquinoline in Part C. The crude product was recrystallized from acetonitrile and then from toluene to provide pure product as a brown solid, mp 128-130° C. $^1$H NMR (300 MHz, DMSO-d$_6$) δ 8.24 (d, J=9.4 Hz, 1H), 7.71 (s, 1H), 7.31 (d, J=8.7 Hz, 1H), 6.81 (br s, 2H), 4.87 (br s, 2H), 4.78 (s, 2H), 4.76 (s, 1H), 3.52 (q, J=6.9 Hz, 2H), 1.66 (m, 4H), 1.51 (m, 4H), 1.13 (t, J=6.9 Hz, 3H); MS (APCI) m/z 420 (M+H)$^+$; Anal. calcd for C$_{19}$H$_{23}$BrN$_4$O$_2$: C, 54.42; H, 5.53; N, 13.36. Found: C, 54.18; H, 5.29; N, 13.10.

Example 154

1-[(4-Amino-1H-imidazo[4,5-c]quinolin-1-yl)methyl]cyclopentanol

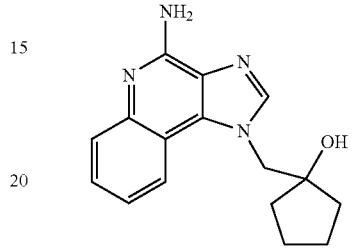

Part A

A mixture of 1-{{(3-aminoquinolin-1-yl)amino]methyl}cyclopentanol (2.00 g, 7.8 mmol, Example 3 Parts A through D), triethyl orthoformate (1.36 mL, 8.2 mmol), pyridine hydrochloride (0.2 g), and toluene (20 mL) was heated at reflux for 3.5 hours. The reaction mixture was allowed to cool to ambient temperature. A solid was isolated by filtration and dried. The solid was triturated with a minimum amount of saturated aqueous sodium bicarbonate for 1 hour. The solid was filtered and then dried to provide 1.85 g of 1-[(1H-imidazo[4,5-c]quinolin-1-yl)methyl]cyclopentanol as a white solid.

Part B

The material from Part A was oxidized and then aminated according to the general methods of Parts B and C of Example 62. The crude product was isolated by filtration, rinsed with methanol, triturated with 1N aqueous sodium hydroxide, isolated by filtration, and then dried in a vacuum oven at 100° C. to provide 1-[(4-amino-1H-imidazo[4,5-c]quinolin-1-yl)methyl]cyclopentanol as a white solid, mp 253.5-255.0° C. $^1$H NMR (300 MHz, DMSO-d$_6$) δ 8.31 (d, J=8.1 Hz, 1H), 8.14 (s, 1H), 7.59 (d, J=7.5 Hz, 1H), 7.40 (t, J=7.5 Hz, 1H), 7.21 (t, J=7.5 Hz, 1H), 6.50, (br s, 2H), 4.79 (s, 1H), 4.67 (s, 2H), 4.69 (m, 4H), 4.55 (m, 4H); MS (APCI) m/z 283 (M+H)$^+$; Anal. calcd for C$_{16}$H$_{18}$N$_4$O: C, 68.06; H, 6.43; N, 19.84. Found: C, 67.89; H, 6.29; N, 20.07.

Example 155

1-[(4-Amino-7-bromo-2-ethoxymethyl-1H-imidazo[4,5-c][1,5]napthyridin-1-yl)methyl]cyclopentanol

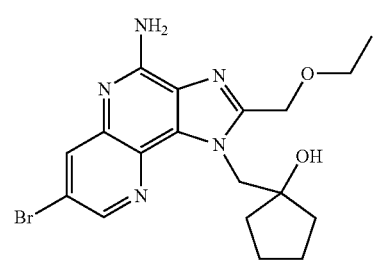 [SMILES: CCOCc1nc2c(N)nc3cc(Br)cnc3c2n1CC1(O)CCCC1]

Part A

A mixture of triethyl orthoformate (10 mL, 60.1 mmol) and 2,2-dimethyl-[1,3]-dioxane-4,6-dione (40.9 g, 0.23 mol) (Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C. $^1$H NMR (300 MHz, CDCl$_3$) δ 11.26 (d, J=14.3 Hz, 1H), 8.80 (d, J=2.3 Hz, 1H), 8.62 (d, J=14.3 Hz, 1H), 8.56 (d, J=1.9 Hz, 1H), 8.44-8.40 (m, 1H), 1.68 (s, 6H).

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder.

$^1$H NMR (300 MHz, CDCl$_3$) δ 11.81 (br s, 1H), 8.69 (d, J=1.9 Hz, 1H), 8.21 (d, J=1.9 Hz, 1H), 7.95 (d, J=7.7 Hz, 1H), 6.22 (d, J=7.5 Hz, 1H).

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and neutralized to pH 2-3 with a solution of 50% aqueous NaOH. The resulting precipitate was filtered, washed with water, and dried over vacuum for 3 days to yield 25.1 g of 7-bromo-3-nitro[1,5]naphthyridin-4-ol as a yellow crystalline solid.

$^1$H NMR (300 MHz, CDCl$_3$) δ 13.06 (br s, 1H), 9.26 (s, 1H), 8.88 (d, J=2.0 Hz, 1H), 8.37 (d, J=2.0 Hz, 1H).

Part D

Phosphorous oxychloride (24 mL, 257.7 mmol) was added slowly dropwise to a 0° C. suspension of 7-bromo-3-nitro[1,5]naphthyridin-4-ol (60.00 g, 222.2 mmol) in N,N-dimethylformamide (DMF; 410 mL), maintaining the temperature below 10° C. After addition was completed, the reaction was allowed to warm to ambient temperature over a 3 hour period. The reaction mixture was then added to ice water (1700 mL) with stirring. A solid precipitate formed, which was isolated by vacuum filtration and rinsed with water. The material was partitioned between chloroform (3 Liters) and saturated aqueous sodium bicarbonate (300 mL). The organic phase was isolated, dried over anhydrous sodium sulfate, then concentrated under reduced pressure to yield 54.42 g of 7-bromo-4-chloro-3-nitro[1,5]naphthyridine as short, off-white needles.

$^1$H NMR (300 MHz, CDCl$_3$) δ 9.32 (s, 1H), 9.21 (d, J=2.5 Hz, 1H), 8.71 (d, J=2.5 Hz, 1H).

Part E

1-[(4-Amino-7-bromo-2-ethoxymethyl-1H-imidazo[4,5-c][1,5]napthyridin-1-yl)methyl]cyclopentanol was prepared according to the general methods of Example 3 using 7-bromo-4-chloro-3-nitro[1,5]naphthyridine in lieu of 4-chloro-3-nitroquinoline in Part C. The crude product was triturated with hot acetonitrile. The acetonitrile phase was concentrated under reduced pressure. The residue was dissolved in chloroform, washed with 1% aqueous sodium bicarbonate, dried over sodium sulfate, and concentrated under reduced pressure. The residue was purified by column chromatography eluting with 1.5% methanol in chloroform. The resulting material was triturated with hot acetonitrile. The mixture was cooled to ambient temperature and a solid was isolated by filtration and dried in a vacuum oven at 110° C. to provide 1-[(4-amino-7-bromo-2-ethoxymethyl-1H-imidazo[4,5-c][1,5]napthyridin-1-yl)methyl]cyclopentanol as a white solid, mp 166-167.5° C. $^1$H NMR (300 MHz, DMSO-d$_6$) δ 8.53 (s, 1H), 8.10 (s, 1H), 7.15 (br s, 2H), 5.05 (br s, 2H), 4.95 (s, 2H), 4.82 (s, 1H), 3.52 (q, J=6.9 Hz, 2H), 4.64 (m, 6H), 1.39 (s, 2H), 1.14 (t, J=6.9 Hz, 3H); MS (APCI) m/z 421 (M+H)$^+$; Anal. calcd for C$_{18}$H$_{22}$BrN$_5$O$_2$: C, 51.44; H, 5.28; N, 16.66. Found: C, 51.32; H, 5.24; N, 16.63.

Example 156

4-[(4-Amino-2-propyl-1H-imidazo[4,5-c]quinolin-1-yl)methyl]-1-methylpiperidin-4-ol

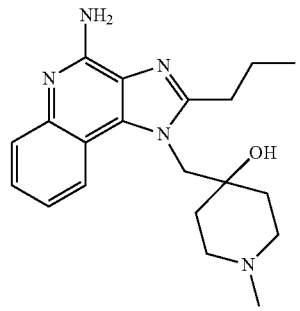 [SMILES: CCCc1nc2c(N)nc3ccccc3c2n1CC1(O)CCN(C)CC1]

Part A

Nitromethane (6.6 mL, 122.0 mmol) and sodium methoxide (0.94 mL of 25 wt % in methanol, 4.1 mmol) were added to a solution of 1-methyl-4-piperidone (10 mL, 81.3 mmol) in ethanol (10 mL). After 30 minutes more ethanol (15 mL) was added to facilitate stirring. The reaction mixture was stirred at ambient temperature for 2 days and then filtered. The isolated solid was rinsed with ether to provide 10.39 g of 1-methyl-4-nitromethylpiperidin-4-ol as a white powder. An additional 1.18 g was isolated from the filtrate.

Part B

Palladium hydroxide (2.3 g of 20% on carbon) was added to a solution of 1-methyl-4-nitromethylpiperidin-4-ol (11.57 g) in ethanol (120 mL). The mixture was placed under hydrogen pressure (50 psi, 3.4×10$^5$ Pa) on a Parr apparatus for 55 hours. The reaction mixture was filtered through a layer of CELITE filter aid and the filter cake was rinsed with methanol (100 mL). The filtrate was concentrated under reduced pressure to provide 10.18 g of 4-aminomethyl-1-methylpiperidin-4-ol as a thick oil.

Part C

Triethylamine (10.9 mL, 78.5 mmol) was added to a suspension of 2,4-dichloro-3-nitroquinoline (14.7 g, 60.4 mmol) in dichloromethane (180 mL). The mixture was cooled to 5° C. and a solution of the material from Part B (66.4 mmol) in dichloromethane (70 mL) was added over a period of 15 minutes. The reaction mixture was stirred at 5° C. for 1 hour and then at ambient temperature overnight. The reaction mixture was concentrated under reduced pressure. The residue was combined with water (500 mL), stirred for 1 hour, and then filtered. The isolated solid was triturated with acetonitrile to provide 13.25 g of 4-{[(2-chloro-3-nitroquinolin-4-yl)amino]methyl}-1-methylpiperidin-4-ol as a bright yellow solid.

Part D

A mixture of 4-{[(2-chloro-3-nitroquinolin-4-yl)amino]methyl}-1-methylpiperidin-4-ol (14.05 g), 5% platinum on carbon (1.1 g), acetonitrile (280 mL), and isopropanol (84 mL) was placed under hydrogen pressure on a Parr apparatus overnight.

The reaction mixture was filtered through a layer of CELITE filter aid. The filtrate was concentrated under reduced pressure to provide crude 4-{[(3-amino-2-chloro-quinolin-4-yl)amino]methyl}-1-methylpiperidin-4-ol. This material was dissolved in 240 mL of acetonitrile.

Part E

Butyryl chloride (1.19 mL, 1.15 eq) was added to a 60 mL portion of the solution from Part D. An hour later more butyryl chloride (0.1 eq) was added. The reaction mixture was concentrated under reduced pressure. The residue was triturated with diethyl ether, isolated by filtration, and dried to provide crude N-(2-chloro-4-{[(4-hydroxy-1-methylpiperidin-4-yl)methyl]amino}quinolin-3-yl)butanamide.

Part F

A solution of 50% aqueous sodium hydroxide (2.39 g) in water (10.2 mL) was added to a solution of the material from Part E in ethanol (30 mL). The reaction mixture was refluxed for 1 hour and then concentrated under reduced pressure. The residue was partitioned between chloroform and water. The organic layer was dried over sodium sulfate and then concentrated under reduced pressure. The residue was purified by HPFC eluting with a gradient of 20-50% CMA in chloroform. The residue was recrystallized from acetonitrile and the mixture was filtered. The filtrate was concentrated under reduced pressure to provide 4-[(4-chloro-2-propyl-1H-imidazo[4,5-c]quinolin-1-yl)methyl]-1-methylpiperidin-4-ol.

Part G

The material from Part F was combined with a solution of 7N ammonia in methanol (16 mL) in a pressure vessel. The vessel was sealed and then heated at 150° C. for 18 hours. The reaction mixture was concentrated under reduced pressure. The residue was purified by HPFC eluting with a gradient of 25-100% solution over 6 L of 30% methanol in chloroform, triturated with acetonitrile, and dried. The resulting material was dissolved in water. The pH of the solution was adjusted to pH 2 with 1N hydrochloric acid and then to pH 14 with 50% aqueous sodium hydroxide and then chloroform was added. The organic phase was separated and concentrated under reduced pressure. The residue was triturated with hot chloroform and the filtered while still hot. The isolated solid was combined with chloroform (400 mL), washed with aqueous sodium bicarbonate (2×60 mL), dried over sodium sulfate, and concentrated under reduced pressure. The residue was dried under vacuum at 110° C. to provide 0.33 g of 4-[(4-amino-2-propyl-1H-imidazo[4,5-c]quinolin-1-yl)methyl]-1-methylpiperidin-4-ol as an off-white solid, mp 241-242° C. $^1$H NMR (300 MHz, DMSO-$d_6$) δ 8.28 (d, J=8.1 Hz, 1H), 7.57 (d, J=8.1 Hz, 1H), 7.36 (t, J=8.1 Hz, 1H), 7.19 (t, J=8.1 Hz, 1H), 6.37, (br s, 2H), 4.60 (s, 1H), 4.54 (br s, 1H), 3.00 (t, J=7.5 Hz, 2H), 2.40 (s, 2H), 2.08 (s, 3H), 2.08 (m, 2H), 1.83 (hex, J=7.5 Hz, 2H), 1.72 (m, 4H), 1.31 (br s, 1H), 1.00 (t, J=7.5 Hz, 3H); MS (APCI) m/z 354 (M+H)$^+$; Anal. calcd for $C_{20}H_{27}N_5O$: C, 67.96; H, 7.70; N, 19.81. Found: C, 67.86; H, 7.67; N, 19.85.

Example 157

4-[(4-Amino-2-ethyl-1H-imidazo[4,5-c]quinolin-1-yl)methyl]-1-methylpiperidin-4-ol

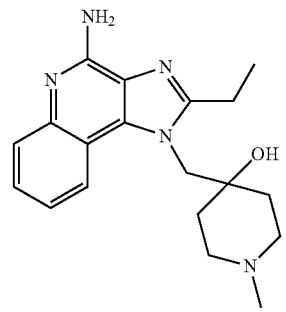 [SMILES: CCc1nc2c(N)nc3ccccc3c2n1CC1(O)CCN(C)CC1]

4-[(4-Amino-2-ethyl-1H-imidazo[4,5-c]quinolin-1-yl)methyl]-1-methylpiperidin-4-ol was prepared according to the general method of Example 156 using propionyl chloride in lieu of butyryl chloride in Part E. The crude product was triturated with chloroform. The resulting material was dissolved in water. The pH of the solution was adjusted to pH 2 with 1N hydrochloric acid and then to pH 14 with 50% aqueous sodium hydroxide and then chloroform was added. The mixture was filtered to provide a gray solid. The organic phase from the filtrate was concentrated under reduced pressure. The residue was triturated with chloroform. The resulting solid was combined with the gray solid, triturated with chloroform, and dried to provide pure product as a gray solid, mp 233-234° C. $^1$H NMR (300 MHz, DMSO-$d_6$) δ 8.29 (d, J=8.1 Hz, 1H), 7.58 (d, J=8.1 Hz, 1H), 7.37 (t, J=8.1 Hz, 1H), 7.19 (t, J=8.1 Hz, 1H), 6.38, (br s, 2H), 4.61 (s, 1H), 4.55 (br s, 1H), 3.05 (q, J=7.5 Hz, 2H), 2.40 (s, 2H), 2.08 (s, 3H), 2.08 (m, 2H), 1.73 (m, 4H), 1.32 (br s, 1H), 1.35 (t, J=7.5 Hz, 3H); MS (APCI) m/z 340 (M+H)$^+$; Anal. calcd for $C_{19}H_{25}N_5O$: C, 67.23; H, 7.42; N, 20.63. Found: C, 66.91; H, 7.70; N, 20.66.

Example 158

4-[(4-Amino-2-ethoxymethyl-1H-imidazo[4,5-c]quinolin-1-yl)methyl]-1-methylpiperidin-4-ol

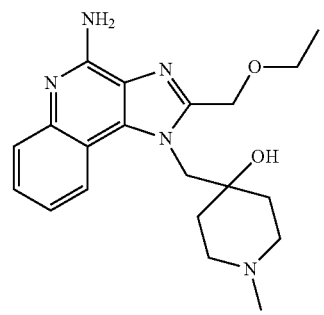 [SMILES: CCOCc1nc2c(N)nc3ccccc3c2n1CC1(O)CCN(C)CC1]

4-[(4-Amino-2-ethoxymethyl-1H-imidazo[4,5-c]quinolin-1-yl)methyl]-1-methylpiperidin-4-ol was prepared according to the general method of Example 156 using ethoxyacetyl chloride in lieu of butyryl chloride in Part E. The crude product was triturated with hot acetonitrile; the

Example 159

2-Ethoxymethyl-1-({4-[2-(methyl sulfonyl)ethoxy]tetrahydro-2H-pyran-4-yl}methyl)-1H-imidazo[4,5-c]quinolin-4-amine

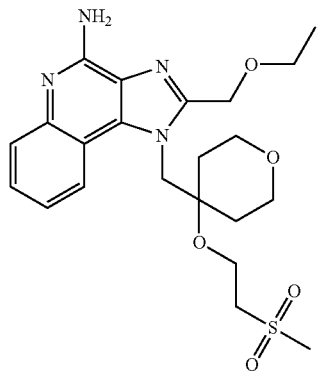 [SMILES: CCOCc1nc2c(N)nc3ccccc3c2n1CC1(OCCS(C)(=O)=O)CCOCC1]

4-[(2-Ethoxymethyl-1H-imidazo[4,5-c]quinolin-1-yl)methyl]tetrahydro-2H-pyran-4-ol (4.05 g, Example 10 Parts A through E) was converted to 2-ethoxymethyl-1-({4-[2-(methylsulfonyl)ethoxy]tetrahydro-2H-pyran-4-yl}methyl)-1H-imidazo[4,5-c]quinolin-4-amine according to the general methods of Example 13 using 4-[(2-ethoxymethyl-1H-imidazo[4,5-c]quinolin-1-yl)methyl]tetrahydro-2H-pyran-4-ol in lieu of tert-butyl [(2-ethoxymethyl-1H-imidazo[4,5-c]quinolin-1-yl)methyl]-4-hydroxyypiperidine-1-carboxylate in Part A. The crude product was purified by column chromatography (silica gel eluting with 95/5 dichloromethane/methanol) to provide a white foam. This material was recrystallized from acetonitrile, isolated by filtration, washed with acetonitrile, and then dried under vacuum at 65° C. to provide 50 mg of pure product as a white powder. MS (APCI) m/z 463 (M+H)+; Anal. Cacld for $C_{22}H_{30}N_4O_5S$: C, 57.12; H, 6.54: N, 12.11. Found: C, 57.08; H, 6.75; N, 12.04.

Previous example continuation:
mixture was allowed to cool and a solid was isolated by filtration. The solid was dissolved in water. The pH of the solution was adjusted to pH 2 with 1N hydrochloric acid and then to pH 14 with 50% aqueous sodium hydroxide and then chloroform was added. The organic phase was separated and concentrated under reduced pressure to provide a yellow solid. This material was recrystallized from acetonitrile and then dried under vacuum at 105° C. to provide pure product as a light brown solid, mp 197.5-198.5° C. $^1$H NMR (300 MHz, DMSO-$d_6$) δ 8.30 (d, J=8.1 Hz, 1H), 7.59 (d, J=8.1 Hz, 1H), 7.40 (t, J=6.9 Hz, 1H), 7.21 (t, J=6.9 Hz, 1H), 6.54, (br s, 2H), 4.88 (br s, 2H), 4.71 (s, 2H), 4.67 (br s, 1H), 3.51 (q, J=6.9 Hz, 2H), 2.40 (m, 2H), 2.08 (s, 3H), 2.08 (m, 2H), 1.76 (m, 2H), 1.30 (br s, 2H), 1.13 (t, J=6.9 Hz, 3H); MS (APCI) m/z 370 (M+H)+; Anal. calcd for $C_{20}H_{27}N_5O_2$: C, 65.02; H, 7.37; N, 18.96. Found: C, 64.75; H, 7.45; N, 19.15.

Example 160

3-[(4-Amino-2-propyl-1H-imidazo[4,5-c][1,5]naphthyridin-1-yl)methyl]tetrahydrofuran-3-ol

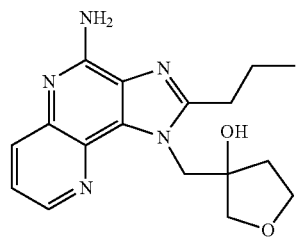 [SMILES: CCCc1nc2c(N)nc3cccnc3c2n1CC1(O)CCOC1]

Part A

Pyridinium chlorochromate (85.8 g, 3.5 eq) was added in portions over a period of 5 minutes to a solution of 3-hydroxytetrahydrofuran (10.02 g, 1.0 eq) in dichloromethane (115 mL). The reaction mixture was stirred at ambient temperature for 3.5 hours and then applied directly to a column of silica gel (325 g). The column was eluted with diethyl ether. The fractions containing product were combined and the solvent was removed by atmospheric distillation to provide 5.22 g of tetrahydrofuran-3-one.

Part B

Potassium cyanide (50 mg, 0.02 eq.) and 18-crown-6 macrocyclic polyether (203 mg, 0.02 eq) were dissolved in methanol (8 mL). The solution was stirred for 5 minutes and then concentrated under reduced pressure. The resulting white solid was dissolved in trimethylsilyl cyanide (5.5 mL, 1.0 eq.) and the solution was added dropwise over a period of 1 minute to the material from Part A (1.0 eq). The reaction was cooled with an ice bath during the addition. The reaction mixture was stirred in the ice bath for 2 minutes, allowed to warm to ambient temperature, and stirred for 15 minutes.

Part C

The reaction mixture from Part B (1.0 eq) was diluted with tetrahydrofuran (THF) and cooled to 0° C. Solid lithium aluminum hydride (1.46 g, 1.0 eq) was added in portions over a period of 5 minutes. After 1 hour water (1.5 mL) was added dropwise; the ice bath was removed, and the reaction was stirred for several minutes. Sodium hydroxide (1.5 mL of 10%) and water (4.5 mL) were added and the reaction mixture was stirred for 30 minutes. Magnesium sulfate was added and the reaction mixture was stirred for another 10 minutes. The reaction mixture was filtered through a layer of CELITE filter aid. The filter cake was rinsed with THF (2×100 mL). The filtrate was concentrated under vacuum to provide a light yellow liquid. This material was concentrated from acetonitrile (2×100 mL) to provide 5.19 g of a mixture of 3-(aminomethyl)tetrahydrofuran-3-ol and (3-trimethylsilyloxytetrahydrofuran-3-yl)methylamine.

Part D

4-Chloro-3-nitronaphthyridine (7.13 g, 1.1 eq) and triethylamine (5.21 mL, 1.1 eq) were added sequentially to a solution of the material from Part C (1.0 eq) in dichloromethane (113 mL). The reaction mixture was cooled briefly with an ice bath to control an exotherm and then stirred at ambient temperature overnight. The reaction mixture was diluted with water (200 mL) and dichloromethane (350 mL). The aqueous layer was extracted with dichloromethane (400 mL). The combined organics were dried over magnesium sulfate and then concentrated under reduced pressure to provide 10.96 g of a yellow solid. This material was dissolved in methanol (350 mL). Potassium carbonate (5.0 g) was added; the resulting suspension was stirred for 20 minutes and then concentrated under reduced pressure. The residue was slurried with water (130 mL) overnight and then filtered. The isolated solid was rinsed with water (2×70 mL) and dried under vacuum to provide 8.27 g of 3-[3-nitro[1,5]napthyridin-4-yl)methyl]tetrahydrofuran-3-ol as a yellow solid.

Part E

A suspension of 3-[3-nitro[1,5]napthyridin-4-yl)methyl] tetrahydrofuran-3-ol (2.00 g) and 10% palladium on carbon (200 mg) in ethanol (68 mL) was placed under hydrogen pressure (50 psi, 3.4×10$^5$ Pa) on a Parr apparatus for 4 hours. The reaction mixture was sparged with nitrogen for 15 minutes and then filtered through a layer of CELITE filter aid. The filtrate was concentrated under reduced pressure. The residue was reconcentrated from acetonitrile (2×75 mL) and dichloromethane (2×50 mL) and then dried under high vacuum to provide 1.79 g of 3-[3-amino[1,5]napthyridin-4-yl)methyl]tetrahydrofuran-3-ol as a yellow foam.

Part F

Toluene (29 mL), trimethyl orthobutyrate (0.56 mL, 1.1 eq), and pyridine hydrochloride (37 mg, 0.1 eq) were added to a suspension of 3-[3-amino[1,5]napthyridin-4-yl)methyl] tetrahydrofuran-3-ol (0.83 g, 1.0 eq) in chloroform (3 mL). The reaction mixture was heated at reflux with stirring for 16 hours, allowed to cool to ambient temperature, and then concentrated under reduced pressure. The residue was triturated with acetonitrile (about 6 mL) and filtered. The isolated solid was rinsed with acetonitrile (3×4 mL) to provide 0.80 g of a tan solid. A portion (112 mg) was purified by HPFC (silica gel eluting with 20% CMA in chloroform) to provide 88 mg of 3-[(2-propyl-1H-imidazo[4,5-c][1,5]naphthyridin-1-yl)methyl]tetrahydrofuran-3-ol as light tan needles, mp 151-152° C. $^1$H NMR (300 MHz, DMSO-d$_6$): δ 9.25 (s, 1H), 8.96 (dd, J=1.6, 4.3 Hz, 1H), 8.51 (dd, J=1.6, 8.5 Hz, 1H), 7.73 (dd, J=4.3, 8.5 Hz, 1H), 5.37 (s, 1H), 5.30 (m, 1H), 5.08 (m, 1H), 3.80 (m, 3H), 3.46 (d, J=8.9 Hz, 1H), 3.12 (t, J=7.5 Hz, 2H), 2.12 (m, 1H), 1.91 (m, 2H), 1.66 (m, 1H), 1.03 (t, J=7.4 Hz, 3H); MS (APCI) m/z 313 (M+H)$^+$; Anal. calcd for C$_{17}$H$_{20}$N$_4$O$_2$: C, 65.37; H, 6.45; N, 17.94. Found: C, 65.13; H, 6.18; N, 17.88.

Part G

3-Chloroperbenzoic acid (0.60 g of 77%, 1.1 eq) was added to a solution of 3-[(2-propyl-1H-imidazo[4,5-c][1,5] naphthyridin-1-yl)methyl]tetrahydrofuran-3-ol (0.68 g, 1.0 eq) in chloroform. The reaction mixture was stirred at ambient temperature for 3.5 hours. Ammonium hydroxide (22 mL) and p-toluenesulfonyl chloride (0.50 g, 1.2 eq) were added sequentially and the reaction mixture was stirred at ambient temperature for 2 hours. The reaction mixture was diluted with water (20 mL) and chloroform (30 mL). The aqueous layer was extracted with chloroform (30 mL). The combined organics were dried over magnesium sulfate and then concentrated under reduced pressure to provide a brown foam. This material was triturated with ethyl acetate (about 12 mL). A solid was isolated by filtration, rinsed with ethyl acetate (4×5 mL), and then dried under vacuum to provide 383 mg of a yellow solid. This material was triturated with warm ethyl acetate (about 15 mL). A solid was isolated by filtration, rinsed with ethyl acetate (3×5 mL), and then dried under vacuum to provide 260 mg of 3-[(4-amino-2-propyl-1H-imidazo[4,5-c][1,5]-naphthyridin-1-yl)methyl]tetrahydrofuran-3-ol as a tan powder, mp 171-173° C. $^1$H NMR (300 MHz, DMSO-d$_6$): δ 8.47 (dd, J=1.5, 4.3 Hz, 1H), 7.91 (dd, J=1.5, 8.4 Hz, 1H), 7.43 (dd, 1H), 6.75 (s, 2H), 5.46 (s, 1H), 5.22 (m, 1H), 4.98 (m, 1H), 3.80 (m, 3H), 3.45 (d, J=8.9 Hz, 1H), 3.04 (t, J=7.6 Hz, 2H), 2.09 (m, 1H), 1.85 (sextet, J=7.5 Hz, 2H), 1.66 (m, 1H), 1.01 (t, J=7.4 Hz, 3H); MS (APCI) m/z 328 (M+H)$^+$; Anal. calcd for C$_{17}$H$_{21}$N$_5$O$_2$: C, 62.37; H, 6.47; N, 21.39. Found: C, 62.14; H, 6.33; N, 21.31.

Example 161

3-[(4-Amino-2-ethyl-1H-imidazo[4,5-c][1,5]naphthyridin-1-yl)methyl]tetrahydrofuran-3-ol

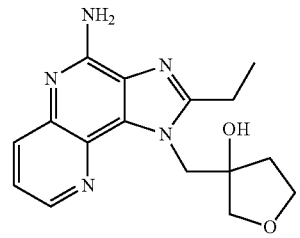 [SMILES: CCc1nc2c(N)nc3cccnc3c2n1CC1(O)CCOC1]

Part A

3-[(2-ethyl-1H-imidazo[4,5-c][1,5]naphthyridin-1-yl) methyl]tetrahydrofuran-3-ol was prepared according to the methods of Parts A through F in Example 160 using triethyl orthoformate in lieu of trimethyl orthobutyrate in Part F. The crude product was triturated with ethyl acetate (about 6 mL). A solid was isolated by filtration, rinsed with ethyl acetate (4×5 mL), and then dried under vacuum to provide 839 mg of a tan powder.

Part B

The material from Part A was oxidized and then aminated according to the methods of Part G of Example 160. The crude product was triturated with ethyl acetate (about 15 mL). A solid was isolated by filtration, rinsed with ethyl acetate, and then dried under vacuum to provide 610 mg of a light orange solid. This material was recrystallized from acetonitrile (about 60 mL), isolated by filtration, rinsed with acetonitrile (3×10 mL), and then dried under high vacuum to provide 462 mg of 3-[(4-amino-2-ethyl-1H-imidazo[4,5-c] [1,5]naphthyridin-1-yl)methyl]tetrahydrofuran-3-ol as off white needles, mp 234-236° C. $^1$H NMR (300 MHz, DMSO-d$_6$): δ 8.47 (dd, J=1.6, 4.3 Hz, 1H), 7.92 (dd, J=1.6, 8.4 Hz, 1H), 7.43 (dd, J=4.3, 8.4 Hz, 1H), 6.76 (s, 2H), 5.47 (s, 1H), 5.21 (m, 1H), 4.97 (m, 1H), 3.79 (m, 3H), 3.45 (d, J=8.9 Hz, 1H), 3.08 (q, J=7.5 Hz, 2H), 2.11 (m, 1H), 1.66 (m, 1H), 1.37 (t, J=7.5 Hz, 3H); MS (APCI) m/z 314 (M+H)$^+$; Anal. calcd for C$_{16}$H$_{19}$N$_5$O$_2$: C, 61.33; H, 6.11; N, 22.35. Found: C, 61.27; H, 6.02; N, 22.58.

Example 162

3-{[4-Amino-2-(fluoromethyl)-1H-imidazo[4,5-c][1,5]naphthyridin-1-yl]methyl}tetrahydrofuran-3-ol

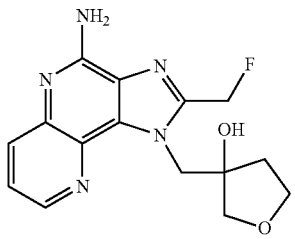 [SMILES: Nc1nc2cccnc2c2c1nc(CF)n2CC1(O)CCOC1]

Part A

Fluoroacetyl chloride (0.36 mL, 1.1 eq) was added dropwise over a period of 2 minutes to a chilled (0° C. suspension of 3-[3-amino[1,5]napthyridin-4-yl)methyl]tetrahydrofuran-3-ol (1.14 g, 1.0 eq) in dichloromethane (44 mL). After 30 minutes the reaction mixture was allowed to warm to ambient temperature. The reaction mixture was stirred for an additional 30 minutes and was then concentrated under reduced pressure to provide 2-fluoro-N-(4-{[(3-hydroxytetrahydrofuran-3-yl)methyl]amino}[1,5]naphthyridin-3-yl)acetamide hydrochloride as a yellow foam.

Part B

Triethylamine (1.83 mL, 3.0 eq) was added to a suspension of the material from Part A (1.0 eq) in ethanol (30 mL). The reaction mixture was heated at 70° C. for 2.5 hours and then at reflux for another hour. The reaction mixture was allowed to cool to ambient temperature and then concentrated under reduced pressure. The residue was suspended in 10% CMA in chloroform, filtered through a cotton plug to remove solids, and then purified by chromatography eluting with 10% CMA in chloroform for 2 column volumes, with a gradient of 10-25% CMA for 8 column volumes, and finally with 25% CMA in chloroform for 4 column volumes to provide 0.69 g of 3-{[2-(fluoromethyl)-1H-imidazo[4,5-c][1,5]naphthyridin-1-yl]methyl}tetrahydrofuran-3-ol.

Part C

The material from Part B was oxidized and then aminated according to the methods of Part G of Example 160. The crude product was triturated with ethyl acetate (about 8 mL). A solid was isolated by filtration, rinsed with ethyl acetate (4×56 mL), and then dried under vacuum to provide 345 mg of an orange foam. This material was dissolved in hot 20% CMA in chloroform (10 mL) and then purified by chromatography eluting with 20% CMA in chloroform for 8 column volumes to provide 270 mg of an off white solid. This material was triturated with ethyl acetate (about 8 mL). A solid was isolated by filtration, rinsed with ethyl acetate (2×2 mL), and then dried under vacuum to provide 196 mg of 3-{[4-amino-2-(fluoromethyl)-1H-imidazo[4,5-c][1,5]naphthyridin-1-yl]methyl}tetrahydrofuran-3-ol as an off white powder, mp 209-210° C. $^1$H NMR (300 MHz, DMSO-$d_6$): δ 8.51 (dd, J=1.5, 4.3 Hz, 1H), 7.94 (dd, J=1.5, 8.4 Hz, 1H), 7.49 (dd, J=4.3, 8.4 Hz, 1H), 7.00 (br s, 2H), 5.86 (m, 2H), 5.54 (s, 1H), 5.36 (d, J=14.3 Hz, 1H), 5.10 (d, J=14.3 Hz, 1H), 3.82 (m, 3H), 3.43 (d, J=9.0 Hz, 1H), 2.14 (ddd, J=8.5, 8.5, 12.6 Hz, 1H), 1.62 (m, 1H); MS (APCI) m/z 318 (M+H)$^+$; Anal. calcd for $C_{15}H_{16}FN_5O_2 \cdot 0.38H_2O$: C, 55.58; H, 5.21; N, 21.60. Found: C, 55.96; H, 4.89; N, 21.72.

Example 163

3-{[4-Amino-2-(fluoromethyl)-1H-imidazo[4,5-c]quinolin-1-yl]methyl}tetrahydrofuran-3-ol

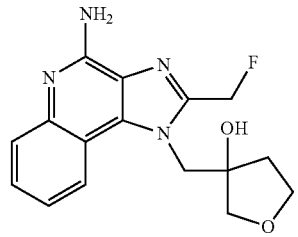 [SMILES: Nc1nc2ccccc2c2c1nc(CF)n2CC1(O)CCOC1]

Part A

A mixture of 3-[3-nitroquinolin-4-yl)methyl]tetrahydrofuran-3-ol (2.5 g, Parts A through D of Example 160 using 4-chloro-3-nitroquinoline in lieu of 4-chloro-3-nitro[1,5]naphthyridine in Part D), 5% platinum on carbon (0.25 g), and ethyl acetate (150 mL) was placed under hydrogen pressure (40 psi, 2.8×10$^5$ Pa) on a Parr apparatus for 4 hours. The reaction mixture was filtered through a layer of CELITE filter aid. The filtrate was concentrated under reduced pressure and then dried under high vacuum to provide 2.20 g of 3-[3-aminoquinolin-4-yl)methyl]tetrahydrofuran-3-ol as a brown foam.

Part B

Fluoroacetyl chloride (0.578 g, 1.2 eq) was added dropwise over a period of 3 minutes to a chilled (0° C. suspension of 3-[3-aminoquinolin-4-yl)methyl]tetrahydrofuran-3-ol (1.3 g, 1.0 eq) in dichloromethane (50 mL). After 30 minutes the reaction mixture was allowed to warm to ambient temperature. The reaction mixture was stirred overnight at ambient temperature and then concentrated under reduced pressure to provide 2-fluoro-N-(4-{[(3-hydroxytetrahydrofuran-3-yl)methyl]amino}quinolin-3-yl)acetamide hydrochloride as a brown solid.

Part C

Triethylamine (2.1 mL, 3.0 eq) was added to a mixture of the material from Part B (1.0 eq) and methanol (50 mL). The reaction mixture was heated at 80° C. for 2 hours, allowed to cool to ambient temperature, and then concentrated under reduced pressure to provide a brown solid. This material was combined with the product from another run, dissolved in chloroform, and purified by HPFC eluting with a gradient of 0-50% CMA in chloroform for 600 mL and then with 50% CMA in chloroform for 1200 mL to provide 800 mg of 3-{[2-(fluoromethyl)-1H-imidazo[4,5-c]quinolin-1-yl]methyl}tetrahydrofuran-3-ol as an orange solid.

Part D

The material from Part D was oxidized and then aminated according to the methods of Part G of Example 160. The crude product was triturated with chloroform and then filtered. The filtrate was concentrated under reduced pressure. The residue was purified by HPFC eluting sequentially with chloroform for 4 column volumes, a gradient of 0-50% CMA in chloroform for 6 column volumes, and 50% CMA in chloroform for 6 column volumes to provide a yellow solid. This material was triturated with methanol. A solid was isolated by filtration and dried under high vacuum to provide 148 mg of 3-{[4-amino-2-(fluoromethyl)-1H-imidazo[4,5-c]quinolin-1-yl]methyl}tetrahydrofuran-3-ol as a light orange solid, mp 169-171° C. $^1$H NMR (300 MHz, DMSO-$d_6$): 8.30 (d, J=7.9 Hz, 1H), 7.61 (dd, J=8.3, 1.1 Hz, 1H), 7.45 (dt, J=7.5, 0.8 Hz, 1H), 7.23 (t, J=7.6, 1.1 Hz, 1H), 6.67 (s, 2H), 5.83 (d, J=48.0 Hz, 2H), 5.48 (s, 1H), 4.89 (s, 2H), 3.83 (m, 2H), 3.59 (dd, J=103.8, 9.1 Hz, 2H), 1.91 (m, 2H); MS (EI) m/z 316 (M+H)$^+$; Anal. calcd for $C_{16}H_{17}FN_4O_2 \cdot 0.58H_2O$: C, 58.81; H, 5.60; N, 17.14. Found: C, 58.92; H, 5.72; N, 17.01.

Example 164

3-[(4-Amino-2-propyl-1H-imidazo[4,5-c]quinolin-1-yl)methyl]tetrahydrofuran-3-ol

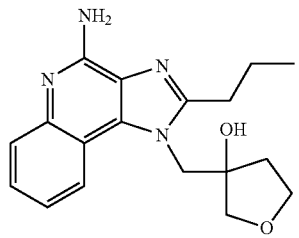 [SMILES: CCCc1nc2c(N)nc3ccccc3c2n1CC1(O)CCOC1]

Part A

3-[(2-Propyl-1H-imidazo[4,5-c]quinolin-1-yl)methyl]tetrahydrofuran-3-ol was prepared using the method of Part F of Example 160 using 3-[3-aminoquinolin-4-yl)methyl]tetrahydrofuran-3-ol in lieu of 3-[3-amino[1,5]napthyridin-4-yl)methyl]tetrahydrofuran-3-ol. The crude product was triturated with acetonitrile (about 10 mL) to provide 500 mg of pure product. An additional 190 mg was isolated from the filtrate.

Part B

The material from Part A was oxidized and then aminated according to the methods of Part G of Example 160. The crude product was triturated with chloroform and then filtered. The filtrate was concentrated under reduced pressure. The residue was purified by HPFC eluting sequentially with chloroform for 3 column volumes and a gradient of 0-50% CMA in chloroform for 10 column volumes to provide a yellow-orange solid. This material was triturated with methanol. A solid was isolated by filtration. This material was triturated with 10% aqueous sodium hydroxide (10 mL) to provide an orange solid. This material was combined with acetonitrile, heated to reflux, and then allowed to cool to ambient temperature. A solid was isolated by filtration and dried under high vacuum to provide 3-[(4-amino-2-propyl-1H-imidazo[4,5-c]quinolin-1-yl)methyl]tetrahydrofuran-3-ol as a tan solid, mp 201-203° C. $^1$H NMR (300 MHz, DMSO-$d_6$): 8.25 (d, J=7.4 Hz, 1H), 7.59 (dd, J=8.3, 1.1 Hz, 1H), 7.38 (t, J=7.7 Hz, 1H), 7.19 (td, J=7.6, 1.2 Hz, 1H), 6.41 (s, 2H), 5.33 (s, 1H), 4.75 (s, 2H), 3.80 (m, 2H), 3.58 (dd, J=73.4, 9.0 Hz, 2H), 2.98 (t, J=7.4 Hz, 2H), 1.94 (m, 2H), 1.83 (m, J=7.5 Hz, 2H), 1.01 (t, J=7.4 Hz, 3H); MS (EI) m/z 327 (M+H)$^+$; Anal. calcd for $C_{18}H_{22}N_4O_2$: C, 66.24; H, 6.79; N, 17.17. Found: C, 65.86; H, 6.82; N, 17.25.

Example 165

3-[(4-Amino-2-ethyl-1H-imidazo[4,5-c]quinolin-1-yl)methyl]tetrahydrofuran-3-ol

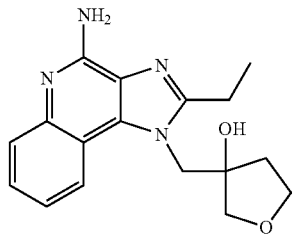 [SMILES: CCc1nc2c(N)nc3ccccc3c2n1CC1(O)CCOC1]

Part A

3-[(2-Ethyl-1H-imidazo[4,5-c]quinolin-1-yl)methyl]tetrahydrofuran-3-ol was prepared using the method of Part F of Example 160 using 3-[3-aminoquinolin-4-yl)methyl]tetrahydrofuran-3-ol in lieu of 3-[3-amino[1,5]napthyridin-4-yl)methyl]tetrahydrofuran-3-ol and trimethyl orthopropionate in lieu of trimethyl orthobutyrate. The crude product was triturated with acetonitrile (about 10 mL) to provide 737 mg of pure product. An additional 210 mg was isolated from the filtrate.

Part B

The material from Part A was oxidized and then aminated according to the methods of Part G of Example 160. The crude product was triturated with acetonitrile (about 2 mL) to provide a tan solid. This material was combined with the material from another run and dissolved in refluxing acetonitrile (50 mL). The solution was filtered and then cooled to −20° C. A solid was isolated by filtration and then dried under high vacuum to provide 3-[(4-amino-2-ethyl-1H-imidazo[4,5-c]quinolin-1-yl)methyl]tetrahydrofuran-3-ol as a light tan solid, mp 245-247° C. $^1$H NMR (300 MHz, DMSO-$d_6$): 8.25 (d, J=7.6 Hz, 1H), 7.59 (dd, J=8.3, 1.2 Hz, 1H), 7.38 (t, J=7.6, 1.0 Hz, 1H), 7.19 (t, J=7.6, 1.2 Hz, 1H), 6.41 (s, 2H), 5.33 (s, 1H), 4.75 (s, 2H), 3.81 (m, 2H), 3.58 (dd, J=75.4, 9.0 Hz, 2H), 3.02 (q, J=7.4 Hz, 2H), 1.89 (m, 2H), 1.36 (t, J=7.4 Hz, 3H); MS (EI) m/z 312 (M+H)$^+$; Anal. calcd for $C_{17}H_{20}N_4O_2$: C, 65.37; H, 6.45; N, 17.94. Found: C, 65.30; H, 6.29; N, 18.00.

Example 166

3-[(4-Amino-2-methyl-1H-imidazo[4,5-c]quinolin-1-yl)methyl]tetrahydrofuran-3-ol

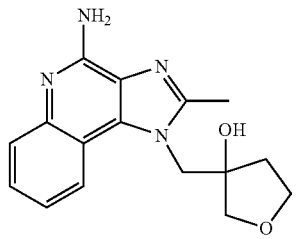 [SMILES: Cc1nc2c(N)nc3ccccc3c2n1CC1(O)CCOC1]

Part A

3-[(2-Methyl-1H-imidazo[4,5-c]quinolin-1-yl)methyl]tetrahydrofuran-3-ol was prepared using the method of Part F of Example 160 using 3-[3-aminoquinolin-4-yl)methyl] tetrahydrofuran-3-ol in lieu of 3-[3-amino[1,5]napthyridin-4-yl)methyl]tetrahydrofuran-3-ol and trimethyl orthoacetate in lieu of trimethyl orthobutyrate. The crude product was dissolved in chloroform and purified by HPFC eluting with chloroform for 3 column volumes and then with a gradient of 0-50% CMA in chloroform for 8 column volumes to provide 0.87 g of product as an off white foam.

Part B

The material from Part A was oxidized and then aminated according to the methods of Part G of Example 160. The crude product was isolated by filtration and triturated with 10% sodium hydroxide. The resulting solid was isolated by filtration, rinsed with water, and then refluxed with acetonitrile. The purification procedure was repeated and the resulting solid was isolated by filtration and then dried under high vacuum to provide 3-[(4-amino-2-methyl-1H-imidazo[4,5-c]quinolin-1-yl)methyl]tetrahydrofuran-3-ol as a light tan solid, mp 278° C. (dec). $^1$H NMR (300 MHz, DMSO-$d_6$): 8.24 (d, J=8.0 Hz, 1H), 7.59 (d, J=8.7 Hz, 1H), 7.38 (t, J=7.4 Hz, 1H), 7.19 (t, J=7.2 Hz, 1H), 6.45 (s, 2H), 5.36 (s, 1H), 4.74 (s, 2H), 3.82 (m, 2H), 3.50 (dd, J=77.6, 9.0 Hz, 2H), 2.65 (s, 3H), 1.92 (m, 2H); MS (EI) m/z 298 (M+H)$^+$; Anal. calcd for $C_{16}H_{18}N_4O_2 \cdot 0.52H_2O$: C, 62.45; H, 6.24; N, 18.21. Found: C, 62.39; H, 5.95; N, 17.81.

Examples 167-190

Part A

A suspension of 1-aminomethyl-1-cyclohexanol hydrochloride (20.0 g, 121 mmol) and 4-chloro-3-nitroquinoline (24.0 g, 115 mmol) in dichloromethane (550 mL) was cooled to 0° C., and triethylamine (40 mL, 290 mmol) was added dropwise over a period of 30 minutes. The reaction was allowed to warm to room temperature over two hours. An analysis by HPLC indicated that the 4-chloro-3-nitroquinoline starting material actually contained some 3-nitroquinolin-4-ol, and additional pure 4-chloro-3-nitroquinoline (12.0 g, 57.5 mmol) was added. The reaction was stirred for four hours, and additional 1-aminomethyl-1-cyclohexanol hydrochloride (2.0 g, 12 mmol) was added, and the resulting suspension was stirred for three days. The solvent was removed under reduced pressure, and the residue was triturated in water for one hour and isolated by filtration. The resulting solid was triturated with hot dichloromethane and isolated by filtration from the hot mixture to provide 36.5 g of 1-{[(3-nitroquinolin-4-yl)amino]methyl}cyclohexanol as a bright yellow powder.

Part B

A suspension of 1-{[(3-nitroquinolin-4-yl)amino] methyl}cyclohexanol (15.0 g, 49.8 mmol) in ethyl acetate (225 mL) in a Parr vessel was purged with nitrogen; 5% platinum on carbon (1.5 g) was added. The reaction was placed under hydrogen pressure (35 psi, 2.4×10$^5$ Pa) for 3.5 hours and then filtered through a layer of CELITE filter agent. The filter cake was washed with ethyl acetate (100 mL), and the filtrate was concentrated under reduced pressure to provide 1-{[(3-aminoquinolin-4-yl)amino] methyl}cyclohexanol as a yellow solid.

Part C

A solution of the material from Part B in dichloromethane (200 mL) was cooled to 0° C., and chloroacetyl chloride (4.4 mL, 55 mmol) was added over a period of ten minutes. The reaction was stirred for one hour at 0° C. and then concentrated under reduced pressure to provide 2-chloro-N-(4-{[(1-hydroxycyclohexyl)methyl]amino}quinolin-3-yl)acetamide hydrochloride as a yellow solid.

Part D

Triethylamine (21 mL, 150 mmol) was added to a solution of the material from Part C in ethanol (200 mL), and the reaction was heated at 60° C. for four hours. The solvent was removed under reduced pressure, and the residue was partitioned between dichloromethane (150 mL) and saturated aqueous sodium bicarbonate (125 mL). The aqueous layer was separated and extracted with dichloromethane (2×50 mL), and the combined organic fractions were dried over magnesium sulfate, filtered, and concentrated under reduced pressure to provide 14.2 g of an orange solid. The solid was triturated with acetonitrile and isolated by filtration to provide 10.74 g of 1-{[2-(chloromethyl)-1H-imidazo[4,5-c]quinolin-1-yl]methyl}cyclohexanol as a pale yellow solid.

Part E

3-Chloroperoxybenzoic acid (8.37 g of 70% pure material, 34 mmol) was added to a suspension of 1-{[2-(chloromethyl)-1H-imidazo[4,5-c]quinolin-1-yl] methyl}cyclohexanol (8.0 g, 24 mmol) in chloroform (100 mL), and the reaction was stirred at room temperature for four hours. Saturated aqueous sodium bicarbonate (100 mL) was added, and the mixture was stirred for 15 minutes. A precipitate formed and was isolated by filtration to provide 1-{[2-(chloromethyl)-5-oxido-1H-imidazo[4,5-c]quinolin-1-yl]methyl}cyclohexanol as a white solid.

Part F

Ammonium hydroxide (8 mL of 15 M) was added to a suspension of the material from Part E in methanol (100 mL). The mixture was cooled to 0° C., and benzenesulfonyl chloride (6.5 mL, 51 mmol) was added dropwise over a period of eight minutes. The reaction was stirred at 0° C. for one hour, and an analysis by HPLC indicated the presence of starting material. Additional benzenesulfonyl chloride (6.5 mL, 51 mmol) was added in two portions over two hours. The reaction was allowed to warm to room temperature slowly and stirred overnight. A precipitate was present and was isolated by filtration, stirred with saturated aqueous sodium bicarbonate (100 mL), isolated by filtration, washed with water (50 mL), and dried to provide 6.14 g of 1-{[4-amino-2-(chloromethyl)-1H-imidazo[4,5-c]quinolin-1-yl] methyl}cyclohexanol.

Part G

Potassium phthalimide (2.59 g, 14.0 mmol) was added to a solution of 1-{[4-amino-2-(chloromethyl)-1H-imidazo[4,5-c]quinolin-1-yl]methyl}cyclohexanol (5.07 g, 13.3 mmol) in DMF (50 mL), and the reaction mixture was stirred at room temperature overnight. An analysis by HPLC indicated the presence of starting material, and additional potassium phthalimide (1 g) was added. The reaction was stirred for an additional five hours, and then concentrated under reduced pressure. The residue was triturated with methanol, and the resulting white solid was isolated by filtration. The filtrate was concentrated under reduced pressure, and the residue was triturated with methanol to afford additional white solid, which was isolated by filtration. The two solids were combined to provide 2-({4-amino-1-[(1-hydroxycyclohexyl) methyl]-1H-imidazo[4,5-c]quinolin-2-yl}methyl)-1H-isoindole-1,3(2H)-dione.

Part H

Hydrazine (2.1 mL, 66 mmol) was added to a suspension of the material from Part G in ethanol (50 mL), and the reaction was stirred for 24 hours at room temperature. The ethanol was removed under reduced pressure, and the resulting white solid was sonicated with hydrochloric acid (50 mL of 1M). The resulting suspension was filtered to remove a solid, and the filtrate was adjusted to pH 8 with the addition of solid sodium bicarbonate. A precipitate formed and was isolated by filtration and dried at 50° C. overnight in a vacuum oven to provide 2.99 g of 1-{[4-amino-2-(aminomethyl)-1H-imidazo[4,5-c]quinolin-1-yl]methyl}cyclohexanol as a white powder.

Part I

A reagent (0.11 mmol, 1.1 equivalents) from the table below was added to a test tube containing 1-{[4-amino-2-(aminomethyl)-1H-imidazo[4,5-c]quinoline-1-yl]methyl}cyclohexanol (33 mg, 0.10 mmol) and N,N-diisopropylethylamine (0.035 mL, 0.20 mmol) in N,N-dimethylacetamide (DMA) (1 mL). The test tube was capped and shaken overnight at ambient temperature. The solvent was then removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 167 | Propionyl chloride | -C(O)CH₂CH₃ | 382.2239 |
| 168 | Methyl chloroformate | -C(O)OCH₃ | 384.2025 |
| 169 | Cyclopropanecarbonyl chloride | -C(O)-cyclopropyl | 394.2232 |
| 170 | Butyryl chloride | -C(O)CH₂CH₂CH₃ | 396.2399 |
| 171 | Isobutyryl chloride | -C(O)CH(CH₃)₂ | 396.2392 |
| 172 | Cyclobutanecarbonyl chloride | -C(O)-cyclobutyl | 408.2421 |
| 173 | Benzoyl chloride | -C(O)-phenyl | 430.2243 |
| 174 | 2-Chlorobenzoyl chloride | -C(O)-(2-Cl-phenyl) | 464.1848 |
| 175 | 3-Chlorobenzoyl chloride | -C(O)-(3-Cl-phenyl) | 464.1852 |
| 176 | Isonicotinoyl chloride hydrochloride | -C(O)-(4-pyridyl) | 431.2201 |
| 177 | Nicotinoyl chloride hydrochloride | -C(O)-(3-pyridyl) | 431.2199 |
| 178 | Picolinoyl chloride hydrochloride | -C(O)-(2-pyridyl) | 431.2203 |

189
-continued

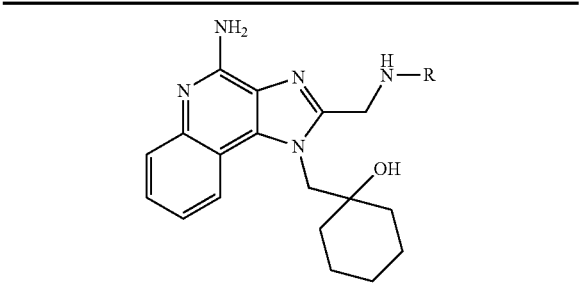

| Example | Reagent | R | Measured Mass (M + H) |
|---|---|---|---|
| 179 | trans-2-Phenyl-1-Cyclopropanecarbonyl chloride | | 470.2561 |
| 180 | 3,4-Dichlorobenzoyl chloride | | 498.1449 |
| 181 | Methanesulfonyl chloride | | 404.1746 |
| 182 | Ethanesulfonyl chloride | | 418.1910 |
| 183 | 1-Propanesulfonyl chloride | | 432.2058 |
| 184 | Isopropylsulfonyl chloride | | 432.2075 |
| 185 | Dimethylsulfamoyl chloride | | 433.2028 |

190
-continued

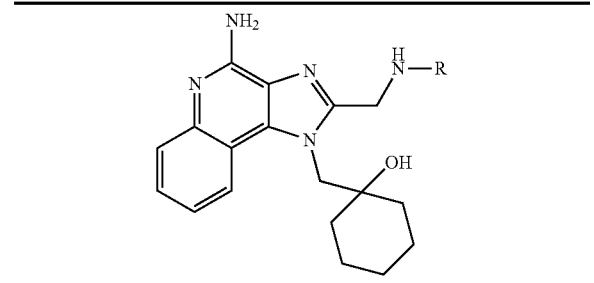

| Example | Reagent | R | Measured Mass (M + H) |
|---|---|---|---|
| 186 | Benzenesulfonyl chloride | | 466.1906 |
| 187 | 1-Methylimidazole-4-sulfonyl chloride | | 470.1980 |
| 188 | alpha-Toluenesulfonyl chloride | | 480.2076 |
| 189 | 3-Chlorobenzenesulfonyl chloride | | 500.1516 |
| 190 | 4-Chlorobenzenesulfonyl chloride | | 500.1518 |

Examples 191-205

Part A

Under a nitrogen atmosphere, nitromethane (116 mL, 2.14 mol) and sodium ethoxide (2.6 g of 96% pure material, 36 mmol) were sequentially added to a solution of cyclobutanone (50.0 g, 713 mmol) in ethanol (71 mL), and the resulting solution was stirred at room temperature for 4 days. Some of the ethanol was removed under reduced pressure, and water (100 mL) was added. The resulting mixture was extracted with ethyl acetate (3×150 mL). The combined extracts were washed sequentially with water (2×80 mL) and brine (40 mL), dried over sodium sulfate, filtered, and concentrated under reduced pressure. The residue was purified by vacuum distillation under high vacuum at 70° C. to provide 46.1 g of 1-(nitromethyl)cyclobutanol as an orange liquid.

Part B

A mixture of 1-(nitromethyl)cyclobutanol (46.0 g, 351 mmol), 20% palladium hydroxide on carbon (6.9 g) and ethanol (1 L) was placed under hydrogen pressure (30 psi, $2.1 \times 10^5$ Pa) on a Parr apparatus for two days. An analysis by nuclear magnetic resonance spectroscopy indicated the reaction was incomplete, and additional 20% palladium hydroxide on carbon (5 g) was added. The reaction was placed under hydrogen pressure (30 psi, $2.1 \times 10^5$ Pa) for four days. The reaction mixture was filtered through a layer of CELITE filter agent, and the filter cake was washed with methanol. The filtrate was concentrated under reduced pressure to provide 34.8 g of 1-(aminomethyl)cyclobutanol as a white solid.

Part C A solution of 4-chloro-3-nitroquinoline (30.0 g, 144 mmol) in dichloromethane (350 mL) was cooled to 0° C. under a nitrogen atmosphere, and triethylamine (22.1 mL, 158 mmol) was added. A solution of 1-(aminomethyl)cyclobutanol (16.0 g, 158 mmol) in dichloromethane (130 mL) was then added over a period of one hour, followed by a rinse of dichloromethane (100 mL). The reaction was stirred at room temperature overnight. The solvent was removed under reduced pressure, and the residue was triturated in water (500 mL) and saturated aqueous sodium bicarbonate (200 mL) for two hours. A solid was present and was isolated by filtration, washed with a large amount of water, and dried in a vacuum oven at 55° C. to provide 38.7 g of 1-{[(3-nitroquinolin-4-yl)amino]methyl}cyclobutanol as a yellow solid.

Part D

1-{[(3-Nitroquinolin-4-yl)amino]methyl}cyclobutanol (14.0 g, 51.2 mmol) was hydrogenated (50 psi, $3.5 \times 10^5$ Pa) according to the method described in Part B of Examples 167-190 to provide 1-{[(3-aminoquinolin-4-yl)amino]methyl}cyclobutanol as a yellow solid.

Part E

A solution of the material from Part D in dichloromethane (250 mL) was cooled to 0° C., and chloroacetyl chloride (4.50 mL, 56.4 mmol) was added over a period of 15 minutes. The reaction was allowed to warm to room temperature and stirred for four hours. An analysis by LC/MS indicated the presence of starting material, and additional chloroacetyl chloride (1 mL) was added. The reaction was stirred overnight at room temperature and then concentrated under reduced pressure to provide 2-chloro-N-(4-{[(1-hydroxycyclobutyl)methyl]amino}quinolin-3-yl)acetamide hydrochloride.

Part F

The method described in Part D of Examples 167-190 was used to treat the material from Part E with triethylamine (21.4 mL, 154 mmol) with the modifications that the reaction was heated at 50° C. for four hours, chloroform was used in the work-up procedure, and following the work-up procedure, the product was not purified by trituration. 1-{[2-(Chloromethyl)-1H-imidazo[4,5-c]quinolin-1-yl]methyl}cyclobutanol (16.5 g) was obtained as a yellow solid containing small amounts of chloroform and triethylamine.

Part G

3-Chloroperoxybenzoic acid (9.15 g of 70% pure material, 37.1 mmol) was added to a suspension of 1-{[2-(chloromethyl)-1H-imidazo[4,5-c]quinolin-1-yl]methyl}cyclobutanol (8.00 g, 26.5 mmol) in chloroform (100 mL) under a nitrogen atmosphere, and the reaction was stirred at room temperature overnight. Additional chloroform (200 mL) was added, and the solution was washed sequentially with saturated aqueous sodium bicarbonate (2×80 mL) and brine (20 mL), dried over magnesium sulfate, filtered, and concentrated under reduced pressure to provide 1-{[2-(chloromethyl)-5-oxido-1H-imidazo[4,5-c]quinolin-1-yl]methyl}cyclobutanol as a yellow solid.

Part H

Ammonium hydroxide (8.83 mL of 15 M) was added to a solution of the material from Part G in methanol (100 mL). The mixture was cooled to 0° C. under a nitrogen atmosphere, and benzenesulfonyl chloride (7.10 mL, 55.7 mmol) was added dropwise over a period of eight minutes. The reaction was stirred at 0° C. for two hours, combined with material from another run, and concentrated under reduced pressure. The residue was dissolved in chloroform (300 mL), and the resulting solution was washed sequentially with saturated aqueous sodium carbonate (2×80 mL) and brine (40 mL), dried over sodium sulfate, filtered, and concentrated under reduced pressure. The crude product was purified by prep HPLC using a HORIZON HPFC system (silica cartridge, eluting with chloroform:CMA in a gradient from 100:0 to 70:30) to provide 4.00 g of 1-{[4-amino-2-(chloromethyl)-1H-imidazo[4,5-c]quinolin-1-yl]methyl}cyclobutanol as a yellow solid.

Part I

Under a nitrogen atmosphere, potassium phthalimide (1.21 g, 6.52 mmol) was added to a solution of 1-{[4-amino-2-(chloromethyl)-1H-imidazo[4,5-c]quinolin-1-yl]methyl}cyclobutanol (1.88 g, 5.93 mmol) in DMF (30 mL), and the reaction mixture was stirred at room temperature overnight and then concentrated under reduced pressure. The residue was partitioned between chloroform (200 mL) and water (25 mL)/saturated aqueous sodium bicarbonate (2×40 mL). The organic layer was washed with brine (2×40 mL), dried over sodium sulfate, filtered, and concentrated under reduced pressure to provide 2.42 g of 2-({4-amino-1-[(1-hydroxycyclobutyl)methyl]-1H-imidazo[4,5-c]quinolin-2-yl}methyl)-1H-isoindole-1,3 (2H)-dione.

Part J

Under a nitrogen atmosphere, hydrazine (0.89 mL, 28 mmol) was added to a suspension of 2-({4-amino-1-[(1-hydroxycyclobutyl)methyl]-1H-imidazo[4,5-c]quinolin-2-yl}methyl)-1H-isoindole-1,3(2H)-dione (2.42 g, 5.66 mmol) in ethanol (57 mL), and the reaction was stirred for two hours at room temperature. The ethanol was removed under reduced pressure, and the resulting white solid was triturated with 2 N hydrochloric acid.

The resulting suspension was filtered to remove a solid, and the filter cake was washed with water. The filtrate was made basic with the addition of solid sodium bicarbonate. A precipitate formed and was isolated by filtration, washed with water, and dried at 50° C. for three days in a vacuum oven to provide 0.994 g of 1-{[4-amino-2-(aminomethyl)-1H-imidazo[4,5-c]quinolin-1-yl]methyl}cyclobutanol as a yellow solid.

Part K

A reagent (0.11 mmol, 1.1 equivalents) from the table below was added to a test tube containing 1-{[4-amino-2-(aminomethyl)-1H-imidazo[4,5-c]quinolin-1-yl]methyl}cyclobutanol (30 mg, 0.10 mmol) and N,N-diisopropylethylamine (0.036 mL, 0.20 mmol) in DMA (1 mL). The test tube was capped and vortexed overnight at ambient temperature. Two drops of water were added to each reaction, and the solvent was then removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

| Example | Reagent | R | Measured Mass (M + H) |
|---------|---------|---|------------------------|
| 191 | Propionyl chloride | -C(O)CH₂CH₃ | 354.1905 |
| 192 | Cyclopropanecarbonyl chloride | -C(O)-cyclopropyl | 366.1926 |
| 193 | Isobutyryl chloride | -C(O)CH(CH₃)₂ | 368.2078 |
| 194 | Benzoyl chloride | -C(O)Ph | 402.1927 |
| 195 | 4-Methoxybenzoyl chloride | -C(O)-C₆H₄-OCH₃ | 432.2044 |
| 196 | 4-Chlorobenzoyl chloride | -C(O)-C₆H₄-Cl | 436.1553 |
| 197 | Nicotinoyl chloride hydrochloride | -C(O)-3-pyridyl | 403.1879 |
| 198 | 3,4-Dichlorobenzoyl chloride | -C(O)-C₆H₃-Cl₂ | 470.1158 |
| 199 | Methanesulfonyl chloride | -S(O)₂CH₃ | 376.1445 |
| 200 | Ethanesulfonyl chloride | -S(O)₂CH₂CH₃ | 390.1597 |
| 201 | Isopropylsulfonyl chloride | -S(O)₂CH(CH₃)₂ | 404.1769 |
| 202 | Dimethylsulfamoyl chloride | -S(O)₂N(CH₃)₂ | 405.1712 |
| 203 | Benzenesulfonyl chloride | -S(O)₂Ph | 438.1631 |
| 204 | 1-Methylimidazole-4-sulfonyl chloride | -S(O)₂-(1-methylimidazol-4-yl) | 442.1665 |
| 205 | 2,2,2-Trifluoroethanesulfonyl chloride | -S(O)₂CH₂CF₃ | 444.1327 |

Examples 206-248

A reagent (0.11 mmol, 1.1 eq) from the table below was added to a test tube. A solution of 4-[4-amino-2-methyl-1H-imidazo[4,5-c][1,5]napthyridin-1-yl)methyl]piperidine-4-ol dihydrochloride (38 mg, 0.10 mmol, 1.0 eq. Example 125 Part A) and N,N-diisopropylethylamine (0.086 mL, 5 eq)) in DMA (1 mL) and chloroform (1 mL) was added. The test tube was capped and shaken overnight at ambient temperature. The reaction was quenched with water (2 drops). The solvent was then removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 206 | Cyclopropanecarbonyl chloride | cyclopropyl-C(=O)- | 381.2019 |
| 207 | Butyryl chloride | -C(=O)CH₂CH₂CH₃ | 383.2228 |
| 208 | Isobutyryl chloride | -C(=O)CH(CH₃)₂ | 383.2212 |
| 209 | Cyclobutanecarbonyl chloride | cyclobutyl-C(=O)- | 395.2163 |
| 210 | Cyclopentanecarbonyl chloride | cyclopentyl-C(=O)- | 409.2366 |
| 211 | Benzoyl chloride | phenyl-C(=O)- | 417.2057 |
| 212 | Cyclohexanecarbonyl chloride | cyclohexyl-C(=O)- | 423.2545 |

-continued
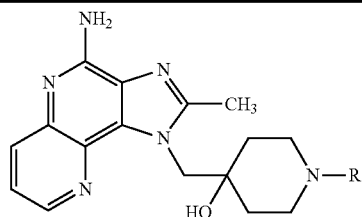
| Example | Reagent | R | Measured Mass (M + H) |
|---|---|---|---|
| 213 | 3-Cyanobenzoyl chloride | 3-cyanobenzoyl | 442.1995 |
| 214 | 3-Methoxybenzoyl chloride | 3-methoxybenzoyl | 447.2169 |
| 215 | 4-Methoxybenzoyl chloride | 4-methoxybenzoyl | 447.2149 |
| 216 | 3-Chlorobenzoyl chloride | 3-chlorobenzoyl | 451.1666 |
| 217 | 4-Chlorobenzoyl chloride | 4-chlorobenzoyl | 451.1650 |
| 218 | Isonicotinoyl chloride hydrochloride | isonicotinoyl | 418.1962 |
| 219 | Nicotinoyl chloride hydrochloride | nicotinoyl | 418.2012 |

-continued

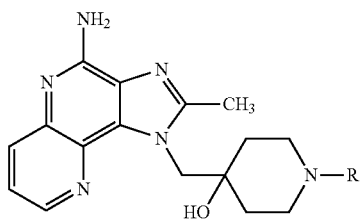

| Example | Reagent | R | Measured Mass (M + H) |
|---|---|---|---|
| 220 | Methanesulfonyl chloride | —S(=O)(=O)—CH₃ | 391.1589 |
| 221 | Ethanesulfonyl chloride | —S(=O)(=O)—CH₂CH₃ | 405.1729 |
| 222 | 1-Propanesulfonyl chloride | —S(=O)(=O)—CH₂CH₂CH₃ | 419.1881 |
| 223 | Isopropylsulfonyl chloride | —S(=O)(=O)—CH(CH₃)₂ | 419.1894 |
| 224 | Dimethylsulfamoyl chloride | —S(=O)(=O)—N(CH₃)₂ | 420.1837 |
| 225 | Benzenesulfonyl chloride | —S(=O)(=O)—Ph | 453.1713 |
| 226 | 1-Methylimidazole-4-sulfonyl chloride | —S(=O)(=O)-(1-methylimidazol-4-yl) | 457.1778 |
| 227 | 3-Cyanobenzenesulfonyl chloride | —S(=O)(=O)-(3-cyanophenyl) | 478.1635 |

-continued

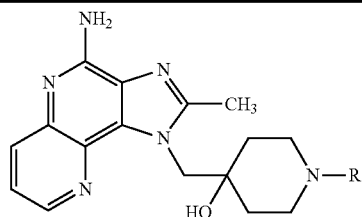

| Example | Reagent | R | Measured Mass (M + H) |
|---|---|---|---|
| 228 | 4-Cyanobenzenesulfonyl chloride | 4-cyanophenylsulfonyl | 478.1655 |
| 229 | 3-Methoxybenzenesulfonyl chloride | 3-methoxyphenylsulfonyl | 483.1805 |
| 230 | 4-Methoxybenzenesulfonyl chloride | 4-methoxyphenylsulfonyl | 483.1801 |
| 231 | 3-Chlorobenzenesulfonyl chloride | 3-chlorophenylsulfonyl | 487.1300 |
| 232 | 4-Chlorobenzenesulfonyl chloride | 4-chlorophenylsulfonyl | 487.1334 |
| 233 | Ethyl isocyanate | C(O)NHCH$_2$CH$_3$ | 384.2174 |

-continued

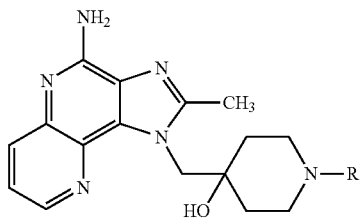

| Example | Reagent | R | Measured Mass (M + H) |
|---|---|---|---|
| 234 | Isopropyl isocyanate | -C(=O)-NH-CH(CH₃)₂ | 398.2327 |
| 235 | n-Propyl isocyanate | -C(=O)-NH-CH₂CH₂CH₃ | 398.2311 |
| 236 | Cyclopentyl isocyanate | -C(=O)-NH-cyclopentyl | 424.2468 |
| 237 | Phenyl isocyanate | -C(=O)-NH-phenyl | 432.2142 |
| 238 | Cyclohexyl isocyanate | -C(=O)-NH-cyclohexyl | 438.2636 |
| 239 | 4-Cyanophenyl isocyanate | -C(=O)-NH-(4-CN-phenyl) | 457.2062 |
| 240 | 2-Methoxyphenyl isocyanate | -C(=O)-NH-(2-OCH₃-phenyl) | 462.2251 |
| 241 | 3-Methoxyphenyl isocyanate | -C(=O)-NH-(3-OCH₃-phenyl) | 462.2230 |

-continued

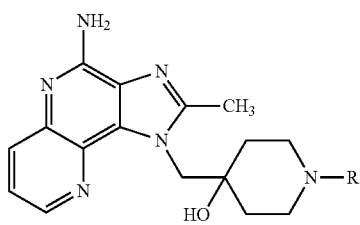

| Example | Reagent | R | Measured Mass (M + H) |
|---|---|---|---|
| 242 | 4-Methoxyphenyl isocyanate | ![acetamide with 4-methoxyphenyl] | 462.2254 |
| 243 | 2-Chlorophenyl isocyanate | ![acetamide with 2-chlorophenyl] | 466.1767 |
| 244 | 3-Chlorophenyl isocyanate | ![acetamide with 3-chlorophenyl] | 466.1758 |
| 245 | 4-Chlorophenyl isocyanate | ![acetamide with 4-chlorophenyl] | 466.1754 |
| 246 | 1-Pyrrolidinecarbonyl chloride | ![acyl pyrrolidine] | 410.2304 |
| 247 | 1-Piperidinecarbonyl chloride | ![acyl piperidine] | 424.2472 |
| 248 | 4-Morpholinylcarbonyl chloride | ![acyl morpholine] | 426.2259 |

Examples 249-285

A reagent (0.11 mmol, 1.1 eq) from the table below was added to a test tube. A solution of 4-[4-amino-2-ethyl-1H-imidazo[4,5-c][1,5]napthyridin-1-yl)methyl]piperidine-4-ol dihydrochloride (40 mg, 0.10 mmol, 1.0 eq. Example 121 Part A) and N,N-diisopropylethylamine (0.086 mL, 5 eq)) in DMA (1 mL) and chloroform (1 mL) was added. The test tube was capped and shaken overnight at ambient temperature. Ammonium hydroxide (100 µL) was added to the tube and the tube was vortexed for 4 hours. The solvent was then removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

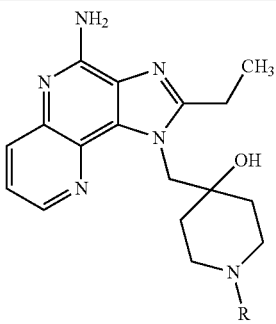

| Example | Reagent | R | Measured Mass (M + H) |
|---|---|---|---|
| 249 | Cyclopropanecarbonyl chloride | | 395.2208 |
| 250 | Butyryl chloride | | 397.2383 |
| 251 | Isobutyryl chloride | | 397.2387 |
| 252 | Cyclopentanecarbonyl chloride | | 423.2492 |
| 253 | Benzoyl chloride | | 431.2166 |
| 254 | 3-Methoxybenzoyl chloride | | 461.2286 |
| 255 | p-Anisoyl chloride | | 461.2288 |

-continued

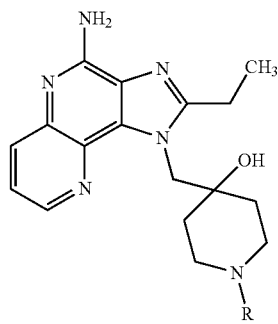

| Example | Reagent | R | Measured Mass (M + H) |
|---|---|---|---|
| 256 | 2-Chlorobenzoyl chloride | 2-chlorobenzoyl | 465.1803 |
| 257 | 3-Chlorobenzoyl chloride | 3-chlorobenzoyl | 465.1821 |
| 258 | 4-Chlorobenzoyl chloride | 4-chlorobenzoyl | 465.1801 |
| 259 | Isonicotinoyl chloride hydrochloride | isonicotinoyl | 432.2170 |
| 260 | Nicotinoyl chloride hydrochloride | nicotinoyl | 432.2142 |
| 261 | Methanesulfonyl chloride | methanesulfonyl | 405.1687 |
| 262 | Ethanesulfonyl chloride | ethanesulfonyl | 419.1889 |
| 263 | 1-Propanesulfonyl chloride | 1-propanesulfonyl | 433.2048 |

-continued

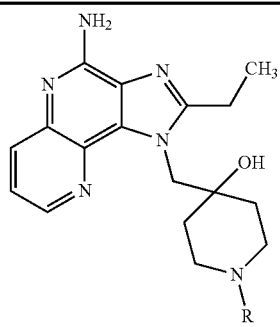

| Example | Reagent | R | Measured Mass (M + H) |
|---|---|---|---|
| 264 | Isopropylsulfonyl chloride | (isopropylsulfonyl group) | 433.2039 |
| 265 | Dimethylsulfamoyl chloride | (dimethylsulfamoyl group) | 434.1998 |
| 266 | 1-Butanesulfonyl chloride | (butylsulfonyl group) | 447.2179 |
| 267 | Benzenesulfonyl chloride | (phenylsulfonyl group) | 467.1826 |
| 268 | 1-Methylimidazole-4-sulfonyl chloride | (1-methylimidazol-4-ylsulfonyl group) | 471.1924 |
| 269 | 3-Methoxybenzenesulfonyl chloride | (3-methoxyphenylsulfonyl group) | 497.1972 |
| 270 | 4-Methoxybenzenesulfonyl chloride | (4-methoxyphenylsulfonyl group) | 497.1990 |

-continued

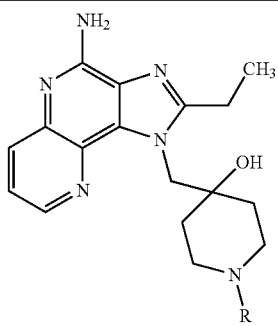

| Example | Reagent | R | Measured Mass (M + H) |
|---|---|---|---|
| 271 | 2-Chlorobenzenesulfonyl chloride | 2-chlorophenylsulfonyl | 501.1467 |
| 272 | 3-Chlorobenzenesulfonyl chloride | 3-chlorophenylsulfonyl | 501.1501 |
| 273 | 4-Chlorobenzenesulfonyl chloride | 4-chlorophenylsulfonyl | 501.1434 |
| 274 | Methyl isocyanate | C(=O)NHCH$_3$ | 384.2187 |
| 275 | Isopropyl isocyanate | C(=O)NHCH(CH$_3$)$_2$ | 412.2495 |
| 276 | N-Propyl isocyanate | C(=O)NHCH$_2$CH$_2$CH$_3$ | 412.2497 |
| 277 | Cyclopentyl isocyanate | C(=O)NH-cyclopentyl | 438.2639 |

-continued
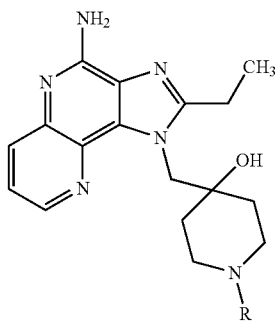
| Example | Reagent | R | Measured Mass (M + H) |
|---|---|---|---|
| 278 | Cyclohexyl isocyanate | -C(=O)NH-cyclohexyl | 452.2793 |
| 279 | 3-Methoxyphenyl isocyanate | -C(=O)NH-(3-methoxyphenyl) | 476.2431 |
| 280 | 4-Methoxyphenyl isocyanate | -C(=O)NH-(4-methoxyphenyl) | 476.2431 |
| 281 | 4-Chlorophenyl isocyanate | -C(=O)NH-(4-chlorophenyl) | 480.1892 |
| 282 | 1-Pyrrolidinecarbonyl chloride | -C(=O)-pyrrolidinyl | 424.2480 |
| 283 | 1-Piperidinecarbonyl chloride | -C(=O)-piperidinyl | 438.2584 |

-continued

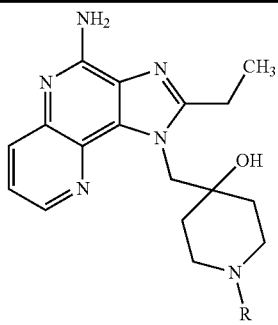

| Example | Reagent | R | Measured Mass (M + H) |
|---|---|---|---|
| 284 | 4-Morpholinylcarbonyl chloride | ![structure] | 440.2442 |
| 285 | 4-Methyl-1-piperazinecarbonyl chloride | ![structure] | 453.2715 |

Examples 286-330

Part A

Tert-Butyl {1-[(2-ethoxymethyl-1H-imidazo[4,5-c]quinolin-1-yl)methyl]cyclopropyl}carbamate (3.40 g, Parts A through H of Example 92) was oxidized and then aminated according to the general method of Part I of Example 12. The crude product was purified by HPFC eluting with a gradient of 0-30% CMA in chloroform to provide a yellow solid. This material was recrystallized from dichloromethane/hexanes to provide 2.60 g of tert-butyl {1-[(4-amino-2-ethoxymethyl-1H-imidazo[4,5-c]quinolin-1-yl)methyl]cyclopropyl}carbamate as a pale yellow solid.

Part B

Aqueous hydrochloric acid (6 mL of 6M) was added to a solution of the material from Part A in ethanol (12 mL). The reaction mixture was heated at 50° C. for 4 hours and then concentrated under reduced pressure. The residue was concentrated from methanol 3 times and then triturated with acetonitrile to provide 2.43 g of 1-[(1-aminocyclopropyl)methyl]-2-ethoxymethyl-1H-imidazo[4,5-c]quinolin-4-amine hydrochloride.

Part C

A reagent (1.1 eq) from the table below was added to a test tube containing a solution of 1-[(1-aminocyclopropyl)methyl]-2-ethoxymethyl-1H-imidazo[4,5-c]quinolin-4-amine hydrochloride (33 mg, 0.010 mmol, 1 eq) and N,N-diisopropylethylamine (0.083 mL, 5 eq) in N,N-dimethylacetamide (1 mL). The test tube was capped and shaken overnight at ambient temperature. The reaction was quenched with water (2 drops). The solvent was then removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

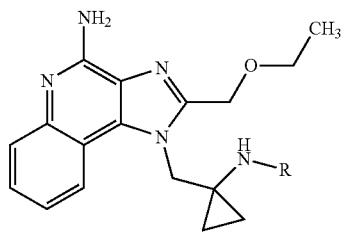

| Example | Reagent | R | Measured Mass (M + H) |
|---|---|---|---|
| 286 | Cyclopropanecarbonyl chloride | ![structure] | 380.2065 |

-continued

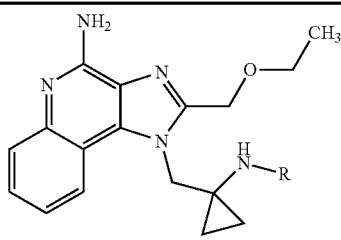

| Example | Reagent | R | Measured Mass (M + H) |
|---|---|---|---|
| 287 | Butyryl chloride | propan-1-yl methyl ketone (CH₃CH₂CH₂C(O)−) | 382.2237 |
| 288 | Isobutyryl chloride | isopropyl methyl ketone ((CH₃)₂CHC(O)−) | 382.2235 |
| 289 | Cyclobutanecarbonyl chloride | cyclobutyl methyl ketone | 394.2235 |
| 290 | Cyclopentanecarbonyl chloride | cyclopentyl methyl ketone | 408.2385 |
| 291 | Benzoyl chloride | phenyl methyl ketone | 416.2090 |
| 292 | Cyclohexanecarbonyl chloride | cyclohexyl methyl ketone | 422.2563 |
| 293 | Hydrocinnamoyl chloride | 4-phenylbutan-2-one | 444.2401 |
| 294 | 3-Methoxybenzoyl chloride | 3-methoxyphenyl methyl ketone | 446.2193 |

-continued

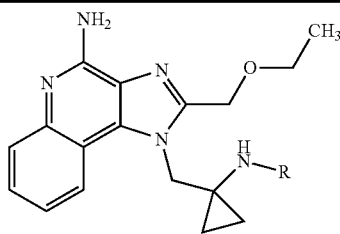

| Example | Reagent | R | Measured Mass (M + H) |
|---|---|---|---|
| 295 | 4-Methoxybenzoyl chloride | 4-methoxybenzoyl group | 446.2207 |
| 296 | 3-Chlorobenzoyl chloride | 3-chlorobenzoyl group | 450.1702 |
| 297 | 4-Chlorobenzoyl chloride | 4-chlorobenzoyl group | 450.1710 |
| 298 | Isonicotinoyl chloride hydrochloride | isonicotinoyl group | 417.2043 |
| 299 | Nicotinoyl chloride hydrochloride | nicotinoyl group | 417.2057 |
| 300 | Picolinoyl chloride hydrochloride | picolinoyl group | 417.2023 |
| 301 | trans-2-Phenyl-1-cyclopropanecarbonyl chloride | trans-2-phenylcyclopropanecarbonyl group | 456.2364 |

-continued

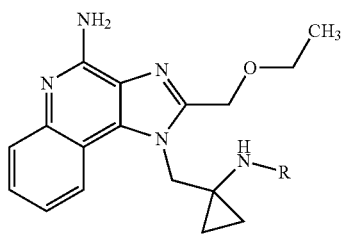

| Example | Reagent | R | Measured Mass (M + H) |
|---|---|---|---|
| 302 | 3,4-Dichlorobenzoyl chloride | 3,4-dichlorobenzoyl | 484.1310 |
| 303 | Methanesulfonyl chloride | methanesulfonyl | 390.1560 |
| 304 | Ethanesulfonyl chloride | ethanesulfonyl | 404.1773 |
| 305 | 1-Propanesulfonyl chloride | propanesulfonyl | 418.1898 |
| 306 | 1-Butanesulfonyl chloride | butanesulfonyl | 432.2047 |
| 307 | Benzenesulfonyl chloride | phenylsulfonyl | 452.1747 |
| 308 | 1-Methylimidazole-4-sulfonyl chloride | 1-methylimidazol-4-ylsulfonyl | 456.1817 |
| 309 | alpha-Toluenesulfonyl chloride | benzylsulfonyl | 466.1900 |

-continued

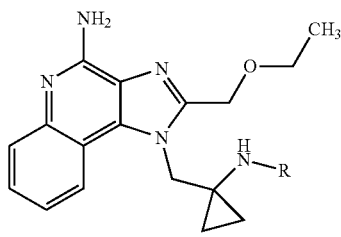

| Example | Reagent | R | Measured Mass (M + H) |
|---|---|---|---|
| 310 | 3-Cyanobenzenesulfonyl chloride | 3-cyano-phenylsulfonyl | 477.1700 |
| 311 | 3-Methoxybenzenesulfonyl chloride | 3-methoxy-phenylsulfonyl | 482.1856 |
| 312 | 4-Methoxybenzenesulfonyl chloride | 4-methoxy-phenylsulfonyl | 482.1843 |
| 313 | 3-Chlorobenzenesulfonyl chloride | 3-chloro-phenylsulfonyl | 486.1353 |
| 314 | 4-Chlorobenzenesulfonyl chloride | 4-chloro-phenylsulfonyl | 486.1349 |
| 315 | Methyl isocyanate | N-methylcarbamoyl | 369.2036 |

-continued

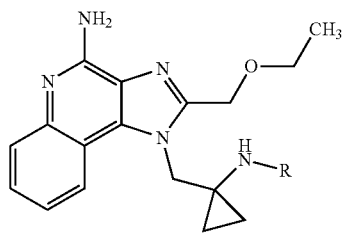

| Example | Reagent | R | Measured Mass (M + H) |
|---|---|---|---|
| 316 | Ethyl isocyanate | -C(O)NH-CH₂CH₃ | 383.2194 |
| 317 | Isopropyl isocyanate | -C(O)NH-CH(CH₃)₂ | 397.2347 |
| 318 | N-Propyl isocyanate | -C(O)NH-CH₂CH₂CH₃ | 397.2359 |
| 319 | Cyclopentyl isocyanate | -C(O)NH-cyclopentyl | 423.2502 |
| 320 | Phenyl isocyanate | -C(O)NH-phenyl | 431.2188 |
| 321 | Cyclohexyl isocyanate | -C(O)NH-cyclohexyl | 437.2674 |
| 322 | (R)-(+)-alpha-Methylbenzyl isocyanate | -C(O)NH-CH(CH₃)(phenyl) | 459.2507 |
| 323 | (S)-(−)-alpha-Methylbenzyl isocyanate | -C(O)NH-CH(CH₃)(phenyl) | 459.2516 |
| 324 | 3-Methoxyphenyl isocyanate | -C(O)NH-(3-methoxyphenyl) | 461.2294 |

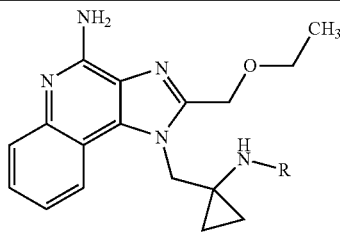

| Example | Reagent | R | Measured Mass (M + H) |
|---|---|---|---|
| 325 | 4-Methoxyphenyl isocyanate | -C(O)NH-C6H4-OCH3 (para) | 461.2318 |
| 326 | 3-Chlorophenyl isocyanate | -C(O)NH-C6H4-Cl (meta) | 465.1809 |
| 327 | 4-Chlorophenyl isocyanate | -C(O)NH-C6H4-Cl (para) | 465.1796 |
| 328 | N,N-Dimethylcarbamoyl chloride | -C(O)N(CH3)2 | 383.2202 |
| 329 | 1-Piperidinecarbonyl chloride | -C(O)-piperidinyl | 423.2494 |
| 330 | 4-Morpholinylcarbonyl chloride | -C(O)-morpholinyl | 425.2287 |

Examples 331-338

Part A

A reagent (1.1 eq) from the table below was added to a test tube containing a solution of 1-[(1-aminocyclopropyl) methyl]-2-ethoxymethyl-1H-imidazo[4,5-c]quinolin-4-amine hydrochloride (3.6 mg, 0.1 mmol, 1 eq) and N,N-diisopropylethylamine (0.083 mL, 5 eq) in N,N-dimethylacetamide (1 mL). The test tube was capped and shaken for 4 hours at ambient temperature. The solvent was then removed by vacuum centrifugation. The residue was purified by solid-supported liquid-liquid extraction according to the following procedure. The residue was dissolved in chloroform (1 mL) and then loaded onto diatomaceous earth that had been equilibrated with water (1 mL) for 20 minutes. After 10 minutes chloroform (5 mL) was added to elute the product from the diatomaceous earth into a test tube. The solvent was then removed by vacuum centrifugation.

Part B

Dichloromethane (1 mL) was added to the test tube and the test tube was shaken to bring all material into solution. The solution was cooled to 0° C. Boron tribromide (400 L of 1M in dichloromethane) was added to the test tube. The test tube was shaken and then placed into an ice bath for 30 minutes. The reaction mixture was stirred at ambient temperature overnight. Methanol (1 mL) and hydrochloric acid (500 L of 6N) were added to the test tube and the test tube was shaken. The solvents were removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 331 | Cyclopropane-carbonyl chloride | cyclopropyl-C(=O)- | 352.1752 |
| 332 | Benzoyl chloride | phenyl-C(=O)- | 388.1777 |
| 333 | Methanesulfonyl chloride | -S(=O)$_2$CH$_3$ | 362.1293 |
| 334 | Benzenesulfonyl chloride | -S(=O)$_2$-phenyl | 424.1436 |
| 335 | Phenyl isocyanate | -C(=O)NH-phenyl | 403.1885 |
| 336 | 4-Morpholinyl-carbonyl chloride | morpholinyl-C(=O)- | 397.1995 |
| 337 | Methyl isocyanate | -C(=O)NHCH$_3$ | 341.1703 |
| 338 | Isopropyl isocyanate | -C(=O)NHCH(CH$_3$)$_2$ | 369.2047 |

Examples 339-378

Part A

Trimethyl orthobutyrate (5.0 mL, 1.3 eq) and pyridine hydrochloride (0.14 g, 0.05 eq) were added to a suspension of ethyl 1-[(3-aminoquinolin-4-ylamino)methyl]cyclobutyrate (24.3 mmol, 1.0 eq, prepared according to the general methods of Parts A through D of Example 92 using 1,3-dibromopropane in lieu of 1,2-dibromoethane in Part A) in tolune (100 mL). The mixture was heated at reflux for 2 hours, allowed to cool to ambient temperature, and then concentrated under reduced pressure. The residue was triturated with acetonitrile. A solid was isolated by filtration to provide 7.55 g of ethyl 1-[(2-propyl-1H-imidazo[4,5-c]quinolin-1-yl)methyl]cyclobutyrate as a white solid.

Part B

The material from Part A was converted to tert-butyl {1-[(2-propyl-1H-imidazo[4,5-c]quinolin-1-yl)methyl]cyclobutyl}carbamate according to the general methods of Parts G and H of Example 92. The crude product was triturated with acetonitrile to provide 4.36 g of tert-butyl {1-[(2-propyl-1H-imidazo[4,5-c]quinolin-1-yl)methyl]cyclobutyl}carbamate as a white solid.

Part C

The material from Part B was oxidized and then aminated according to the general methods of Part I of Example 12. The crude product was triturated with acetonitrile to provide 2.91 g of tert-butyl {1-[(4-amino-2-propyl-1H-imidazo[4,5-c]quinolin-1-yl)methyl]cyclobutyl}carbamate as a tan powder.

Part D

Aqueous hydrochloric acid (6 mL of 6M) was added to a solution of the material from Part C in ethanol (12 mL). The reaction mixture was heated at 60° C. for 8 hours and then concentrated under reduced pressure. The residue was concentrated from methanol 3 times and then triturated with acetonitrile to provide 2.99 g of 1-[(1-aminocyclobutyl)methyl]-2-propyl-1H-imidazo[4,5-c]quinolin-4-amine hydrochloride.

Part E

A reagent (1.1 eq) from the table below was added to a test tube containing a solution of 1-[(1-aminocyclobutyl)methyl]-2-propyl-1H-imidazo[4,5-c]quinolin-4-amine hydrochloride (42 mg, 0.010 mmol, 1 eq) and N,N-diisopropylethylamine (0.087 mL, 5 eq) in N,N-dimethylacetamide (1 mL). The test tube was capped and shaken overnight at ambient temperature. The reaction was quenched with water (2 drops). The solvent was then removed by vacuum centrifugation.

The compounds were purified by prep HPLC according to the method described in Examples 16-53. The table below shows the reagent added to each test tube, the structure of the resulting compound, and the observed accurate mass for the isolated trifluoroacetate salt.

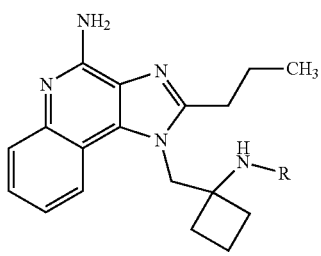

| Example | Reagent | R | Measured Mass (M + H) |
|---|---|---|---|
| 339 | Propionyl chloride | -C(O)CH₂CH₃ | 366.2293 |
| 340 | Cyclopropanecarbonyl chloride | -C(O)-cyclopropyl | 378.2281 |
| 341 | Cyclobutanecarbonyl chloride | -C(O)-cyclobutyl | 392.2454 |
| 342 | Cyclopentanecarbonyl chloride | -C(O)-cyclopentyl | 406.2603 |
| 343 | Phenylacetyl chloride | -C(O)CH₂-phenyl | 428.2433 |
| 344 | 2-Methoxybenzoyl chloride | -C(O)-(2-methoxyphenyl) | 444.2429 |
| 345 | 3-Chlorobenzoyl chloride | -C(O)-(3-chlorophenyl) | 448.1901 |
| 346 | 4-Chlorobenzoyl chloride | -C(O)-(4-chlorophenyl) | 448.1914 |

-continued

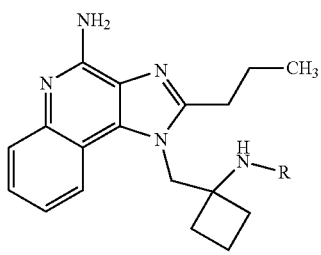

| Example | Reagent | R | Measured Mass (M + H) |
|---|---|---|---|
| 347 | Picolinoyl chloride hydrochloride | 2-pyridyl-C(=O)- | 415.2257 |
| 348 | 3,4-Dimethoxybenzoyl chloride | 3,4-dimethoxyphenyl-C(=O)- | 474.2503 |
| 349 | 3,4-Dichlorobenzoyl chloride | 3,4-dichlorophenyl-C(=O)- | 482.1516 |
| 350 | Methanesulfonyl chloride | CH₃-S(=O)₂- | 388.1819 |
| 351 | Dimethylsulfamoyl chloride | (CH₃)₂N-S(=O)₂- | 417.2081 |
| 352 | 1-Methylimidazole-4-sulfonyl chloride | (1-methylimidazol-4-yl)-S(=O)₂- | 454.2015 |
| 353 | 2,2,2-Trifluoroethanesulfonyl chloride | CF₃CH₂-S(=O)₂- | 456.1696 |

-continued
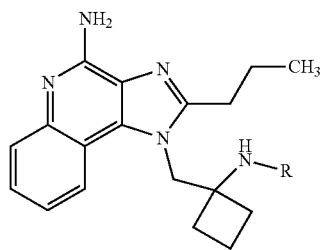
| Example | Reagent | R | Measured Mass (M + H) |
|---|---|---|---|
| 354 | 3-Fluorobenzenesulfonyl chloride | 3-F-C6H4-SO2- | 468.1885 |
| 355 | 4-Fluorobenzenesulfonyl chloride | 4-F-C6H4-SO2- | 468.1908 |
| 356 | 3-Cyanobenzenesulfonyl chloride | 3-NC-C6H4-SO2- | 475.1916 |
| 357 | 4-Cyanobenzenesulfonyl chloride | 4-NC-C6H4-SO2- | 475.1931 |
| 358 | 4-Methoxybenzenesulfonyl chloride | 4-MeO-C6H4-SO2- | 480.2073 |

-continued

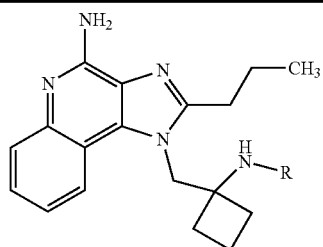

| Example | Reagent | R | Measured Mass (M + H) |
|---|---|---|---|
| 359 | 3-Chlorobenzenesulfonyl chloride | 3-chlorophenyl-SO$_2$- | 484.1579 |
| 360 | 3,4-Dimethoxybenzenesulfonyl chloride | 3,4-dimethoxyphenyl-SO$_2$- | 510.2143 |
| 361 | 3,4-Dichlorobenzenesulfonyl chloride | 3,4-dichlorophenyl-SO$_2$- | 518.1169 |
| 362 | Ethyl isocyanate | -C(O)NH-CH$_2$CH$_3$ | 381.2421 |
| 363 | Isopropyl isocyanate | -C(O)NH-CH(CH$_3$)$_2$ | 395.2561 |
| 364 | n-Propyl isocyanate | -C(O)NH-CH$_2$CH$_2$CH$_3$ | 395.2554 |
| 365 | n-Butyl isocyanate | -C(O)NH-(CH$_2$)$_3$CH$_3$ | 409.2722 |
| 366 | Cyclopentyl isocyanate | -C(O)NH-cyclopentyl | 421.2711 |

-continued

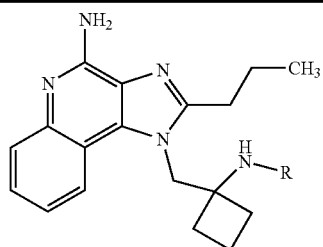

| Example | Reagent | R | Measured Mass (M + H) |
|---|---|---|---|
| 367 | Phenyl isocyanate | -C(O)NH-phenyl | 429.2395 |
| 368 | Cyclohexyl isocyanate | -C(O)NH-cyclohexyl | 435.2869 |
| 369 | 3-Pyridyl isothiocyanate | -C(S)NH-(3-pyridyl) | 446.2140 |
| 370 | (R)-(+)-alpha-Methylbenzyl isocyanate | -C(O)NH-CH(CH₃)-phenyl | 457.2723 |
| 371 | (S)-(−)-alpha-Methylbenzyl isocyanate | -C(O)NH-CH(CH₃)-phenyl | 457.2736 |
| 372 | 3-Methoxyphenyl isocyanate | -C(O)NH-(3-methoxyphenyl) | 459.2513 |
| 373 | 4-Methoxyphenyl isocyanate | -C(O)NH-(4-methoxyphenyl) | 459.2504 |
| 374 | 4-Chlorophenyl isocyanate | -C(O)NH-(4-chlorophenyl) | 463.2012 |
| 375 | N,N-Dimethylcarbamoyl chloride | -C(O)N(CH₃)₂ | 381.2413 |

-continued

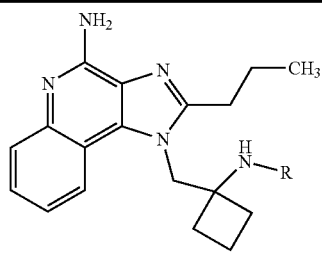

| Example | Reagent | R | Measured Mass (M + H) |
|---|---|---|---|
| 376 | 1-Piperidinecarbonyl chloride | | 421.2741 |
| 377 | 2-Oxo-1-imidazolidinecarbonyl chloride | | 422.2295 |
| 378 | 4-Morpholinylcarbonyl chloride | | 423.2523 |

Example 379

Tert-butyl 3-[(4-amino-2-propyl-1H-imidazo[4,5-c][1,5]naphthyridin-1-yl)methyl]-3-hydroxyazetidine-1-carboxylate

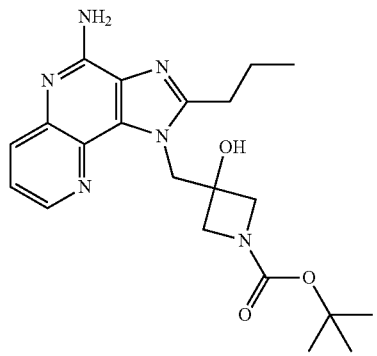 [SMILES: CCCc1nc2c(N)nc3cccnc3c2n1CC1(O)CN(C(=O)OC(C)(C)C)C1]

Part A

A mixture of 1-benzhydrylazetidin-3-ol (5.00 g, 20.9 mmol, prepared according to A. G. Anderson, Jr. and R. Lok, J. Org. Chem., 37, 3953 (1972)), ammonium formate (6.59 g, 104.5 mmol), and 10% palladium on carbon (1.00 g) in ethanol (100 mL) was heated at 70° C. overnight. The reaction mixture was filtered through CELITE filter agent, which was rinsed with methanol and the filtrate was concentrated in vacuo to give crude azetidin-3-ol.

Part B

Under a nitrogen atmosphere a mixture of the material from Part A, di(tert-butyl) dicarbonate (11.4 g, 52.2 mmol), N,N-dimethylpyridin-4-amine (255 mg, 2.09 mmol) and N,N-dimethylformamide (75 mL) was stirred at room temperature for 3 hours. The reaction mixture was concentrated under reduced pressure and the residue dissolved in ethyl acetate (100 mL), washed with water (2×50 mL) and saturated aqueous sodium chloride (30 mL), dried over sodium sulfate, filtered and concentrated under reduced pressure. The material was purified by HPFC eluting with a gradient of 0-20% ethyl acetate in hexanes to give 3.70 g of a clear oil. The oil was dissolved in methanol (200 mL), aqueous sodium hydroxide (12.6 mL of 2N) was added and the solution was stirred at room temperature for 3 hours. The solvent was partially removed under reduced pressure, water (20 mL) was added and the solution was extracted with chloroform (3×100 mL). The combined organics were washed with saturated aqueous sodium chloride (30 mL), dried over sodium sulfate, filtered and concentrated under reduced pressure to provide 2.30 g of tert-butyl 3-hydroxyazetidine-1-carboxylate as a clear oil.

Part C

Under a nitrogen atmosphere sulfur trioxide pyridine complex (6.34 g, 39.8 mmol) was added portionwise to a chilled (0° C.) solution of tert-butyl 3-hydroxyazetidine-1-carboxylate (2.30 g) and triethylamine (5.55 mL, 39.8 mmol) in dimethyl sulfoxide (11.5 mL) and dichloromethane (23 mL). The solution was stirred at 0° C. for another hour, poured into 70 mL of saturated aqueous ammonium chloride and then extracted with diethyl ether (3×100 mL). The combined organics were washed with water (2×30 mL) and brine (20 mL), dried over sodium sulfate, filtered and concentrated under reduced pressure to give tert-butyl 3-oxoazetidine-1-carboxylate as a clear oil.

Part D

The material from part C was converted to tert-butyl 3-(aminomethyl)-3-hydroxyazetidine-1-carboxylate according to the general methods of Parts A and B of Example 4. The product was isolated as 1.48 g of a white solid.

Part E

Tert-butyl 3-[(4-amino-2-propyl-1H-imidazo[4,5-c][1,5]naphthyridin-1-yl)methyl]-3-hydroxyazetidine-1-carboxylate was prepared according to the methods of Parts A through D of Example 120 using tert-butyl 3-(aminomethyl)-3-hydroxyazetidine-1-carboxylate in lieu of tert-butyl 4-(aminomethyl)-4-hydroxypiperidine-1-carboxylate in part A and using trimethylorthobutyrate in lieu of triethylorthopropionate in Part C. The crude product was purified by HPFC eluting with a gradient of 0-25% CMA in chloroform. Trituration with acetonitrile provided 620 mg of the pure product as an off-white powder, mp 134.0-135.0° C. HRMS (EI) calcd for $C_{21}H_{28}N_6O_3$+H, 413.2301, found 413.2319.

TABLE 1

Exemplary Compounds
Certain exemplary compounds, including some of those described above in the Examples, have the following Formulas (II-1, III-1, IV-1, and V-1) wherein $R_2$, Z, R', and m are defined immediately below in the table. In this table, for each ring system, each row represents one specific compound.

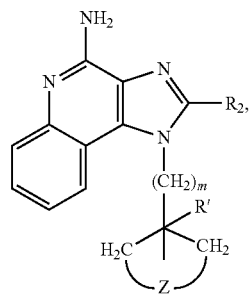

II-1

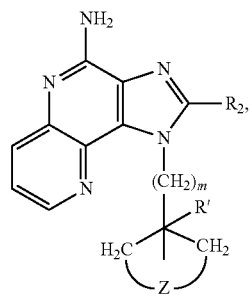

V-1

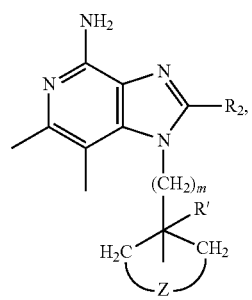

IV-1

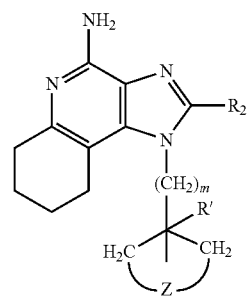

III-1

TABLE 1-continued

| $R_2$ | Z | R' | m |
|---|---|---|---|
| H | Bond | —OH | 1 |
| H | Bond | —OH | 2 |
| H | Bond | —OH | 3 |
| H | Bond | —OCH$_3$ | 1 |
| H | Bond | —OCH$_3$ | 2 |
| H | Bond | —OCH$_3$ | 3 |
| H | Bond | —NH$_2$ | 1 |
| H | Bond | —NH$_2$ | 2 |
| H | Bond | —NH$_2$ | 3 |
| H | —CH$_2$— | —OH | 1 |
| H | —CH$_2$— | —OH | 2 |
| H | —CH$_2$— | —OH | 3 |
| H | —CH$_2$— | —OCH$_3$ | 1 |
| H | —CH$_2$— | —OCH$_3$ | 2 |
| H | —CH$_2$— | —OCH$_3$ | 3 |
| H | —CH$_2$— | —NH$_2$ | 1 |
| H | —CH$_2$— | —NH$_2$ | 2 |
| H | —CH$_2$— | —NH$_2$ | 3 |
| H | —CH$_2$CH$_2$— | —OH | 1 |
| H | —CH$_2$CH$_2$— | —OH | 2 |
| H | —CH$_2$CH$_2$— | —OH | 3 |
| H | —CH$_2$CH$_2$— | —OCH$_3$ | 1 |
| H | —CH$_2$CH$_2$— | —OCH$_3$ | 2 |
| H | —CH$_2$CH$_2$— | —OCH$_3$ | 3 |
| H | —CH$_2$CH$_2$— | —NH$_2$ | 1 |
| H | —CH$_2$CH$_2$— | —NH$_2$ | 2 |
| H | —CH$_2$CH$_2$— | —NH$_2$ | 3 |
| H | —CH$_2$CH$_2$CH$_2$— | —OH | 1 |
| H | —CH$_2$CH$_2$CH$_2$— | —OH | 2 |
| H | —CH$_2$CH$_2$CH$_2$— | —OH | 3 |
| H | —CH$_2$CH$_2$CH$_2$— | —OCH$_3$ | 1 |
| H | —CH$_2$CH$_2$CH$_2$— | —OCH$_3$ | 2 |
| H | —CH$_2$CH$_2$CH$_2$— | —OCH$_3$ | 3 |
| H | —CH$_2$CH$_2$CH$_2$— | —NH$_2$ | 1 |
| H | —CH$_2$CH$_2$CH$_2$— | —NH$_2$ | 2 |
| H | —CH$_2$CH$_2$CH$_2$— | —NH$_2$ | 3 |
| H | —CH$_2$—O—CH$_2$— | —OH | 1 |
| H | —CH$_2$—O—CH$_2$— | —OH | 2 |
| H | —CH$_2$—O—CH$_2$— | —OH | 3 |
| H | —CH$_2$—O—CH$_2$— | —OCH$_3$ | 1 |
| H | —CH$_2$—O—CH$_2$— | —OCH$_3$ | 2 |
| H | —CH$_2$—O—CH$_2$— | —OCH$_3$ | 3 |
| H | —CH$_2$—O—CH$_2$— | —NH$_2$ | 1 |
| H | —CH$_2$—O—CH$_2$— | —NH$_2$ | 2 |
| H | —CH$_2$—O—CH$_2$— | —NH$_2$ | 3 |
| methyl | Bond | —OH | 1 |
| methyl | Bond | —OH | 2 |
| methyl | Bond | —OH | 3 |
| methyl | Bond | —OCH$_3$ | 1 |
| methyl | Bond | —OCH$_3$ | 2 |
| methyl | Bond | —OCH$_3$ | 3 |
| methyl | Bond | —NH$_2$ | 1 |
| methyl | Bond | —NH$_2$ | 2 |
| methyl | Bond | —NH$_2$ | 3 |
| methyl | —CH$_2$— | —OH | 1 |
| methyl | —CH$_2$— | —OH | 2 |
| methyl | —CH$_2$— | —OH | 3 |
| methyl | —CH$_2$— | —OCH$_3$ | 1 |
| methyl | —CH$_2$— | —OCH$_3$ | 2 |
| methyl | —CH$_2$— | —OCH$_3$ | 3 |
| methyl | —CH$_2$— | —NH$_2$ | 1 |
| methyl | —CH$_2$— | —NH$_2$ | 2 |
| methyl | —CH$_2$— | —NH$_2$ | 3 |
| methyl | —CH$_2$CH$_2$— | —OH | 1 |
| methyl | —CH$_2$CH$_2$— | —OH | 2 |
| methyl | —CH$_2$CH$_2$— | —OH | 3 |
| methyl | —CH$_2$CH$_2$— | —OCH$_3$ | 1 |
| methyl | —CH$_2$CH$_2$— | —OCH$_3$ | 2 |
| methyl | —CH$_2$CH$_2$— | —OCH$_3$ | 3 |
| methyl | —CH$_2$CH$_2$— | —NH$_2$ | 1 |
| methyl | —CH$_2$CH$_2$— | —NH$_2$ | 2 |
| methyl | —CH$_2$CH$_2$— | —NH$_2$ | 3 |
| methyl | —CH$_2$CH$_2$CH$_2$— | —OH | 1 |
| methyl | —CH$_2$CH$_2$CH$_2$— | —OH | 2 |
| methyl | —CH$_2$CH$_2$CH$_2$— | —OH | 3 |
| methyl | —CH$_2$CH$_2$CH$_2$— | —OCH$_3$ | 1 |
| methyl | —CH$_2$CH$_2$CH$_2$— | —OCH$_3$ | 2 |

TABLE 1-continued

| | | | |
|---|---|---|---|
| methyl | —CH$_2$CH$_2$CH$_2$— | —OCH$_3$ | 3 |
| methyl | —CH$_2$CH$_2$CH$_2$— | —NH$_2$ | 1 |
| methyl | —CH$_2$CH$_2$CH$_2$— | —NH$_2$ | 2 |
| methyl | —CH$_2$CH$_2$CH$_2$— | —NH$_2$ | 3 |
| methyl | —CH$_2$—O—CH$_2$— | —OH | 1 |
| methyl | —CH$_2$—O—CH$_2$— | —OH | 2 |
| methyl | —CH$_2$—O—CH$_2$— | —OH | 3 |
| methyl | —CH$_2$—O—CH$_2$— | —OCH$_3$ | 1 |
| methyl | —CH$_2$—O—CH$_2$— | —OCH$_3$ | 2 |
| methyl | —CH$_2$—O—CH$_2$— | —OCH$_3$ | 3 |
| methyl | —CH$_2$—O—CH$_2$— | —NH$_2$ | 1 |
| methyl | —CH$_2$—O—CH$_2$— | —NH$_2$ | 2 |
| methyl | —CH$_2$—O—CH$_2$— | —NH$_2$ | 3 |
| ethyl | Bond | —OH | 1 |
| ethyl | Bond | —OH | 2 |
| ethyl | Bond | —OH | 3 |
| ethyl | Bond | —OCH$_3$ | 1 |
| ethyl | Bond | —OCH$_3$ | 2 |
| ethyl | Bond | —OCH$_3$ | 3 |
| ethyl | Bond | —NH$_2$ | 1 |
| ethyl | Bond | —NH$_2$ | 2 |
| ethyl | Bond | —NH$_2$ | 3 |
| ethyl | —CH$_2$— | —OH | 1 |
| ethyl | —CH$_2$— | —OH | 2 |
| ethyl | —CH$_2$— | —OH | 3 |
| ethyl | —CH$_2$— | —OCH$_3$ | 1 |
| ethyl | —CH$_2$— | —OCH$_3$ | 2 |
| ethyl | —CH$_2$— | —OCH$_3$ | 3 |
| ethyl | —CH$_2$— | —NH$_2$ | 1 |
| ethyl | —CH$_2$— | —NH$_2$ | 2 |
| ethyl | —CH$_2$— | —NH$_2$ | 3 |
| ethyl | —CH$_2$CH$_2$— | —OH | 1 |
| ethyl | —CH$_2$CH$_2$— | —OH | 2 |
| ethyl | —CH$_2$CH$_2$— | —OH | 3 |
| ethyl | —CH$_2$CH$_2$— | —OCH$_3$ | 1 |
| ethyl | —CH$_2$CH$_2$— | —OCH$_3$ | 2 |
| ethyl | —CH$_2$CH$_2$— | —OCH$_3$ | 3 |
| ethyl | —CH$_2$CH$_2$— | —NH$_2$ | 1 |
| ethyl | —CH$_2$CH$_2$— | —NH$_2$ | 2 |
| ethyl | —CH$_2$CH$_2$— | —NH$_2$ | 3 |
| ethyl | —CH$_2$CH$_2$CH$_2$— | —OH | 1 |
| ethyl | —CH$_2$CH$_2$CH$_2$— | —OH | 2 |
| ethyl | —CH$_2$CH$_2$CH$_2$— | —OH | 3 |
| ethyl | —CH$_2$CH$_2$CH$_2$— | —OCH$_3$ | 1 |
| ethyl | —CH$_2$CH$_2$CH$_2$— | —OCH$_3$ | 2 |
| ethyl | —CH$_2$CH$_2$CH$_2$— | —OCH$_3$ | 3 |
| ethyl | —CH$_2$CH$_2$CH$_2$— | —NH$_2$ | 1 |
| ethyl | —CH$_2$CH$_2$CH$_2$— | —NH$_2$ | 2 |
| ethyl | —CH$_2$CH$_2$CH$_2$— | —NH$_2$ | 3 |
| ethyl | —CH$_2$—O—CH$_2$— | —OH | 1 |
| ethyl | —CH$_2$—O—CH$_2$— | —OH | 2 |
| ethyl | —CH$_2$—O—CH$_2$— | —OH | 3 |
| ethyl | —CH$_2$—O—CH$_2$— | —OCH$_3$ | 1 |
| ethyl | —CH$_2$—O—CH$_2$— | —OCH$_3$ | 2 |
| ethyl | —CH$_2$—O—CH$_2$— | —OCH$_3$ | 3 |
| ethyl | —CH$_2$—O—CH$_2$— | —NH$_2$ | 1 |
| ethyl | —CH$_2$—O—CH$_2$— | —NH$_2$ | 2 |
| ethyl | —CH$_2$—O—CH$_2$— | —NH$_2$ | 3 |
| n-propyl | Bond | —OH | 1 |
| n-propyl | Bond | —OH | 2 |
| n-propyl | Bond | —OH | 3 |
| n-propyl | Bond | —OCH$_3$ | 1 |
| n-propyl | Bond | —OCH$_3$ | 2 |
| n-propyl | Bond | —OCH$_3$ | 3 |
| n-propyl | Bond | —NH$_2$ | 1 |
| n-propyl | Bond | —NH$_2$ | 2 |
| n-propyl | Bond | —NH$_2$ | 3 |
| n-propyl | —CH$_2$— | —OH | 1 |
| n-propyl | —CH$_2$— | —OH | 2 |
| n-propyl | —CH$_2$— | —OH | 3 |
| n-propyl | —CH$_2$— | —OCH$_3$ | 1 |
| n-propyl | —CH$_2$— | —OCH$_3$ | 2 |
| n-propyl | —CH$_2$— | —OCH$_3$ | 3 |
| n-propyl | —CH$_2$— | —NH$_2$ | 1 |
| n-propyl | —CH$_2$— | —NH$_2$ | 2 |
| n-propyl | —CH$_2$— | —NH$_2$ | 3 |
| n-propyl | —CH$_2$CH$_2$— | —OH | 1 |
| n-propyl | —CH$_2$CH$_2$— | —OH | 2 |
| n-propyl | —CH$_2$CH$_2$— | —OH | 3 |
| n-propyl | —CH$_2$CH$_2$— | —OCH$_3$ | 1 |

TABLE 1-continued

| | | | |
|---|---|---|---|
| n-propyl | —CH$_2$CH$_2$— | —OCH$_3$ | 2 |
| n-propyl | —CH$_2$CH$_2$— | —OCH$_3$ | 3 |
| n-propyl | —CH$_2$CH$_2$— | —NH$_2$ | 1 |
| n-propyl | —CH$_2$CH$_2$— | —NH$_2$ | 2 |
| n-propyl | —CH$_2$CH$_2$— | —NH$_2$ | 3 |
| n-propyl | —CH$_2$CH$_2$CH$_2$— | —OH | 1 |
| n-propyl | —CH$_2$CH$_2$CH$_2$— | —OH | 2 |
| n-propyl | —CH$_2$CH$_2$CH$_2$— | —OH | 3 |
| n-propyl | —CH$_2$CH$_2$CH$_2$— | —OCH$_3$ | 1 |
| n-propyl | —CH$_2$CH$_2$CH$_2$— | —OCH$_3$ | 2 |
| n-propyl | —CH$_2$CH$_2$CH$_2$— | —OCH$_3$ | 3 |
| n-propyl | —CH$_2$CH$_2$CH$_2$— | —NH$_2$ | 1 |
| n-propyl | —CH$_2$CH$_2$CH$_2$— | —NH$_2$ | 2 |
| n-propyl | —CH$_2$CH$_2$CH$_2$— | —NH$_2$ | 3 |
| n-propyl | —CH$_2$—O—CH$_2$— | —OH | 1 |
| n-propyl | —CH$_2$—O—CH$_2$— | —OH | 2 |
| n-propyl | —CH$_2$—O—CH$_2$— | —OH | 3 |
| n-propyl | —CH$_2$—O—CH$_2$— | —OCH$_3$ | 1 |
| n-propyl | —CH$_2$—O—CH$_2$— | —OCH$_3$ | 2 |
| n-propyl | —CH$_2$—O—CH$_2$— | —OCH$_3$ | 3 |
| n-propyl | —CH$_2$—O—CH$_2$— | —NH$_2$ | 1 |
| n-propyl | —CH$_2$—O—CH$_2$— | —NH$_2$ | 2 |
| n-propyl | —CH$_2$—O—CH$_2$— | —NH$_2$ | 3 |
| n-butyl | Bond | —OH | 1 |
| n-butyl | Bond | —OH | 2 |
| n-butyl | Bond | —OH | 3 |
| n-butyl | Bond | —OCH$_3$ | 1 |
| n-butyl | Bond | —OCH$_3$ | 2 |
| n-butyl | Bond | —OCH$_3$ | 3 |
| n-butyl | Bond | —NH$_2$ | 1 |
| n-butyl | Bond | —NH$_2$ | 2 |
| n-butyl | Bond | —NH$_2$ | 3 |
| n-butyl | —CH$_2$— | —OH | 1 |
| n-butyl | —CH$_2$— | —OH | 2 |
| n-butyl | —CH$_2$— | —OH | 3 |
| n-butyl | —CH$_2$— | —OCH$_3$ | 1 |
| n-butyl | —CH$_2$— | —OCH$_3$ | 2 |
| n-butyl | —CH$_2$— | —OCH$_3$ | 3 |
| n-butyl | —CH$_2$— | —NH$_2$ | 1 |
| n-butyl | —CH$_2$— | —NH$_2$ | 2 |
| n-butyl | —CH$_2$— | —NH$_2$ | 3 |
| n-butyl | —CH$_2$CH$_2$— | —OH | 1 |
| n-butyl | —CH$_2$CH$_2$— | —OH | 2 |
| n-butyl | —CH$_2$CH$_2$— | —OH | 3 |
| n-butyl | —CH$_2$CH$_2$— | —OCH$_3$ | 1 |
| n-butyl | —CH$_2$CH$_2$— | —OCH$_3$ | 2 |
| n-butyl | —CH$_2$CH$_2$— | —OCH$_3$ | 3 |
| n-butyl | —CH$_2$CH$_2$— | —NH$_2$ | 1 |
| n-butyl | —CH$_2$CH$_2$— | —NH$_2$ | 2 |
| n-butyl | —CH$_2$CH$_2$— | —NH$_2$ | 3 |
| n-butyl | —CH$_2$CH$_2$CH$_2$— | —OH | 1 |
| n-butyl | —CH$_2$CH$_2$CH$_2$— | —OH | 2 |
| n-butyl | —CH$_2$CH$_2$CH$_2$— | —OH | 3 |
| n-butyl | —CH$_2$CH$_2$CH$_2$— | —OCH$_3$ | 1 |
| n-butyl | —CH$_2$CH$_2$CH$_2$— | —OCH$_3$ | 2 |
| n-butyl | —CH$_2$CH$_2$CH$_2$— | —OCH$_3$ | 3 |
| n-butyl | —CH$_2$CH$_2$CH$_2$— | —NH$_2$ | 1 |
| n-butyl | —CH$_2$CH$_2$CH$_2$— | —NH$_2$ | 2 |
| n-butyl | —CH$_2$CH$_2$CH$_2$— | —NH$_2$ | 3 |
| n-butyl | —CH$_2$—O—CH$_2$— | —OH | 1 |
| n-butyl | —CH$_2$—O—CH$_2$— | —OH | 2 |
| n-butyl | —CH$_2$—O—CH$_2$— | —OH | 3 |
| n-butyl | —CH$_2$—O—CH$_2$— | —OCH$_3$ | 1 |
| n-butyl | —CH$_2$—O—CH$_2$— | —OCH$_3$ | 2 |
| n-butyl | —CH$_2$—O—CH$_2$— | —OCH$_3$ | 3 |
| n-butyl | —CH$_2$—O—CH$_2$— | —NH$_2$ | 1 |
| n-butyl | —CH$_2$—O—CH$_2$— | —NH$_2$ | 2 |
| n-butyl | —CH$_2$—O—CH$_2$— | —NH$_2$ | 3 |
| ethoxymethyl | Bond | —OH | 1 |
| ethoxymethyl | Bond | —OH | 2 |
| ethoxymethyl | Bond | —OH | 3 |
| ethoxymethyl | Bond | —OCH$_3$ | 1 |
| ethoxymethyl | Bond | —OCH$_3$ | 2 |
| ethoxymethyl | Bond | —OCH$_3$ | 3 |
| ethoxymethyl | Bond | —NH$_2$ | 1 |
| ethoxymethyl | Bond | —NH$_2$ | 2 |
| ethoxymethyl | Bond | —NH$_2$ | 3 |
| ethoxymethyl | —CH$_2$— | —OH | 1 |
| ethoxymethyl | —CH$_2$— | —OH | 2 |
| ethoxymethyl | —CH$_2$— | —OH | 3 |

TABLE 1-continued

| | | | |
|---|---|---|---|
| ethoxymethyl | —CH$_2$— | —OCH$_3$ | 1 |
| ethoxymethyl | —CH$_2$— | —OCH$_3$ | 2 |
| ethoxymethyl | —CH$_2$— | —OCH$_3$ | 3 |
| ethoxymethyl | —CH$_2$— | —NH$_2$ | 1 |
| ethoxymethyl | —CH$_2$— | —NH$_2$ | 2 |
| ethoxymethyl | —CH$_2$— | —NH$_2$ | 3 |
| ethoxymethyl | —CH$_2$CH$_2$— | —OH | 1 |
| ethoxymethyl | —CH$_2$CH$_2$— | —OH | 2 |
| ethoxymethyl | —CH$_2$CH$_2$— | —OH | 3 |
| ethoxymethyl | —CH$_2$CH$_2$— | —OCH$_3$ | 1 |
| ethoxymethyl | —CH$_2$CH$_2$— | —OCH$_3$ | 2 |
| ethoxymethyl | —CH$_2$CH$_2$— | —OCH$_3$ | 3 |
| ethoxymethyl | —CH$_2$CH$_2$— | —NH$_2$ | 1 |
| ethoxymethyl | —CH$_2$CH$_2$— | —NH$_2$ | 2 |
| ethoxymethyl | —CH$_2$CH$_2$— | —NH$_2$ | 3 |
| ethoxymethyl | —CH$_2$CH$_2$CH$_2$— | —OH | 1 |
| ethoxymethyl | —CH$_2$CH$_2$CH$_2$— | —OH | 2 |
| ethoxymethyl | —CH$_2$CH$_2$CH$_2$— | —OH | 3 |
| ethoxymethyl | —CH$_2$CH$_2$CH$_2$— | —OCH$_3$ | 1 |
| ethoxymethyl | —CH$_2$CH$_2$CH$_2$— | —OCH$_3$ | 2 |
| ethoxymethyl | —CH$_2$CH$_2$CH$_2$— | —OCH$_3$ | 3 |
| ethoxymethyl | —CH$_2$CH$_2$CH$_2$— | —NH$_2$ | 1 |
| ethoxymethyl | —CH$_2$CH$_2$CH$_2$— | —NH$_2$ | 2 |
| ethoxymethyl | —CH$_2$CH$_2$CH$_2$— | —NH$_2$ | 3 |
| ethoxymethyl | —CH$_2$—O—CH$_2$— | —OH | 1 |
| ethoxymethyl | —CH$_2$—O—CH$_2$— | —OH | 2 |
| ethoxymethyl | —CH$_2$—O—CH$_2$— | —OH | 3 |
| ethoxymethyl | —CH$_2$—O—CH$_2$— | —OCH$_3$ | 1 |
| ethoxymethyl | —CH$_2$—O—CH$_2$— | —OCH$_3$ | 2 |
| ethoxymethyl | —CH$_2$—O—CH$_2$— | —OCH$_3$ | 3 |
| ethoxymethyl | —CH$_2$—O—CH$_2$— | —NH$_2$ | 1 |
| ethoxymethyl | —CH$_2$—O—CH$_2$— | —NH$_2$ | 2 |
| ethoxymethyl | —CH$_2$—O—CH$_2$— | —NH$_2$ | 3 |
| 2-methoxyethyl | Bond | —OH | 1 |
| 2-methoxyethyl | Bond | —OH | 2 |
| 2-methoxyethyl | Bond | —OH | 3 |
| 2-methoxyethyl | Bond | —OCH$_3$ | 1 |
| 2-methoxyethyl | Bond | —OCH$_3$ | 2 |
| 2-methoxyethyl | Bond | —OCH$_3$ | 3 |
| 2-methoxyethyl | Bond | —NH$_2$ | 1 |
| 2-methoxyethyl | Bond | —NH$_2$ | 2 |
| 2-methoxyethyl | Bond | —NH$_2$ | 3 |
| 2-methoxyethyl | —CH$_2$— | —OH | 1 |
| 2-methoxyethyl | —CH$_2$— | —OH | 2 |
| 2-methoxyethyl | —CH$_2$— | —OH | 3 |
| 2-methoxyethyl | —CH$_2$— | —OCH$_3$ | 1 |
| 2-methoxyethyl | —CH$_2$— | —OCH$_3$ | 2 |
| 2-methoxyethyl | —CH$_2$— | —OCH$_3$ | 3 |
| 2-methoxyethyl | —CH$_2$— | —NH$_2$ | 1 |
| 2-methoxyethyl | —CH$_2$— | —NH$_2$ | 2 |
| 2-methoxyethyl | —CH$_2$— | —NH$_2$ | 3 |
| 2-methoxyethyl | —CH$_2$CH$_2$— | —OH | 1 |
| 2-methoxyethyl | —CH$_2$CH$_2$— | —OH | 2 |
| 2-methoxyethyl | —CH$_2$CH$_2$— | —OH | 3 |
| 2-methoxyethyl | —CH$_2$CH$_2$— | —OCH$_3$ | 1 |
| 2-methoxyethyl | —CH$_2$CH$_2$— | —OCH$_3$ | 2 |
| 2-methoxyethyl | —CH$_2$CH$_2$— | —OCH$_3$ | 3 |
| 2-methoxyethyl | —CH$_2$CH$_2$— | —NH$_2$ | 1 |
| 2-methoxyethyl | —CH$_2$CH$_2$— | —NH$_2$ | 2 |
| 2-methoxyethyl | —CH$_2$CH$_2$— | —NH$_2$ | 3 |
| 2-methoxyethyl | —CH$_2$CH$_2$CH$_2$— | —OH | 1 |
| 2-methoxyethyl | —CH$_2$CH$_2$CH$_2$— | —OH | 2 |
| 2-methoxyethyl | —CH$_2$CH$_2$CH$_2$— | —OH | 3 |
| 2-methoxyethyl | —CH$_2$CH$_2$CH$_2$— | —OCH$_3$ | 1 |
| 2-methoxyethyl | —CH$_2$CH$_2$CH$_2$— | —OCH$_3$ | 2 |
| 2-methoxyethyl | —CH$_2$CH$_2$CH$_2$— | —OCH$_3$ | 3 |
| 2-methoxyethyl | —CH$_2$CH$_2$CH$_2$— | —NH$_2$ | 1 |
| 2-methoxyethyl | —CH$_2$CH$_2$CH$_2$— | —NH$_2$ | 2 |
| 2-methoxyethyl | —CH$_2$CH$_2$CH$_2$— | —NH$_2$ | 3 |
| 2-methoxyethyl | —CH$_2$—O—CH$_2$— | —OH | 1 |
| 2-methoxyethyl | —CH$_2$—O—CH$_2$— | —OH | 2 |
| 2-methoxyethyl | —CH$_2$—O—CH$_2$— | —OH | 3 |
| 2-methoxyethyl | —CH$_2$—O—CH$_2$— | —OCH$_3$ | 1 |
| 2-methoxyethyl | —CH$_2$—O—CH$_2$— | —OCH$_3$ | 2 |
| 2-methoxyethyl | —CH$_2$—O—CH$_2$— | —OCH$_3$ | 3 |
| 2-methoxyethyl | —CH$_2$—O—CH$_2$— | —NH$_2$ | 1 |
| 2-methoxyethyl | —CH$_2$—O—CH$_2$— | —NH$_2$ | 2 |
| 2-methoxyethyl | —CH$_2$—O—CH$_2$— | —NH$_2$ | 3 |

TABLE 2
Exemplary Compounds
Certain exemplary compounds, including some of those described above in the Examples, have the following Formulas (II-2, III-2, IV-2, and V-2) wherein $R_2$, Q, R', $R_4$, and m are defined immediately below in the table. In this table, for each ring system, each row represents one specific compound.
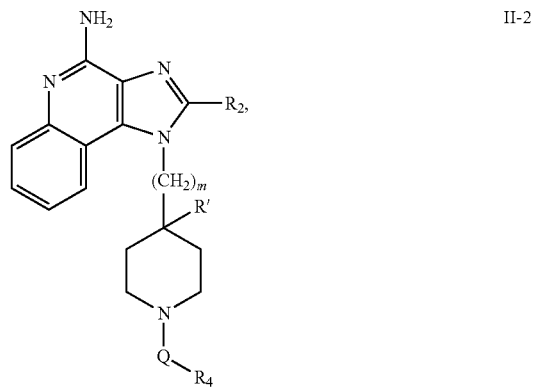
II-2
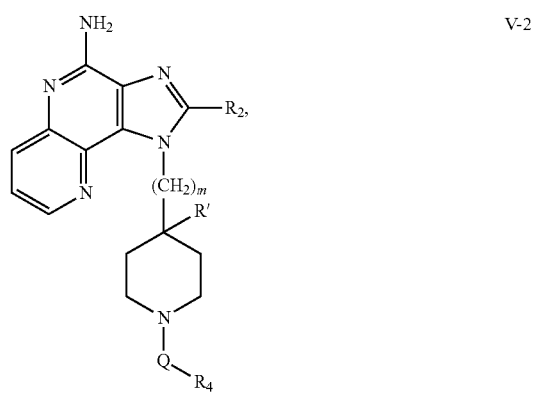
V-2
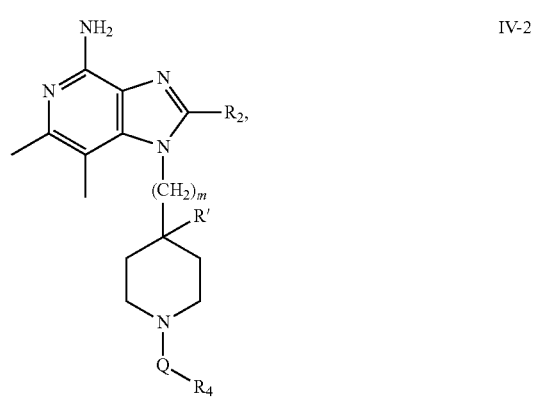
IV-2

TABLE 2-continued

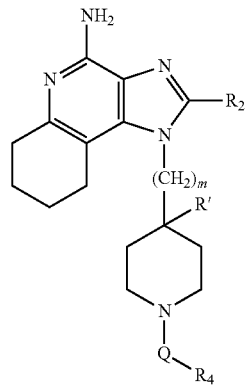

III-2

| R₂ | Q | R₄ | R' | m |
|---|---|---|---|---|
| H | Bond | Methyl | —OH | 1 |
| H | Bond | Methyl | —OH | 2 |
| H | Bond | Methyl | —OH | 3 |
| H | Bond | Methyl | —OCH₃ | 1 |
| H | Bond | methyl | —OCH₃ | 2 |
| H | Bond | methyl | —OCH₃ | 3 |
| H | Bond | ethyl | —OH | 1 |
| H | Bond | ethyl | —OH | 2 |
| H | Bond | ethyl | —OH | 3 |
| H | Bond | ethyl | —OCH₃ | 1 |
| H | Bond | ethyl | —OCH₃ | 2 |
| H | Bond | ethyl | —OCH₃ | 3 |
| H | Bond | isopropyl | —OH | 1 |
| H | Bond | isopropyl | —OH | 2 |
| H | Bond | isopropyl | —OH | 3 |
| H | Bond | isopropyl | —OCH₃ | 1 |
| H | Bond | isopropyl | —OCH₃ | 2 |
| H | Bond | isopropyl | —OCH₃ | 3 |
| H | Bond | phenyl | —OH | 1 |
| H | Bond | phenyl | —OH | 2 |
| H | Bond | phenyl | —OH | 3 |
| H | Bond | phenyl | —OCH₃ | 1 |
| H | Bond | phenyl | —OCH₃ | 2 |
| H | Bond | phenyl | —OCH₃ | 3 |
| H | —C(O)— | methyl | —OH | 1 |
| H | —C(O)— | methyl | —OH | 2 |
| H | —C(O)— | methyl | —OH | 3 |
| H | —C(O)— | methyl | —OCH₃ | 1 |
| H | —C(O)— | methyl | —OCH₃ | 2 |
| H | —C(O)— | methyl | —OCH₃ | 3 |
| H | —C(O)— | ethyl | —OH | 1 |
| H | —C(O)— | ethyl | —OH | 2 |
| H | —C(O)— | ethyl | —OH | 3 |
| H | —C(O)— | ethyl | —OCH₃ | 1 |
| H | —C(O)— | ethyl | —OCH₃ | 2 |
| H | —C(O)— | ethyl | —OCH₃ | 3 |
| H | —C(O)— | isopropyl | —OH | 1 |
| H | —C(O)— | isopropyl | —OH | 2 |
| H | —C(O)— | isopropyl | —OH | 3 |
| H | —C(O)— | isopropyl | —OCH₃ | 1 |
| H | —C(O)— | isopropyl | —OCH₃ | 2 |
| H | —C(O)— | isopropyl | —OCH₃ | 3 |
| H | —C(O)— | phenyl | —OH | 1 |
| H | —C(O)— | phenyl | —OH | 2 |
| H | —C(O)— | phenyl | —OH | 3 |
| H | —C(O)— | phenyl | —OCH₃ | 1 |
| H | —C(O)— | phenyl | —OCH₃ | 2 |
| H | —C(O)— | phenyl | —OCH₃ | 3 |
| H | —S(O)₂— | methyl | —OH | 1 |
| H | —S(O)₂— | methyl | —OH | 2 |
| H | —S(O)₂— | methyl | —OH | 3 |
| H | —S(O)₂— | methyl | —OCH₃ | 1 |
| H | —S(O)₂— | methyl | —OCH₃ | 2 |
| H | —S(O)₂— | methyl | —OCH₃ | 3 |
| H | —S(O)₂— | ethyl | —OH | 1 |
| H | —S(O)₂— | ethyl | —OH | 2 |
| H | —S(O)₂— | ethyl | —OH | 3 |
| H | —S(O)₂— | ethyl | —OCH₃ | 1 |
| H | —S(O)₂— | ethyl | —OCH₃ | 2 |

TABLE 2-continued

| | | | | |
|---|---|---|---|---|
| H | —S(O)$_2$— | ethyl | —OCH$_3$ | 3 |
| H | —S(O)$_2$— | isopropyl | —OH | 1 |
| H | —S(O)$_2$— | isopropyl | —OH | 2 |
| H | —S(O)$_2$— | isopropyl | —OH | 3 |
| H | —S(O)$_2$— | isopropyl | —OCH$_3$ | 1 |
| H | —S(O)$_2$— | isopropyl | —OCH$_3$ | 2 |
| H | —S(O)$_2$— | isopropyl | —OCH$_3$ | 3 |
| H | —S(O)$_2$— | phenyl | —OH | 1 |
| H | —S(O)$_2$— | phenyl | —OH | 2 |
| H | —S(O)$_2$— | phenyl | —OH | 3 |
| H | —S(O)$_2$— | phenyl | —OCH$_3$ | 1 |
| H | —S(O)$_2$— | phenyl | —OCH$_3$ | 2 |
| H | —S(O)$_2$— | phenyl | —OCH$_3$ | 3 |
| H | —C(O)—NH— | methyl | —OH | 1 |
| H | —C(O)—NH— | methyl | —OH | 2 |
| H | —C(O)—NH— | methyl | —OH | 3 |
| H | —C(O)—NH— | methyl | —OCH$_3$ | 1 |
| H | —C(O)—NH— | methyl | —OCH$_3$ | 2 |
| H | —C(O)—NH— | methyl | —OCH$_3$ | 3 |
| H | —C(O)—NH— | ethyl | —OH | 1 |
| H | —C(O)—NH— | ethyl | —OH | 2 |
| H | —C(O)—NH— | ethyl | —OH | 3 |
| H | —C(O)—NH— | ethyl | —OCH$_3$ | 1 |
| H | —C(O)—NH— | ethyl | —OCH$_3$ | 2 |
| H | —C(O)—NH— | ethyl | —OCH$_3$ | 3 |
| H | —C(O)—NH— | isopropyl | —OH | 1 |
| H | —C(O)—NH— | isopropyl | —OH | 2 |
| H | —C(O)—NH— | isopropyl | —OH | 3 |
| H | —C(O)—NH— | isopropyl | —OCH$_3$ | 1 |
| H | —C(O)—NH— | isopropyl | —OCH$_3$ | 2 |
| H | —C(O)—NH— | isopropyl | —OCH$_3$ | 3 |
| H | —C(O)—NH— | phenyl | —OH | 1 |
| H | —C(O)—NH— | phenyl | —OH | 2 |
| H | —C(O)—NH— | phenyl | —OH | 3 |
| H | —C(O)—NH— | phenyl | —OCH$_3$ | 1 |
| H | —C(O)—NH— | phenyl | —OCH$_3$ | 2 |
| H | —C(O)—NH— | phenyl | —OCH$_3$ | 3 |
| methyl | Bond | methyl | —OH | 1 |
| methyl | Bond | methyl | —OH | 2 |
| methyl | Bond | methyl | —OH | 3 |
| methyl | Bond | methyl | —OCH$_3$ | 1 |
| methyl | Bond | methyl | —OCH$_3$ | 2 |
| methyl | Bond | methyl | —OCH$_3$ | 3 |
| methyl | Bond | ethyl | —OH | 1 |
| methyl | Bond | ethyl | —OH | 2 |
| methyl | Bond | ethyl | —OH | 3 |
| methyl | Bond | ethyl | —OCH$_3$ | 1 |
| methyl | Bond | ethyl | —OCH$_3$ | 2 |
| methyl | Bond | ethyl | —OCH$_3$ | 3 |
| methyl | Bond | isopropyl | —OH | 1 |
| methyl | Bond | isopropyl | —OH | 2 |
| methyl | Bond | isopropyl | —OH | 3 |
| methyl | Bond | isopropyl | —OCH$_3$ | 1 |
| methyl | Bond | isopropyl | —OCH$_3$ | 2 |
| methyl | Bond | isopropyl | —OCH$_3$ | 3 |
| methyl | Bond | phenyl | —OH | 1 |
| methyl | Bond | phenyl | —OH | 2 |
| methyl | Bond | phenyl | —OH | 3 |
| methyl | Bond | phenyl | —OCH$_3$ | 1 |
| methyl | Bond | phenyl | —OCH$_3$ | 2 |
| methyl | Bond | phenyl | —OCH$_3$ | 3 |
| methyl | —C(O)— | methyl | —OH | 1 |
| methyl | —C(O)— | methyl | —OH | 2 |
| methyl | —C(O)— | methyl | —OH | 3 |
| methyl | —C(O)— | methyl | —OCH$_3$ | 1 |
| methyl | —C(O)— | methyl | —OCH$_3$ | 2 |
| methyl | —C(O)— | methyl | —OCH$_3$ | 3 |
| methyl | —C(O)— | ethyl | —OH | 1 |
| methyl | —C(O)— | ethyl | —OH | 2 |
| methyl | —C(O)— | ethyl | —OH | 3 |
| methyl | —C(O)— | ethyl | —OCH$_3$ | 1 |
| methyl | —C(O)— | ethyl | —OCH$_3$ | 2 |
| methyl | —C(O)— | ethyl | —OCH$_3$ | 3 |
| methyl | —C(O)— | isopropyl | —OH | 1 |
| methyl | —C(O)— | isopropyl | —OH | 2 |
| methyl | —C(O)— | isopropyl | —OH | 3 |
| methyl | —C(O)— | isopropyl | —OCH$_3$ | 1 |
| methyl | —C(O)— | isopropyl | —OCH$_3$ | 2 |
| methyl | —C(O)— | isopropyl | —OCH$_3$ | 3 |
| methyl | —C(O)— | phenyl | —OH | 1 |

TABLE 2-continued

| | | | | |
|---|---|---|---|---|
| methyl | —C(O)— | phenyl | —OH | 2 |
| methyl | —C(O)— | phenyl | —OH | 3 |
| methyl | —C(O)— | phenyl | —OCH$_3$ | 1 |
| methyl | —C(O)— | phenyl | —OCH$_3$ | 2 |
| methyl | —C(O)— | phenyl | —OCH$_3$ | 3 |
| methyl | —S(O)$_2$— | methyl | —OH | 1 |
| methyl | —S(O)$_2$— | methyl | —OH | 2 |
| methyl | —S(O)$_2$— | methyl | —OH | 3 |
| methyl | —S(O)$_2$— | methyl | —OCH$_3$ | 1 |
| methyl | —S(O)$_2$— | methyl | —OCH$_3$ | 2 |
| methyl | —S(O)$_2$— | methyl | —OCH$_3$ | 3 |
| methyl | —S(O)$_2$— | ethyl | —OH | 1 |
| methyl | —S(O)$_2$— | ethyl | —OH | 2 |
| methyl | —S(O)$_2$— | ethyl | —OH | 3 |
| methyl | —S(O)$_2$— | ethyl | —OCH$_3$ | 1 |
| methyl | —S(O)$_2$— | ethyl | —OCH$_3$ | 2 |
| methyl | —S(O)$_2$— | ethyl | —OCH$_3$ | 3 |
| methyl | —S(O)$_2$— | isopropyl | —OH | 1 |
| methyl | —S(O)$_2$— | isopropyl | —OH | 2 |
| methyl | —S(O)$_2$— | isopropyl | —OH | 3 |
| methyl | —S(O)$_2$— | isopropyl | —OCH$_3$ | 1 |
| methyl | —S(O)$_2$— | isopropyl | —OCH$_3$ | 2 |
| methyl | —S(O)$_2$— | isopropyl | —OCH$_3$ | 3 |
| methyl | —S(O)$_2$— | phenyl | —OH | 1 |
| methyl | —S(O)$_2$— | phenyl | —OH | 2 |
| methyl | —S(O)$_2$— | phenyl | —OH | 3 |
| methyl | —S(O)$_2$— | phenyl | —OCH$_3$ | 1 |
| methyl | —S(O)$_2$— | phenyl | —OCH$_3$ | 2 |
| methyl | —S(O)$_2$— | phenyl | —OCH$_3$ | 3 |
| methyl | —C(O)—NH— | methyl | —OH | 1 |
| methyl | —C(O)—NH— | methyl | —OH | 2 |
| methyl | —C(O)—NH— | methyl | —OH | 3 |
| methyl | —C(O)—NH— | methyl | —OCH$_3$ | 1 |
| methyl | —C(O)—NH— | methyl | —OCH$_3$ | 2 |
| methyl | —C(O)—NH— | methyl | —OCH$_3$ | 3 |
| methyl | —C(O)—NH— | ethyl | —OH | 1 |
| methyl | —C(O)—NH— | ethyl | —OH | 2 |
| methyl | —C(O)—NH— | ethyl | —OH | 3 |
| methyl | —C(O)—NH— | ethyl | —OCH$_3$ | 1 |
| methyl | —C(O)—NH— | ethyl | —OCH$_3$ | 2 |
| methyl | —C(O)—NH— | ethyl | —OCH$_3$ | 3 |
| methyl | —C(O)—NH— | isopropyl | —OH | 1 |
| methyl | —C(O)—NH— | isopropyl | —OH | 2 |
| methyl | —C(O)—NH— | isopropyl | —OH | 3 |
| methyl | —C(O)—NH— | isopropyl | —OCH$_3$ | 1 |
| methyl | —C(O)—NH— | isopropyl | —OCH$_3$ | 2 |
| methyl | —C(O)—NH— | isopropyl | —OCH$_3$ | 3 |
| methyl | —C(O)—NH— | phenyl | —OH | 1 |
| methyl | —C(O)—NH— | phenyl | —OH | 2 |
| methyl | —C(O)—NH— | phenyl | —OH | 3 |
| methyl | —C(O)—NH— | phenyl | —OCH$_3$ | 1 |
| methyl | —C(O)—NH— | phenyl | —OCH$_3$ | 2 |
| methyl | —C(O)—NH— | phenyl | —OCH$_3$ | 3 |
| ethyl | Bond | methyl | —OH | 1 |
| ethyl | Bond | methyl | —OH | 2 |
| ethyl | Bond | methyl | —OH | 3 |
| ethyl | Bond | methyl | —OCH$_3$ | 1 |
| ethyl | Bond | methyl | —OCH$_3$ | 2 |
| ethyl | Bond | methyl | —OCH$_3$ | 3 |
| ethyl | Bond | ethyl | —OH | 1 |
| ethyl | Bond | ethyl | —OH | 2 |
| ethyl | Bond | ethyl | —OH | 3 |
| ethyl | Bond | ethyl | —OCH$_3$ | 1 |
| ethyl | Bond | ethyl | —OCH$_3$ | 2 |
| ethyl | Bond | ethyl | —OCH$_3$ | 3 |
| ethyl | Bond | isopropyl | —OH | 1 |
| ethyl | Bond | isopropyl | —OH | 2 |
| ethyl | Bond | isopropyl | —OH | 3 |
| ethyl | Bond | isopropyl | —OCH$_3$ | 1 |
| ethyl | Bond | isopropyl | —OCH$_3$ | 2 |
| ethyl | Bond | isopropyl | —OCH$_3$ | 3 |
| ethyl | Bond | phenyl | —OH | 1 |
| ethyl | Bond | phenyl | —OH | 2 |
| ethyl | Bond | phenyl | —OH | 3 |
| ethyl | Bond | phenyl | —OCH$_3$ | 1 |
| ethyl | Bond | phenyl | —OCH$_3$ | 2 |
| ethyl | Bond | phenyl | —OCH$_3$ | 3 |
| ethyl | —C(O)— | methyl | —OH | 1 |
| ethyl | —C(O)— | methyl | —OH | 2 |
| ethyl | —C(O)— | methyl | —OH | 3 |

TABLE 2-continued

| | | | | |
|---|---|---|---|---|
| ethyl | —C(O)— | methyl | —OCH$_3$ | 1 |
| ethyl | —C(O)— | methyl | —OCH$_3$ | 2 |
| ethyl | —C(O)— | methyl | —OCH$_3$ | 3 |
| ethyl | —C(O)— | ethyl | —OH | 1 |
| ethyl | —C(O)— | ethyl | —OH | 2 |
| ethyl | —C(O)— | ethyl | —OH | 3 |
| ethyl | —C(O)— | ethyl | —OCH$_3$ | 1 |
| ethyl | —C(O)— | ethyl | —OCH$_3$ | 2 |
| ethyl | —C(O)— | ethyl | —OCH$_3$ | 3 |
| ethyl | —C(O)— | isopropyl | —OH | 1 |
| ethyl | —C(O)— | isopropyl | —OH | 2 |
| ethyl | —C(O)— | isopropyl | —OH | 3 |
| ethyl | —C(O)— | isopropyl | —OCH$_3$ | 1 |
| ethyl | —C(O)— | isopropyl | —OCH$_3$ | 2 |
| ethyl | —C(O)— | isopropyl | —OCH$_3$ | 3 |
| ethyl | —C(O)— | phenyl | —OH | 1 |
| ethyl | —C(O)— | phenyl | —OH | 2 |
| ethyl | —C(O)— | phenyl | —OH | 3 |
| ethyl | —C(O)— | phenyl | —OCH$_3$ | 1 |
| ethyl | —C(O)— | phenyl | —OCH$_3$ | 2 |
| ethyl | —C(O)— | phenyl | —OCH$_3$ | 3 |
| ethyl | —S(O)$_2$— | methyl | —OH | 1 |
| ethyl | —S(O)$_2$— | methyl | —OH | 2 |
| ethyl | —S(O)$_2$— | methyl | —OH | 3 |
| ethyl | —S(O)$_2$— | methyl | —OCH$_3$ | 1 |
| ethyl | —S(O)$_2$— | methyl | —OCH$_3$ | 2 |
| ethyl | —S(O)$_2$— | methyl | —OCH$_3$ | 3 |
| ethyl | —S(O)$_2$— | ethyl | —OH | 1 |
| ethyl | —S(O)$_2$— | ethyl | —OH | 2 |
| ethyl | —S(O)$_2$— | ethyl | —OH | 3 |
| ethyl | —S(O)$_2$— | ethyl | —OCH$_3$ | 1 |
| ethyl | —S(O)$_2$— | ethyl | —OCH$_3$ | 2 |
| ethyl | —S(O)$_2$— | ethyl | —OCH$_3$ | 3 |
| ethyl | —S(O)$_2$— | isopropyl | —OH | 1 |
| ethyl | —S(O)$_2$— | isopropyl | —OH | 2 |
| ethyl | —S(O)$_2$— | isopropyl | —OH | 3 |
| ethyl | —S(O)$_2$— | isopropyl | —OCH$_3$ | 1 |
| ethyl | —S(O)$_2$— | isopropyl | —OCH$_3$ | 2 |
| ethyl | —S(O)$_2$— | isopropyl | —OCH$_3$ | 3 |
| ethyl | —S(O)$_2$— | phenyl | —OH | 1 |
| ethyl | —S(O)$_2$— | phenyl | —OH | 2 |
| ethyl | —S(O)$_2$— | phenyl | —OH | 3 |
| ethyl | —S(O)$_2$— | phenyl | —OCH$_3$ | 1 |
| ethyl | —S(O)$_2$— | phenyl | —OCH$_3$ | 2 |
| ethyl | —S(O)$_2$— | phenyl | —OCH$_3$ | 3 |
| ethyl | —C(O)—NH— | methyl | —OH | 1 |
| ethyl | —C(O)—NH— | methyl | —OH | 2 |
| ethyl | —C(O)—NH— | methyl | —OH | 3 |
| ethyl | —C(O)—NH— | methyl | —OCH$_3$ | 1 |
| ethyl | —C(O)—NH— | methyl | —OCH$_3$ | 2 |
| ethyl | —C(O)—NH— | methyl | —OCH$_3$ | 3 |
| ethyl | —C(O)—NH— | ethyl | —OH | 1 |
| ethyl | —C(O)—NH— | ethyl | —OH | 2 |
| ethyl | —C(O)—NH— | ethyl | —OH | 3 |
| ethyl | —C(O)—NH— | ethyl | —OCH$_3$ | 1 |
| ethyl | —C(O)—NH— | ethyl | —OCH$_3$ | 2 |
| ethyl | —C(O)—NH— | ethyl | —OCH$_3$ | 3 |
| ethyl | —C(O)—NH— | isopropyl | —OH | 1 |
| ethyl | —C(O)—NH— | isopropyl | —OH | 2 |
| ethyl | —C(O)—NH— | isopropyl | —OH | 3 |
| ethyl | —C(O)—NH— | isopropyl | —OCH$_3$ | 1 |
| ethyl | —C(O)—NH— | isopropyl | —OCH$_3$ | 2 |
| ethyl | —C(O)—NH— | isopropyl | —OCH$_3$ | 3 |
| ethyl | —C(O)—NH— | phenyl | —OH | 1 |
| ethyl | —C(O)—NH— | phenyl | —OH | 2 |
| ethyl | —C(O)—NH— | phenyl | —OH | 3 |
| ethyl | —C(O)—NH— | phenyl | —OCH$_3$ | 1 |
| ethyl | —C(O)—NH— | phenyl | —OCH$_3$ | 2 |
| ethyl | —C(O)—NH— | phenyl | —OCH$_3$ | 3 |
| n-propyl | Bond | methyl | —OH | 1 |
| n-propyl | Bond | methyl | —OH | 2 |
| n-propyl | Bond | methyl | —OH | 3 |
| n-propyl | Bond | methyl | —OCH$_3$ | 1 |
| n-propyl | Bond | methyl | —OCH$_3$ | 2 |
| n-propyl | Bond | methyl | —OCH$_3$ | 3 |
| n-propyl | Bond | ethyl | —OH | 1 |
| n-propyl | Bond | ethyl | —OH | 2 |
| n-propyl | Bond | ethyl | —OH | 3 |
| n-propyl | Bond | ethyl | —OCH$_3$ | 1 |
| n-propyl | Bond | ethyl | —OCH$_3$ | 2 |

TABLE 2-continued

| | | | | |
|---|---|---|---|---|
| n-propyl | Bond | ethyl | —OCH₃ | 3 |
| n-propyl | Bond | isopropyl | —OH | 1 |
| n-propyl | Bond | isopropyl | —OH | 2 |
| n-propyl | Bond | isopropyl | —OH | 3 |
| n-propyl | Bond | isopropyl | —OCH₃ | 1 |
| n-propyl | Bond | isopropyl | —OCH₃ | 2 |
| n-propyl | Bond | isopropyl | —OCH₃ | 3 |
| n-propyl | Bond | phenyl | —OH | 1 |
| n-propyl | Bond | phenyl | —OH | 2 |
| n-propyl | Bond | phenyl | —OH | 3 |
| n-propyl | Bond | phenyl | —OCH₃ | 1 |
| n-propyl | Bond | phenyl | —OCH₃ | 2 |
| n-propyl | Bond | phenyl | —OCH₃ | 3 |
| n-propyl | —C(O)— | methyl | —OH | 1 |
| n-propyl | —C(O)— | methyl | —OH | 2 |
| n-propyl | —C(O)— | methyl | —OH | 3 |
| n-propyl | —C(O)— | methyl | —OCH₃ | 1 |
| n-propyl | —C(O)— | methyl | —OCH₃ | 2 |
| n-propyl | —C(O)— | methyl | —OCH₃ | 3 |
| n-propyl | —C(O)— | ethyl | —OH | 1 |
| n-propyl | —C(O)— | ethyl | —OH | 2 |
| n-propyl | —C(O)— | ethyl | —OH | 3 |
| n-propyl | —C(O)— | ethyl | —OCH₃ | 1 |
| n-propyl | —C(O)— | ethyl | —OCH₃ | 2 |
| n-propyl | —C(O)— | ethyl | —OCH₃ | 3 |
| n-propyl | —C(O)— | isopropyl | —OH | 1 |
| n-propyl | —C(O)— | isopropyl | —OH | 2 |
| n-propyl | —C(O)— | isopropyl | —OH | 3 |
| n-propyl | —C(O)— | isopropyl | —OCH₃ | 1 |
| n-propyl | —C(O)— | isopropyl | —OCH₃ | 2 |
| n-propyl | —C(O)— | isopropyl | —OCH₃ | 3 |
| n-propyl | —C(O)— | phenyl | —OH | 1 |
| n-propyl | —C(O)— | phenyl | —OH | 2 |
| n-propyl | —C(O)— | phenyl | —OH | 3 |
| n-propyl | —C(O)— | phenyl | —OCH₃ | 1 |
| n-propyl | —C(O)— | phenyl | —OCH₃ | 2 |
| n-propyl | —C(O)— | phenyl | —OCH₃ | 3 |
| n-propyl | —S(O)₂— | methyl | —OH | 1 |
| n-propyl | —S(O)₂— | methyl | —OH | 2 |
| n-propyl | —S(O)₂— | methyl | —OH | 3 |
| n-propyl | —S(O)₂— | methyl | —OCH₃ | 1 |
| n-propyl | —S(O)₂— | methyl | —OCH₃ | 2 |
| n-propyl | —S(O)₂— | methyl | —OCH₃ | 3 |
| n-propyl | —S(O)₂— | ethyl | —OH | 1 |
| n-propyl | —S(O)₂— | ethyl | —OH | 2 |
| n-propyl | —S(O)₂— | ethyl | —OH | 3 |
| n-propyl | —S(O)₂— | ethyl | —OCH₃ | 1 |
| n-propyl | —S(O)₂— | ethyl | —OCH₃ | 2 |
| n-propyl | —S(O)₂— | ethyl | —OCH₃ | 3 |
| n-propyl | —S(O)₂— | isopropyl | —OH | 1 |
| n-propyl | —S(O)₂— | isopropyl | —OH | 2 |
| n-propyl | —S(O)₂— | isopropyl | —OH | 3 |
| n-propyl | —S(O)₂— | isopropyl | —OCH₃ | 1 |
| n-propyl | —S(O)₂— | isopropyl | —OCH₃ | 2 |
| n-propyl | —S(O)₂— | isopropyl | —OCH₃ | 3 |
| n-propyl | —S(O)₂— | phenyl | —OH | 1 |
| n-propyl | —S(O)₂— | phenyl | —OH | 2 |
| n-propyl | —S(O)₂— | phenyl | —OH | 3 |
| n-propyl | —S(O)₂— | phenyl | —OCH₃ | 1 |
| n-propyl | —S(O)₂— | phenyl | —OCH₃ | 2 |
| n-propyl | —S(O)₂— | phenyl | —OCH₃ | 3 |
| n-propyl | —C(O)—NH— | methyl | —OH | 1 |
| n-propyl | —C(O)—NH— | methyl | —OH | 2 |
| n-propyl | —C(O)—NH— | methyl | —OH | 3 |
| n-propyl | —C(O)—NH— | methyl | —OCH₃ | 1 |
| n-propyl | —C(O)—NH— | methyl | —OCH₃ | 2 |
| n-propyl | —C(O)—NH— | methyl | —OCH₃ | 3 |
| n-propyl | —C(O)—NH— | ethyl | —OH | 1 |
| n-propyl | —C(O)—NH— | ethyl | —OH | 2 |
| n-propyl | —C(O)—NH— | ethyl | —OH | 3 |
| n-propyl | —C(O)—NH— | ethyl | —OCH₃ | 1 |
| n-propyl | —C(O)—NH— | ethyl | —OCH₃ | 2 |
| n-propyl | —C(O)—NH— | ethyl | —OCH₃ | 3 |
| n-propyl | —C(O)—NH— | isopropyl | —OH | 1 |
| n-propyl | —C(O)—NH— | isopropyl | —OH | 2 |
| n-propyl | —C(O)—NH— | isopropyl | —OH | 3 |
| n-propyl | —C(O)—NH— | isopropyl | —OCH₃ | 1 |
| n-propyl | —C(O)—NH— | isopropyl | —OCH₃ | 2 |
| n-propyl | —C(O)—NH— | isopropyl | —OCH₃ | 3 |
| n-propyl | —C(O)—NH— | phenyl | —OH | 1 |

TABLE 2-continued

| | | | | |
|---|---|---|---|---|
| n-propyl | —C(O)—NH— | phenyl | —OH | 2 |
| n-propyl | —C(O)—NH— | phenyl | —OH | 3 |
| n-propyl | —C(O)—NH— | phenyl | —OCH$_3$ | 1 |
| n-propyl | —C(O)—NH— | phenyl | —OCH$_3$ | 2 |
| n-propyl | —C(O)—NH— | phenyl | —OCH$_3$ | 3 |
| n-butyl | Bond | methyl | —OH | 1 |
| n-butyl | Bond | methyl | —OH | 2 |
| n-butyl | Bond | methyl | —OH | 3 |
| n-butyl | Bond | methyl | —OCH$_3$ | 1 |
| n-butyl | Bond | methyl | —OCH$_3$ | 2 |
| n-butyl | Bond | methyl | —OCH$_3$ | 3 |
| n-butyl | Bond | ethyl | —OH | 1 |
| n-butyl | Bond | ethyl | —OH | 2 |
| n-butyl | Bond | ethyl | —OH | 3 |
| n-butyl | Bond | ethyl | —OCH$_3$ | 1 |
| n-butyl | Bond | ethyl | —OCH$_3$ | 2 |
| n-butyl | Bond | ethyl | —OCH$_3$ | 3 |
| n-butyl | Bond | isopropyl | —OH | 1 |
| n-butyl | Bond | isopropyl | —OH | 2 |
| n-butyl | Bond | isopropyl | —OH | 3 |
| n-butyl | Bond | isopropyl | —OCH$_3$ | 1 |
| n-butyl | Bond | isopropyl | —OCH$_3$ | 2 |
| n-butyl | Bond | isopropyl | —OCH$_3$ | 3 |
| n-butyl | Bond | phenyl | —OH | 1 |
| n-butyl | Bond | phenyl | —OH | 2 |
| n-butyl | Bond | phenyl | —OH | 3 |
| n-butyl | Bond | phenyl | —OCH$_3$ | 1 |
| n-butyl | Bond | phenyl | —OCH$_3$ | 2 |
| n-butyl | Bond | phenyl | —OCH$_3$ | 3 |
| n-butyl | —C(O)— | methyl | —OH | 1 |
| n-butyl | —C(O)— | methyl | —OH | 2 |
| n-butyl | —C(O)— | methyl | —OH | 3 |
| n-butyl | —C(O)— | methyl | —OCH$_3$ | 1 |
| n-butyl | —C(O)— | methyl | —OCH$_3$ | 2 |
| n-butyl | —C(O)— | methyl | —OCH$_3$ | 3 |
| n-butyl | —C(O)— | ethyl | —OH | 1 |
| n-butyl | —C(O)— | ethyl | —OH | 2 |
| n-butyl | —C(O)— | ethyl | —OH | 3 |
| n-butyl | —C(O)— | ethyl | —OCH$_3$ | 1 |
| n-butyl | —C(O)— | ethyl | —OCH$_3$ | 2 |
| n-butyl | —C(O)— | ethyl | —OCH$_3$ | 3 |
| n-butyl | —C(O)— | isopropyl | —OH | 1 |
| n-butyl | —C(O)— | isopropyl | —OH | 2 |
| n-butyl | —C(O)— | isopropyl | —OH | 3 |
| n-butyl | —C(O)— | isopropyl | —OCH$_3$ | 1 |
| n-butyl | —C(O)— | isopropyl | —OCH$_3$ | 2 |
| n-butyl | —C(O)— | isopropyl | —OCH$_3$ | 3 |
| n-butyl | —C(O)— | phenyl | —OH | 1 |
| n-butyl | —C(O)— | phenyl | —OH | 2 |
| n-butyl | —C(O)— | phenyl | —OH | 3 |
| n-butyl | —C(O)— | phenyl | —OCH$_3$ | 1 |
| n-butyl | —C(O)— | phenyl | —OCH$_3$ | 2 |
| n-butyl | —C(O)— | phenyl | —OCH$_3$ | 3 |
| n-butyl | —S(O)$_2$— | methyl | —OH | 1 |
| n-butyl | —S(O)$_2$— | methyl | —OH | 2 |
| n-butyl | —S(O)$_2$— | methyl | —OH | 3 |
| n-butyl | —S(O)$_2$— | methyl | —OCH$_3$ | 1 |
| n-butyl | —S(O)$_2$— | methyl | —OCH$_3$ | 2 |
| n-butyl | —S(O)$_2$— | methyl | —OCH$_3$ | 3 |
| n-butyl | —S(O)$_2$— | ethyl | —OH | 1 |
| n-butyl | —S(O)$_2$— | ethyl | —OH | 2 |
| n-butyl | —S(O)$_2$— | ethyl | —OH | 3 |
| n-butyl | —S(O)$_2$— | ethyl | —OCH$_3$ | 1 |
| n-butyl | —S(O)$_2$— | ethyl | —OCH$_3$ | 2 |
| n-butyl | —S(O)$_2$— | ethyl | —OCH$_3$ | 3 |
| n-butyl | —S(O)$_2$— | isopropyl | —OH | 1 |
| n-butyl | —S(O)$_2$— | isopropyl | —OH | 2 |
| n-butyl | —S(O)$_2$— | isopropyl | —OH | 3 |
| n-butyl | —S(O)$_2$— | isopropyl | —OCH$_3$ | 1 |
| n-butyl | —S(O)$_2$— | isopropyl | —OCH$_3$ | 2 |
| n-butyl | —S(O)$_2$— | isopropyl | —OCH$_3$ | 3 |
| n-butyl | —S(O)$_2$— | phenyl | —OH | 1 |
| n-butyl | —S(O)$_2$— | phenyl | —OH | 2 |
| n-butyl | —S(O)$_2$— | phenyl | —OH | 3 |
| n-butyl | —S(O)$_2$— | phenyl | —OCH$_3$ | 1 |
| n-butyl | —S(O)$_2$— | phenyl | —OCH$_3$ | 2 |
| n-butyl | —S(O)$_2$— | phenyl | —OCH$_3$ | 3 |
| n-butyl | —C(O)—NH— | methyl | —OH | 1 |
| n-butyl | —C(O)—NH— | methyl | —OH | 2 |
| n-butyl | —C(O)—NH— | methyl | —OH | 3 |

TABLE 2-continued

| | | | | |
|---|---|---|---|---|
| n-butyl | —C(O)—NH— | methyl | —OCH$_3$ | 1 |
| n-butyl | —C(O)—NH— | methyl | —OCH$_3$ | 2 |
| n-butyl | —C(O)—NH— | methyl | —OCH$_3$ | 3 |
| n-butyl | —C(O)—NH— | ethyl | —OH | 1 |
| n-butyl | —C(O)—NH— | ethyl | —OH | 2 |
| n-butyl | —C(O)—NH— | ethyl | —OH | 3 |
| n-butyl | —C(O)—NH— | ethyl | —OCH$_3$ | 1 |
| n-butyl | —C(O)—NH— | ethyl | —OCH$_3$ | 2 |
| n-butyl | —C(O)—NH— | ethyl | —OCH$_3$ | 3 |
| n-butyl | —C(O)—NH— | isopropyl | —OH | 1 |
| n-butyl | —C(O)—NH— | isopropyl | —OH | 2 |
| n-butyl | —C(O)—NH— | isopropyl | —OH | 3 |
| n-butyl | —C(O)—NH— | isopropyl | —OCH$_3$ | 1 |
| n-butyl | —C(O)—NH— | isopropyl | —OCH$_3$ | 2 |
| n-butyl | —C(O)—NH— | isopropyl | —OCH$_3$ | 3 |
| n-butyl | —C(O)—NH— | phenyl | —OH | 1 |
| n-butyl | —C(O)—NH— | phenyl | —OH | 2 |
| n-butyl | —C(O)—NH— | phenyl | —OH | 3 |
| n-butyl | —C(O)—NH— | phenyl | —OCH$_3$ | 1 |
| n-butyl | —C(O)—NH— | phenyl | —OCH$_3$ | 2 |
| n-butyl | —C(O)—NH— | phenyl | —OCH$_3$ | 3 |
| ethoxymethyl | Bond | methyl | —OH | 1 |
| ethoxymethyl | Bond | methyl | —OH | 2 |
| ethoxymethyl | Bond | methyl | —OH | 3 |
| ethoxymethyl | Bond | methyl | —OCH$_3$ | 1 |
| ethoxymethyl | Bond | methyl | —OCH$_3$ | 2 |
| ethoxymethyl | Bond | methyl | —OCH$_3$ | 3 |
| ethoxymethyl | Bond | ethyl | —OH | 1 |
| ethoxymethyl | Bond | ethyl | —OH | 2 |
| ethoxymethyl | Bond | ethyl | —OH | 3 |
| ethoxymethyl | Bond | ethyl | —OCH$_3$ | 1 |
| ethoxymethyl | Bond | ethyl | —OCH$_3$ | 2 |
| ethoxymethyl | Bond | ethyl | —OCH$_3$ | 3 |
| ethoxymethyl | Bond | isopropyl | —OH | 1 |
| ethoxymethyl | Bond | isopropyl | —OH | 2 |
| ethoxymethyl | Bond | isopropyl | —OH | 3 |
| ethoxymethyl | Bond | isopropyl | —OCH$_3$ | 1 |
| ethoxymethyl | Bond | isopropyl | —OCH$_3$ | 2 |
| ethoxymethyl | Bond | isopropyl | —OCH$_3$ | 3 |
| ethoxymethyl | Bond | phenyl | —OH | 1 |
| ethoxymethyl | Bond | phenyl | —OH | 2 |
| ethoxymethyl | Bond | phenyl | —OH | 3 |
| ethoxymethyl | Bond | phenyl | —OCH$_3$ | 1 |
| ethoxymethyl | Bond | phenyl | —OCH$_3$ | 2 |
| ethoxymethyl | Bond | phenyl | —OCH$_3$ | 3 |
| ethoxymethyl | —C(O)— | methyl | —OH | 1 |
| ethoxymethyl | —C(O)— | methyl | —OH | 2 |
| ethoxymethyl | —C(O)— | methyl | —OH | 3 |
| ethoxymethyl | —C(O)— | methyl | —OCH$_3$ | 1 |
| ethoxymethyl | —C(O)— | methyl | —OCH$_3$ | 2 |
| ethoxymethyl | —C(O)— | methyl | —OCH$_3$ | 3 |
| ethoxymethyl | —C(O)— | ethyl | —OH | 1 |
| ethoxymethyl | —C(O)— | ethyl | —OH | 2 |
| ethoxymethyl | —C(O)— | ethyl | —OH | 3 |
| ethoxymethyl | —C(O)— | ethyl | —OCH$_3$ | 1 |
| ethoxymethyl | —C(O)— | ethyl | —OCH$_3$ | 2 |
| ethoxymethyl | —C(O)— | ethyl | —OCH$_3$ | 3 |
| ethoxymethyl | —C(O)— | isopropyl | —OH | 1 |
| ethoxymethyl | —C(O)— | isopropyl | —OH | 2 |
| ethoxymethyl | —C(O)— | isopropyl | —OH | 3 |
| ethoxymethyl | —C(O)— | isopropyl | —OCH$_3$ | 1 |
| ethoxymethyl | —C(O)— | isopropyl | —OCH$_3$ | 2 |
| ethoxymethyl | —C(O)— | isopropyl | —OCH$_3$ | 3 |
| ethoxymethyl | —C(O)— | phenyl | —OH | 1 |
| ethoxymethyl | —C(O)— | phenyl | —OH | 2 |
| ethoxymethyl | —C(O)— | phenyl | —OH | 3 |
| ethoxymethyl | —C(O)— | phenyl | —OCH$_3$ | 1 |
| ethoxymethyl | —C(O)— | phenyl | —OCH$_3$ | 2 |
| ethoxymethyl | —C(O)— | phenyl | —OCH$_3$ | 3 |
| ethoxymethyl | —S(O)$_2$— | methyl | —OH | 1 |
| ethoxymethyl | —S(O)$_2$— | methyl | —OH | 2 |
| ethoxymethyl | —S(O)$_2$— | methyl | —OH | 3 |
| ethoxymethyl | —S(O)$_2$— | methyl | —OCH$_3$ | 1 |
| ethoxymethyl | —S(O)$_2$— | methyl | —OCH$_3$ | 2 |
| ethoxymethyl | —S(O)$_2$— | methyl | —OCH$_3$ | 3 |
| ethoxymethyl | —S(O)$_2$— | ethyl | —OH | 1 |
| ethoxymethyl | —S(O)$_2$— | ethyl | —OH | 2 |
| ethoxymethyl | —S(O)$_2$— | ethyl | —OH | 3 |
| ethoxymethyl | —S(O)$_2$— | ethyl | —OCH$_3$ | 1 |
| ethoxymethyl | —S(O)$_2$— | ethyl | —OCH$_3$ | 2 |

TABLE 2-continued

| | | | | |
|---|---|---|---|---|
| ethoxymethyl | —S(O)$_2$— | ethyl | —OCH$_3$ | 3 |
| ethoxymethyl | —S(O)$_2$— | isopropyl | —OH | 1 |
| ethoxymethyl | —S(O)$_2$— | isopropyl | —OH | 2 |
| ethoxymethyl | —S(O)$_2$— | isopropyl | —OH | 3 |
| ethoxymethyl | —S(O)$_2$— | isopropyl | —OCH$_3$ | 1 |
| ethoxymethyl | —S(O)$_2$— | isopropyl | —OCH$_3$ | 2 |
| ethoxymethyl | —S(O)$_2$— | isopropyl | —OCH$_3$ | 3 |
| ethoxymethyl | —S(O)$_2$— | phenyl | —OH | 1 |
| ethoxymethyl | —S(O)$_2$— | phenyl | —OH | 2 |
| ethoxymethyl | —S(O)$_2$— | phenyl | —OH | 3 |
| ethoxymethyl | —S(O)$_2$— | phenyl | —OCH$_3$ | 1 |
| ethoxymethyl | —S(O)$_2$— | phenyl | —OCH$_3$ | 2 |
| ethoxymethyl | —S(O)$_2$— | phenyl | —OCH$_3$ | 3 |
| ethoxymethyl | —C(O)—NH— | methyl | —OH | 1 |
| ethoxymethyl | —C(O)—NH— | methyl | —OH | 2 |
| ethoxymethyl | —C(O)—NH— | methyl | —OH | 3 |
| ethoxymethyl | —C(O)—NH— | methyl | —OCH$_3$ | 1 |
| ethoxymethyl | —C(O)—NH— | methyl | —OCH$_3$ | 2 |
| ethoxymethyl | —C(O)—NH— | methyl | —OCH$_3$ | 3 |
| ethoxymethyl | —C(O)—NH— | ethyl | —OH | 1 |
| ethoxymethyl | —C(O)—NH— | ethyl | —OH | 2 |
| ethoxymethyl | —C(O)—NH— | ethyl | —OH | 3 |
| ethoxymethyl | —C(O)—NH— | ethyl | —OCH$_3$ | 1 |
| ethoxymethyl | —C(O)—NH— | ethyl | —OCH$_3$ | 2 |
| ethoxymethyl | —C(O)—NH— | ethyl | —OCH$_3$ | 3 |
| ethoxymethyl | —C(O)—NH— | isopropyl | —OH | 1 |
| ethoxymethyl | —C(O)—NH— | isopropyl | —OH | 2 |
| ethoxymethyl | —C(O)—NH— | isopropyl | —OH | 3 |
| ethoxymethyl | —C(O)—NH— | isopropyl | —OCH$_3$ | 1 |
| ethoxymethyl | —C(O)—NH— | isopropyl | —OCH$_3$ | 2 |
| ethoxymethyl | —C(O)—NH— | isopropyl | —OCH$_3$ | 3 |
| ethoxymethyl | —C(O)—NH— | phenyl | —OH | 1 |
| ethoxymethyl | —C(O)—NH— | phenyl | —OH | 2 |
| ethoxymethyl | —C(O)—NH— | phenyl | —OH | 3 |
| ethoxymethyl | —C(O)—NH— | phenyl | —OCH$_3$ | 1 |
| ethoxymethyl | —C(O)—NH— | phenyl | —OCH$_3$ | 2 |
| ethoxymethyl | —C(O)—NH— | phenyl | —OCH$_3$ | 3 |
| 2-methoxyethyl | Bond | methyl | —OH | 1 |
| 2-methoxyethyl | Bond | methyl | —OH | 2 |
| 2-methoxyethyl | Bond | methyl | —OH | 3 |
| 2-methoxyethyl | Bond | methyl | —OCH$_3$ | 1 |
| 2-methoxyethyl | Bond | methyl | —OCH$_3$ | 2 |
| 2-methoxyethyl | Bond | methyl | —OCH$_3$ | 3 |
| 2-methoxyethyl | Bond | ethyl | —OH | 1 |
| 2-methoxyethyl | Bond | ethyl | —OH | 2 |
| 2-methoxyethyl | Bond | ethyl | —OH | 3 |
| 2-methoxyethyl | Bond | ethyl | —OCH$_3$ | 1 |
| 2-methoxyethyl | Bond | ethyl | —OCH$_3$ | 2 |
| 2-methoxyethyl | Bond | ethyl | —OCH$_3$ | 3 |
| 2-methoxyethyl | Bond | isopropyl | —OH | 1 |
| 2-methoxyethyl | Bond | isopropyl | —OH | 2 |
| 2-methoxyethyl | Bond | isopropyl | —OH | 3 |
| 2-methoxyethyl | Bond | isopropyl | —OCH$_3$ | 1 |
| 2-methoxyethyl | Bond | isopropyl | —OCH$_3$ | 2 |
| 2-methoxyethyl | Bond | isopropyl | —OCH$_3$ | 3 |
| 2-methoxyethyl | Bond | phenyl | —OH | 1 |
| 2-methoxyethyl | Bond | phenyl | —OH | 2 |
| 2-methoxyethyl | Bond | phenyl | —OH | 3 |
| 2-methoxyethyl | Bond | phenyl | —OCH$_3$ | 1 |
| 2-methoxyethyl | Bond | phenyl | —OCH$_3$ | 2 |
| 2-methoxyethyl | Bond | phenyl | —OCH$_3$ | 3 |
| 2-methoxyethyl | —C(O)— | methyl | —OH | 1 |
| 2-methoxyethyl | —C(O)— | methyl | —OH | 2 |
| 2-methoxyethyl | —C(O)— | methyl | —OH | 3 |
| 2-methoxyethyl | —C(O)— | methyl | —OCH$_3$ | 1 |
| 2-methoxyethyl | —C(O)— | methyl | —OCH$_3$ | 2 |
| 2-methoxyethyl | —C(O)— | methyl | —OCH$_3$ | 3 |
| 2-methoxyethyl | —C(O)— | ethyl | —OH | 1 |
| 2-methoxyethyl | —C(O)— | ethyl | —OH | 2 |
| 2-methoxyethyl | —C(O)— | ethyl | —OH | 3 |
| 2-methoxyethyl | —C(O)— | ethyl | —OCH$_3$ | 1 |
| 2-methoxyethyl | —C(O)— | ethyl | —OCH$_3$ | 2 |
| 2-methoxyethyl | —C(O)— | ethyl | —OCH$_3$ | 3 |
| 2-methoxyethyl | —C(O)— | isopropyl | —OH | 1 |
| 2-methoxyethyl | —C(O)— | isopropyl | —OH | 2 |
| 2-methoxyethyl | —C(O)— | isopropyl | —OH | 3 |
| 2-methoxyethyl | —C(O)— | isopropyl | —OCH$_3$ | 1 |
| 2-methoxyethyl | —C(O)— | isopropyl | —OCH$_3$ | 2 |
| 2-methoxyethyl | —C(O)— | isopropyl | —OCH$_3$ | 3 |
| 2-methoxyethyl | —C(O)— | phenyl | —OH | 1 |

TABLE 2-continued

| | | | | |
|---|---|---|---|---|
| 2-methoxyethyl | —C(O)— | phenyl | —OH | 2 |
| 2-methoxyethyl | —C(O)— | phenyl | —OH | 3 |
| 2-methoxyethyl | —C(O)— | phenyl | —OCH$_3$ | 1 |
| 2-methoxyethyl | —C(O)— | phenyl | —OCH$_3$ | 2 |
| 2-methoxyethyl | —C(O)— | phenyl | —OCH$_3$ | 3 |
| 2-methoxyethyl | —S(O)$_2$— | methyl | —OH | 1 |
| 2-methoxyethyl | —S(O)$_2$— | methyl | —OH | 2 |
| 2-methoxyethyl | —S(O)$_2$— | methyl | —OH | 3 |
| 2-methoxyethyl | —S(O)$_2$— | methyl | —OCH$_3$ | 1 |
| 2-methoxyethyl | —S(O)$_2$— | methyl | —OCH$_3$ | 2 |
| 2-methoxyethyl | —S(O)$_2$— | methyl | —OCH$_3$ | 3 |
| 2-methoxyethyl | —S(O)$_2$— | ethyl | —OH | 1 |
| 2-methoxyethyl | —S(O)$_2$— | ethyl | —OH | 2 |
| 2-methoxyethyl | —S(O)$_2$— | ethyl | —OH | 3 |
| 2-methoxyethyl | —S(O)$_2$— | ethyl | —OCH$_3$ | 1 |
| 2-methoxyethyl | —S(O)$_2$— | ethyl | —OCH$_3$ | 2 |
| 2-methoxyethyl | —S(O)$_2$— | ethyl | —OCH$_3$ | 3 |
| 2-methoxyethyl | —S(O)$_2$— | isopropyl | —OH | 1 |
| 2-methoxyethyl | —S(O)$_2$— | isopropyl | —OH | 2 |
| 2-methoxyethyl | —S(O)$_2$— | isopropyl | —OH | 3 |
| 2-methoxyethyl | —S(O)$_2$— | isopropyl | —OCH$_3$ | 1 |
| 2-methoxyethyl | —S(O)$_2$— | isopropyl | —OCH$_3$ | 2 |
| 2-methoxyethyl | —S(O)$_2$— | isopropyl | —OCH$_3$ | 3 |
| 2-methoxyethyl | —S(O)$_2$— | phenyl | —OH | 1 |
| 2-methoxyethyl | —S(O)$_2$— | phenyl | —OH | 2 |
| 2-methoxyethyl | —S(O)$_2$— | phenyl | —OH | 3 |
| 2-methoxyethyl | —S(O)$_2$— | phenyl | —OCH$_3$ | 1 |
| 2-methoxyethyl | —S(O)$_2$— | phenyl | —OCH$_3$ | 2 |
| 2-methoxyethyl | —S(O)$_2$— | phenyl | —OCH$_3$ | 3 |
| 2-methoxyethyl | —C(O)—NH— | methyl | —OH | 1 |
| 2-methoxyethyl | —C(O)—NH— | methyl | —OH | 2 |
| 2-methoxyethyl | —C(O)—NH— | methyl | —OH | 3 |
| 2-methoxyethyl | —C(O)—NH— | methyl | —OCH$_3$ | 1 |
| 2-methoxyethyl | —C(O)—NH— | methyl | —OCH$_3$ | 2 |
| 2-methoxyethyl | —C(O)—NH— | methyl | —OCH$_3$ | 3 |
| 2-methoxyethyl | —C(O)—NH— | ethyl | —OH | 1 |
| 2-methoxyethyl | —C(O)—NH— | ethyl | —OH | 2 |
| 2-methoxyethyl | —C(O)—NH— | ethyl | —OH | 3 |
| 2-methoxyethyl | —C(O)—NH— | ethyl | —OCH$_3$ | 1 |
| 2-methoxyethyl | —C(O)—NH— | ethyl | —OCH$_3$ | 2 |
| 2-methoxyethyl | —C(O)—NH— | ethyl | —OCH$_3$ | 3 |
| 2-methoxyethyl | —C(O)—NH— | isopropyl | —OH | 1 |
| 2-methoxyethyl | —C(O)—NH— | isopropyl | —OH | 2 |
| 2-methoxyethyl | —C(O)—NH— | isopropyl | —OH | 3 |
| 2-methoxyethyl | —C(O)—NH— | isopropyl | —OCH$_3$ | 1 |
| 2-methoxyethyl | —C(O)—NH— | isopropyl | —OCH$_3$ | 2 |
| 2-methoxyethyl | —C(O)—NH— | isopropyl | —OCH$_3$ | 3 |
| 2-methoxyethyl | —C(O)—NH— | phenyl | —OH | 1 |
| 2-methoxyethyl | —C(O)—NH— | phenyl | —OH | 2 |
| 2-methoxyethyl | —C(O)—NH— | phenyl | —OH | 3 |
| 2-methoxyethyl | —C(O)—NH— | phenyl | —OCH$_3$ | 1 |
| 2-methoxyethyl | —C(O)—NH— | phenyl | —OCH$_3$ | 2 |
| 2-methoxyethyl | —C(O)—NH— | phenyl | —OCH$_3$ | 3 |

TABLE 3

Exemplary Compounds

Certain exemplary compounds, including some of those described above in the Examples, have the following Formulas (II-3, III-3, IV-3, and V-3) wherein $R_2$, Z, Q, $R_4$, and m are defined immediately below in the table. In this table, for each ring system, each row represents one specific compound.

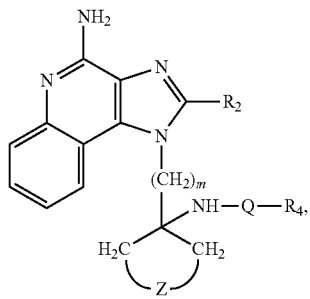

II-3

TABLE 3-continued

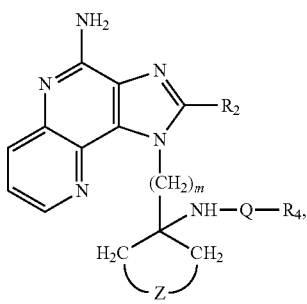

V-3

TABLE 3-continued

IV-3

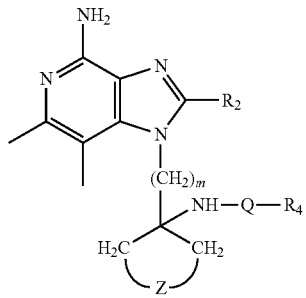

III-3

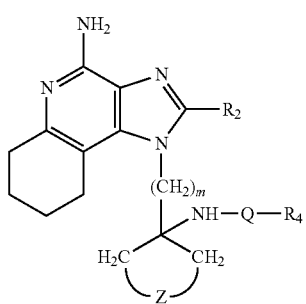

| R₂ | Q | Z | R₄ | m |
|---|---|---|---|---|
| H | Bond | —CH₂CH₂CH₂— | methyl | 1 |
| H | Bond | —CH₂CH₂CH₂— | methyl | 2 |
| H | Bond | —CH₂CH₂CH₂— | methyl | 3 |
| H | Bond | —CH₂CH₂CH₂— | ethyl | 1 |
| H | Bond | —CH₂CH₂CH₂— | ethyl | 2 |
| H | Bond | —CH₂CH₂CH₂— | ethyl | 3 |
| H | Bond | —CH₂—O—CH₂— | methyl | 1 |
| H | Bond | —CH₂—O—CH₂— | methyl | 2 |
| H | Bond | —CH₂—O—CH₂— | methyl | 3 |
| H | Bond | —CH₂—O—CH₂— | ethyl | 1 |
| H | Bond | —CH₂—O—CH₂— | ethyl | 2 |
| H | Bond | —CH₂—O—CH₂— | ethyl | 3 |
| H | —C(O)— | —CH₂CH₂CH₂— | methyl | 1 |
| H | —C(O)— | —CH₂CH₂CH₂— | methyl | 2 |
| H | —C(O)— | —CH₂CH₂CH₂— | methyl | 3 |
| H | —C(O)— | —CH₂CH₂CH₂— | ethyl | 1 |
| H | —C(O)— | —CH₂CH₂CH₂— | ethyl | 2 |
| H | —C(O)— | —CH₂CH₂CH₂— | ethyl | 3 |
| H | —C(O)— | —CH₂—O—CH₂— | methyl | 1 |
| H | —C(O)— | —CH₂—O—CH₂— | methyl | 2 |
| H | —C(O)— | —CH₂—O—CH₂— | methyl | 3 |
| H | —C(O)— | —CH₂—O—CH₂— | ethyl | 1 |
| H | —C(O)— | —CH₂—O—CH₂— | ethyl | 2 |
| H | —C(O)— | —CH₂—O—CH₂— | ethyl | 3 |
| H | —S(O)₂— | —CH₂CH₂CH₂— | methyl | 1 |
| H | —S(O)₂— | —CH₂CH₂CH₂— | methyl | 2 |
| H | —S(O)₂— | —CH₂CH₂CH₂— | methyl | 3 |
| H | —S(O)₂— | —CH₂CH₂CH₂— | ethyl | 1 |
| H | —S(O)₂— | —CH₂CH₂CH₂— | ethyl | 2 |
| H | —S(O)₂— | —CH₂CH₂CH₂— | ethyl | 3 |
| H | —S(O)₂— | —CH₂—O—CH₂— | methyl | 1 |
| H | —S(O)₂— | —CH₂—O—CH₂— | methyl | 2 |
| H | —S(O)₂— | —CH₂—O—CH₂— | methyl | 3 |
| H | —S(O)₂— | —CH₂—O—CH₂— | ethyl | 1 |
| H | —S(O)₂— | —CH₂—O—CH₂— | ethyl | 2 |
| H | —S(O)₂— | —CH₂—O—CH₂— | ethyl | 3 |
| H | —C(O)—NH— | —CH₂CH₂CH₂— | methyl | 1 |
| H | —C(O)—NH— | —CH₂CH₂CH₂— | methyl | 2 |
| H | —C(O)—NH— | —CH₂CH₂CH₂— | methyl | 3 |
| H | —C(O)—NH— | —CH₂CH₂CH₂— | ethyl | 1 |
| H | —C(O)—NH— | —CH₂CH₂CH₂— | ethyl | 2 |
| H | —C(O)—NH— | —CH₂CH₂CH₂— | ethyl | 3 |
| H | —C(O)—NH— | —CH₂—O—CH₂— | methyl | 1 |
| H | —C(O)—NH— | —CH₂—O—CH₂— | methyl | 2 |
| H | —C(O)—NH— | —CH₂—O—CH₂— | methyl | 3 |
| H | —C(O)—NH— | —CH₂—O—CH₂— | ethyl | 1 |
| H | —C(O)—NH— | —CH₂—O—CH₂— | ethyl | 2 |
| H | —C(O)—NH— | —CH₂—O—CH₂— | ethyl | 3 |
| methyl | Bond | —CH₂CH₂CH₂— | methyl | 1 |
| methyl | Bond | —CH₂CH₂CH₂— | methyl | 2 |
| methyl | Bond | —CH₂CH₂CH₂— | methyl | 3 |
| methyl | Bond | —CH₂CH₂CH₂— | ethyl | 1 |
| methyl | Bond | —CH₂CH₂CH₂— | ethyl | 2 |
| methyl | Bond | —CH₂CH₂CH₂— | ethyl | 3 |
| methyl | Bond | —CH₂—O—CH₂— | methyl | 1 |
| methyl | Bond | —CH₂—O—CH₂— | methyl | 2 |
| methyl | Bond | —CH₂—O—CH₂— | methyl | 3 |
| methyl | Bond | —CH₂—O—CH₂— | ethyl | 1 |
| methyl | Bond | —CH₂—O—CH₂— | ethyl | 2 |
| methyl | Bond | —CH₂—O—CH₂— | ethyl | 3 |
| methyl | —C(O)— | —CH₂CH₂CH₂— | methyl | 1 |
| methyl | —C(O)— | —CH₂CH₂CH₂— | methyl | 2 |
| methyl | —C(O)— | —CH₂CH₂CH₂— | methyl | 3 |
| methyl | —C(O)— | —CH₂CH₂CH₂— | ethyl | 1 |
| methyl | —C(O)— | —CH₂CH₂CH₂— | ethyl | 2 |
| methyl | —C(O)— | —CH₂CH₂CH₂— | ethyl | 3 |
| methyl | —C(O)— | —CH₂—O—CH₂— | methyl | 1 |
| methyl | —C(O)— | —CH₂—O—CH₂— | methyl | 2 |
| methyl | —C(O)— | —CH₂—O—CH₂— | methyl | 3 |
| methyl | —C(O)— | —CH₂—O—CH₂— | ethyl | 1 |
| methyl | —C(O)— | —CH₂—O—CH₂— | ethyl | 2 |
| methyl | —C(O)— | —CH₂—O—CH₂— | ethyl | 3 |
| methyl | —S(O)₂— | —CH₂CH₂CH₂— | methyl | 1 |
| methyl | —S(O)₂— | —CH₂CH₂CH₂— | methyl | 2 |
| methyl | —S(O)₂— | —CH₂CH₂CH₂— | methyl | 3 |
| methyl | —S(O)₂— | —CH₂CH₂CH₂— | ethyl | 1 |
| methyl | —S(O)₂— | —CH₂CH₂CH₂— | ethyl | 2 |
| methyl | —S(O)₂— | —CH₂CH₂CH₂— | ethyl | 3 |
| methyl | —S(O)₂— | —CH₂—O—CH₂— | methyl | 1 |
| methyl | —S(O)₂— | —CH₂—O—CH₂— | methyl | 2 |
| methyl | —S(O)₂— | —CH₂—O—CH₂— | methyl | 3 |
| methyl | —S(O)₂— | —CH₂—O—CH₂— | ethyl | 1 |
| methyl | —S(O)₂— | —CH₂—O—CH₂— | ethyl | 2 |
| methyl | —S(O)₂— | —CH₂—O—CH₂— | ethyl | 3 |
| methyl | —C(O)—NH— | —CH₂CH₂CH₂— | methyl | 1 |
| methyl | —C(O)—NH— | —CH₂CH₂CH₂— | methyl | 2 |
| methyl | —C(O)—NH— | —CH₂CH₂CH₂— | methyl | 3 |
| methyl | —C(O)—NH— | —CH₂CH₂CH₂— | ethyl | 1 |
| methyl | —C(O)—NH— | —CH₂CH₂CH₂— | ethyl | 2 |
| methyl | —C(O)—NH— | —CH₂CH₂CH₂— | ethyl | 3 |
| methyl | —C(O)—NH— | —CH₂—O—CH₂— | methyl | 1 |
| methyl | —C(O)—NH— | —CH₂—O—CH₂— | methyl | 2 |
| methyl | —C(O)—NH— | —CH₂—O—CH₂— | methyl | 3 |
| methyl | —C(O)—NH— | —CH₂—O—CH₂— | ethyl | 1 |
| methyl | —C(O)—NH— | —CH₂—O—CH₂— | ethyl | 2 |
| methyl | —C(O)—NH— | —CH₂—O—CH₂— | ethyl | 3 |
| ethyl | Bond | —CH₂CH₂CH₂— | methyl | 1 |
| ethyl | Bond | —CH₂CH₂CH₂— | methyl | 2 |
| ethyl | Bond | —CH₂CH₂CH₂— | methyl | 3 |
| ethyl | Bond | —CH₂CH₂CH₂— | ethyl | 1 |
| ethyl | Bond | —CH₂CH₂CH₂— | ethyl | 2 |
| ethyl | Bond | —CH₂CH₂CH₂— | ethyl | 3 |
| ethyl | Bond | —CH₂—O—CH₂— | methyl | 1 |
| ethyl | Bond | —CH₂—O—CH₂— | methyl | 2 |
| ethyl | Bond | —CH₂—O—CH₂— | methyl | 3 |
| ethyl | Bond | —CH₂—O—CH₂— | ethyl | 1 |
| ethyl | Bond | —CH₂—O—CH₂— | ethyl | 2 |
| ethyl | Bond | —CH₂—O—CH₂— | ethyl | 3 |
| ethyl | —C(O)— | —CH₂CH₂CH₂— | methyl | 1 |
| ethyl | —C(O)— | —CH₂CH₂CH₂— | methyl | 2 |
| ethyl | —C(O)— | —CH₂CH₂CH₂— | methyl | 3 |
| ethyl | —C(O)— | —CH₂CH₂CH₂— | ethyl | 1 |
| ethyl | —C(O)— | —CH₂CH₂CH₂— | ethyl | 2 |
| ethyl | —C(O)— | —CH₂CH₂CH₂— | ethyl | 3 |
| ethyl | —C(O)— | —CH₂—O—CH₂— | methyl | 1 |
| ethyl | —C(O)— | —CH₂—O—CH₂— | methyl | 2 |
| ethyl | —C(O)— | —CH₂—O—CH₂— | methyl | 3 |
| ethyl | —C(O)— | —CH₂—O—CH₂— | ethyl | 1 |
| ethyl | —C(O)— | —CH₂—O—CH₂— | ethyl | 2 |
| ethyl | —C(O)— | —CH₂—O—CH₂— | ethyl | 3 |
| ethyl | —S(O)₂— | —CH₂CH₂CH₂— | methyl | 1 |
| ethyl | —S(O)₂— | —CH₂CH₂CH₂— | methyl | 2 |
| ethyl | —S(O)₂— | —CH₂CH₂CH₂— | methyl | 3 |
| ethyl | —S(O)₂— | —CH₂CH₂CH₂— | ethyl | 1 |
| ethyl | —S(O)₂— | —CH₂CH₂CH₂— | ethyl | 2 |
| ethyl | —S(O)₂— | —CH₂CH₂CH₂— | ethyl | 3 |

TABLE 3-continued

| | | | | |
|---|---|---|---|---|
| ethyl | —S(O)₂— | —CH₂—O—CH₂— | methyl | 1 |
| ethyl | —S(O)₂— | —CH₂—O—CH₂— | methyl | 2 |
| ethyl | —S(O)₂— | —CH₂—O—CH₂— | methyl | 3 |
| ethyl | —S(O)₂— | —CH₂—O—CH₂— | ethyl | 1 |
| ethyl | —S(O)₂— | —CH₂—O—CH₂— | ethyl | 2 |
| ethyl | —S(O)₂— | —CH₂—O—CH₂— | ethyl | 3 |
| ethyl | —C(O)—NH— | —CH₂CH₂CH₂— | methyl | 1 |
| ethyl | —C(O)—NH— | —CH₂CH₂CH₂— | methyl | 2 |
| ethyl | —C(O)—NH— | —CH₂CH₂CH₂— | methyl | 3 |
| ethyl | —C(O)—NH— | —CH₂CH₂CH₂— | ethyl | 1 |
| ethyl | —C(O)—NH— | —CH₂CH₂CH₂— | ethyl | 2 |
| ethyl | —C(O)—NH— | —CH₂CH₂CH₂— | ethyl | 3 |
| ethyl | —C(O)—NH— | —CH₂—O—CH₂— | methyl | 1 |
| ethyl | —C(O)—NH— | —CH₂—O—CH₂— | methyl | 2 |
| ethyl | —C(O)—NH— | —CH₂—O—CH₂— | methyl | 3 |
| ethyl | —C(O)—NH— | —CH₂—O—CH₂— | ethyl | 1 |
| ethyl | —C(O)—NH— | —CH₂—O—CH₂— | ethyl | 2 |
| ethyl | —C(O)—NH— | —CH₂—O—CH₂— | ethyl | 3 |
| n-propyl | Bond | —CH₂CH₂CH₂— | methyl | 1 |
| n-propyl | Bond | —CH₂CH₂CH₂— | methyl | 2 |
| n-propyl | Bond | —CH₂CH₂CH₂— | methyl | 3 |
| n-propyl | Bond | —CH₂CH₂CH₂— | ethyl | 1 |
| n-propyl | Bond | —CH₂CH₂CH₂— | ethyl | 2 |
| n-propyl | Bond | —CH₂CH₂CH₂— | ethyl | 3 |
| n-propyl | Bond | —CH₂—O—CH₂— | methyl | 1 |
| n-propyl | Bond | —CH₂—O—CH₂— | methyl | 2 |
| n-propyl | Bond | —CH₂—O—CH₂— | methyl | 3 |
| n-propyl | Bond | —CH₂—O—CH₂— | ethyl | 1 |
| n-propyl | Bond | —CH₂—O—CH₂— | ethyl | 2 |
| n-propyl | Bond | —CH₂—O—CH₂— | ethyl | 3 |
| n-propyl | —C(O)— | —CH₂CH₂CH₂— | methyl | 1 |
| n-propyl | —C(O)— | —CH₂CH₂CH₂— | methyl | 2 |
| n-propyl | —C(O)— | —CH₂CH₂CH₂— | methyl | 3 |
| n-propyl | —C(O)— | —CH₂CH₂CH₂— | ethyl | 1 |
| n-propyl | —C(O)— | —CH₂CH₂CH₂— | ethyl | 2 |
| n-propyl | —C(O)— | —CH₂CH₂CH₂— | ethyl | 3 |
| n-propyl | —C(O)— | —CH₂—O—CH₂— | methyl | 1 |
| n-propyl | —C(O)— | —CH₂—O—CH₂— | methyl | 2 |
| n-propyl | —C(O)— | —CH₂—O—CH₂— | methyl | 3 |
| n-propyl | —C(O)— | —CH₂—O—CH₂— | ethyl | 1 |
| n-propyl | —C(O)— | —CH₂—O—CH₂— | ethyl | 2 |
| n-propyl | —C(O)— | —CH₂—O—CH₂— | ethyl | 3 |
| n-propyl | —S(O)₂— | —CH₂CH₂CH₂— | methyl | 1 |
| n-propyl | —S(O)₂— | —CH₂CH₂CH₂— | methyl | 2 |
| n-propyl | —S(O)₂— | —CH₂CH₂CH₂— | methyl | 3 |
| n-propyl | —S(O)₂— | —CH₂CH₂CH₂— | ethyl | 1 |
| n-propyl | —S(O)₂— | —CH₂CH₂CH₂— | ethyl | 2 |
| n-propyl | —S(O)₂— | —CH₂CH₂CH₂— | ethyl | 3 |
| n-propyl | —S(O)₂— | —CH₂—O—CH₂— | methyl | 1 |
| n-propyl | —S(O)₂— | —CH₂—O—CH₂— | methyl | 2 |
| n-propyl | —S(O)₂— | —CH₂—O—CH₂— | methyl | 3 |
| n-propyl | —S(O)₂— | —CH₂—O—CH₂— | ethyl | 1 |
| n-propyl | —S(O)₂— | —CH₂—O—CH₂— | ethyl | 2 |
| n-propyl | —S(O)₂— | —CH₂—O—CH₂— | ethyl | 3 |
| n-propyl | —C(O)—NH— | —CH₂CH₂CH₂— | methyl | 1 |
| n-propyl | —C(O)—NH— | —CH₂CH₂CH₂— | methyl | 2 |
| n-propyl | —C(O)—NH— | —CH₂CH₂CH₂— | methyl | 3 |
| n-propyl | —C(O)—NH— | —CH₂CH₂CH₂— | ethyl | 1 |
| n-propyl | —C(O)—NH— | —CH₂CH₂CH₂— | ethyl | 2 |
| n-propyl | —C(O)—NH— | —CH₂CH₂CH₂— | ethyl | 3 |
| n-propyl | —C(O)—NH— | —CH₂—O—CH₂— | methyl | 1 |
| n-propyl | —C(O)—NH— | —CH₂—O—CH₂— | methyl | 2 |
| n-propyl | —C(O)—NH— | —CH₂—O—CH₂— | methyl | 3 |
| n-propyl | —C(O)—NH— | —CH₂—O—CH₂— | ethyl | 1 |
| n-propyl | —C(O)—NH— | —CH₂—O—CH₂— | ethyl | 2 |
| n-propyl | —C(O)—NH— | —CH₂—O—CH₂— | ethyl | 3 |
| n-butyl | Bond | —CH₂CH₂CH₂— | methyl | 1 |
| n-butyl | Bond | —CH₂CH₂CH₂— | methyl | 2 |
| n-butyl | Bond | —CH₂CH₂CH₂— | methyl | 3 |
| n-butyl | Bond | —CH₂CH₂CH₂— | ethyl | 1 |
| n-butyl | Bond | —CH₂CH₂CH₂— | ethyl | 2 |
| n-butyl | Bond | —CH₂CH₂CH₂— | ethyl | 3 |
| n-butyl | Bond | —CH₂—O—CH₂— | methyl | 1 |
| n-butyl | Bond | —CH₂—O—CH₂— | methyl | 2 |
| n-butyl | Bond | —CH₂—O—CH₂— | methyl | 3 |
| n-butyl | Bond | —CH₂—O—CH₂— | ethyl | 1 |
| n-butyl | Bond | —CH₂—O—CH₂— | ethyl | 2 |
| n-butyl | Bond | —CH₂—O—CH₂— | ethyl | 3 |
| n-butyl | —C(O)— | —CH₂CH₂CH₂— | methyl | 1 |
| n-butyl | —C(O)— | —CH₂CH₂CH₂— | methyl | 2 |
| n-butyl | —C(O)— | —CH₂CH₂CH₂— | methyl | 3 |
| n-butyl | —C(O)— | —CH₂CH₂CH₂— | ethyl | 1 |
| n-butyl | —C(O)— | —CH₂CH₂CH₂— | ethyl | 2 |
| n-butyl | —C(O)— | —CH₂CH₂CH₂— | ethyl | 3 |
| n-butyl | —C(O)— | —CH₂—O—CH₂— | methyl | 1 |
| n-butyl | —C(O)— | —CH₂—O—CH₂— | methyl | 2 |
| n-butyl | —C(O)— | —CH₂—O—CH₂— | methyl | 3 |
| n-butyl | —C(O)— | —CH₂—O—CH₂— | ethyl | 1 |
| n-butyl | —C(O)— | —CH₂—O—CH₂— | ethyl | 2 |
| n-butyl | —C(O)— | —CH₂—O—CH₂— | ethyl | 3 |
| n-butyl | —S(O)₂— | —CH₂CH₂CH₂— | methyl | 1 |
| n-butyl | —S(O)₂— | —CH₂CH₂CH₂— | methyl | 2 |
| n-butyl | —S(O)₂— | —CH₂CH₂CH₂— | methyl | 3 |
| n-butyl | —S(O)₂— | —CH₂CH₂CH₂— | ethyl | 1 |
| n-butyl | —S(O)₂— | —CH₂CH₂CH₂— | ethyl | 2 |
| n-butyl | —S(O)₂— | —CH₂CH₂CH₂— | ethyl | 3 |
| n-butyl | —S(O)₂— | —CH₂—O—CH₂— | methyl | 1 |
| n-butyl | —S(O)₂— | —CH₂—O—CH₂— | methyl | 2 |
| n-butyl | —S(O)₂— | —CH₂—O—CH₂— | methyl | 3 |
| n-butyl | —S(O)₂— | —CH₂—O—CH₂— | ethyl | 1 |
| n-butyl | —S(O)₂— | —CH₂—O—CH₂— | ethyl | 2 |
| n-butyl | —S(O)₂— | —CH₂—O—CH₂— | ethyl | 3 |
| n-butyl | —C(O)—NH— | —CH₂CH₂CH₂— | methyl | 1 |
| n-butyl | —C(O)—NH— | —CH₂CH₂CH₂— | methyl | 2 |
| n-butyl | —C(O)—NH— | —CH₂CH₂CH₂— | methyl | 3 |
| n-butyl | —C(O)—NH— | —CH₂CH₂CH₂— | ethyl | 1 |
| n-butyl | —C(O)—NH— | —CH₂CH₂CH₂— | ethyl | 2 |
| n-butyl | —C(O)—NH— | —CH₂CH₂CH₂— | ethyl | 3 |
| n-butyl | —C(O)—NH— | —CH₂—O—CH₂— | methyl | 1 |
| n-butyl | —C(O)—NH— | —CH₂—O—CH₂— | methyl | 2 |
| n-butyl | —C(O)—NH— | —CH₂—O—CH₂— | methyl | 3 |
| n-butyl | —C(O)—NH— | —CH₂—O—CH₂— | ethyl | 1 |
| n-butyl | —C(O)—NH— | —CH₂—O—CH₂— | ethyl | 2 |
| n-butyl | —C(O)—NH— | —CH₂—O—CH₂— | ethyl | 3 |
| ethoxymethyl | Bond | —CH₂CH₂CH₂— | methyl | 1 |
| ethoxymethyl | Bond | —CH₂CH₂CH₂— | methyl | 2 |
| ethoxymethyl | Bond | —CH₂CH₂CH₂— | methyl | 3 |
| ethoxymethyl | Bond | —CH₂CH₂CH₂— | ethyl | 1 |
| ethoxymethyl | Bond | —CH₂CH₂CH₂— | ethyl | 2 |
| ethoxymethyl | Bond | —CH₂CH₂CH₂— | ethyl | 3 |
| ethoxymethyl | Bond | —CH₂—O—CH₂— | methyl | 1 |
| ethoxymethyl | Bond | —CH₂—O—CH₂— | methyl | 2 |
| ethoxymethyl | Bond | —CH₂—O—CH₂— | methyl | 3 |
| ethoxymethyl | Bond | —CH₂—O—CH₂— | ethyl | 1 |
| ethoxymethyl | Bond | —CH₂—O—CH₂— | ethyl | 2 |
| ethoxymethyl | Bond | —CH₂—O—CH₂— | ethyl | 3 |
| ethoxymethyl | —C(O)— | —CH₂CH₂CH₂— | methyl | 1 |
| ethoxymethyl | —C(O)— | —CH₂CH₂CH₂— | methyl | 2 |
| ethoxymethyl | —C(O)— | —CH₂CH₂CH₂— | methyl | 3 |
| ethoxymethyl | —C(O)— | —CH₂CH₂CH₂— | ethyl | 1 |
| ethoxymethyl | —C(O)— | —CH₂CH₂CH₂— | ethyl | 2 |
| ethoxymethyl | —C(O)— | —CH₂CH₂CH₂— | ethyl | 3 |
| ethoxymethyl | —C(O)— | —CH₂—O—CH₂— | methyl | 1 |
| ethoxymethyl | —C(O)— | —CH₂—O—CH₂— | methyl | 2 |
| ethoxymethyl | —C(O)— | —CH₂—O—CH₂— | methyl | 3 |
| ethoxymethyl | —C(O)— | —CH₂—O—CH₂— | ethyl | 1 |
| ethoxymethyl | —C(O)— | —CH₂—O—CH₂— | ethyl | 2 |
| ethoxymethyl | —C(O)— | —CH₂—O—CH₂— | ethyl | 3 |
| ethoxymethyl | —S(O)₂— | —CH₂CH₂CH₂— | methyl | 1 |
| ethoxymethyl | —S(O)₂— | —CH₂CH₂CH₂— | methyl | 2 |
| ethoxymethyl | —S(O)₂— | —CH₂CH₂CH₂— | methyl | 3 |
| ethoxymethyl | —S(O)₂— | —CH₂CH₂CH₂— | ethyl | 1 |
| ethoxymethyl | —S(O)₂— | —CH₂CH₂CH₂— | ethyl | 2 |
| ethoxymethyl | —S(O)₂— | —CH₂CH₂CH₂— | ethyl | 3 |
| ethoxymethyl | —S(O)₂— | —CH₂—O—CH₂— | methyl | 1 |
| ethoxymethyl | —S(O)₂— | —CH₂—O—CH₂— | methyl | 2 |
| ethoxymethyl | —S(O)₂— | —CH₂—O—CH₂— | methyl | 3 |
| ethoxymethyl | —S(O)₂— | —CH₂—O—CH₂— | ethyl | 1 |
| ethoxymethyl | —S(O)₂— | —CH₂—O—CH₂— | ethyl | 2 |
| ethoxymethyl | —S(O)₂— | —CH₂—O—CH₂— | ethyl | 3 |
| ethoxymethyl | —C(O)—NH— | —CH₂CH₂CH₂— | methyl | 1 |
| ethoxymethyl | —C(O)—NH— | —CH₂CH₂CH₂— | methyl | 2 |
| ethoxymethyl | —C(O)—NH— | —CH₂CH₂CH₂— | methyl | 3 |
| ethoxymethyl | —C(O)—NH— | —CH₂CH₂CH₂— | ethyl | 1 |
| ethoxymethyl | —C(O)—NH— | —CH₂CH₂CH₂— | ethyl | 2 |
| ethoxymethyl | —C(O)—NH— | —CH₂CH₂CH₂— | ethyl | 3 |
| ethoxymethyl | —C(O)—NH— | —CH₂—O—CH₂— | methyl | 1 |
| ethoxymethyl | —C(O)—NH— | —CH₂—O—CH₂— | methyl | 2 |
| ethoxymethyl | —C(O)—NH— | —CH₂—O—CH₂— | methyl | 3 |
| ethoxymethyl | —C(O)—NH— | —CH₂—O—CH₂— | ethyl | 1 |

TABLE 3-continued

| | | | | |
|---|---|---|---|---|
| ethoxymethyl | —C(O)—NH— | —CH$_2$—O—CH$_2$— | ethyl | 2 |
| ethoxymethyl | —C(O)—NH— | —CH$_2$—O—CH$_2$— | ethyl | 3 |
| 2-methoxyethyl | Bond | —CH$_2$CH$_2$CH$_2$— | methyl | 1 |
| 2-methoxyethyl | Bond | —CH$_2$CH$_2$CH$_2$— | methyl | 2 |
| 2-methoxyethyl | Bond | —CH$_2$CH$_2$CH$_2$— | methyl | 3 |
| 2-methoxyethyl | Bond | —CH$_2$CH$_2$CH$_2$— | ethyl | 1 |
| 2-methoxyethyl | Bond | —CH$_2$CH$_2$CH$_2$— | ethyl | 2 |
| 2-methoxyethyl | Bond | —CH$_2$CH$_2$CH$_2$— | ethyl | 3 |
| 2-methoxyethyl | Bond | —CH$_2$—O—CH$_2$— | methyl | 1 |
| 2-methoxyethyl | Bond | —CH$_2$—O—CH$_2$— | methyl | 2 |
| 2-methoxyethyl | Bond | —CH$_2$—O—CH$_2$— | methyl | 3 |
| 2-methoxyethyl | Bond | —CH$_2$—O—CH$_2$— | ethyl | 1 |
| 2-methoxyethyl | Bond | —CH$_2$—O—CH$_2$— | ethyl | 2 |
| 2-methoxyethyl | Bond | —CH$_2$—O—CH$_2$— | ethyl | 3 |
| 2-methoxyethyl | —C(O)— | —CH$_2$CH$_2$CH$_2$— | methyl | 1 |
| 2-methoxyethyl | —C(O)— | —CH$_2$CH$_2$CH$_2$— | methyl | 2 |
| 2-methoxyethyl | —C(O)— | —CH$_2$CH$_2$CH$_2$— | methyl | 3 |
| 2-methoxyethyl | —C(O)— | —CH$_2$CH$_2$CH$_2$— | ethyl | 1 |
| 2-methoxyethyl | —C(O)— | —CH$_2$CH$_2$CH$_2$— | ethyl | 2 |
| 2-methoxyethyl | —C(O)— | —CH$_2$CH$_2$CH$_2$— | ethyl | 3 |
| 2-methoxyethyl | —C(O)— | —CH$_2$—O—CH$_2$— | methyl | 1 |
| 2-methoxyethyl | —C(O)— | —CH$_2$—O—CH$_2$— | methyl | 2 |
| 2-methoxyethyl | —C(O)— | —CH$_2$—O—CH$_2$— | methyl | 3 |
| 2-methoxyethyl | —C(O)— | —CH$_2$—O—CH$_2$— | ethyl | 1 |
| 2-methoxyethyl | —C(O)— | —CH$_2$—O—CH$_2$— | ethyl | 2 |
| 2-methoxyethyl | —C(O)— | —CH$_2$—O—CH$_2$— | ethyl | 3 |
| 2-methoxyethyl | —S(O)$_2$— | —CH$_2$CH$_2$CH$_2$— | methyl | 1 |
| 2-methoxyethyl | —S(O)$_2$— | —CH$_2$CH$_2$CH$_2$— | methyl | 2 |
| 2-methoxyethyl | —S(O)$_2$— | —CH$_2$CH$_2$CH$_2$— | methyl | 3 |
| 2-methoxyethyl | —S(O)$_2$— | —CH$_2$CH$_2$CH$_2$— | ethyl | 1 |
| 2-methoxyethyl | —S(O)$_2$— | —CH$_2$CH$_2$CH$_2$— | ethyl | 2 |
| 2-methoxyethyl | —S(O)$_2$— | —CH$_2$CH$_2$CH$_2$— | ethyl | 3 |
| 2-methoxyethyl | —S(O)$_2$— | —CH$_2$—O—CH$_2$— | methyl | 1 |
| 2-methoxyethyl | —S(O)$_2$— | —CH$_2$—O—CH$_2$— | methyl | 2 |
| 2-methoxyethyl | —S(O)$_2$— | —CH$_2$—O—CH$_2$— | methyl | 3 |
| 2-methoxyethyl | —S(O)$_2$— | —CH$_2$—O—CH$_2$— | ethyl | 1 |
| 2-methoxyethyl | —S(O)$_2$— | —CH$_2$—O—CH$_2$— | ethyl | 2 |
| 2-methoxyethyl | —S(O)$_2$— | —CH$_2$—O—CH$_2$— | ethyl | 3 |
| 2-methoxyethyl | —C(O)—NH— | —CH$_2$CH$_2$CH$_2$— | methyl | 1 |
| 2-methoxyethyl | —C(O)—NH— | —CH$_2$CH$_2$CH$_2$— | methyl | 2 |
| 2-methoxyethyl | —C(O)—NH— | —CH$_2$CH$_2$CH$_2$— | methyl | 3 |
| 2-methoxyethyl | —C(O)—NH— | —CH$_2$CH$_2$CH$_2$— | ethyl | 1 |
| 2-methoxyethyl | —C(O)—NH— | —CH$_2$CH$_2$CH$_2$— | ethyl | 2 |
| 2-methoxyethyl | —C(O)—NH— | —CH$_2$CH$_2$CH$_2$— | ethyl | 3 |
| 2-methoxyethyl | —C(O)—NH— | —CH$_2$—O—CH$_2$— | methyl | 1 |
| 2-methoxyethyl | —C(O)—NH— | —CH$_2$—O—CH$_2$— | methyl | 2 |
| 2-methoxyethyl | —C(O)—NH— | —CH$_2$—O—CH$_2$— | methyl | 3 |
| 2-methoxyethyl | —C(O)—NH— | —CH$_2$—O—CH$_2$— | ethyl | 1 |
| 2-methoxyethyl | —C(O)—NH— | —CH$_2$—O—CH$_2$— | ethyl | 2 |
| 2-methoxyethyl | —C(O)—NH— | —CH$_2$—O—CH$_2$— | ethyl | 3 |

TABLE 4

Exemplary Compounds
Certain exemplary compounds, including some of those described above in the Examples, have the following Formulas (II-4, III-4, IV-4, and V-4) wherein R$_2$, Z, and m are defined immediately below in the table. In this table, for each ring system, each row represents one specific compound.

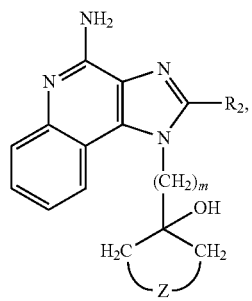

II-4

TABLE 4-continued

V-4

IV-4

III-4

| R$_2$ | Z | m |
|---|---|---|
| hydroxymethyl | Bond | 1 |
| hydroxymethyl | Bond | 2 |
| 2-hydroxyethyl | Bond | 1 |
| 2-hydroxyethyl | Bond | 2 |
| hydroxymethyl | —CH$_2$— | 1 |
| hydroxymethyl | —CH$_2$— | 2 |
| 2-hydroxyethyl | —CH$_2$— | 1 |
| 2-hydroxyethyl | —CH$_2$— | 2 |
| hydroxymethyl | —CH$_2$CH$_2$— | 1 |
| hydroxymethyl | —CH$_2$CH$_2$— | 2 |
| 2-hydroxyethyl | —CH$_2$CH$_2$— | 1 |
| 2-hydroxyethyl | —CH$_2$CH$_2$— | 2 |
| hydroxymethyl | —CH$_2$CH$_2$CH$_2$— | 1 |
| hydroxymethyl | —CH$_2$CH$_2$CH$_2$— | 2 |
| 2-hydroxyethyl | —CH$_2$CH$_2$CH$_2$— | 1 |
| 2-hydroxyethyl | —CH$_2$CH$_2$CH$_2$— | 2 |
| hydroxymethyl | —CH$_2$—O—CH$_2$— | 1 |
| hydroxymethyl | —CH$_2$—O—CH$_2$— | 2 |
| 2-hydroxyethyl | —CH$_2$—O—CH$_2$— | 1 |
| 2-hydroxyethyl | —CH$_2$—O—CH$_2$— | 2 |
| H | —CH$_2$—O— | 1 |
| H | —CH$_2$—O— | 2 |
| methyl | —CH$_2$—O— | 1 |
| methyl | —CH$_2$—O— | 2 |
| ethyl | —CH$_2$—O— | 1 |
| ethyl | —CH$_2$—O— | 2 |
| n-propyl | —CH$_2$—O— | 1 |
| n-propyl | —CH$_2$—O— | 2 |
| n-butyl | —CH$_2$—O— | 1 |

TABLE 4-continued

| | | |
|---|---|---|
| n-butyl | —$CH_2$—O— | 2 |
| ethoxymethyl | —$CH_2$—O— | 1 |
| ethoxymethyl | —$CH_2$—O— | 2 |
| hydroxymethyl | —$CH_2$—O— | 1 |
| hydroxymethyl | —$CH_2$—O— | 2 |
| 2-hydroxyethyl | —$CH_2$—O— | 1 |
| 2-hydroxyethyl | —$CH_2$—O— | 2 |
| H | —O— | 1 |
| H | —O— | 2 |
| methyl | —O— | 1 |
| methyl | —O— | 2 |
| ethyl | —O— | 1 |
| ethyl | —O— | 2 |
| n-propyl | —O— | 1 |
| n-propyl | —O— | 2 |
| n-butyl | —O— | 1 |
| n-butyl | —O— | 2 |
| ethoxymethyl | —O— | 1 |
| ethoxymethyl | —O— | 2 |
| hydroxymethyl | —O— | 1 |
| hydroxymethyl | —O— | 2 |
| 2-hydroxyethyl | —O— | 1 |
| 2-hydroxyethyl | —O— | 2 |

TABLE 5

Certain exemplary compounds, including some of those described above in the Examples, have the following Formulas (II-5, III-5, IV-5, and V-5) wherein $R_2$, and m are defined immediately below in the table. In this table, for each ring system, each row represents one specific compound.

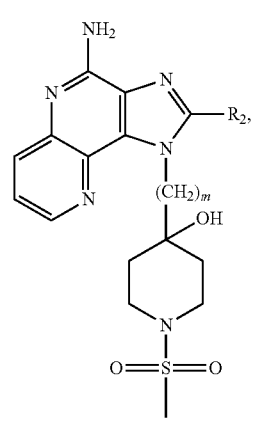

| $R_2$ | m |
|---|---|
| hydroxymethyl | 1 |
| hydroxymethyl | 2 |
| 2-hydroxyethyl | 1 |
| 2-hydroxyethyl | 2 |

Compounds of the invention have been found to induce biosynthesis when tested using the method described below.

CYTOKINE INDUCTION IN HUMAN CELLS

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

CYTOKINE INDUCTION IN HUMAN CELLS

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's Sector HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula (I):

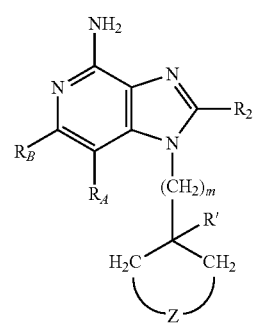

I wherein:
  m is an integer from 1 to 5;
  R' is selected from the group consisting of:
    hydroxy,
    thiol,
    —S(O)$_{0-2}$-alkyl,
    —S(O)$_2$—NH—R$_9$,
    alkoxy,
    —N(R$_9$)$_2$, and
    —NH-Q-R$_4$;
  Z is selected from the group consisting of:
    a bond,
    C$_{1-5}$ alkylene,

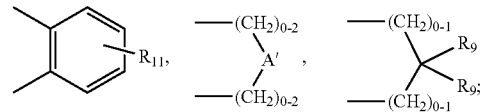

A' is selected from the group consisting of:
    —O—,
    —C(O)—,
    —N(R$_8$)—,
    —N(Q-R$_4$)—,
    —N(C$_{1-5}$ alkylene-NH-Q-R$_4$)—,
    —N(C$_{1-5}$ alkylene-W—NH—R$_8$)—, and
    —S(O)$_{0-2}$-;
  R$_2$ is selected from the group consisting of hydrogen, alkyl, alkoxyalkylenyl, haloalkyl, hydroxyalkylenyl, and —X—Y-alkyl wherein X is C$_{1-2}$ alkylene, and Y

287 is selected from the group consisting of —N(R$_8$)—SO$_2$—, —N(R$_8$)—C(R$_6$)—, and —N(R$_8$)—SO$_2$—N(R$_8$)—;

taken together, R$_A$ and R$_B$ form a fused aryl or heteroaryl ring containing one heteroatom selected from the group consisting of N and S wherein the aryl or heteroaryl ring is unsubstituted or substituted by one or more R groups;

or taken together, R$_A$ and R$_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N(R$_9$)$_2$;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

R$_6$ is selected from the group consisting of =O and =S;

R$_8$ is selected from the group consisting of hydrogen, alkyl, alkoxyalkylenyl, and arylalkylenyl;

R$_9$ is selected from the group consisting of hydrogen and alkyl;

R$_{11}$ is selected from the group consisting of hydrogen, alkyl, halogen, and trifluoromethyl;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—; and W is selected from the group consisting of a bond, —C(O)—, and —S(O)$_2$—; and or a pharmaceutically acceptable salt thereof.

288

2. A compound of the Formula (II):

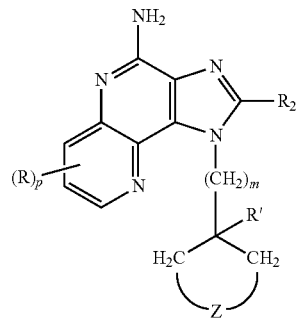

V wherein:
m is an integer from 1 to 5;
n is an integer from 0 to 4;
R' is selected from the group consisting of:
hydroxy,
thiol,
—S(O)$_{0-2}$-alkyl,
—S(O)$_2$—NH—R$_9$,
alkoxy,
—N(R$_9$)$_2$, and
—NH-Q-R$_4$;

Z is selected from the group consisting of:
a bond,
C$_{1-5}$ alkylene,

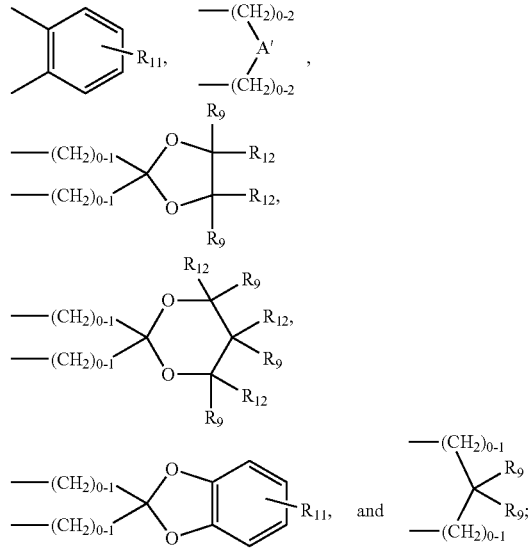

A' is selected from the group consisting of:
—O—,
—C(O)—,
—N(R$_8$)—,
—N(Q-R$_4$)—,
—N(C$_{1-5}$ alkylene-NH-Q-R$_4$)—,
—N(C$_{1-5}$ alkylene-W—NH—R$_8$)—, and
—S(O)$_{0-2}$—;

R$_2$ is selected from the group consisting of hydrogen, alkyl, alkoxyalkylenyl, haloalkyl, hydroxyalkylenyl, and —X—Y-alkyl wherein X is C$_{1-2}$ alkylene, and Y is selected from the group consisting of —N(R$_8$)—SO$_2$—, —N(R$_8$)—C(R$_6$)—, and —N(R$_8$)—SO$_2$—N(R$_8$)—;

R is selected from the group consisting of:
halogen,
hydroxy,
alkyl,
alkenyl,
haloalkyl,
alkoxy,
alkylthio, and
—N($R_9$)$_2$;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;
$R_6$ is selected from the group consisting of =O and =S;
$R_8$ is selected from the group consisting of hydrogen, alkyl, alkoxyalkylenyl, and arylalkylenyl;
$R_9$ is selected from the group consisting of hydrogen and alkyl;
$R_{11}$ is selected from the group consisting of hydrogen, alkyl, halogen, and trifluoromethyl;
Q is selected from the group consisting of a bond, —C($R_6$)—, —C($R_6$)—C($R_6$), —S(O)$_2$—, —C($R_6$)—N($R_8$)—W—, —S(O)$_2$—N($R_8$)—, —C($R_6$)—O—, and —C($R_6$)—N(O$R_9$)—; and
W is selected from the group consisting of a bond, —C(O)—, and —S(O)$_2$—; and
or a pharmaceutically acceptable salt thereof.

3. The compound or salt of claim 2 wherein n is 0.
4. The compound or salt of claim 2 wherein m is 1.
5. The compound or salt of claim 2 wherein Z is selected from the group consisting of a bond and $C_{1-5}$ alkylene.
6. The compound or salt of claim 2 wherein m is 1, and n is 0.
7. The compound or salt of claim 6 wherein A' is —O—.
8. The compound or salt of claim 6 wherein A' is —N($R_8$)— or —N(Q-$R_4$)—.
9. The compound or salt of claim 2 wherein:
Z is a bond or G1-4 $C_{1-5}$ alkylene; and
$R_2$ is selected from the group consisting of hydrogen, $C_{1-4}$ alkyl, HO—$C_{1-4}$ alkylenyl, and $C_{1-4}$ alkyl-O$C_{1-4}$ alkylenyl; and
R' is hydroxyl, —N($R_9$)$_2$, or —NH-Q-$R_4$.
10. The compound or salt of claim 9 wherein Q is —S(O)$_2$— or —C($R_6$)—.
11. The compound or salt of claim 9 wherein R' is —N($R_9$)$_2$.
12. The compound or salt of claim 2 wherein R' is —N($R_9$)$_2$—, and each $R_9$ is hydrogen.
13. The compound or salt of claim 2 wherein $R_2$ is hydrogen, alkyl, alkoxyalkylenyl, haloalkyl, or hydroxyalkyl.
14. The compound or salt of claim 2, wherein R' is —NH-Q-$R_4$, wherein:
Q is selected from the group consisting of —C($R_6$)—, —S(O)$_2$—, and —C($R_6$)—N($R_8$).

15. A pharmaceutical composition comprising a therapeutically effective amount of a compound or salt of claim 1 in combination with a pharmaceutically acceptable carrier.

16. The compound or salt of claim 1 selected from the group of N-{[4-(4-Amino-2-(ethoxymethyl)-1H-imidazo[4,5-c]quinolin-1-yl)methyl]tetrahydropyran-4-yl}methanesulfonamide; N-{[4-(4-Amino-2-(2-methoxyethyl)-1H-imidazo[4,5-c]quinolin-1-yl)methyl]tetrahydropyran-4-yl}methanesulfonamide; N-{[4-(4-Amino-2-butyl-1H-imidazo[4,5-c]quinolin-1-yl)methyl]tetrahydropyran-4-yl}methanesulfonamide; N-{[4-(4-Amino-2-propyl-1H-imidazo[4,5-c]quinolin-1-yl)methyl]tetrahydropyran-4-yl}methanesulfonamide; N-{[4-(4-Amino-2-ethyl-1H-imidazo[4,5-c]quinolin-1-yl)methyl]tetrahydropyran-4-yl}methanesulfonamide; N-{[4-(4-Amino-2-methyl-1H-imidazo[4,5-c]quinolin-1-yl)methyl]tetrahydropyran-4-yl}methanesulfonamide; N-{[4-(4-Amino-2-hydroxymethyl-1H-imidazo[4,5-c]quinolin-1-yl)methyl]tetrahydropyran-4-yl}methanesulfonamide; N-{[4-(4-Amino-2-(2-hydroxyethyl)-1H-imidazo[4,5-c]quinolin-1-yl)methyl]tetrahydropyran-4-yl}methanesulfonamide; N-{[4-(4-Amino-1H-imidazo[4,5-c]quinolin-1-yl)methyl]tetrahydropyran-4-yl}methanesulfonamide N-(1-{[4-Amino-2-(ethoxymethyl)-1H-imidazo[4,5-c]quinolin-1-yl]methyl}cyclopentyl)methanesulfonamide; N-(1-{[4-Amino-2-(2-methoxyethyl)-1H-imidazo[4,5-c]quinolin-1-yl]methyl}cyclopentyl)methanesulfonamide; N-(1-{[4-Amino-2-butyl-1H-imidazo[4,5-c]quinolin-1-yl]methyl}cyclopentyl)methanesulfonamide; N-(1-{[4-Amino-2-propyl-1H-imidazo[4,5-c]quinolin-1-yl]methyl}cyclopentyl)methanesulfonamide; N-(1-{[4-Amino-2-ethyl-1H-imidazo[4,5-c]quinolin-1-yl]methyl}cyclopentyl)methanesulfonamide; N-(1-{[4-Amino-2-methyl-1H-imidazo[4,5-c]quinolin-1-yl]methyl}cyclopentyl)methanesulfonamide; N-(1-{[4-Amino-2-hydroxymethyl-1H-imidazo[4,5-c]quinolin-1-yl]methyl}cyclopentyl)methanesulfonamide; N-(1-{[4-Amino-2-(2-hydroxyethyl)-1H-imidazo[4,5-c]quinolin-1-yl]methyl}cyclopentyl)methanesulfonamide; and N-(1-{[4-Amino-1H-imidazo[4,5-c]quinolin-1-yl]methyl}cyclopentyl)methanesulfonamide.

17. The compound or salt of claim 1 selected from the group of N-(1-{[4-Amino-2-(ethoxymethyl)-1H-imidazo[4,5-c]quinolin-1-yl]methyl}cyclohexyl)acetamide; N-(1-{[4-Amino-2-(2-methoxyethyl)-1H-imidazo[4,5-c]quinolin-1-yl]methyl}cyclohexyl)acetamide; N-(1-{[4-Amino-2-butyl-1H-imidazo[4,5-c]quinolin-1-yl]methyl}cyclohexyl)acetamide; N-(1-{[4-Amino-2-propyl-1H-imidazo[4,5-c]quinolin-1-yl]methyl}cyclohexyl)acetamide; N-(1-{[4-Amino-2-ethyl-1H-imidazo[4,5-c]quinolin-1-yl]methyl}cyclohexyl)acetamide; N-(1-{[4-Amino-2-methyl-1H-imidazo[4,5-c]quinolin-1-yl]methyl}cyclohexyl)acetamide; N-(1-{[4-Amino-2-hydroxymethyl-1H-imidazo[4,5-c]quinolin-1-yl]methyl}cyclohexyl)acetamide; N-(1-{[4-Amino-2-(2-hydroxyethyl)-1H-imidazo[4,5-c]quinolin-1-yl]methyl}cyclohexyl)acetamide; and N-(1-{[4-Amino-1H-imidazo[4,5-c]quinolin-1-yl]methyl}cyclohexyl)acetamide.

18. The compound or salt of claim 1 selected from the group of N-(1-{[4-Amino-2-(ethoxymethyl)-1H-imidazo[4,5-c]quinolin-1-yl]methyl}cyclohexyl)methanesulfonamide; N-(1-{[4-Amino-2-(2-methoxyethyl)-1H-imidazo[4,5-c]quinolin-1-yl]methyl}cyclohexyl)methanesulfonamide; N-(1-{[4-Amino-2-butyl-1H-imidazo[4,5-c]quinolin-1-yl]methyl}cyclohexyl)methanesulfonamide; N-(1-{[4-Amino- 2-propyl-1H-imidazo[4,5-c]quinolin-1-yl]methyl}cyclohexyl)methanesulfonamide; N-(1-{[4-Amino-2-ethyl-1H-imidazo[4,5-c]quinolin-1-yl]methyl}cyclohexyl)methanesulfonamide; N-(1-{[4-Amino-2-methyl-1H-imidazo[4,5-c]quinolin-1-yl]methyl}cyclohexyl)methanesulfonamide; N-(1-{[4-Amino-2-hydroxymethyl-1H-imidazo[4,5-c]quinolin-1-yl]methyl}cyclohexyl)methanesulfonamide; N-(1-{[4-Amino-2-(2-hydroxyethyl)-1H-imidazo[4,5-c]quinolin-1-yl]methyl}cyclohexyl)methanesulfonamide; and N-(1-{[4-Amino-1H-imidazo[4,5-c]quinolin-1-yl]methyl}cyclohexyl)methanesulfonamide.

19. The compound or salt of claim 1 selected from the group of N-(1-{[4-Amino-2-(ethoxymethyl)-1H-imidazo[4,5-c]quinolin-1-yl]methyl}cyclohexyl)-N'-isopropylurea; N-(1-{[4-Amino-2-(2-methoxyethyl)-1H-imidazo[4,5-c]quinolin-1-yl]methyl}cyclohexyl)-N'-isopropylurea; N-(1-{[4-Amino-2-butyl-1H-imidazo[4,5-c]quinolin-1-yl]methyl}cyclohexyl)-N'-isopropylurea; N-(1-{[4-Amino-2-propyl-1H-imidazo[4,5-c]quinolin-1-yl]methyl}cyclohexyl)-N'-isopropylurea; N-(1-{[4-Amino-2-ethyl-1H-imidazo[4,5-c]quinolin-1-yl]methyl}cyclohexyl)-N'-isopropylurea; N-(1-{[4-Amino-2-methyl-1H-imidazo[4,5-c]quinolin-1-yl]methyl}cyclohexyl)-N'-isopropylurea; N-(1-{[4-Amino-2-hydroxymethyl-1H-imidazo[4,5-c]quinolin-1-yl]methyl}cyclohexyl)-N'-isopropylurea; N-(1-{[4-Amino-2-(2-hydroxyethyl)-1H-imidazo[4,5-c]quinolin-1-yl]methyl}cyclohexyl)-N'-isopropylurea; and N-(1-{[4-Amino-1H-imidazo[4,5-c]quinolin-1-yl]methyl}cyclohexyl)-N'-isopropylurea.

20. The compound or salt of claim 1 selected from the group of; N-(1-{[4-Amino-2-(ethoxymethyl)-1H-imidazo[4,5-c]quinolin-1-yl]methyl}cyclobutyl)methanesulfonamide; N-(1-{[4-Amino-2-(2-methoxyethyl)-1H-imidazo[4,5-c]quinolin-1-yl]methyl}cyclobutyl)methanesulfonamide; N-(1-{[4-Amino-2-butyl-1H-imidazo[4,5-c]quinolin-1-yl]methyl}cyclobutyl)methanesulfonamide; N-(1-{[4-Amino-2-propyl-1H-imidazo[4,5-c]quinolin-1-yl]methyl}cyclobutyl)methanesulfonamide; N-(1-{[4-Amino-2-ethyl-1H-imidazo[4,5-c]quinolin-1-yl]methyl}cyclobutyl)methanesulfonamide; N-(1-{[4-Amino-2-methyl-1H-imidazo[4,5-c]quinolin-1-yl]methyl}cyclobutyl)methanesulfonamide; N-(1-{[4-Amino-2-hydroxymethyl-1H-imidazo[4,5-c]quinolin-1-yl]methyl}cyclobutyl)methanesulfonamide; N-(1-{[4-Amino-2-(2-hydroxyethyl)-1H-imidazo[4,5-c]quinolin-1-yl]methyl}cyclobutyl)methanesulfonamide; N-(1-{[4-Amino-1H-imidazo[4,5-c]quinolin-1-yl]methyl}cyclobutyl)methanesulfonamide; N-(1-{[4-Amino-2-(ethoxymethyl)-1H-imidazo[4,5-c]quinolin-1-yl]methyl}cyclopropyl)methanesulfonamide; N-(1-{[4-Amino-2-(2-methoxyethyl)-1H-imidazo[4,5-c]quinolin-1-yl]methyl}cyclopropyl)methanesulfonamide; N-(1-{[4-Amino-2-butyl-1H-imidazo[4,5-c]quinolin-1-yl]methyl}cyclopropyl)methanesulfonamide; N-(1-{[4-Amino-2-propyl-1H-imidazo[4,5-c]quinolin-1-yl]methyl}cyclopropyl)methanesulfonamide; N-(1-{[4-Amino-2-ethyl-1H-imidazo[4,5-c]quinolin-1-yl]methyl}cyclopropyl)methanesulfonamide; N-(1-{[4-Amino-2-methyl-1H-imidazo[4,5-c]quinolin-1-yl]methyl}cyclopropyl)methanesulfonamide; N-(1-{[4-Amino-2-hydroxymethyl-1H-imidazo[4,5-c]quinolin-1-yl]methyl}cyclopropyl)methanesulfonamide; N-(1-{[4-Amino-2-(2-hydroxyethyl)-1H-imidazo[4,5-c]quinolin-1-yl]methyl}cyclopropyl)methanesulfonamide; and N-(1-{[4-Amino-1H-imidazo[4,5-c]quinolin-1-yl]methyl}cyclopropyl)methanesulfonamide.

* * * * *